(12) United States Patent
Whitten et al.

(10) Patent No.: US 9,079,891 B2
(45) Date of Patent: Jul. 14, 2015

(54) COMPOUNDS THAT MODULATE INTRACELLULAR CALCIUM

(75) Inventors: Jeffrey P. Whitten, Santee, CA (US); Yazhong Pei, San Diego, CA (US); Jianguo Cao, San Diego, CA (US); Zhijun Wang, San Diego, CA (US); Evan Rogers, San Diego, CA (US); Brian Dyck, San Diego, CA (US); Jonathan Grey, San Diego, CA (US)

(73) Assignee: CALCIMEDICA, INC., La Jolla, CA (US)

( * ) Notice: Subject to any disclaimer, the term of this patent is extended or adjusted under 35 U.S.C. 154(b) by 33 days.

(21) Appl. No.: 13/219,393

(22) Filed: Aug. 26, 2011

(65) Prior Publication Data

US 2012/0053210 A1    Mar. 1, 2012

Related U.S. Application Data

(60) Provisional application No. 61/377,842, filed on Aug. 27, 2010.

(51) Int. Cl.

| | | |
|---|---|---|
| C07D 277/34 | (2006.01) | |
| A61K 31/426 | (2006.01) | |
| C07D 413/04 | (2006.01) | |
| C07D 413/14 | (2006.01) | |
| C07D 417/04 | (2006.01) | |
| C07D 417/14 | (2006.01) | |
| A61K 9/00 | (2006.01) | |
| A61K 9/02 | (2006.01) | |
| A61K 9/48 | (2006.01) | |
| C07D 409/04 | (2006.01) | |
| C07D 409/14 | (2006.01) | |

(52) U.S. Cl.
CPC .............. *C07D 413/04* (2013.01); *A61K 9/007* (2013.01); *A61K 9/0014* (2013.01); *A61K 9/0019* (2013.01); *A61K 9/0031* (2013.01); *A61K 9/0048* (2013.01); *A61K 9/02* (2013.01); *A61K 9/4866* (2013.01); *C07D 409/04* (2013.01); *C07D 409/14* (2013.01); *C07D 413/14* (2013.01); *C07D 417/04* (2013.01); *C07D 417/14* (2013.01)

(58) Field of Classification Search
CPC .................................... A61K 31/426
USPC .................... 548/400, 195; 514/371
See application file for complete search history.

(56) References Cited

U.S. PATENT DOCUMENTS

| | | | |
|---|---|---|---|
| 4,658,040 A | 4/1987 | Baird et al. | |
| 6,323,227 B1 | 11/2001 | Klein et al. | |
| 6,348,480 B1 | 2/2002 | Kubota et al. | |
| 6,506,747 B1 | 1/2003 | Betageri et al. | |
| 6,919,359 B2 | 7/2005 | Piotrowski | |
| 6,958,339 B2 | 10/2005 | Kubota et al. | |
| 7,378,420 B2* | 5/2008 | Pajouhesh et al. | 514/253.12 |
| 7,709,518 B2 | 5/2010 | Chen et al. | |
| 7,816,535 B2 | 10/2010 | Bohnert et al. | |
| 8,546,403 B2 | 10/2013 | Whitten | |
| 2001/0044445 A1 | 11/2001 | Bamaung et al. | |
| 2004/0142980 A1 | 7/2004 | Finzel et al. | |
| 2005/0085531 A1 | 4/2005 | Hodge et al. | |
| 2006/0014811 A1* | 1/2006 | Muto et al. | 514/369 |
| 2006/0030567 A1 | 2/2006 | Ehrenfreund et al. | |
| 2006/0100245 A1 | 5/2006 | Bakthavatchalam et al. | |
| 2006/0199845 A1 | 9/2006 | Sun et al. | |
| 2006/0223812 A1 | 10/2006 | Mandelkow et al. | |
| 2006/0270720 A1 | 11/2006 | Gopalsamy et al. | |
| 2007/0105867 A1 | 5/2007 | Chidambaram et al. | |
| 2007/0249050 A1 | 10/2007 | Chen et al. | |
| 2007/0249051 A1 | 10/2007 | Bohnert et al. | |
| 2007/0249609 A1 | 10/2007 | Chen et al. | |
| 2007/0249661 A1 | 10/2007 | Chen et al. | |
| 2007/0254363 A1 | 11/2007 | Chen et al. | |
| 2007/0254912 A1 | 11/2007 | Chen et al. | |
| 2007/0254925 A1 | 11/2007 | Vo et al. | |
| 2007/0254926 A1 | 11/2007 | Jiang et al. | |
| 2008/0064874 A1 | 3/2008 | Dunkel et al. | |
| 2008/0293092 A1 | 11/2008 | Stauderman et al. | |
| 2009/0069288 A1 | 3/2009 | Breinlinger et al. | |
| 2009/0137659 A1 | 5/2009 | Velicelebi et al. | |
| 2010/0041762 A1 | 2/2010 | Bohnert et al. | |
| 2010/0130510 A1 | 5/2010 | Chen et al. | |
| 2010/0130522 A1 | 5/2010 | Jiang et al. | |
| 2010/0152241 A1 | 6/2010 | Whitten | |

(Continued)

FOREIGN PATENT DOCUMENTS

| | | |
|---|---|---|
| EP | 1024138 | 8/2000 |
| EP | 1754483 A1 | 2/2007 |

(Continued)

OTHER PUBLICATIONS

STN display Muto et al., US 2006/0014811 (2006).*
STN/CAS online results, Muto et al. US 20060035944 (2006).*
PCT/US2011/049424 International Search Report and Written Opinion dated Mar. 26, 2012.
Buchstaller, et al. "Synthesis of Thieno [2, 3-b] Pyridinones Acting as Cytoprotectants . . . " Journal of Medicinal Chemistry 49(3), pp. 864-871 (2006).

(Continued)

*Primary Examiner* — Yong Chu
*Assistant Examiner* — Sonya Wright
(74) *Attorney, Agent, or Firm* — Wilson Sonsini Goodrich & Rosati

(57) ABSTRACT

Described herein are compounds and pharmaceutical compositions containing such compounds, which modulate the activity of store-operated calcium (SOC) channels. Also described herein are methods of using such SOC channel modulators, alone and in combination with other compounds, for treating diseases or conditions that would benefit from inhibition of SOC channel activity.

13 Claims, 2 Drawing Sheets

(56) References Cited

U.S. PATENT DOCUMENTS

| | | |
|---|---|---|
| 2010/0273744 A1 | 10/2010 | Gore et al. |
| 2010/0286103 A1 | 11/2010 | Chen et al. |
| 2010/0292252 A1 | 11/2010 | Chen et al. |
| 2010/0311787 A1 | 12/2010 | Chen et al. |
| 2011/0015184 A1 | 1/2011 | Bohnert et al. |
| 2011/0052643 A1 | 3/2011 | Che et al. |
| 2011/0105447 A1 | 5/2011 | Muthuppalaniappan et al. |
| 2011/0112058 A1 | 5/2011 | Muthuppalaniappan et al. |
| 2011/0263612 A1 | 10/2011 | Whitten et al. |
| 2012/0035237 A1 | 2/2012 | Coe et al. |
| 2012/0289587 A1 | 11/2012 | Velecelibi et al. |
| 2013/0345193 A1 | 12/2013 | Whitten |
| 2013/0345240 A1 | 12/2013 | Whitten |

FOREIGN PATENT DOCUMENTS

| | | | |
|---|---|---|---|
| EP | 1921077 | | 5/2008 |
| ES | 371373 | | 4/1972 |
| JP | WO 2007/037543 | * | 4/2007 |
| WO | WO94/12505 | | 6/1994 |
| WO | WO98/06719 | | 2/1998 |
| WO | WO98/54116 | | 12/1998 |
| WO | WO99/51580 | | 10/1999 |
| WO | WO01/49663 | | 7/2001 |
| WO | WO02/48131 | | 6/2002 |
| WO | WO03/101979 A1 | | 12/2003 |
| WO | WO2004/041813 A1 | | 5/2004 |
| WO | WO-2004/056774 | | 7/2004 |
| WO | WO2005/009539 | | 2/2005 |
| WO | WO2005/009954 | | 2/2005 |
| WO | WO2005/033102 A2 | | 4/2005 |
| WO | WO2006/007864 A1 | | 1/2006 |
| WO | WO2006/012642 A2 | | 2/2006 |
| WO | WO2006/034402 | | 3/2006 |
| WO | WO2006/081389 | | 8/2006 |
| WO | WO2006/081391 | | 8/2006 |
| WO | WO2006/083477 | | 8/2006 |
| WO | WO2006/089177 | | 8/2006 |
| WO | WO2006/124887 A1 | | 11/2006 |
| WO | WO-2007/056341 | | 5/2007 |
| WO | WO2007/083689 A1 | | 7/2007 |
| WO | WO2007/087427 | | 8/2007 |
| WO | WO2007/087429 | | 8/2007 |
| WO | WO-2007/093542 | | 8/2007 |
| WO | WO2007/112093 | | 10/2007 |
| WO | WO-2007/120600 | | 10/2007 |
| WO | WO2008/063504 | | 5/2008 |
| WO | WO-2009/020642 | | 2/2009 |
| WO | WO2010/034011 | | 3/2010 |
| WO | WO2010/122089 | | 10/2010 |
| WO | WO2011/063277 | | 5/2011 |
| WO | WO-2011/139489 | | 11/2011 |
| WO | WO2012/170951 | | 12/2012 |

OTHER PUBLICATIONS

Bundgaard, Design of Prodrugs, (1985), Elsevier, Chapter 1, p. 1-4.
Henry, "Calcium antagonists as antiatherogenic agents", Ann N Y Acad Sci. 522:411-9, 1988.
Kharizomenova, "Functional derivatives of thiophone," Khimiya Geterotsiklicheskikh Soedininii, vol. 1, p. 45-46 (1980)(includes English Translation).
Kharizomenova, Caplus 93:71666, 1980.
Koebel, Synthesis of Thieno [2, 3-b]azepin-4-ones as Potential Antineoplaxic Agents, (1975) Jounral of Medicinal Chemistry, vol. 18, No. 2, p. 192-194.

Mashlovskii M.D. "Lekarstvennie sredstva." 1993, *Medicina*, part I, p. 8 Moscow (includes English translation).
PCT/US2008/073392 International Search Report dated Feb. 11, 2009.
PCT/US2009/055247 International Search Report dated Mar. 10, 2011.
PCT/US2011/049424 International Search Report mailed Mar. 26, 2012.
Perissin, Caplus 113:17485 (1990).
Perissin, M. et al., "Synthesis and Pharmacology of 2-amino-3-ethoxycarbony-4-phenithiophene derivatives," European Journal of Medicinal Chemistry, Jan. 1, 1980, pp. 563-565, vol. 15, No. 6, Editions Scientifique Elsevier, Paris, FR.
Pittala, A facile synthesis of new 2-carboxamido-3-carboxythiophene, Il Farmaco, vol. 60, p. 711-720 (2005).
Putney, 2010, Molecular Interventions, vol. 10(4), p. 209-218.
Russian Application No. 2010112967/04 Office Action dated Apr. 14, 2011 (English translation only).
Schepetkin et al., "High-throughput screening for small-molecule activators of neutrophils: identification of novel N-formyl peptide receptor agonists," Mol Pharmacol. 71(4):1061-74, 2007.
Sweeney et al., "Small-molecule inhibitors of store-operated calcium entry," ChemMedChem. 4(5):706-18, 2009.
Yonetoku et al., "Novel potent and selective $Ca^{2+}$ release-activated $Ca^{2+}$ (CRAC) channel inhibitors. Part 3: synthesis and CRAC channel inhibitory activity of 4'-[(trifluoromethyl)pyrazol-1-yl]carboxanilides," Bioorg Med Chem. 16(21):9457-66, 2008.
Yonetoku et al., "Novel potent and selective calcium-release-activated calcium (CRAC) channel inhibitors. Part 1: synthesis and inhibitory activity of 5-(1-methyl-3-trifluoromethyl-1H-pyrazol-5-yl)-2-thiophenecarboxamides," Bioorg Med Chem. 14(14):4750-60, 2006.
Yonetoku et al., "Novel potent and selective calcium-release-activated calcium (CRAC) channel inhibitors. Part 2: Synthesis and inhibitory activity of aryl-3-trifluoromethylpyrazoles," Bioorg Med Chem. 14(15):5370-83, 2006.
Australian Patent Application No. 2011248877 Examination Report dated Jun. 10, 2014.
Chinese Application No. 201180050485.X Office Action dated Jul. 18, 2014.
EP11820751.3 Extended Search Report dated May 21, 2014.
Long et al. Pyrazolylthiazole as ΔF508-Cystic Fibrosis Transmemberane Conductance Regulator Correctors with Improved Hydrophilicity Compared to Bithiazoles. J Medicinal Chemistry 53(9):3772-3781 (2010).
U.S. Appl. No. 13/969,401 Office Action dated Jul. 8, 2014.
Arthritis, 2014, http://en.wikipedia.org/wiki/Arthritis.
AU 2011293201 Exam Report dated Mar. 4, 2014.
Colitis, 2014, http://www.healthline.com/health/ulterative-colitis-take-control-can-it-be-cured.
EP11777791 Search Report dated Aug. 8, 2013.
Patani et al., "Bioisosterism: A Rational Approach in Drug Design," Chem. Rev., vol. 96, pp. 3147-3176 (1996).
PCT/US2011/031992 Search Report mailed Dec. 7, 2011.
PCT/US2011/031992 International Preliminary Report on Patentability mailed Nov. 8, 2012.
PCT/US2011/049424 International Preliminary Report on Patentability mailed Mar. 5, 2013.
Taiwanese Appl. No. 100114497 Search Report dated Feb. 19, 2013.
U.S. Appl. No. 13/085,324 Office Action dated Feb. 8, 2013.
U.S. Appl. No. 13/975,238 Office Action dated Jan. 27, 2014.
U.S. Appl. No. 13/975,238 Office Action dated Jun. 9, 2014.
U.S. Appl. No. 13/969,401 Office Action dated Mar. 17, 2014.

* cited by examiner

COMPOUNDS THAT MODULATE INTRACELLULAR CALCIUM

CROSS-REFERENCE

This application claims the benefit of U.S. provisional application No. 61/377,842, filed Aug. 27, 2010, which is incorporated by reference in its entirety.

FIELD OF THE INVENTION

Described herein are compounds, pharmaceutical compositions and medicaments that include such compounds, and methods of using such compounds to modulate store-operated calcium (SOC) channel activity.

BACKGROUND OF THE INVENTION

Calcium plays a vital role in cell function and survival. For example, calcium is a key element in the transduction of signals into and within cells. Cellular responses to growth factors, neurotransmitters, hormones and a variety of other signal molecules are initiated through calcium-dependent processes.

Virtually all cell types depend in some manner upon the generation of cytoplasmic $Ca^{2+}$ signals to regulate cell function, or to trigger specific responses. Cytosolic $Ca^{2+}$ signals control a wide array of cellular functions ranging from short-term responses such as contraction and secretion to longer-term regulation of cell growth and proliferation. Usually, these signals involve some combination of release of $Ca^{2+}$ from intracellular stores, such as the endoplasmic reticulum (ER), and influx of $Ca^{2+}$ across the plasma membrane. In one example, cell activation begins with an agonist binding to a surface membrane receptor, which is coupled to phospholipase C (PLC) through a G-protein mechanism. PLC activation leads to the production of inositol 1,4,5-triphosphate ($IP_3$), which in turn activates the $IP_3$ receptor causing release of $Ca^{2+}$ from the ER. The fall in ER $Ca^{2+}$ then signals to activate plasma membrane store-operated calcium (SOC) channels.

Store-operated calcium (SOC) influx is a process in cellular physiology that controls such diverse functions such as, but not limited to, refilling of intracellular $Ca^{2+}$ stores (Putney et al. Cell, 75, 199-201, 1993), activation of enzymatic activity (Fagan et al., J. Biol. Chem. 275:26530-26537, 2000), gene transcription (Lewis, Annu. Rev. Immunol. 19:497-521, 2001), cell proliferation (Nunez et al., J. Physiol. 571.1, 57-73, 2006), and release of cytokines (Winslow et al., Curr. Opin. Immunol. 15:299-307, 2003). In some nonexcitable cells, e.g., blood cells, immune cells, hematopoietic cells, T lymphocytes and mast cells, SOC influx occurs through calcium release-activated calcium (CRAC) channels, a type of SOC channel.

The calcium influx mechanism has been referred to as store-operated calcium entry (SOCE). Stromal interaction molecule (STIM) proteins are an essential component of SOC channel function, serving as the sensors for detecting the depletion of calcium from intracellular stores and for activating SOC channels.

SUMMARY OF THE INVENTION

Described herein are compounds of Formula (I), (II), (III), or (IV) compositions that include such compounds, and methods of use thereof, for modulating intracellular calcium. In one aspect, compounds of Formula (I), (II), (III), or (IV) modulate intracellular calcium by inhibition of store-operated calcium channel activity. In one aspect, compounds of Formula (I), (II), (III), or (IV) modulate intracellular calcium by preventing the activity of activated store-operated calcium channel complexes. In one aspect, compounds of Formula (I), (II), (III), or (IV) inhibit activation of store-operated channels. In one aspect, compounds of Formula (I), (II), (III), or (IV) inhibit activation of calcium-release activated calcium channels. In one aspect, compounds of Formula (I), (II), (III), or (IV) modulate an activity of, modulate an interaction of, or modulate the level of, or distribution of, or bind to, or interact with at least one protein of the SOC channel complex. In one aspect, compounds of Formula (I), (II), (III), or (IV) modulate an activity of, modulate an interaction of, or modulate the level of, or distribution of, or bind to, or interact with at least one protein of the CRAC channel complex.

In one aspect is a compound of Formula (I) having the structure:

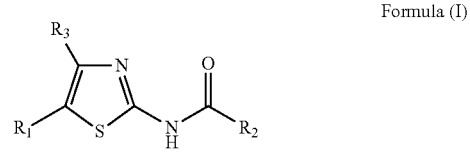

wherein:

$R_1$ is

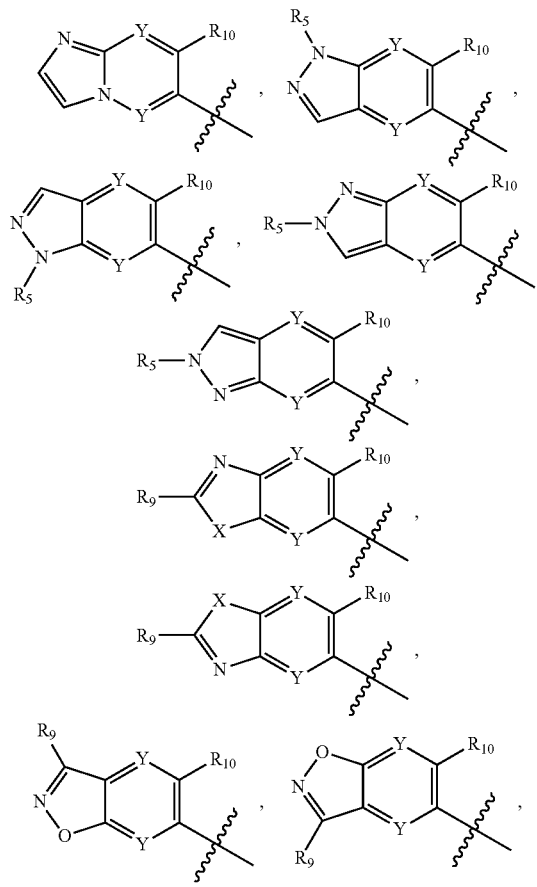

-continued

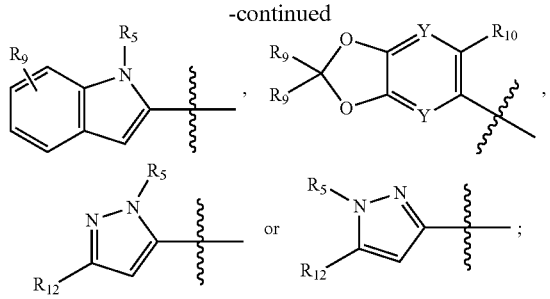

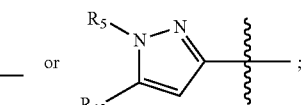 or 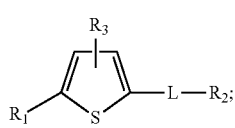;

X is S, O, or NR$_5$;

Y is independently selected from CR$_{10}$ or N;

R$_2$ is aryl, heteroaryl, fused aryl or fused heteroaryl; wherein aryl, heteroaryl, fused aryl or fused heteroaryl is optionally substituted with at least one R$_3$;

R$_3$ is independently selected from H, F, D, Cl, Br, I, —CN, —NO$_2$, —OH, —CF$_3$, —OCF$_3$, —OR$_5$, optionally substituted C$_1$-C$_6$alkyl, optionally substituted C$_3$-C$_8$cycloalkyl, optionally substituted C$_1$-C$_6$heteroalkyl, C$_1$-C$_6$haloalkyl, optionally substituted C$_2$-C$_8$heterocycloalkyl, optionally substituted aryl, optionally substituted O-aryl, and optionally substituted heteroaryl;

R$_5$ is selected from H, C$_1$-C$_6$alkyl, C$_1$-C$_6$haloalkyl, C$_3$-C$_8$cycloalkyl, phenyl, and benzyl;

R$_9$ and R$_{10}$ are each independently selected from H, D, optionally substituted C$_1$-C$_6$alkyl, halogen, C$_1$-C$_6$ alkylcarbonyl, or CF$_3$;

R$_{12}$ is selected from CN, —OR$_5$, optionally substituted C$_1$-C$_6$alkyl, C$_1$-C$_6$haloalkyl, and optionally substituted C$_3$-C$_8$cycloalkyl, optionally substituted aryl, optionally substituted O-aryl, and optionally substituted heteroaryl;

or a pharmaceutically acceptable salt, pharmaceutically acceptable solvate, or pharmaceutically acceptable prodrug thereof.

In another aspect is a compound having the structure of Formula (II):

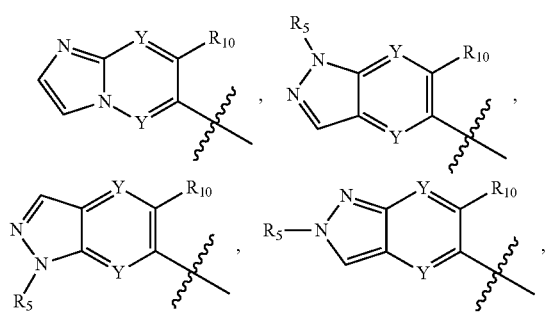

Formula (II)

wherein:

L is —NH—C(═O)—, or —C(═O)NH—;

R$_1$ is

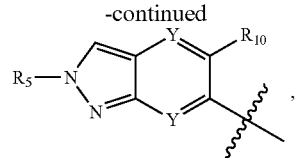,

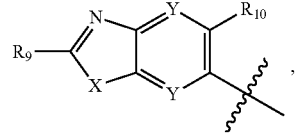,

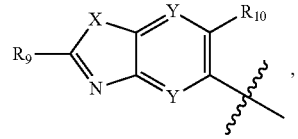,

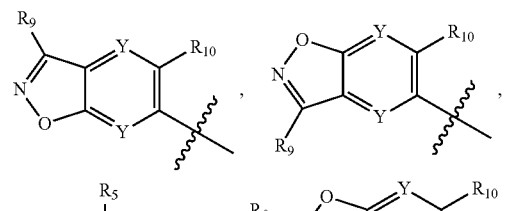

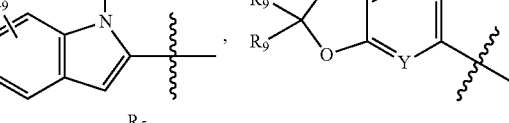

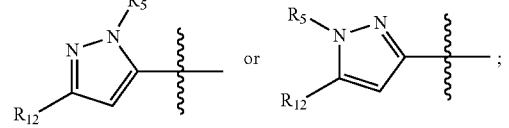

X is S, O, or NR$_5$;

Y is independently selected from CR$_{10}$ or N;

R$_2$ is aryl, heteroaryl, fused aryl or fused heteroaryl; wherein aryl, heteroaryl, fused aryl or fused heteroaryl is optionally substituted with at least one R$_3$;

R$_3$ is independently selected from H, F, D, Cl, Br, I, —CN, —NO$_2$, —OH, —CF$_3$, —OCF$_3$, —OR$_5$, optionally substituted C$_1$-C$_6$alkyl, optionally substituted C$_3$-C$_8$cycloalkyl, optionally substituted C$_1$-C$_6$heteroalkyl, C$_1$-C$_6$haloalkyl, optionally substituted C$_2$-C$_8$heterocycloalkyl, optionally substituted aryl, optionally substituted O-aryl, and optionally substituted heteroaryl;

R$_5$ is selected from H, C$_1$-C$_6$alkyl, C$_1$-C$_6$haloalkyl, C$_3$-C$_8$cycloalkyl, phenyl, and benzyl;

R$_{12}$ is CF$_3$, optionally substituted aryl, optionally substituted O-aryl, or optionally substituted heteroaryl;

R$_9$ and R$_{10}$ are each independently selected from H, D, optionally substituted C$_1$-C$_6$alkyl, halogen, C$_1$-C$_6$alkylcarbonyl, or CF$_3$;

or a pharmaceutically acceptable salt, pharmaceutically acceptable solvate, or pharmaceutically acceptable prodrug thereof.

In another aspect is a compound of Formula (III) having the structure:

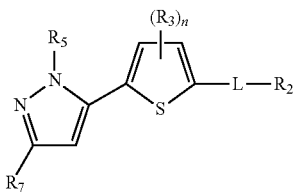

Formula (III)

wherein:
  L is —NH—C(=O)—, or —C(=O)NH—;
  $R_2$ is aryl, heteroaryl, fused aryl or fused heteroaryl; wherein aryl, heteroaryl, fused aryl or fused heteroaryl is optionally substituted with at least one $R_8$;
  $R_8$ is independently selected from F, D, Cl, Br, I, —CN, —NO$_2$, —OH, —CF$_3$, —OCF$_3$, —OR$_5$, optionally substituted C$_1$-C$_6$alkyl, optionally substituted C$_3$-C$_8$cycloalkyl, optionally substituted C$_1$-C$_6$heteroalkyl, C$_1$-C$_6$haloalkyl, optionally substituted C$_2$-C$_8$heterocycloalkyl, optionally substituted aryl, optionally substituted O-aryl, and optionally substituted heteroaryl;
  $R_3$ is independently selected from F, D, Cl, Br, —CN, —NO$_2$, —OH, —NH$_2$, —CF$_3$, and —OCF$_3$;
  $R_5$ is selected from H, C$_1$-C$_6$alkyl, C$_1$-C$_6$haloalkyl, C$_3$-C$_8$cycloalkyl, phenyl, and benzyl;
  $R_7$ is selected from CF$_3$, CN, optionally substituted C$_1$-C$_6$alkyl, C$_1$-C$_6$haloalkyl, and optionally substituted C$_3$-C$_8$cycloalkyl; and n is an integer selected from 1 or 2;
  or a pharmaceutically acceptable salt, pharmaceutically acceptable solvate, or pharmaceutically acceptable prodrug thereof.

In another aspect is a compound of Formula (IV) having the structure:

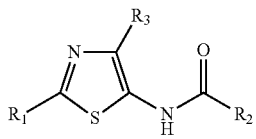

Formula (IV)

wherein:
  $R_1$ is

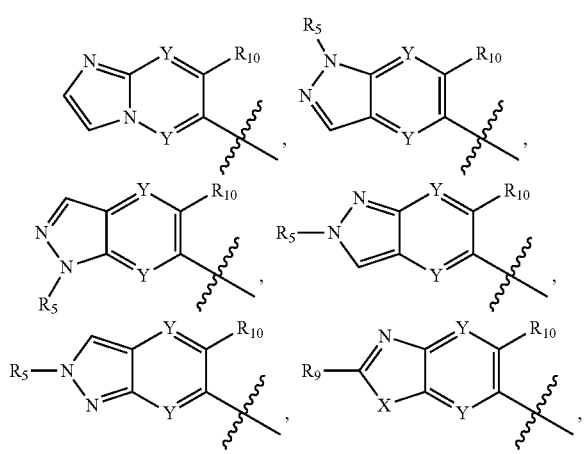

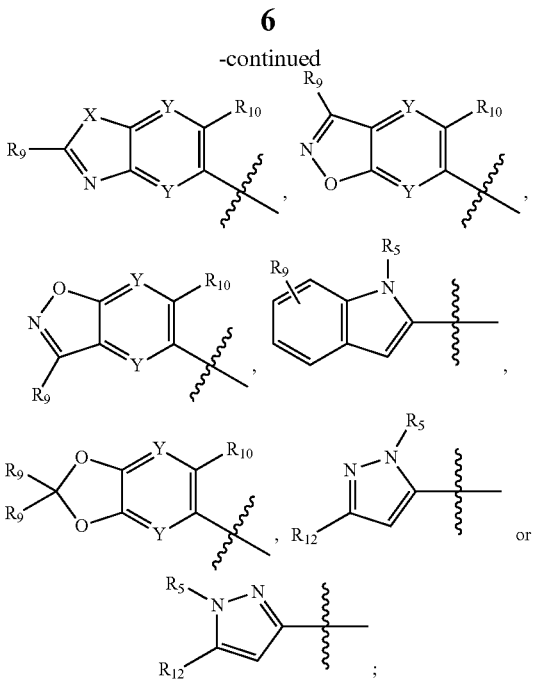

X is S, O, or NR$_5$;
Y is independently selected from CR$_{10}$ or N;
$R_2$ is aryl, heteroaryl, fused aryl or fused heteroaryl; wherein aryl, heteroaryl, fused aryl or fused heteroaryl is optionally substituted with at least one $R_3$;
$R_3$ is independently selected from H, F, D, Cl, Br, I, —CN, —NO$_2$, —OH, —CF$_3$, —OCF$_3$, —OR$_5$, optionally substituted C$_1$-C$_6$alkyl, optionally substituted C$_3$-C$_8$cycloalkyl, optionally substituted C$_1$-C$_6$heteroalkyl, C$_1$-C$_6$haloalkyl, optionally substituted C$_2$-C$_8$heterocycloalkyl, optionally substituted aryl, optionally substituted O-aryl, and optionally substituted heteroaryl;
$R_5$ is selected from H, C$_1$-C$_6$alkyl, C$_1$-C$_6$haloalkyl, C$_3$-C$_8$cycloalkyl, phenyl, and benzyl;
$R_9$ and $R_{10}$ are each independently selected from H, D, optionally substituted C$_1$-C$_6$alkyl, halogen, C$_1$-C$_6$ alkylcarbonyl, or CF$_3$;
$R_{12}$ is selected from CN, —OR$_5$, optionally substituted C$_1$-C$_6$alkyl, C$_1$-C$_6$haloalkyl, and optionally substituted C$_3$-C$_8$cycloalkyl, optionally substituted aryl, optionally substituted O-aryl, and optionally substituted heteroaryl;
or a pharmaceutically acceptable salt, pharmaceutically acceptable solvate, or pharmaceutically acceptable prodrug thereof.

In one embodiment is a compound of Formula (I), (II), (III), or (IV) wherein $R_2$ is aryl. In a further embodiment, aryl is phenyl. In yet a further embodiment, the phenyl group is substituted with at least one substituent selected from D, F, Cl, Br, I, —CN, —NO$_2$, —OH, —CF$_3$, —OCF$_3$, —OR$_5$, C$_1$-C$_6$alkyl, C$_3$-C$_8$cycloalkyl, C$_1$-C$_6$heteroalkyl, C$_1$-C$_6$haloalkyl, C$_2$-C$_8$heterocycloalkyl, optionally substituted aryl, optionally substituted O-aryl, and optionally substituted heteroaryl. In one embodiment, the substituent is fluorine. In one embodiment, phenyl is substituted with at least 2 substituents. In another embodiment, phenyl is substituted with at least 3 substituents.

In another embodiment is a compound of Formula (I), (II), (III), or (IV) wherein $R_2$ is heteroaryl. In a further embodiment, heteroaryl is pyridyl. In yet a further embodiment, the pyridyl group is substituted with at least one substituent selected from D, F, Cl, Br, I, —CN, —NO$_2$, —OH, —CF$_3$, —OCF$_3$, —OR$_5$, C$_1$-C$_6$alkyl, C$_3$-C$_8$cycloalkyl, C$_1$-C$_6$heteroalkyl, C$_1$-C$_6$haloalkyl, C$_2$-C$_8$heterocycloalkyl, optionally substituted aryl, optionally substituted O-aryl, and optionally substituted heteroaryl. In one embodiment, the substituent is fluorine. In one embodiment, pyridyl is substituted with at least 2 substituents. In another embodiment, pyridyl is substituted with at least 3 substituents.

In another embodiment, is a compound of Formula (I), (II), or (IV) wherein R$_1$ is a heteroaryl. In another embodiment, the heteroaryl is selected from pyrazole, indazole, benzothiazole, or benzoxazole.

In another aspect is a pharmaceutical composition comprising a pharmaceutically acceptable diluent, excipient or binder, and a compound having the structure of Formula (I), (II), (III), or (IV) or a pharmaceutically acceptable salt, pharmaceutically acceptable prodrug, or pharmaceutically acceptable solvate thereof.

In another aspect is a method of treating a disease, disorder or condition in a mammal that would benefit from inhibition of store-operated calcium channel activity comprising administering to the mammal a compound having the structure of Formula (I), (II), (III), or (IV) or a pharmaceutically acceptable salt, pharmaceutically acceptable solvate, or pharmaceutically acceptable prodrug thereof, or a pharmaceutical composition comprising same with a pharmaceutically acceptable diluent, excipient or binder.

In another aspect is a method of modulating store-operated calcium (SOC) channel activity comprising contacting the SOC channel complex, or portion thereof, with a compound of Formula (I), (II), (III), or (IV) or a pharmaceutically acceptable salt, pharmaceutically acceptable solvate, or pharmaceutically acceptable prodrug thereof, or a pharmaceutical composition comprising same with a pharmaceutically acceptable diluent, excipient or binder.

In another aspect is a method of modulating calcium release activated calcium channel (CRAC) activity in a mammal comprising administering to the mammal a compound of Formula (I), (II), (III), or (IV) wherein the compound of Formula (I), (II), (III), or (IV) modulates CRAC activity in the mammal.

In another aspect is a method of inhibiting store-operated calcium entry (SOCE) activation of nuclear factor of activated T cells (NFAT) in a mammal comprising administering to the mammal a compound of Formula (I), (II), (III), or (IV) wherein the compound of Formula (I), (II), (III), or (IV) inhibits SOCE activation of NFAT in the mammal.

In yet another aspect is a method of decreasing cytokine release by inhibiting the SOCE activation of NFAT in a mammal comprising administering to the mammal a compound of Formula (I), (II), (III), or (IV) wherein the compound of Formula (I), (II), (III), or (IV) decreases cytokine release in the mammal.

In a further aspect is a method of treating a disease, disorder or condition in a mammal that would benefit from inhibition of store-operated calcium channel activity comprising administering to the mammal a compound of Formula (I), (II), or (III).

In one aspect is a method for treating an autoimmune disease, heteroimmune disease or condition, or inflammatory disease in a mammal comprising administering to the mammal a compound of Formula (I), (II), (III), or (IV) or a pharmaceutically acceptable salt or prodrug thereof.

In one embodiment, the autoimmune disease is inflammatory bowel disease, rheumatoid arthritis, myasthenia gravis, multiple sclerosis, Sjogren's syndrome, type I diabetes, lupus erythematosus, psoriasis, osteoarthritis, scleroderma, and autoimmune hemolytic anemia.

In another embodiment, the heteroimmune disease or condition is graft-versus-host disease, graft rejection, atopic dermatitis, allergic conjunctivitis, organ transplant rejection, allogeneic or xenogenic transplantation, and allergic rhinitis.

In a further embodiment, the inflammatory disease is uveitis, vasculitis, vaginitis, asthma, inflammatory muscle disease, dermatitis, interstitial cystitis, colitis, Crohn's disease, dermatomyositis, hepatitis, and chronic relapsing hepatitis.

In another aspect is a method of treating a disease, disorder or condition in a mammal that would benefit from inhibition of store-operated calcium channel activity comprising administering to the mammal a compound of Formula (I), (II), (III), or (IV) or a pharmaceutically acceptable salt, N-oxide or prodrug thereof.

In one embodiment, the disease, disorder or condition in the mammal is selected from glomerulonephritis, hepatic diseases or disorders, renal diseases or disorders, chronic obstructive pulmonary disease, osteoporosis, eczema, pulmonary fibrosis, thyroiditis, cystic fibrosis, and primary biliary cirrhosis.

Compounds provided herein are used for modulating intracellular calcium. In one aspect, compounds provided herein modulate SOC channel activity. In one aspect, compounds provided herein modulate CRAC channel activity. In another aspect, compounds provided herein modulate STIM protein activity. In another aspect, compounds provided herein modulate Orai protein activity. In another aspect, compounds provided herein modulate the functional interactions of STIM proteins with Orai proteins. In another aspect, compounds provided herein reduce the number of functional SOC channels. In another aspect, compounds provided herein reduce the number of functional CRAC channels. In one aspect, compounds described herein are SOC channel blockers. In one aspect, compounds described herein are CRAC channel blockers or CRAC channel modulators.

In one aspect, compounds of Formula (I), (II), (III), or (IV) are selective inhibitors of CRAC channel activity.

Other objects, features and advantages of the compounds, compositions, methods, and uses described herein will become apparent from the following detailed description. It should be understood, however, that the detailed description and the specific examples, while indicating specific embodiments, are given by way of illustration only, since various changes and modifications within the spirit and scope of the disclosure will become apparent from this detailed description.

DETAILED DESCRIPTION

Figure 1:
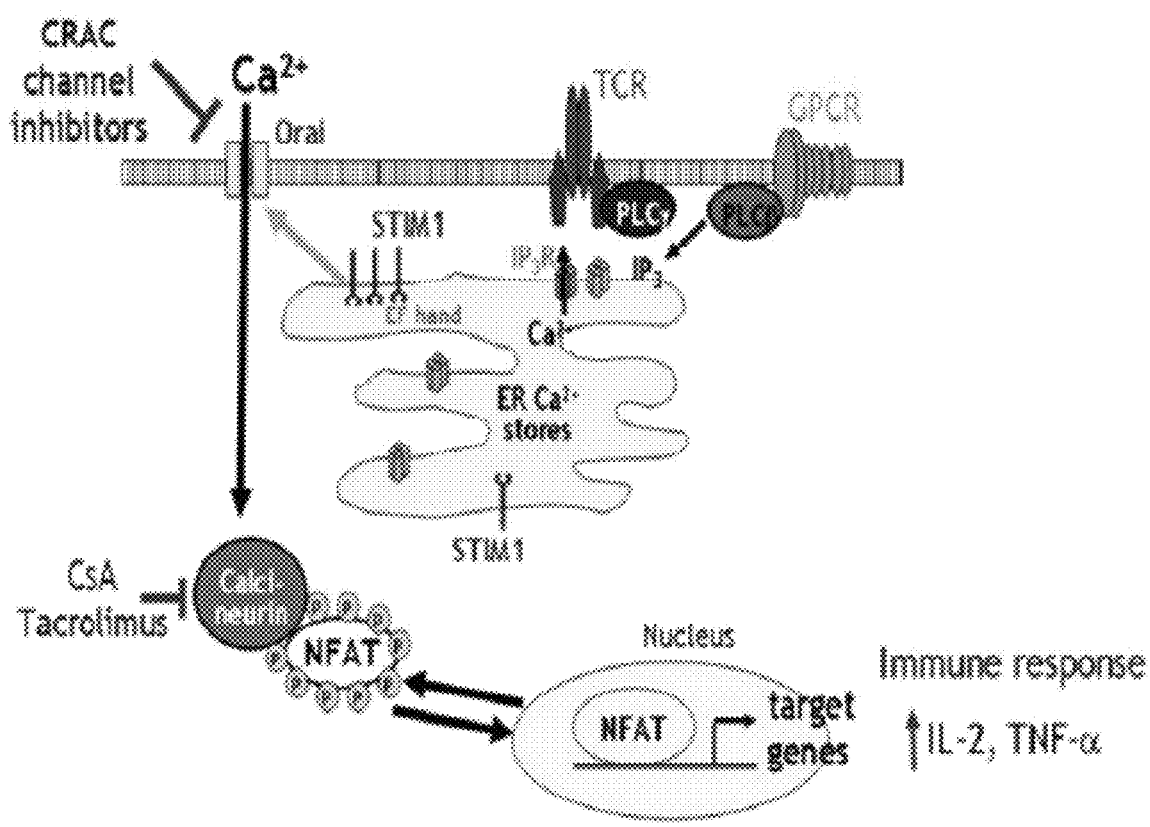
FIG. 1 outlines the I$_{CRAC}$ channel pathway.

Cellular calcium homeostasis is a result of the summation of regulatory systems involved in the control of intracellular calcium levels and movements. Cellular calcium homeostasis is achieved, at least in part, by calcium binding and by movement of calcium into and out of the cell across the plasma membrane and within the cell by movement of calcium across membranes of intracellular organelles including, for example, the endoplasmic reticulum, sarcoplasmic reticulum, mitochondria and endocytic organelles including endosomes and lysosomes.

Movement of calcium across cellular membranes is carried out by specialized proteins. For example, calcium from the extracellular space can enter the cell through various calcium channels and a sodium/calcium exchanger and is actively extruded from the cell by calcium pumps and sodium/calcium exchangers. Calcium can also be released from internal stores through inositol trisphosphate or ryanodine receptors and can be taken up by these organelles by means of calcium pumps.

Calcium can enter cells by any of several general classes of channels, including but not limited to, voltage-operated calcium (VOC) channels, store-operated calcium (SOC) channels, and sodium/calcium exchangers operating in reverse mode. VOC channels are activated by membrane depolarization and are found in excitable cells like nerve and muscle and are for the most part not found in nonexcitable cells. Under some conditions, $Ca^{2+}$ can enter cells via $Na^+$—$Ca^{2+}$ exchangers operating in reverse mode.

Endocytosis provides another process by which cells can take up calcium from the extracellular medium through endosomes. In addition, some cells, e.g., exocrine cells, can release calcium via exocytosis.

Cytosolic calcium concentration is tightly regulated with resting levels usually estimated at approximately 0.1 µM in mammalian cells, whereas the extracellular calcium concentration is typically about 2 mM. This tight regulation facilitates transduction of signals into and within cells through transient calcium flux across the plasma membrane and membranes of intracellular organelles. There is a multiplicity of intracellular calcium transport and buffer systems in cells that serve to shape intracellular calcium signals and maintain the low resting cytoplasmic calcium concentration. In cells at rest, the principal components involved in maintaining basal calcium levels are calcium pumps and leak pathways in both the endoplasmic reticulum and plasma membrane. Disturbance of resting cytosolic calcium levels can affect transmission of calcium-dependent signals and give rise to defects in a number of cellular processes. For example, cell proliferation involves a prolonged calcium signaling sequence. Other cellular processes that involve calcium signaling include, but are not limited to, secretion, transcription factor signaling, and fertilization.

Cell-surface receptors that activate phospholipase C (PLC) create cytosolic $Ca^{2+}$ signals from intra- and extra-cellular sources. An initial transient rise of $[Ca^{2+}]_i$ (intracellular calcium concentration) results from the release of $Ca^{2+}$ from the endoplasmic reticulum (ER), which is triggered by the PLC product, inositol-1,4,5-trisphosphate ($IP_3$), opening $IP_3$ receptors in the ER (Streb et al. Nature, 306, 67-69, 1983). A subsequent phase of sustained $Ca^{2+}$ entry across the plasma membrane then ensues, through specialized store-operated calcium (SOC) channels (in the case of immune cells the SOC channels are calcium release-activated calcium (CRAC) channels) in the plasma membrane. Store-operated $Ca^{2+}$ entry (SOCE) is the process in which the emptying of $Ca^{2+}$ stores itself activates $Ca^{2+}$ channels in the plasma membrane to help refill the stores (Putney, Cell Calcium, 7, 1-12, 1986; Parekh et al., Physiol. Rev. 757-810; 2005). SOCE does more than simply provide $Ca^{2+}$ for refilling stores, but can itself generate sustained $Ca^{2+}$ signals that control such essential functions as gene expression, cell metabolism and exocytosis (Parekh and Putney, Physiol. Rev. 85, 757-810 (2005).

In lymphocytes and mast cells, activation of antigen or Fc receptors, respectively causes the release of $Ca^{2+}$ from intracellular stores, which in turn leads to $Ca^{2+}$ influx through CRAC channels in the plasma membrane. The subsequent rise in intracellular $Ca^{2+}$ activates calcineurin, a phosphatase that regulates the transcription factor NFAT. In resting cells, NFAT is phosphorylated and resides in the cytoplasm, but when dephosphorylated by calcineurin, NFAT translocates to the nucleus and activates different genetic programmes depending on stimulation conditions and cell type. In response to infections and during transplant rejection, NFAT partners with the transcription factor AP-1 (Fos-Jun) in the nucleus of "effector" T cells, thereby transactivating cytokine genes, genes that regulate T cell proliferation and other genes that orchestrate an active immune response (Rao et al., Annu Rev Immunol., 1997; 15:707-47). In contrast, in T cells recognizing self antigens, NFAT is activated in the absence of AP-1, and activates a transcriptional programme known as "anergy" that suppresses autoimmune responses (Macian et al., Transcriptional mechanisms underlying lymphocyte tolerance. Cell. 2002 Jun. 14;109(6):719-31). In a subclass of T cells known as regulatory T cells which suppress autoimmunity mediated by self-reactive effector T cells, NFAT partners with the transcription factor FOXP3 to activate genes responsible for suppressor function (Wu et al., Cell, 2006 Jul. 28;126 (2):375-87; Rudensky A Y, Gavin M, Zheng Y. Cell. 2006 Jul. 28;126(2):253-256).

The endoplasmic reticulum (ER) carries out a variety processes. The ER has a role as both a $Ca^{2+}$ sink and an agonist-sensitive $Ca^{2+}$ store and, protein folding/processing takes place within its lumen. In the latter case, numerous $Ca^{2+}$-dependent chaperone proteins ensure that newly synthesized proteins are folded correctly and sent off to their appropriate destination. The ER is also involved in vesicle trafficking, release of stress signals, regulation of cholesterol metabolism, and apoptosis. Many of these processes require intraluminal $Ca^{2+}$, and protein misfolding, ER stress responses, and apoptosis can all be induced by depleting the ER of $Ca^{2+}$ for prolonged periods of time. Because it contains a finite amount of $Ca^{2+}$, it is clear that ER $Ca^{2+}$ content must fall after release of that $Ca^{2+}$ during stimulation. However, to preserve the functional integrity of the ER, it is vital that the $Ca^{2+}$ content does not fall too low or is maintained at least ar a low level. Replenishment of the ER with $Ca^{2+}$ is therefore a central process to all eukaryotic cells. Because a fall in ER $Ca^{2+}$ content activates store-operated $Ca^{2+}$ channels in the plasma membrane, a major function of this $Ca^{2+}$ entry pathway is believed to be maintenance of ER $Ca^{2+}$ levels that are necessary for proper protein synthesis and folding. However, store-operated $Ca^{2+}$ channels have other important roles.

The understanding of store-operated calcium entry was provided by electrophysiological studies which established that the process of emptying the stores activated a $Ca^{2+}$ current in mast cells called $Ca^{2+}$ release-activated $Ca^{2+}$ current or $I_{CRAC}$. $I_{CRAC}$ is non-voltage activated, inwardly rectifying, and remarkably selective for $Ca^{2+}$. It is found in several cell types mainly of hemapoietic origin. $I_{CRAC}$ is not the only store-operated current, and it is now apparent that store-operated influx encompasses a family of $Ca^{2+}$-permeable channels, with different properties in different cell types. $I_{CRAC}$ was the first store-operated $Ca^{2+}$ current to be described and remains a popular model for studying store-operated influx.

Store-operated calcium channels can be activated by any procedure that empties ER $Ca^{2+}$ stores; it does not seem to matter how the stores are emptied, the net effect is activation of store-operated $Ca^{2+}$ entry. Physiologically, store emptying is evoked by an increase in the levels of $IP_3$ or other $Ca^{2+}$-releasing signals followed by $Ca^{2+}$ release from the stores. But there are several other methods for emptying stores. These methods include the following:

1) elevation of $IP_3$ in the cytosol (following receptor stimulation or, dialyzing the cytosol with $IP_3$ itself or related congeners like the nonmetabolizable analog $Ins(2,4,5)P_3$);
2) application of a $Ca^{2+}$ ionophore (e.g., ionomycin) to permeabilize the ER membrane;
3) dialyzing the cytoplasm with high concentrations of $Ca^{2+}$ chelators (e.g., EGTA or BAPTA), which chelate $Ca^{2+}$ that leaks from the stores and hence prevent store refilling;
4) exposure to the sarcoplasmic/endoplasmic reticulum $Ca^{2+}$-ATPase (SERCA) inhibitors like thapsigargin, cyclopiazonic acid, and di-tert-butylhydroquinone;
5) sensitizing the $IP_3$ receptors to resting levels of $InsP_3$ with agents like thimerosal; and
6) loading membrane-permeable metal $Ca^{2+}$ chelators like N,N,N',N'-tetrakis(2-pyridylmethyl)ethylene diamine (TPEN) directly into the stores.

Through mass action, TPEN lowers free intraluminal Ca2+ concentration without changing total store $Ca^{2+}$ such that the store depletion-dependent signal is generated.

These methods of emptying stores are not devoid of potential problems. The key feature of store-operated $Ca^{2+}$ entry is that it is the fall in $Ca^{2+}$ content within the stores and not the subsequent rise in cytoplasmic $Ca^{2+}$ concentration that activates the channels. However, ionomycin and SERCA pump blockers generally cause a rise in cytoplasmic $Ca^{2+}$ concentration as a consequence of store depletion, and such a rise in $Ca^{2+}$ could open $Ca^{2+}$-activated cation channels permeable to $Ca^{2+}$. One way to avoid such problems is to use agents under conditions where cytoplasmic $Ca^{2+}$ has been strongly buffered with high concentrations of $Ca^{2+}$ chelator such as EGTA or BAPTA.

Store-Operated Calcium Entry

Reduced calcium concentration in intracellular calcium stores such as the endoplasmic reticulum resulting from release of calcium there from provides a signal for influx of calcium from the extracellular medium into the cell. This influx of calcium, which produces a sustained "plateau" elevation of cytosolic calcium concentration, generally does not rely on voltage-gated plasma membrane channels and does not involve activation of calcium channels by calcium. This calcium influx mechanism is referred to as capacitative calcium entry (CCE), calcium release-activated, store-operated or depletion-operated calcium entry. Store-operated calcium entry can be recorded as an ionic current with distinctive properties. This current is referred to as $I_{SOC}$ (store-operated current) or $I_{CRAC}$ (calcium release-activated current).

Electrophysiological analysis of store-operated or calcium release-activated currents reveal distinct biophysical properties (see, e.g., Parekh and Penner (1997) *Physiol. Rev.* 77:901-930) of these currents. For example, the current can be activated by depletion of intracellular calcium stores (e.g., by non-physiological activators such as thapsigargin, CPA, ionomycin and BAPTA, and physiological activators such as $IP_3$) and can be selective for divalent cations, such as calcium, over monovalent ions in physiological solutions or conditions, can be influenced by changes in cytosolic calcium levels, and can show altered selectivity and conductivity in the presence of low extracellular concentrations of divalent cations. The current may also be blocked or enhanced by 2-APB (depending on concentration) and blocked by SKF96365 and $Gd^{3+}$ and generally can be described as a calcium current that is not strictly voltage-gated.

Patch-clamp studies in mast cells and Jurkat leukaemic T cells have established the CRAC entry mechanism as an ion channel with distinctive biophysical characteristics, including a high selectivity for $Ca^{2+}$ paired with an exceedingly low conductance. Furthermore, the CRAC channel was shown to fulfill the rigorous criteria for being store-operated, which is the activation solely by the reduction of $Ca^{2+}$ in the ER rather than by cytosolic $Ca^{2+}$ or other messengers generated by PLC (Prakriya et al., In *Molecular and Cellular Insights into Ion Channel Biology* (ed. Robert Maue) 121-140 (Elsevier Science, Amsterdam, 2004)).

Regulation of Store-Operated Calcium Entry by Intracellular Calcium Stores

Store-operated calcium entry is regulated by the level of calcium within an intracellular calcium store. Intracellular calcium stores can be characterized by sensitivity to agents, which can be physiological or pharmacological, which activate release of calcium from the stores or inhibit uptake of calcium into the stores. Different cells have been studied in characterization of intracellular calcium stores, and stores have been characterized as sensitive to various agents, including, but not limited to, $IP_3$ and compounds that effect the $IP_3$ receptor, thapsigargin, ionomycin and/or cyclic ADP-ribose (cADPR) (see, e.g., Berridge (1993) *Nature* 361:315-325; Churchill and Louis (1999) *Am. J. Physiol.* 276:C426-C434; Dargie et al. (1990) *Cell Regul.* 1:279-290; Gerasimenko et al. (1996) *Cell* 84:473-480; Gromoda et al. (1995) *FEBS Lett.* 360:303-306; Guse et al. (1999) *Nature* 398:70-73).

Accumulation of calcium within endoplasmic reticulum and sarcoplasmic reticulum (SR; a specialized version of the endoplasmic reticulum in striated muscle) storage organelles is achieved through sarcoplasmic-endoplasmic reticulum calcium ATPases (SERCAs), commonly referred to as calcium pumps. During signaling (i.e., when endoplasmic reticulum channels are activated to provide for calcium release from the endoplasmic reticulum into the cytoplasm), endoplasmic reticulum calcium is replenished by the SERCA pump with cytoplasmic calcium that has entered the cell from the extracellular medium (Yu and Hinkle (2000) *J. Biol. Chem.* 275: 23648-23653; Hofer et al. (1998) *EMBO J.* 17:1986-1995).

Calcium release channels associated with $IP_3$ and ryanodine receptors provide for controlled release of calcium from endoplasmic and sarcoplasmic reticulum into the cytoplasm resulting in transient increases in cytoplasmic calcium concentration. $IP_3$ receptor-mediated calcium release is triggered by $IP_3$ formed by the break down of plasma membrane phosphoinositides through the action of phospholipase C, which is activated by binding of an agonist to a plasma membrane G protein-coupled receptor or tyrosine kinase. Ryanodine receptor-mediated calcium release is triggered by an increase in cytoplasmic calcium and is referred to as calcium-induced calcium release (CICR). The activity of ryanodine receptors (which have affinity for ryanodine and caffeine) may also be regulated by cyclic ADP-ribose.

Thus, the calcium levels in the stores, and in the cytoplasm, fluctuate. For example, ER free calcium concentration can decrease from a range of about 60-400 μM to about 1-50 μM when HeLa cells are treated with histamine, an agonist of PLC-linked histamine receptors (Miyawaki et al. (1997) *Nature* 388:882-887). Store-operated calcium entry is activated as the free calcium concentration of the intracellular stores is reduced. Depletion of store calcium, as well as a concomitant increase in cytosolic calcium concentration, can thus regulate store-operated calcium entry into cells.

Cytoplasmic Calcium Buffering

Agonist activation of signaling processes in cells can involve dramatic increases in the calcium permeability of the endoplasmic reticulum, for example, through opening of $IP_3$ receptor channels, and the plasma membrane through store-operated calcium entry. These increases in calcium permeability are associated with an increase in cytosolic calcium concentration that can be separated into two components: a "spike" of calcium release from the endoplasmic reticulum during activation of the IP$_3$ receptor and a plateau phase which is a sustained elevation of calcium levels resulting from entry of calcium into the cytoplasm from the extracellular medium. Upon stimulation, the resting intracellular free calcium concentration of about 100 nM can rise globally to greater than 1 µM and higher in microdomains of the cell. The cell modulates these calcium signals with endogenous calcium buffers, including physiological buffering by organelles such as mitochondria, endoplasmic reticulum and Golgi. Mitochondrial uptake of calcium through a uniporter in the inner membrane is driven by the large negative mitochondrial membrane potential, and the accumulated calcium is released slowly through sodium-dependent and -independent exchangers, and, under some circumstances, the permeability transition pore (PTP). Thus, mitochondria can act as calcium buffers by taking up calcium during periods of cellular activation and can slowly release it later. Uptake of calcium into the endoplasmic reticulum is regulated by the sarcoplasmic and endoplasmic reticulum calcium ATPase (SERCA). Uptake of calcium into the Golgi is mediated by a P-type calcium transport ATPase (PMR1/ATP2C1). Additionally, there is evidence that a significant amount of the calcium released upon IP$_3$ receptor activation is extruded from the cell through the action of the plasma membrane calcium ATPase. For example, plasma membrane calcium ATPases provide the dominant mechanism for calcium clearance in human T cells and Jurkat cells, although sodium/calcium exchange also contributes to calcium clearance in human T cells. Within calcium-storing organelles, calcium ions can be bound to specialized calcium-buffering proteins, such as, for example, calsequestrins, calreticulins and calnexins. Additionally, there are calcium-buffering proteins in the cytosol that modulate calcium spikes and assist in redistribution of calcium ions. Thus, proteins and other molecules that participate in any of these and other mechanisms through which cytosolic calcium levels can be reduced are proteins that are involved in, participate in and/or provide for cytoplasmic calcium buffering. Thus, cytoplasmic calcium buffering helps regulate cytoplasmic Ca$^{2+}$ levels during periods of sustained calcium influx through SOC channels or bursts of Ca$^{2+}$ release. Large increases in cytoplasmic Ca2+ levels or store refilling deactivate SOCE.

Downstream Calcium Entry-Mediated Events

In addition to intracellular changes in calcium stores, store-operated calcium entry affects a multitude of events that are consequent to or in addition to the store-operated changes. For example Ca$^{2+}$ influx results in the activation of a large number of calmodulin-dependent enzymes including the serine phosphatase calcineurin. Activation of calcineurin by an increase in intracellular calcium results in acute secretory processes such as mast cell degranulation. Activated mast cells release preformed granules containing histamine, heparin, TNFα and enzymes such as β-hexosaminidase. Some cellular events, such as B and T cell proliferation, require sustained calcineurin signaling, which requires a sustained increase in intracellular calcium. A number of transcription factors are regulated by calcineurin, including NFAT (nuclear factor of activated T cells), MEF2 and NFκB. NFAT transcription factors play important roles in many cell types, including immune cells. In immune cells NFAT mediates transcription of a large number of molecules, including cytokines, chemokines and cell surface receptors. Transcriptional elements for NFAT have been found within the promoters of cytokines such as IL-2, IL-3, IL-4, IL-5, IL-8, IL-13, as well as tumor necrosis factor alpha (TNFα), granulocyte colony-stimulating factor (G-CSF), and gamma-interferon (γ-IFN).

The activity of NFAT proteins is regulated by their phosphorylation level, which in turn is regulated by both calcineurin and NFAT kinases. Activation of calcineurin by an increase in intracellular calcium levels results in dephosphorylation of NFAT and entry into the nucleus. Rephosphorylation of NFAT masks the nuclear localization sequence of NFAT and prevents its entry into the nucleus. Because of its strong dependence on calcineurin-mediated dephosphorylation for localization and activity, NFAT is a sensitive indicator of intracellular free calcium levels.

Diseases, Disorders or Conditions

Clinical studies demonstrate that the CRAC channel is absolutely required for the activation of genes underlying the T cell response to antigen. Sustained calcium entry is needed for lymphocyte activation and adaptive immune response. Calcium entry into lymphocytes occurs primarily through the CRAC channels. Increased calcium leads to NFAT activation and expression of cytokines required for immune response. Inhibiting the store-operated calcium entry is an efficient way to prevent T cell activation.

Inhibition of CRAC channel activity with the compounds described herein, such as compounds of Formula (I), (II), (III), or (IV) provide a means for providing immunosuppresive therapy as demonstrated by the elimination of store-operated calcium entry noted in patients with severe-combined immunodeficiency (SCID). T cells, fibroblasts, and in some cases B cells, from patients with T cell immunodeficiency or SCID having a principal defect in T cell activation show a strong defect in store-operated calcium entry (Feske et al. (2001) *Nature Immunol.* 2:316-324; Paratiseti et al. (1994) *J. Biol. Chem.* 269:32327-32335; and Le Deist et al. (1995) *Blood* 85:1053-1062). SCID patients lack adaptive immune response, but without any impairment or toxicity in major organs. The SCID patient phenotype indicates that inhibition of CRAC channels is an effective strategy for immunosuppression.

Diseases/Disorders Involving Inflammation and Diseases/Disorders Related to the Immune System Diseases or disorders that can be treated or prevented using the compounds, compositions, and methods provided herein include diseases and disorders involving inflammation and/or that are related to the immune system. These diseases include but are not limited to asthma, chronic obstructive pulmonary disease, rheumatoid arthritis, inflammatory bowel disease, glomerulonephritis, neuroinflammatory diseases such as multiple sclerosis, and disorders of the immune system.

The activation of neutrophils (PMN) by inflammatory mediators is partly achieved by increasing cytosolic calcium concentration. Store-operated calcium influx in particular is thought to play an important role in PMN activation. It has been shown that trauma increases PMN store-operated calcium influx (Hauser et al. (2000) *J. Trauma Injury Infection and Critical Care* 48 (4):592-598) and that prolonged elevations of cytosolic calcium concentration due to enhanced store-operated calcium influx may alter stimulus-response coupling to chemotaxins and contribute to PMN dysfunction after injury. Modulation of PMN cytosolic calcium concentration through store-operated calcium channels might therefore be useful in regulating PMN-mediated inflammation and spare cardiovascular function after injury, shock or sepsis (Hauser et al. (2001) *J. Leukocyte Biology* 69 (1):63-68).

Calcium plays a critical role in lymphocyte activation. Activation of lymphocytes, e.g., by antigen stimulation, results in rapid increases in intracellular free calcium concentration and activation of transcription factors, including nuclear factor of activated T cells (NFAT), NF-κB, JNK1, MEF2 and CREB. NFAT is a key transcriptional regulator of the IL-2 (and other cytokine) genes (see, e.g. Lewis (2001) *Annu. Rev. Immunol* 19:497-521). A sustained elevation of intracellular calcium level is required to keep NFAT in a transcriptionally active state, and is dependent on store-operated calcium entry. Reduction or blocking of store-operated calcium entry in lymphocytes blocks calcium-dependent lymphocyte activation. Thus, modulation of intracellular calcium, and particularly store-operated calcium entry (e.g., reduction in, elimination of store-operated calcium entry), in lymphocytes can be a method for treating immune and immune-related disorders, including, for example, chronic immune diseases/disorders, acute immune diseases/disorders, autoimmune and immunodeficiency diseases/disorders, diseases/disorders involving inflammation, organ transplant graft rejections and graft-versus-host disease and altered (e.g., hyperactive) immune responses. For example treatment of an autoimmune disease/disorder might involve reducing, blocking or eliminating store-operated calcium entry in lymphocytes.

Examples of immune disorders include psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

Cancer and Other Proliferative Diseases

Compounds of Formula (I), (II), (III) or (IV), compositions thereof, and methods provided herein may be used in connection with treatment of malignancies, including, but not limited to, malignancies of lymphoreticular origin, bladder cancer, breast cancer, colon cancer, endometrial cancer, head and neck cancer, lung cancer, melanoma, ovarian cancer, prostate cancer and rectal cancer. Store-operated calcium entry may play an important role in cell proliferation in cancer cells (Weiss et al. (2001) *International Journal of Cancer* 92 (6): 877-882).

Inhibition of SOCE is sufficient to prevent tumor cell proliferation. The pyrazole derivative BTP-2, a direct $I_{CRAC}$ blocker inhibits SOCE and proliferation in Jurkat cells (Zitt et al., *J. Biol. Chem.*, 279, 12427-12437, 2004) and in colon cancer cells. It has been suggested that sustained SOCE requires mitochondrial $Ca^{2+}$ uptake (Nunez et al., *J. Physiol.* 571.1, 57-73, 2006) and that prevention of mitochondrial $Ca^{2+}$ uptake leads to SOCE inhibition (Hoth et al., *P.N.A.S.*, 97, 10607-10612, 2000; Hoth et al., *J. Cell. Biol.* 137, 633-648, 1997; Glitsch et al., *EMBO J.*, 21, 6744-6754, 2002). Stimulation of Jurkat cells induces sustained SOCE and activation of the $Ca^{2+}$-dependent phosphatase calcineurin that dephosphorylates NFAT, promoting expression of interleukin-2 and proliferation. Compounds of Formula (I), (II), (III), or (IV) inhibit SOCE and may be used in the treatment of cancer or other proliferative diseases or conditions.

Liver Diseases and Disorders

Diseases or disorders that can be treated or prevented using the compounds of Formula (I), (II), (III) or (IV), compositions thereof, and methods provided herein include hepatic or liver diseases and disorders. These diseases and disorders include but are not limited to liver injury, for example, due to transplantation, hepatitis and cirrhosis.

Store-operated calcium entry has been implicated in chronic liver disease (Tao et al. (1999) *J. Biol. Chem.*, 274 (34):23761-23769) as well as transplantation injury after cold preservation-warm reoxygenation (Elimadi et al. (2001) *Am J. Physiology*, 281(3 Part 1):G809-G815).

Kidney Diseases and Disorders

Diseases or disorders that can be treated or prevented using the methods provided herein include kidney or renal diseases and disorders. Mesangial cell hyperplasia is often a key feature of such diseases and disorders. Such diseases and disorders may be caused by immunological or other mechanisms of injury, including IgAN, membranoproliferative glomerulonephritis or lupus nephritis. Imbalances in the control of mesangial cell replication also appear to play a key role in the pathogenesis of progressive renal failure.

The turnover of mesangial cells in normal adult kidney is very low with a renewal rate of less than 1%. A prominent feature of glomerular/kidney diseases is mesangial hyperplasia due to elevated proliferation rate or reduced cell loss of mesangial cells. When mesangial cell proliferation is induced without cell loss, for example due to mitogenic stimulation, mesangioproliferative glomerulonephritis can result. Data have indicated that regulators of mesangial cell growth, particularly growth factors, may act by regulating store-operated calcium channels (Ma et al. (2001) *J Am. Soc. Of Nephrology*, 12:(1) 47-53). Modulators of store-operated calcium influx may aid in the treatment of glomerular diseases by inhibiting mesangial cell proliferation.

Store-Operated Calcium Channels

Clinical studies demonstrate that the CRAC channel, a type of SOC channel, is absolutely required for the activation of genes underlying the T cell response to antigen (Partiseti et al., *J Biol. Chem.*, 269, 32327-32335, 1994; Feske et al., *Curr. Biol.* 15, 1235-1241, 2005). SOCE can contribute directly to the elevation of cytosolic $Ca^{2+}$ levels ($[Ca^{2+}]_i$), as in T lymphocytes where CRAC channels generate the sustained $Ca^{2+}$ signals needed to drive gene expression underlying T cell activation by antigen. Sustained calcium entry is needed for lymphocyte activation and adaptive immune response. Calcium entry into lymphocytes occurs primarily through the CRAC channels. Increased calcium levels lead to NFAT activation and expression of cytokines required for immune response.

The CRAC channel has a distinctive biophysical fingerprint, quantifiable store-dependence, and essential function in T cells. Studies have shown that CRAC channels are formed from two component proteins, which interact to form CRAC channels. The CRAC channel is assembled by two functional components, STIM1 and Orai1. STIM1 (stromal interaction molecule 1) was identified as the mammalian ER $Ca^{2+}$ sensor (Liou, J. et al. *Curr. Biol.* 15, 1235-1241 (2005); Roos, *J. et al. J. Cell Biol.* 169, 435-445 (2005); WO 20041078995; US 2007/0031814). Orai1/CRACM1 was identified as a component of the mammalian CRAC channel (Feske, S. et al. *Nature* 441, 179-185 (2006); Vig, M. et al. *Science* 312, 1220-1223 (2006); Zhang, S. L. et al. *Proc. Natl. Acad. Sci. USA* 103, 9357-9362 (2006)).

STIM1 is the sensor of $Ca^{2+}$ within ER $Ca^{2+}$ stores, moving in response to store depletion into ER puncta close to the plasma membrane. Orai1 is a pore forming CRAC channel subunit in the plasma membrane. The two membrane proteins STIM1 and Orai1 have each been shown to be essential for the activation of CRAC channels.

Expression of both STIM1 and Orai1 in human embryonic kidney 293 cells (HEK293 cells) reconstitute functional CRAC channels. Expression of Orai1 alone strongly reduces store-operated $Ca^{2+}$ entry in HEK293 cells and the $Ca^{2+}$ release-activated $Ca^{2+}$ current ($I_{CRAC}$) in rat basophilic leukemia cells. However, expressed along with the store-sensing STIM1 protein, Orai1 causes a massive increase in SOCE, enhancing the rate of $Ca^{2+}$ entry by up to 103-fold. This $Ca^{2+}$ entry is entirely store dependent since the same co-expression causes no measurable store-independent $Ca^{2+}$ entry. The entry is completely blocked by the store-operated channel blocker, 2-aminoethoxydiphenylborate. STIM proteins are mediate $Ca^{2+}$ store-sensing and endoplasmic reticulum-plasma membrane coupling with no intrinsic channel properties. Orai1 contributes the plasma membrane channel component responsible for $Ca^{2+}$ entry. The suppression of CRAC channel function by Orai1 overexpression reflects a required stoichiometry between STIM1 and Orai1 (Soboloff et al., *J. Biol. Chem. Vol.* 281, no. 30, 20661-20665, 2006).

Stromal Interacting Molecule (STIM) Proteins

In an RNAi screen in *Drosophila* S2 cells using thapsigargin-activated $Ca^{2+}$ entry as a marker for store-operated channels one gene gave a substantially reduced $Ca^{2+}$ entry, and that gene coded for the protein stromal interaction molecule (Stim) (Roos, J. et al. *J. Cell Biol.* 169, 435-445, 2005). There are two homologues of Stim in mammalian cells, STIM1 and STIM2, both of which appear to be distributed ubiquitously (Williams et al., *Biochem J.* 2001 Aug. 1; 357(Pt 3):673-85). STIM1 is the ER $Ca^{2+}$ sensor for store-operated $Ca^{2+}$ entry. STIM1 is a 77 kDa type I membrane protein with multiple predicted protein interaction or signaling domains and is located predominantly in the ER, but also to a limited extent in the plasma membrane.

Knockdown of STIM1 by RNAi substantially reduced $I_{CRAC}$ in Jurkat T cells, and store-operated $Ca^{2+}$ entry in HEK293 epithelial cells and SH-SY5Y neuroblastoma cells. However, knockdown of the closely related STIM2 had no effect. These results indicate an essential role of STIM (*Drosophila*) and STIM1 (mammals) in the mechanism of activation of store-operated channels. It is unlikely that STIM1 is the store-operated channel itself. It has no channel-like sequence, and overexpression of the protein only modestly enhances $Ca^{2+}$ entry. STIM1 is located both on the plasma membrane and intracellular membranes like the ER (Manji et al., *Biochim Biophys Acta.* 2000 Aug. 31; 1481(1): 147-55. 2000). The protein sequence suggests that it spans the membrane once, with its $NH_2$ terminus oriented toward the lumen of the ER or the extracellular space. The $NH_2$ terminus contains an EF-hand domain, and functions as the $Ca^{2+}$ sensor in the ER. The protein also contains protein-protein interaction domains, notably coiled-coiled domains in the cytoplasm and a sterile motif (SAM) in the ER (or extracellular space), both near the predicted transmembrane domain. STIM1 can oligomerize and thus the protein in the ER and plasma membrane could interact bridging the two (Roos, J. et al. *J. Cell Biol.* 169, 435-445 (2005)).

Total internal reflection fluorescence (TIRF) and confocal microscopy reveal that STIM1 is distributed throughout the ER when $Ca^{2+}$ stores are full, but redistributes into discrete puncta near the plasma membrane on store depletion. Although the redistribution of STIM1 into junctional ER regions is slow (Liou, J. et al. *Curr. Biol.* 15, 1235-1241 (2005); Zhang, S. L. et al. *Nature* 437, 902-905 (2005), it does precede the opening of CRAC channels by several seconds (Wu et al., *J. Cell Biol.* 174, 803-813 (2006)) and is therefore rapid enough to be an essential step in the activation of CRAC channels.

It has been suggested that store depletion causes the insertion of STIM1 into the plasma membrane where it may control store-operated calcium entry through the CRAC channels (Zhang, S. L. et al. *Nature* 437, 902-905 (2005); Spassova, M. A. et al. *Proc. Natl. Acad. Sci. USA* 103, 4040-4045 (2006)).

The critical evidence for STIM1 as the $Ca^{2+}$ sensor for SOCE is that mutation of predicted $Ca^{2+}$-binding residues of the EF hand structural motif, expected to reduce its affinity for $Ca^{2+}$ and hence mimic the store-depleted state, causes STIM1 to redistribute spontaneously into puncta and trigger constitutive $Ca^{2+}$ influx through SOCs even when stores are full (Spassova, M. A. et al. *Proc. Natl. Acad. Sci. USA* 103, 4040-4045 (2006); Liou, J. et al. *Curr. Biol.* 15, 1235-1241 (2005)).

Orai Proteins

Orai1 (also known as CRACM1) is a widely expressed, 33 kDa plasma membrane protein with 4 transmembrane domains and a lack of significant sequence homology to other ion channels (Vig, M. et al. *Science* 312, 1220-1223 (2006); Zhang, S. L. et al. *Proc. Natl. Acad. Sci. USA* 103, 9357-9362 (2006)).

Studies of T cells from human patients with a severe combined immunodeficiency (SCID) syndrome, in which T cell receptor engagement or store depletion failed to activate $Ca^{2+}$ entry, was shown to be due to a single point mutation in Orai1 (Feske, S. et al. Nature 441, 179-185 (2006)).

Other mammalian Orai homologues exist, e.g. Orai2 and Orai3, however their function is not clearly defined. Orai2 and Orai3 can exhibit SOC channel activity when overexpressed with STIM1 in HEK cells (Mercer, J. C. et al. J. Biol. Chem. 281, 24979-24990 (2006)).

Evidence that Orai1 contributes to the CRAC channel pore was obtained by Orai1 mutagenesis studies. Selectivity of the CRAC channel for $Ca^{2+}$ ions was shown by mutations at either Glu 106 or Glu 190, which weaken the ability of $Ca^{2+}$ binding in order block permeation of monovalent cations (similar to mechanisms described for voltage-gated $Ca^{2+}$ channels) (Yeromin, A. V. et al. *Nature* 443, 226-229 (2006); Vig, M. et al. *Curr. Biol.* 16, 2073-2079 (2006); Prakriya, M. et al. *Nature* 443, 230-233 (2006)).

Neutralizing the charge on a pair of aspartates in the I-II loop (Asp 110 and Asp 112) reduces block by $Gd^{3+}$ and block of outward current by extracellular $Ca^{2+}$, indicating that these negatively charged sites may promote accumulation of polyvalent cations near the mouth of the pore.

Currents observed through overexpression of Orai1 closely resemble $I_{CRAC}$, and the fact that Orai1 can form multimers (Yeromin, A. V. et al. *Nature* 443, 226-229 (2006); Vig, M. et al. *Curr. Biol.* 16, 2073-2079 (2006); Prakriya, M. et al. *Nature* 443, 230-233 (2006)), makes it likely that the native CRAC channel is either a multimer of Orai1 alone or in combination with the closely related subunits Orai2 and/or Orai3.

Functional Store-operated Calcium Channels

The characterization of SOC channels has been largely obtained by one type of SOC channel, the CRAC channel. CRAC channel activity is triggered by the loss of $Ca^{2+}$ from the ER lumen, which is coupled to the opening of CRAC channels in the plasma membrane through the actions of STIM1 and Orai1. Depletion of $Ca^{2+}$ is sensed by STIM1, causing it to accumulate in junctional ER adjacent to the plasma membrane. In a TIRF-based $Ca^{2+}$-imaging study to map the locations of open CRAC channels, $[Ca^{2+}]_i$ elevations were seen to co-localize with STIM1 puncta, showing directly that CRAC channels open only in extreme proximity to these sites (Luik, et al., *J. Cell Biol.* 174, 815-825 (2006)).

In cells co-expressing both STIM1 and Orai1, store depletion causes Orai1 itself to move from a dispersed distribution to accumulate in the plasma membrane directly opposite STIM1, enabling STIM1 to activate the channel (Luik, et al., J. Cell Biol. 174, 815-825 (2006); Xu, P. et al. Biochem. Biophys. Res. Commun. 350, 969-976 (2006)). Thus, CRAC channels are formed by apposed clusters of STIM1 in the ER and Orai1 in the plasma membrane. The junctional gap between the ER and plasma membrane where Orai1/STIM 1 clusters from (about 10-25 nm) may be small enough to permit protein-protein interactions between STIM 1 and Orai1. This is supported by the fact that overexpressed STIM1 and Orai1 can be co-immunoprecipitated (Yeromin, A. V. et al. Nature 443, 226-229 (2006); Vig, M. et al. Curr. Biol. 16, 2073-2079 (2006)).

Thus, STIM1 and Orai1 interact either directly or as members of a multiprotein complex. Support for this was observed when the expression of the cytosolic portion of STIM1 by itself was sufficient to activate CRAC channels in one study (Huang, G. N. et al. Nature Cell Biol. 8, 1003-1010 (2006)), and the effects of deleting the ERM/coiled-coil and other C-terminal domains suggest roles in STIM1 clustering and SOC channel activation (Baba, Y. et al. Proc. Natl. Acad. Sci. USA 103, 16704-16709 (2006)). On the luminal side of STIM1, the isolated EF-SAM region forms dimers and higher-order multimers on removal of $Ca^{2+}$ in vitro, indicating that STIM1 oligomerization may be an early step in store-operated calcium activation (Stathopulos, et al., J. Biol. Chem. 281, 35855-35862 (2006)).

In some embodiments, compounds of Formula (I), (II), (III), or (IV) described herein modulate intracellular calcium, such as, inhibition or reduction of SOCE and/or $I_{CRAC}$. In other embodiments, the modulation by compounds of Formula (I), (II), (III), or (IV) result from a variety of effects, such as, but not limited to, binding to a protein, interaction with a protein, or modulation of interactions, activities, levels or any physical, structural or other property of a protein involved in modulating intracellular calcium (e.g. a STIM protein and/or Orai protein).

For example, methods for assessing binding or interaction of a test agent with a protein involved in modulating intracellular calcium include NMR, mass spectroscopy, fluorescence spectroscopy, scintillation proximity assays, surface plasmon resonance assays and others. Examples of methods for assessing modulation of interactions, activities, levels or any physical, structural or other property of a protein involved in modulating intracellular calcium include, but are not limited to, FRET assays to assess effects on protein interactions, NMR, X-ray crystallography and circular dichroism to assess effects on protein interactions and on physical and structural properties of a protein, and activity assays suitable for assessing a particular activity of a protein.

Monitoring or Assessing Effects on Intracellular Calcium

In some embodiments, monitoring or assessing the effect of a compound of Formula (I), (II), (III), or (IV) on intracellular calcium in any of the screening/identification methods described herein, a direct or indirect evaluation or measurement of cellular (including cytosolic and intracellular organelle or compartment) calcium and/or movement of ions into, within or out of a cell, organelle, calcium store or portions thereof (e.g., a membrane) are conducted. A variety of methods are described herein for evaluating calcium levels and ion movements or flux. The particular method used and the conditions employed depend on whether a particular aspect of intracellular calcium is being monitored or assessed. For example, in some embodiments described herein, reagents and conditions are known, and are used, for specifically evaluating store-operated calcium entry, resting cytosolic calcium levels, calcium buffering and calcium levels and uptake by or release from intracellular organelles and calcium stores. In other embodiments, the effect of a compound of Formula (I), (II), (III), or (IV) on intracellular calcium is monitored or assessed using, for example, a cell, an intracellular organelle or calcium storage compartment, a membrane (including, e.g., a detached membrane patch or a lipid bilayer) or a cell-free assay system (e.g., outside-out membrane vesicle). Generally, some aspect of intracellular calcium is monitored or assessed in the presence of test agent and compared to a control, e.g., intracellular calcium in the absence of test agent.

Methods of Modulating Intracellular Calcium

In some embodiments, modulation of intracellular calcium is any alteration or adjustment in intracellular calcium including but not limited to alteration of calcium concentration or level in the cytoplasm and/or intracellular calcium storage organelles, e.g., endoplasmic reticulum, alteration in the movement of calcium into, out of and within a cell or intracellular calcium store or organelle, alteration in the location of calcium within a cell, and alteration of the kinetics, or other properties, of calcium fluxes into, out of and within cells. In some embodiments, intracellular calcium modulation involves alteration or adjustment, e.g. reduction or inhibition, of store-operated calcium entry, cytosolic calcium buffering, calcium levels in or movement of calcium into, out of or within an intracellular calcium store or organelle, and/or basal or resting cytosolic calcium levels. In some embodiments, modulation of intracellular calcium involves an alteration or adjustment in receptor-mediated ion (e.g., calcium) movement, second messenger-operated ion (e.g., calcium) movement, calcium influx into or efflux out of a cell, and/or ion (e.g., calcium) uptake into or release from intracellular compartments, including, for example, endosomes and lysosomes.

In one aspect, compounds described herein modulate intracellular calcium, such as but not limited to, modulation (e.g. reduction or inhibition) of SOC channel activity, such as inhibition of CRAC channel activity (e.g. inhibition of $I_{CRAC}$, inhibition of SOCE), in an immune system cell (e.g., a lymphocyte, white blood cell, T cell, B cell), a fibroblast (or a cell derived from a fibroblast), or an epidermal, dermal or skin cell (e.g., a keratinocyte). In some embodiments, the step of modulating one or more proteins involved in modulating intracellular calcium (e.g. a STIM protein and/or Orai protein) involves, for example, reducing the level, expression of, an activity of, function of and/or molecular interactions of a protein. For instance, if a cell exhibits an increase in calcium levels or lack of regulation of an aspect of intracellular calcium modulation, e.g., store-operated calcium entry, then in other embodiments, modulating involves reducing the level of, expression of, an activity or function of, or a molecular interaction of a protein, e.g. a STIM protein and/or Orai protein.

Compounds

Compounds described herein modulate intracellular calcium and may be used in the treatment of diseases or conditions where modulation of intracellular calcium has a beneficial effect.

In one embodiment, compounds described herein inhibit store-operated calcium entry. In one embodiment, compounds of Formula (I), (II), (III), or (IV) interrupt the assembly of SOCE units. In another embodiment, compounds of Formula (I), (II), (III), or (IV) alter the functional interactions of proteins that form store-operated calcium channel complexes. In one embodiment, compounds of Formula (I), (II), (III), or (IV) alter the functional interactions of STIM1 with Orai1. In other embodiments, compounds of Formula (I), (II), (III), or (IV) are SOC channel pore blockers. In other embodiments, compounds of Formula (I), (II), (III), or (IV) are CRAC channel pore blockers.

In one aspect, compounds described herein inhibit the electrophysiological current ($I_{SOC}$) directly associated with activated SOC channels. In another aspect, compounds described herein inhibit the electrophysiological current ($I_{CRAC}$) directly associated with activated CRAC channels.

The diseases or disorders that may benefit from modulation of intracellular calcium include, but are not limited to, an immune system-related disease (e.g., an autoimmune disease), a disease or disorder involving inflammation (e.g., asthma, chronic obstructive pulmonary disease, rheumatoid arthritis, inflammatory bowel disease, glomerulonephritis, neuroinflammatory diseases, multiple sclerosis, and disorders of the immune system), cancer or other proliferative disease, kidney disease and liver disease. In one aspect, compounds described herein may be used as immunosuppresants to prevent transplant graft rejections, allogeneic or xenogeneic transplantation rejection (organ, bone marrow, stem cells, other cells and tissues), graft-versus-host disease. Transplant graft rejections can result from tissue or organ transplants. Graft-versus-host disease can result from bone marrow or stem cell transplantation.

Compounds described herein modulate an activity of, modulate an interaction of, or binds to, or interacts with at least one portion of a protein in the store-operated calcium channel complex. In one embodiment, compounds described herein modulate an activity of, modulate an interaction of, or binds to, or interacts with at least one portion of a protein in the calcium release activated calcium channel complex. In one aspect, compounds described herein reduce the level of functional store-operated calcium channel complexes. In one aspect, compounds described herein reduce the level of activated store-operated calcium channel complexes. In one aspect, store-operated calcium channel complexes are calcium release activated calcium channel complexes.

Compounds described herein for treatment of a disease or disorder, when administered to a subject having a disease or disorder effectively reduces, ameliorates or eliminates a symptom or manifestation of the disease or disorder. Compounds described herein can also be administered to a subject predisposed to a disease or disorder who does not yet manifest a symptom of the disease or disorder, prevents or delays development of the symptoms. The agent can have such effects alone or in combination with other agents, or may function to enhance a therapeutic effect of another agent.

Compounds described herein, pharmaceutically acceptable salts, pharmaceutically acceptable prodrugs, or a pharmaceutically acceptable solvates thereof, modulate intracellular calcium, and may be used to treat patients where modulation of intracellular calcium provides benefit.

In one aspect, the compounds described herein are selective inhibitors of CRAC channel activity.

In one aspect is a compound of Formula (I) having the structure:

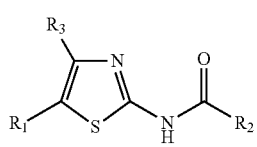

Formula (I)

wherein:
$R_1$ is

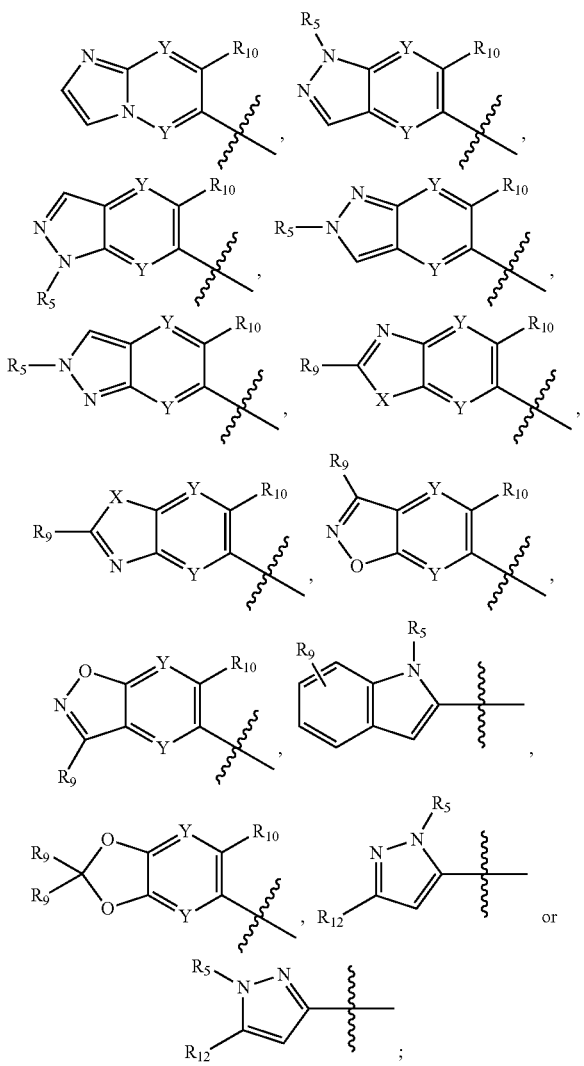

X is S, O, or $NR_5$;
Y is independently selected from $CR_{10}$ or N;
$R_2$ is aryl, heteroaryl, fused aryl or fused heteroaryl; wherein aryl, heteroaryl, fused aryl or fused heteroaryl is optionally substituted with at least one $R_3$;
$R_3$ is independently selected from H, F, D, Cl, Br, I, —CN, —NO$_2$, —OH, —CF$_3$, —OCF$_3$, —OR$_5$, C$_1$-C$_6$alkyl, C$_3$-C$_8$cycloalkyl, C$_1$-C$_6$heteroalkyl, C$_1$-C$_6$haloalkyl, C$_2$-C$_8$heterocycloalkyl, optionally substituted aryl, optionally substituted O-aryl, and optionally substituted heteroaryl;
$R_5$ is selected from H, C$_1$-C$_6$alkyl, C$_1$-C$_6$haloalkyl, C$_3$-C$_8$cycloalkyl, phenyl, and benzyl;
$R_9$ and $R_{10}$ are each independently selected from H, D, C$_1$-C$_6$alkyl, halogen, C$_1$-C$_6$ alkylcarbonyl, or CF$_3$;
$R_{12}$ is selected from CN, —OR$_5$, optionally substituted C$_1$-C$_6$alkyl, C$_1$-C$_6$haloalkyl, C$_3$-C$_8$cycloalkyl, optionally substituted aryl, optionally substituted O-aryl, and optionally substituted heteroaryl;
or a pharmaceutically acceptable salt, pharmaceutically acceptable solvate, or pharmaceutically acceptable prodrug thereof.

In certain embodiments is a compound of Formula (I) wherein $R_1$ is

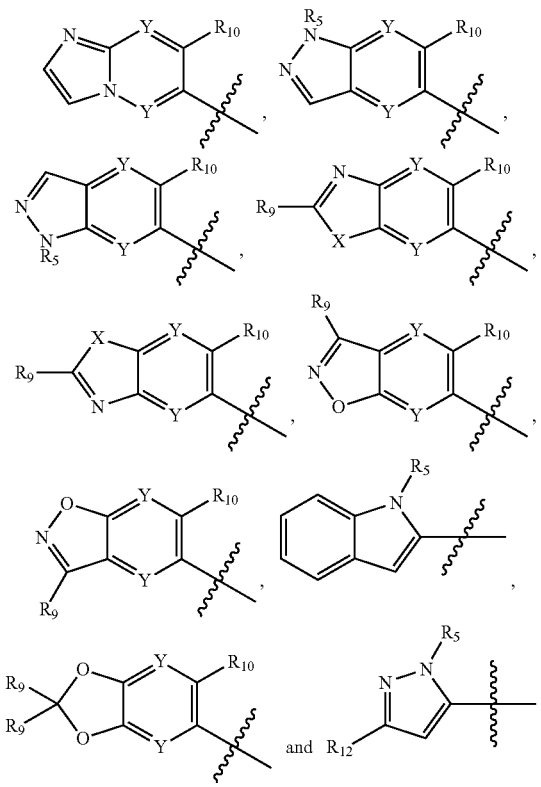

In a further embodiment is a compound of Formula (I) wherein $R_2$ is aryl optionally substituted with at least one $R_3$ independently selected from F, Cl, Br, and I. In another embodiment, $R_2$ is aryl optionally substituted with at least one $R_3$ independently selected from F or Cl. In another embodiment, $R_2$ is aryl optionally substituted with at least one F. In another embodiment, $R_2$ is aryl optionally substituted with at least one Cl. In another embodiment, $R_2$ is phenyl optionally substituted with at least one $R_3$ independently selected from F or Cl. In another embodiment $R_2$ is phenyl optionally substituted with at least one F. In another embodiment, $R_2$ is phenyl optionally substituted with at least one Cl. In another embodiment, $R_3$ is selected from —CN, —$NO_2$, —OH, —$OCF_3$, and —$OR_5$, wherein $R_5$ is $C_1$-$C_6$alkyl. In another embodiment, $R_3$ is —OH. In a further embodiment, $R_3$ is —CN. In another embodiment is a compound of Formula (I) wherein $R_{12}$ is $C_1$-$C_6$haloalkyl. In another embodiment, $R_{12}$ is $C_1$-$C_6$alkyl. In a further embodiment, $C_1$-$C_6$alkyl is methyl, ethyl, n-propyl, iso-propyl, n-butyl, iso-butyl or tert-butyl. In another embodiment $R_5$ is H or $C_1$-$C_6$alkyl. In another embodiment, $R_5$ is methyl, ethyl, n-propyl, iso-propyl, n-butyl, iso-butyl or tert-butyl. In a further embodiment, $R_5$ is H. In yet a further embodiment, $R_5$ is methyl. In another embodiment is a compound of Formula (I) wherein $R_2$ is heteroaryl selected from thienyl, thianthrenyl, furyl, pyranyl, thiadiazolyl, benzothiadiazolyl, isobenzofuranyl, chromenyl, xanthenyl, phenoxathiinyl, pyrrolyl, imidazolyl, pyrazolyl, isothiazolyl, isoxazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinoxalinyl, quinazolinyl, oxazolyl, cinnolinyl, pteridinyl, 4aH-carbazolyl, carbazolyl, carbolinyl, phenanthridinyl, acridinyl, perimidinyl, phenanthrolinyl, phenazinyl, phenarsazinyl, phenothiazinyl, furazanyl, and phenoxazinyl. In a further embodiment, $R_2$ is pyridinyl. In another embodiment, $R_2$ is furyl. In a further embodiment, $R_2$ is pyranyl. In one embodiment is a compound of Formula (I) wherein $R_2$ is heteroaryl substituted with at least one $R_3$ selected from F, Cl, Br, and I. In another embodiment, $R_2$ is heteroaryl substituted with at least two $R_3$ or at least three $R_3$ selected from H, F, Cl, Br, I, —CN, —$NO_2$, —OH, —$CF_3$, —$OCF_3$, —$OR_5$, $C_1$-$C_6$alkyl, and $C_3$-$C_8$cycloalkyl.

Also described herein is a compound of Formula (I) wherein $R_1$ is

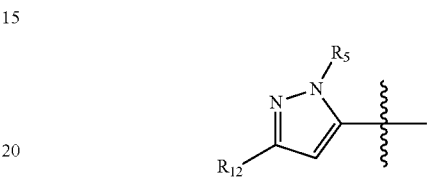

wherein $R_{12}$ is selected from $CF_3$, CN, —$OR_5$, $C_1$-$C_6$alkyl, $C_1$-$C_6$haloalkyl, $C_3$-$C_8$cycloalkyl, optionally substituted aryl, optionally substituted O-aryl, optionally substituted heteroaryl; and $R_5$ is $C_1$-$C_6$alkyl. In one embodiment, $R_5$ is $CH_3$. In another embodiment, $R_{12}$ is —CN. In another embodiment, $R_{12}$ is $CF_3$. In another embodiment, $R_{12}$ is OH. In yet another embodiment, $R_{12}$ is $C_1$-$C_6$alkyl. In a further embodiment, $R_{12}$ is selected from methyl, ethyl, n-propyl, iso-propyl, n-butyl, iso-butyl, and tert-butyl. In one embodiment, $R_{12}$ is methyl. In another embodiment $R_{12}$ is ethyl. In another embodiment, $R_{12}$ is optionally substituted aryl. In a further embodiment, $R_{12}$ is optionally substituted phenyl. In yet another embodiment, $R_{12}$ is optionally substituted heteroaryl. In a further embodiment, $R_{12}$ is selected from optionally substituted furanyl, thienyl, thiazolyl, oxazolyl, oxadiazolyl, pyrazolyl, and pyridinyl. In another embodiment, $R_{12}$ is optionally substituted furanyl. In another embodiment, $R_{12}$ is optionally substituted thienyl. In another embodiment, $R_{12}$ is optionally substituted thiazolyl. In another embodiment, $R_{12}$ is optionally substituted oxazolyl. In another embodiment, $R_{12}$ is optionally substituted oxadiazolyl. In another embodiment, $R_{12}$ is optionally substituted pyrazolyl. In another embodiment, $R_{12}$ is optionally substituted pyridinyl.

In another embodiment is a compound of Formula (I) wherein $R_{12}$ is selected from $CF_3$, CN, —$OR_5$, optionally substituted $C_1$-$C_6$alkyl, $C_1$-$C_6$haloalkyl, $C_3$-$C_8$cycloalkyl, optionally substituted aryl, optionally substituted O-aryl, and optionally substituted heteroaryl. In another embodiment is a compound of Formula (I) wherein $R_{12}$ is selected from $CF_3$, $C_1$-$C_6$alkyl, and $C_3$-$C_8$cycloalkyl. In certain embodiments, $R_{12}$ is $CF_3$. In other embodiments, $R_{12}$ is cyclopropyl. In other embodiments, $R_5$ is $C_1$-$C_6$alkyl. In certain embodiments, $R_5$ is $CH_3$. In certain embodiments, $R_5$ is $C_2H_5$. In certain embodiments, $R_5$ is isopropyl.

In certain embodiments is a compound of Formula (I) wherein $R_1$ is

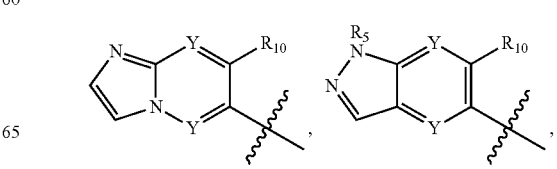

-continued
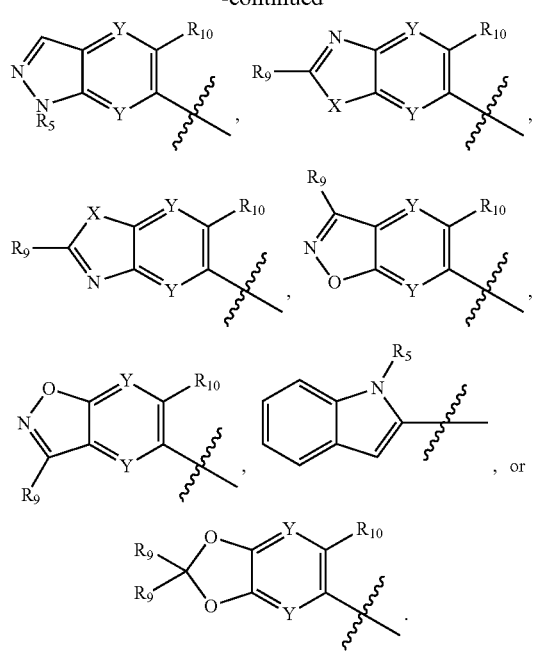
In another aspect is a compound selected from:
-continued
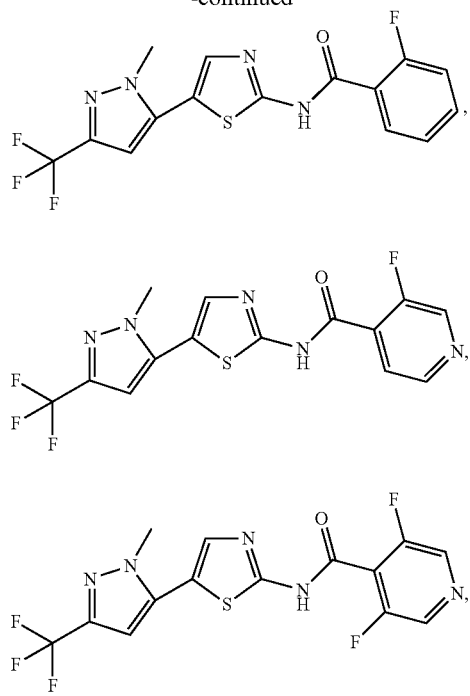
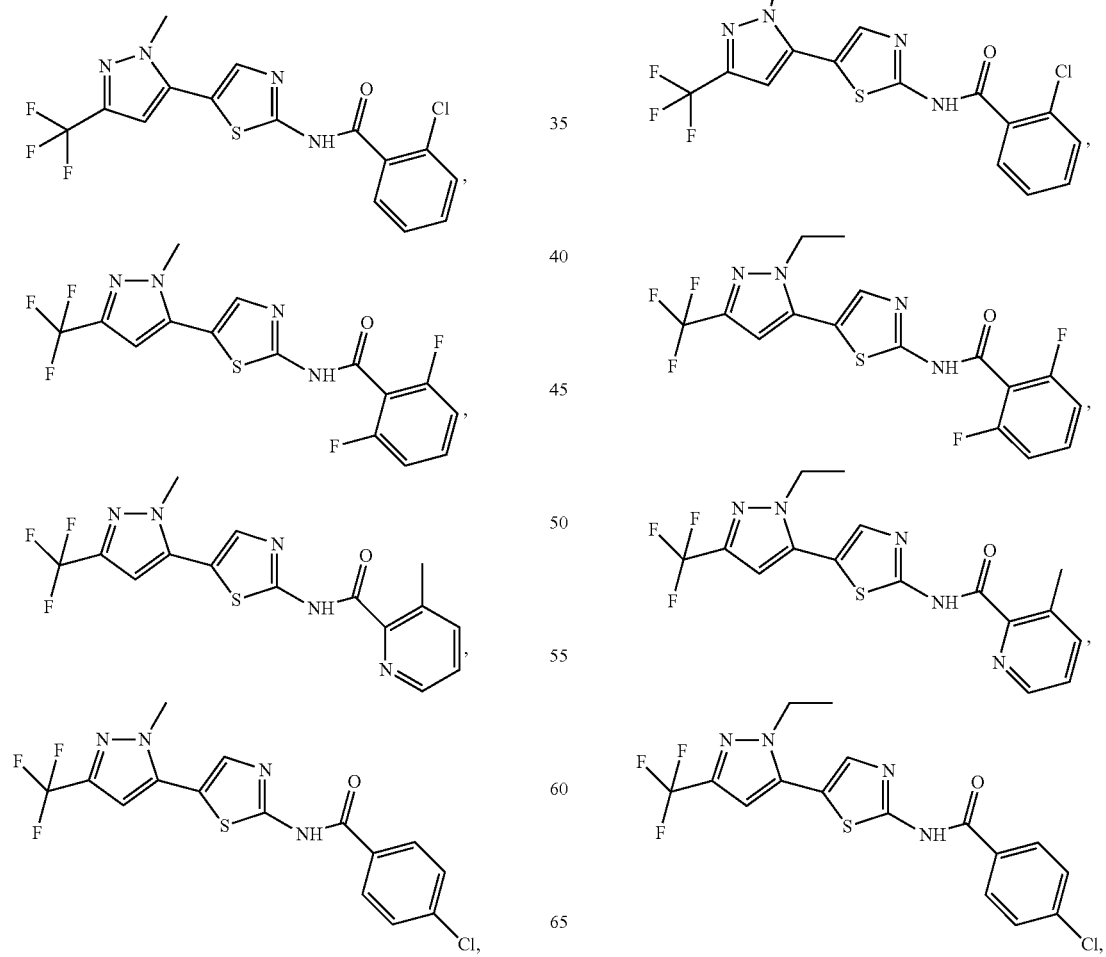

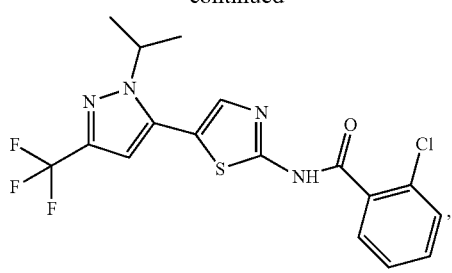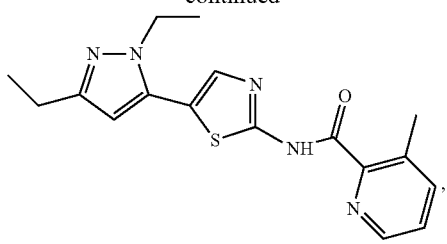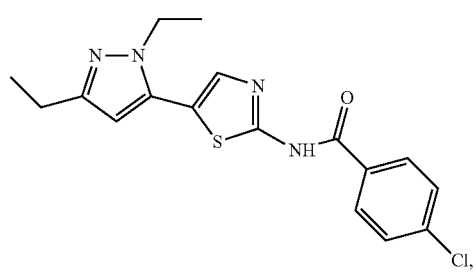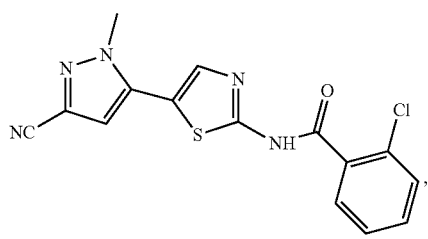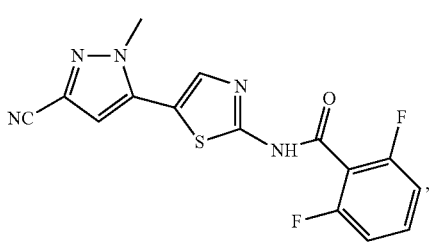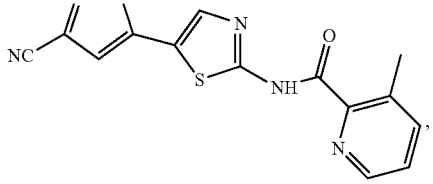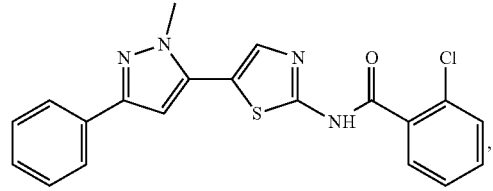

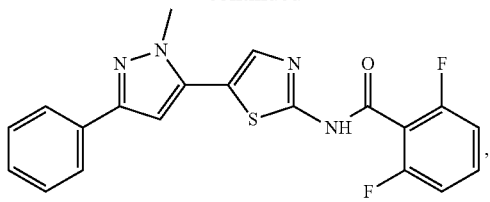
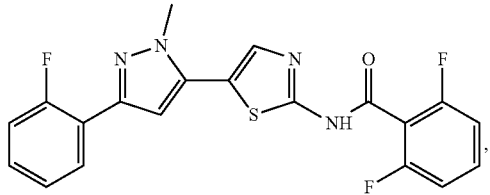
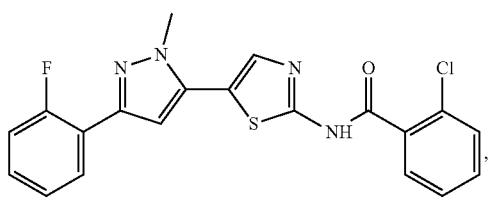
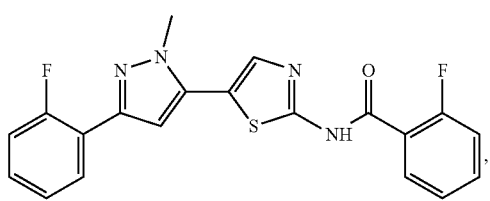
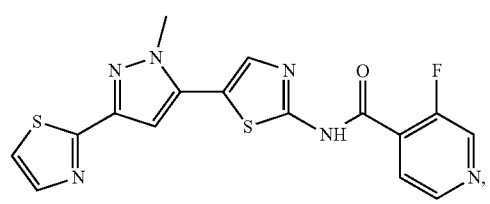
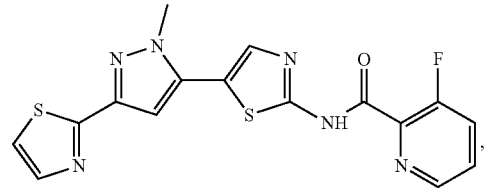
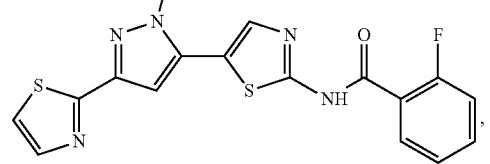
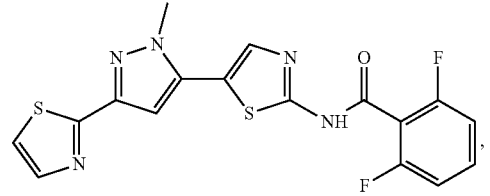
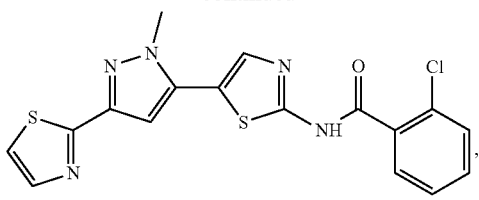
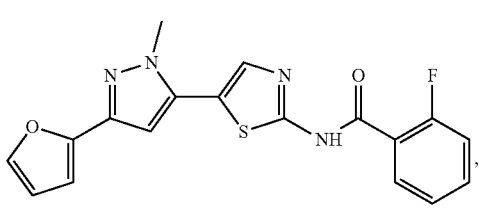
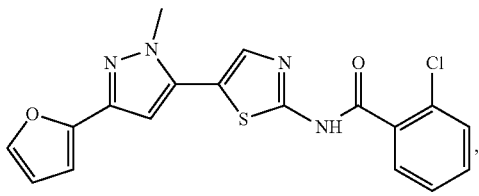
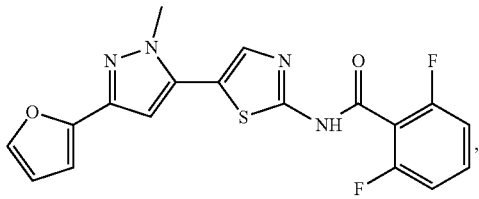
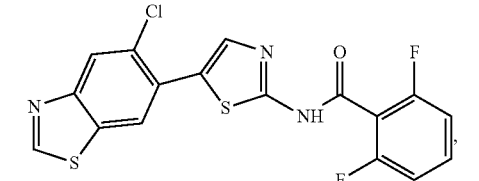
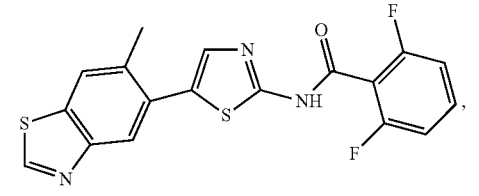
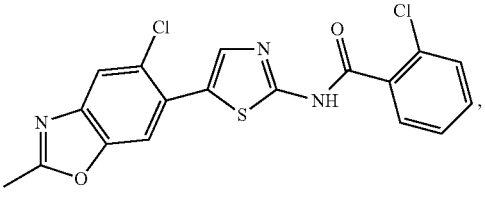
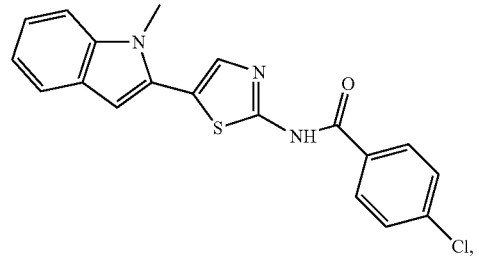

-continued

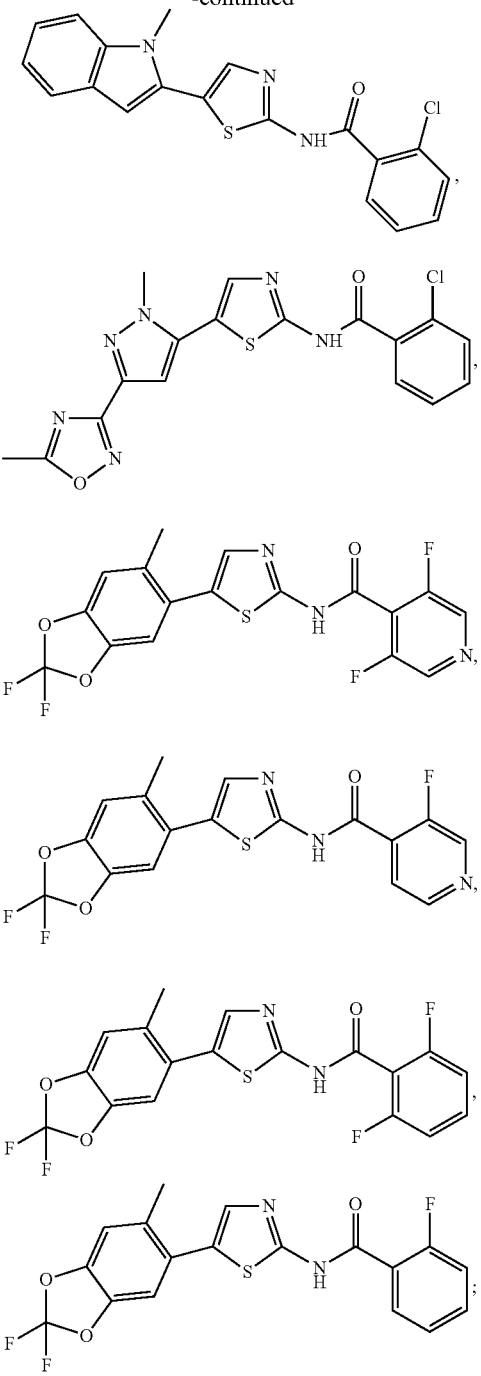

or a pharmaceutically acceptable salt, pharmaceutically acceptable solvate, or pharmaceutically acceptable prodrug In another aspect, described herein is a compound having the structure of Formula (II):

Formula (II)

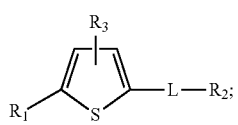

wherein:
L is —NH—C(=O)—, or —C(=O)NH—;
$R_1$

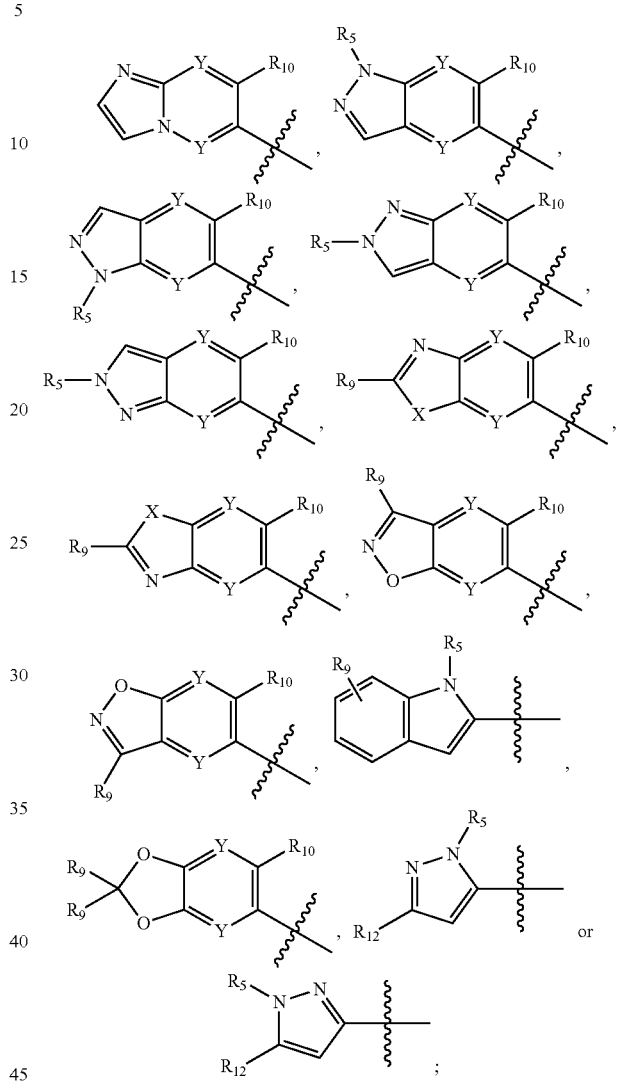

X is S, O, or $NR_5$;
Y is independently selected from $CR_{10}$ or N;
$R_2$ is aryl, heteroaryl, fused aryl or fused heteroaryl; wherein aryl, heteroaryl, fused aryl or fused heteroaryl is optionally substituted with at least one $R_3$;
$R_3$ is independently selected from H, F, D, Cl, Br, I, —CN, —$NO_2$, —OH, —$CF_3$, —$OCF_3$, —$OR_5$, optionally substituted $C_1$-$C_6$alkyl, optionally substituted $C_3$-$C_8$cycloalkyl, optionally substituted $C_1$-$C_6$heteroalkyl, $C_1$-$C_6$haloalkyl, optionally substituted $C_2$-$C_8$heterocycloalkyl, optionally substituted aryl, optionally substituted O-aryl, optionally substituted heteroaryl;
$R_5$ is selected from H, $C_1$-$C_6$alkyl, $C_1$-$C_6$haloalkyl, $C_3$-$C_8$cycloalkyl, phenyl, and benzyl;
$R_{12}$ is $CF_3$, optionally substituted aryl, optionally substituted O-aryl, or optionally substituted heteroaryl;
$R_9$ and $R_{10}$ are each independently selected from H, D, optionally substituted $C_1$-$C_6$alkyl, halogen, $C_1$-$C_6$alkylcarbonyl, or $CF_3$;

or a pharmaceutically acceptable salt, pharmaceutically acceptable solvate, or pharmaceutically acceptable prodrug thereof.

For any and all of the embodiments, substituents are selected from among from a subset of the listed alternatives. For example, in some embodiments, $R_2$ is heteroaryl. In other embodiments, heteroaryl is selected from thienyl, thianthrenyl, furyl, pyranyl, thiadiazolyl, benzothiadiazolyl, isobenzofuranyl, chromenyl, xanthenyl, phenoxathiinyl, pyrrolyl, imidazolyl, pyrazolyl, isothiazolyl, isoxazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinoxalinyl, quinazolinyl, oxazolyl, cinnolinyl, pteridinyl, 4aH-carbazolyl, carbazolyl, carbolinyl, phenanthridinyl, acridinyl, perimidinyl, phenanthrolinyl, phenazinyl, phenarsazinyl, phenothiazinyl, furazanyl, and phenoxazinyl. In one embodiment, $R_2$ is pyrazolyl. In some embodiments, $R_2$ is substituted with at least 2 substituents or at least 3 substituents. In yet another embodiment, $R_2$ is substituted with at least one $R_3$ selected from F, Cl, Br, I, —CN, —NO$_2$, —OH, —CF$_3$, —OCF$_3$, —OR$_5$, $C_1$-$C_6$alkyl, and $C_3$-$C_8$cycloalkyl.

In some embodiments of a compound of Formula (II), $R_1$ is

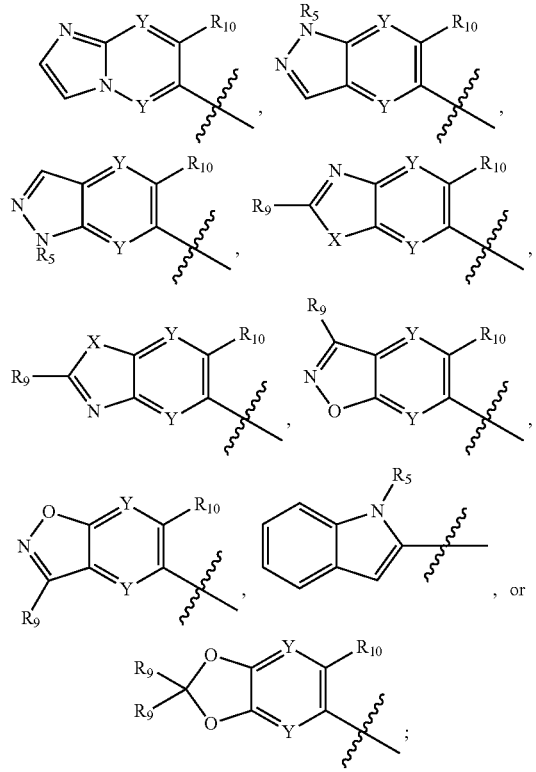

wherein $R_9$ and $R_{10}$ are independently H, $C_1$-$C_6$alkyl, halogen, $C_1$-$C_6$alkylcarbonyl, or CF$_3$ and $R_5$ is selected from H, $C_1$-$C_6$alkyl, $C_1$-$C_6$haloalkyl, $C_3$-$C_8$cycloalkyl, phenyl, and benzyl.

In certain embodiments is a compound of Formula (II), $R_1$ is

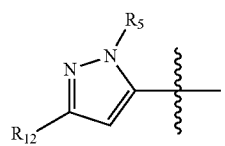

wherein $R_5$ is H, $C_1$-$C_6$alkyl, $C_1$-$C_6$haloalkyl, $C_3$-$C_8$cycloalkyl, phenyl, and benzyl. In another embodiment, $R_5$ is selected from methyl, ethyl, n-propyl, iso-propyl, n-butyl, iso-butyl or tert-butyl. In yet another embodiment, $R_5$ is methyl. In a further embodiment, $R_{12}$ is CF$_3$, optionally substituted aryl, optionally substituted O-aryl, optionally substituted heteroaryl. In one embodiment, $R_{12}$ is CF$_3$. In another embodiment is a compound of Formula (II) wherein $R_{12}$ is optionally substituted aryl, optionally substituted O-aryl, optionally substituted heteroaryl. In one embodiment $R_{12}$ is optionally substituted phenyl. In another embodiment, phenyl is substituted with at least one halogen. In another embodiment, at least two halogens. In another embodiment, $R_{12}$ is selected from optionally substituted thienyl, thianthrenyl, furanyl, pyranyl, thiazolyl, thiadiazolyl, oxadiazolyl, benzothiadiazolyl, isobenzofuranyl, chromenyl, xanthenyl, phenoxathiinyl, pyrrolyl, imidazolyl, pyrazolyl, isothiazolyl, isoxazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinoxalinyl, quinazolinyl, oxazolyl, cinnolinyl, pteridinyl, 4aH-carbazolyl, carbazolyl, carbolinyl, phenanthridinyl, acridinyl, perimidinyl, phenanthrolinyl, phenazinyl, phenarsazinyl, phenothiazinyl, furazanyl, and phenoxazinyl. In a further embodiment, $R_{12}$ is optionally substituted thienyl, furanyl, oxadiazolyl or thiazolyl.

In another embodiment, $R_3$ is selected from F, Cl, Br, and I. In yet a further embodiment, $R_3$ is F. In another embodiment, $R_3$ is Br. In a further embodiment, $R_3$ is Cl. In yet another embodiment $R_3$ is NO$_2$. In another embodiment, $R_3$ is $C_2$-$C_8$heterocycloalkyl, optionally substituted aryl, optionally substituted O-aryl, or optionally substituted heteroaryl. In one embodiment, $R_3$ is optionally substituted heteroaryl selected from thienyl, thianthrenyl, furyl, pyranyl, thiadiazolyl, oxadiazolyl, benzothiadiazolyl, isobenzofuranyl, chromenyl, xanthenyl, phenoxathiinyl, pyrrolyl, imidazolyl, pyrazolyl, isothiazolyl, isoxazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinoxalinyl, quinazolinyl, oxazolyl, cinnolinyl, pteridinyl, 4aH-carbazolyl, carbazolyl, carbolinyl, phenanthridinyl, acridinyl, perimidinyl, phenanthrolinyl, phenazinyl, phenarsazinyl, phenothiazinyl, furazanyl, and phenoxazinyl. In a further embodiment, $R_3$ is oxadiazolyl.

In certain embodiments is a compound of Formula (II) wherein $R_2$ is aryl. In other embodiments, $R_2$ is phenyl. In certain embodiments, the phenyl group is substituted with at least one $R_3$ independently selected from F, Cl, Br, I, —CN, —NO$_2$, —OH, —CF$_3$, —OCF$_3$, —OR$_5$, $C_1$-$C_6$alkyl, $C_3$-$C_8$cycloalkyl, $C_1$-$C_6$heteroalkyl, $C_1$-$C_6$haloalkyl, $C_2$-$C_8$heterocycloalkyl, optionally substituted aryl, optionally substituted O-aryl, and optionally substituted heteroaryl. In certain embodiments, the phenyl group is substituted with at least one $R_3$ independently selected from F and Cl. In some embodiments, phenyl is substituted with at least 2 substituents or at least 3 substituents. In certain embodiments, $R_3$ is fluorine. In other embodiment, $R_3$ is chlorine. In another embodiment, $R_3$ is OR$_5$ wherein $R_5$ is methyl or ethyl.

In certain embodiments is a compound of Formula (II) wherein $R_2$ is heteroaryl. In some embodiments, $R_2$ is pyridyl. In certain embodiments, the pyridyl group is substituted with at least one $R_3$ independently selected from F, Cl, Br, I, —CN, —$NO_2$, —OH, —$CF_3$, —$OCF_3$, —$OR_5$, $C_1$-$C_6$alkyl, $C_3$-$C_8$cycloalkyl, $C_1$-$C_6$heteroalkyl, $C_1$-$C_6$haloalkyl, $C_2$-$C_6$heterocycloalkyl, optionally substituted aryl, optionally substituted O-aryl, and optionally substituted heteroaryl. In certain embodiments, the pyridyl group is substituted with at least one $R_3$ independently selected from F and Cl. In some embodiments, pyridyl is substituted with at least 2 substituents or at least 3 substituents. In certain embodiments, $R_3$ is fluorine. In other embodiment, $R_3$ is chlorine. In another embodiment, $R_3$ is $OR_5$ wherein $R_5$ is methyl or ethyl.

In another embodiment is a compound of Formula (II) wherein $R_3$ is selected from $CF_3$, $C_1$-$C_6$alkyl, and $C_3$-$C_8$cycloalkyl. In certain embodiments, $R_3$ is $CF_3$. In certain embodiments, $R_3$ is cyclopropyl. In other embodiments, $R_3$ is $C_1$-$C_6$alkyl. In certain embodiments, $R_3$ is $CH_3$. In certain embodiments, $R_3$ is $C_2H_5$. In certain embodiments, $R_3$ is isopropyl.

In another embodiment is a compound of Formula (II) wherein L is —C(=O)NH—.

In another embodiment is a compound of Formula (II) wherein L is —NH—C(=O)—.

In another aspect is a compound having the structure of Formula (III):

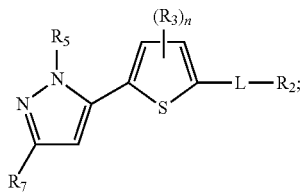

Formula (III)

wherein:
L is —NH—C(=O)—, or —C(=O)NH—;
$R_2$ is aryl, heteroaryl, fused aryl or fused heteroaryl; wherein aryl, heteroaryl, fused aryl or fused heteroaryl is optionally substituted with at least one $R_8$;
$R_8$ is independently selected from F, D, Cl, Br, I, —CN, —$NO_2$, —OH, —$CF_3$, —$OCF_3$, —$OR_5$, optionally substituted $C_1$-$C_6$alkyl, optionally substituted $C_3$-$C_8$cycloalkyl, optionally substituted $C_1$-$C_6$heteroalkyl, $C_1$-$C_6$haloalkyl, optionally substituted $C_2$-$C_8$heterocycloalkyl, optionally substituted aryl, optionally substituted O-aryl, and optionally substituted heteroaryl;
$R_3$ is independently selected from F, D, Cl, Br, —CN, —$NO_2$, —OH, —$NH_2$, —$CF_3$, and —$OCF_3$;
$R_5$ is selected from H, $C_1$-$C_6$alkyl, $C_1$-$C_6$haloalkyl, $C_3$-$C_8$cycloalkyl, phenyl, and benzyl;
$R_7$ is selected from $CF_3$, CN, optionally substituted $C_1$-$C_6$alkyl, $C_1$-$C_6$haloalkyl, and optionally substituted $C_3$-$C_8$cycloalkyl; and n is an integer selected from 1 or 2;
or a pharmaceutically acceptable salt, pharmaceutically acceptable solvate, or pharmaceutically acceptable prodrug thereof.

In one embodiment, $R_5$ is selected from H, $C_1$-$C_6$alkyl, $C_1$-$C_6$haloalkyl, $C_3$-$C_8$cycloalkyl, phenyl, and benzyl. In another embodiment, $R_5$ is selected from methyl, ethyl, n-propyl, iso-propyl, n-butyl, iso-butyl or tert-butyl. In yet another embodiment, $R_5$ is methyl. In one embodiment, $R_7$ is selected from $CF_3$, CN, $C_1$-$C_6$alkyl, $C_1$-$C_6$haloalkyl, and $C_3$-$C_8$cycloalkyl. In another embodiment, $R_7$ is $CF_3$. In another embodiment, $R_7$ is $C_1$-$C_6$alkyl. In another embodiment, $C_1$-$C_6$alkyl is selected from methyl, ethyl, n-propyl, iso-propyl, n-butyl, iso-butyl or tert-butyl. In yet another embodiment, $R_5$ is methyl. In another embodiment, $R_7$ is ethyl.

In another embodiment is a compound of Formula (III) wherein $R_3$ is independently selected from F, D, Cl, Br, —CN, —$NO_2$, —OH, —$NH_2$, —$CF_3$, and —$OCF_3$. In certain embodiments, $R_3$ is $CF_3$. In certain embodiments, $R_3$ is F, Cl, or Br. In yet a further embodiment, $R_3$ is F. In another embodiment, $R_3$ is Br. In a further embodiment, $R_3$ is Cl. In another embodiment, $R_3$ is $NO_2$. In yet another embodiment, $R_3$ is $NH_2$.

In certain embodiments is a compound of Formula (III) wherein $R_2$ is aryl. In other embodiments, $R_2$ is phenyl. In certain embodiments, the phenyl group is substituted with at least one $R_8$ selected from F, Cl, Br, I, —CN, —$NO_2$, —OH, —$CF_3$, —$OCF_3$, —$OR_5$, $C_1$-$C_6$alkyl, $C_3$-$C_8$cycloalkyl, $C_1$-$C_6$heteroalkyl, $C_1$-$C_6$haloalkyl, $C_2$-$C_8$heterocycloalkyl, optionally substituted aryl, optionally substituted O-aryl, and optionally substituted heteroaryl. In some embodiments, phenyl is substituted with at least 2 substituents or at least 3 substituents. In certain embodiments, $R_8$ is fluorine. In another embodiment, $R_8$ is chlorine.

In certain embodiments is a compound of Formula (III) wherein $R_2$ is heteroaryl. In some embodiments, heteroaryl is selected from thienyl, thianthrenyl, furyl, pyranyl, thiadiazolyl, benzothiadiazolyl, isobenzofuranyl, chromenyl, xanthenyl, phenoxathiinyl, pyrrolyl, imidazolyl, pyrazolyl, isothiazolyl, isoxazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinoxalinyl, quinazolinyl, oxazolyl, cinnolinyl, pteridinyl, 4aH-carbazolyl, carbazolyl, carbolinyl, phenanthridinyl, acridinyl, perimidinyl, phenanthrolinyl, phenazinyl, phenarsazinyl, phenothiazinyl, furazanyl, and phenoxazinyl. In another embodiment $R_2$ is pyridinyl. In one embodiment, $R_2$ is pyrazolyl. In some embodiments, $R_2$ is substituted with at least 2 substituents or at least 3 substituents. In yet another embodiment, $R_2$ is substituted with at least one $R_8$ selected from F, Cl, Br, I, —CN, —$NO_2$, —OH, —$CF_3$, —$OCF_3$, —$OR_5$, $C_1$-$C_6$alkyl, and $C_3$-$C_8$cycloalkyl.

In another embodiment is a compound of Formula (III) wherein $R_8$ is selected from F, Cl, Br, $CF_3$, $C_1$-$C_6$alkyl, and $C_3$-$C_8$cycloalkyl. In certain embodiments, $R_8$ is $CF_3$. In certain embodiments, $R_8$ is cyclopropyl. In other embodiments, $R_8$ is $C_1$-$C_6$alkyl. In certain embodiments, $R_8$ is $CH_3$. In certain embodiments, $R_8$ is $C_2H_5$. In certain embodiments, $R_8$ is isopropyl. In another embodiment $R_8$ is F. In a further embodiment $R_8$ is Cl.

In another embodiment is a compound of Formula (III) wherein L is —C(=O)NH—.

In another embodiment is a compound of Formula (III) wherein L is —NH—C(=O)—.

In yet a further aspect is a compound selected from:
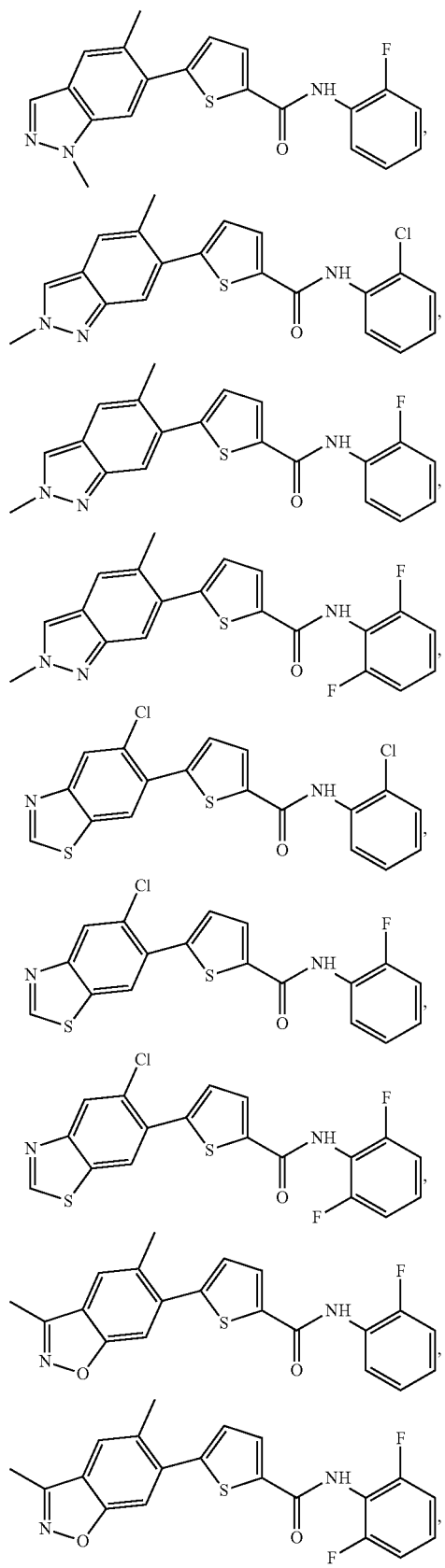
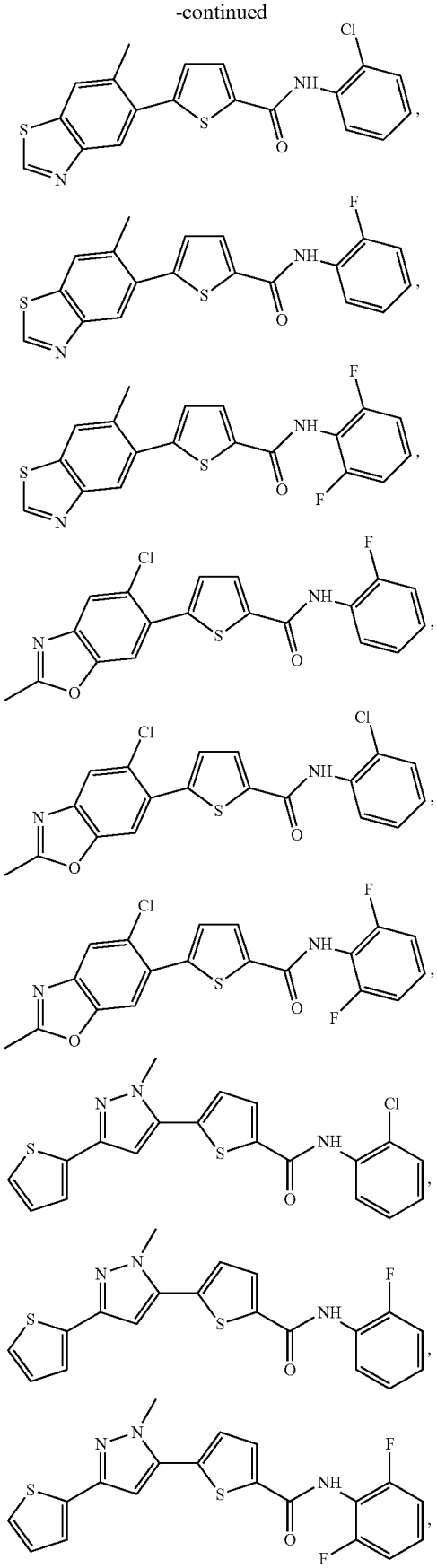

-continued
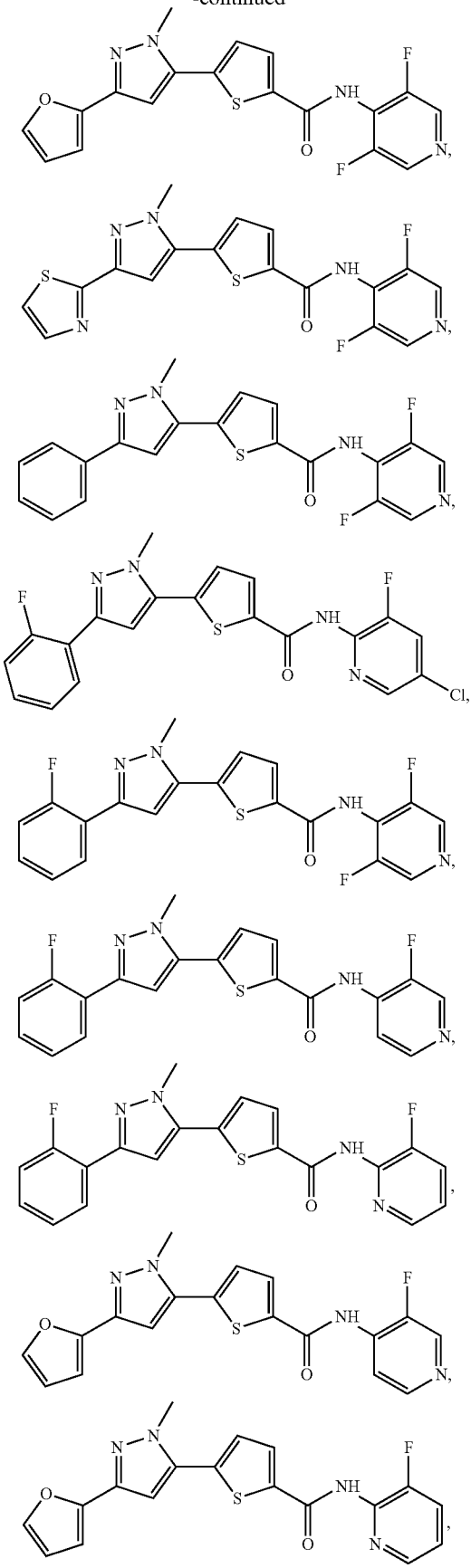
-continued
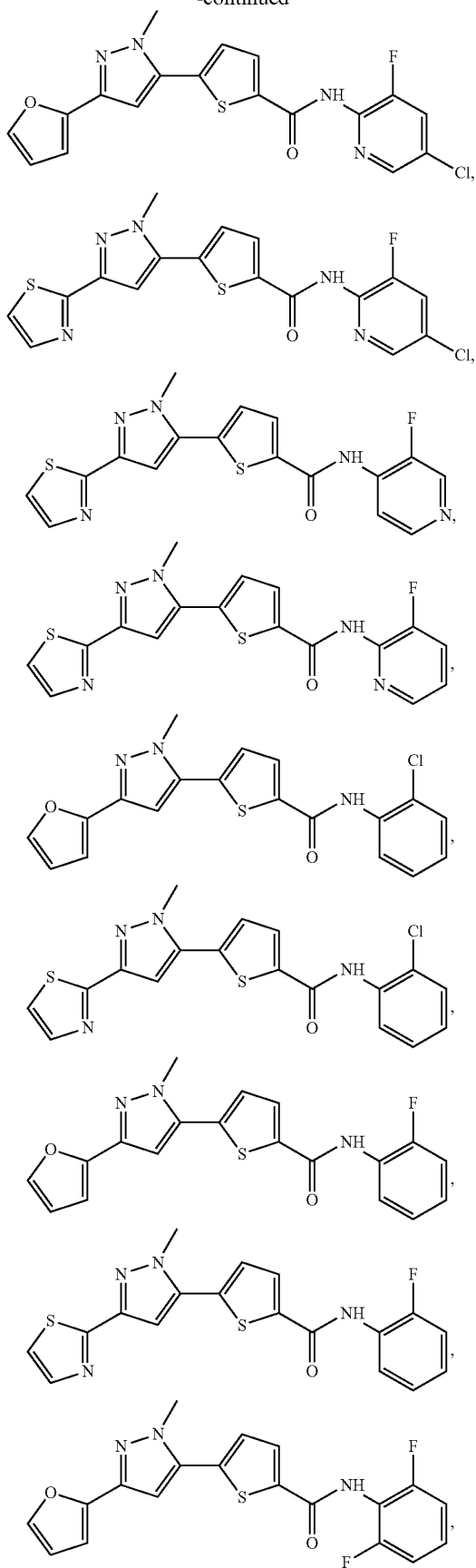

-continued
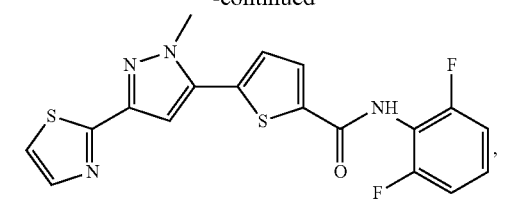
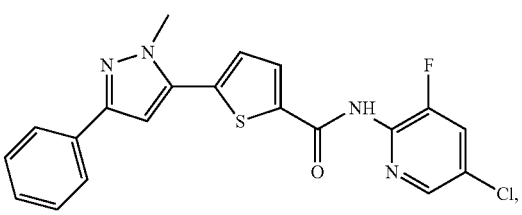
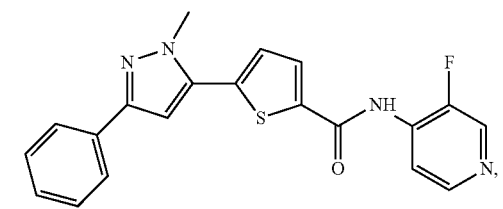
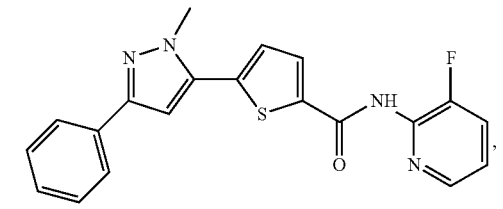
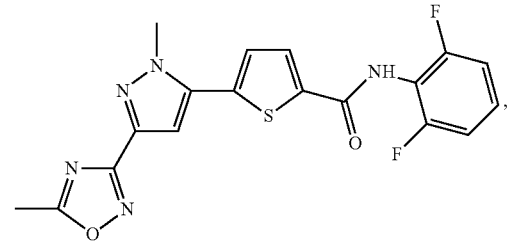
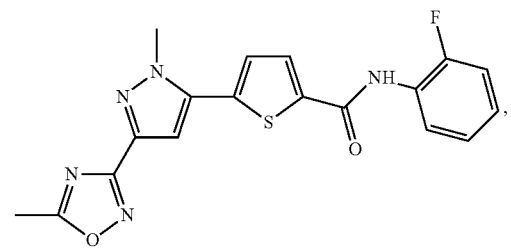
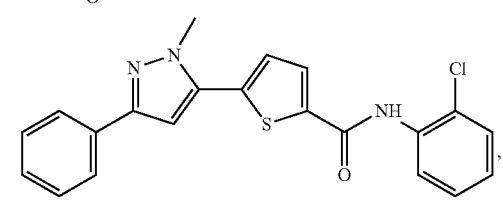
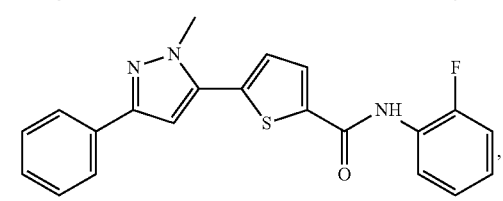
-continued
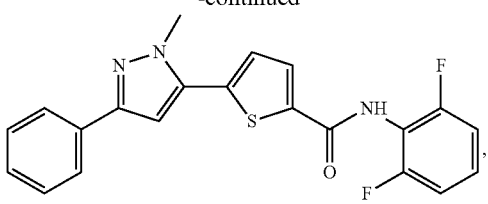
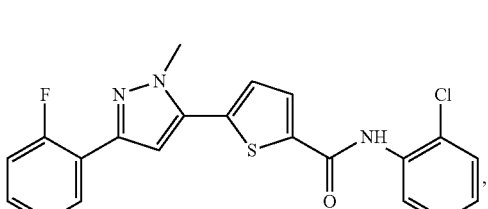
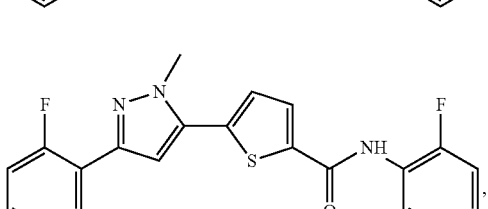
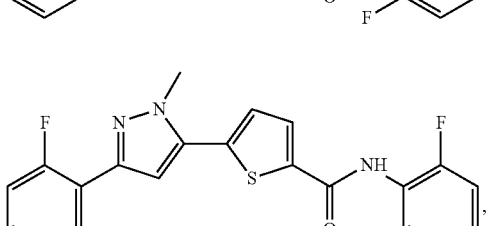
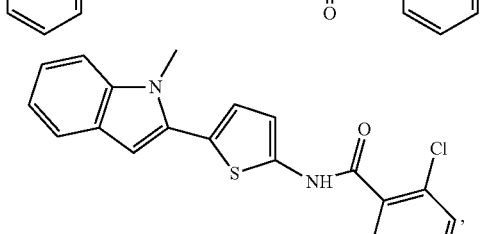
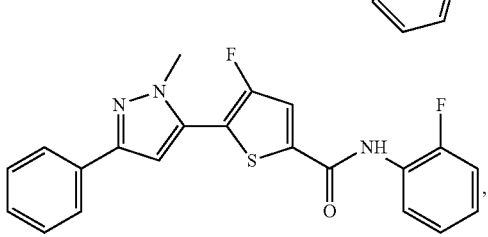
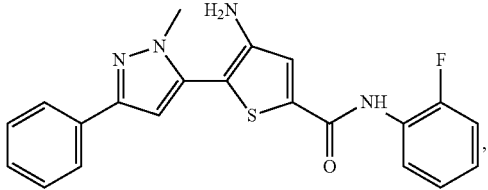
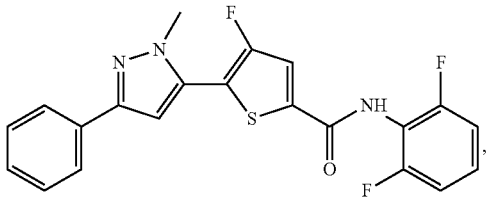

-continued

45
-continued
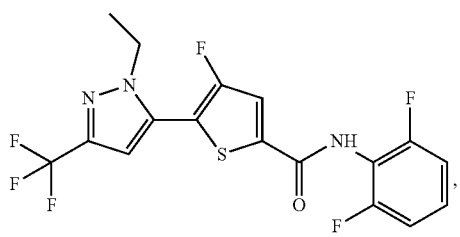
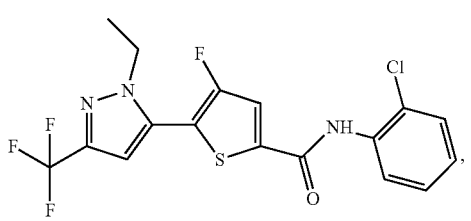
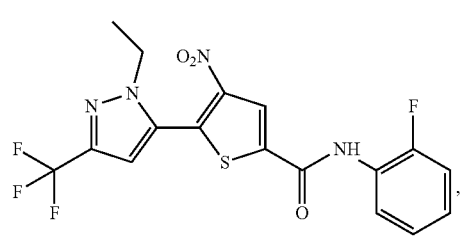
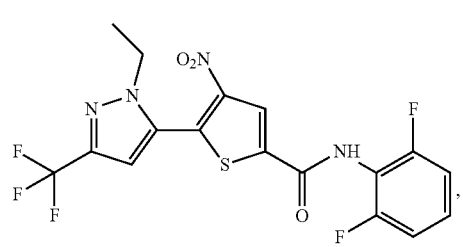
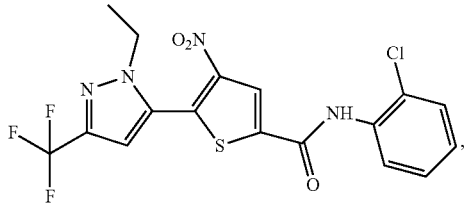
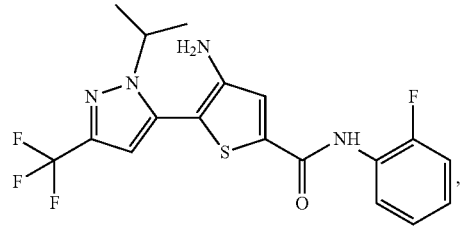
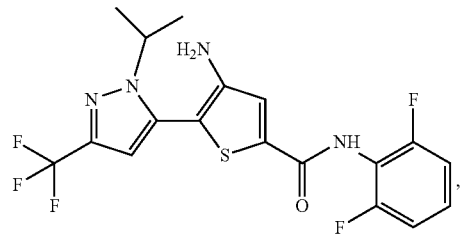
46
-continued
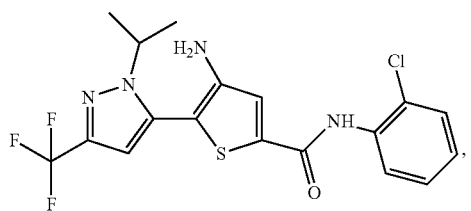
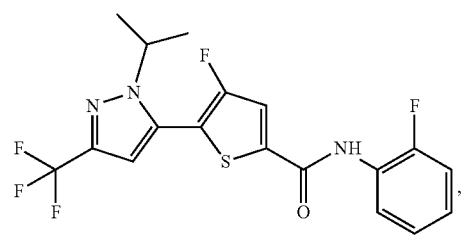
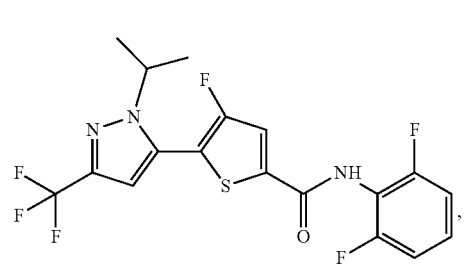
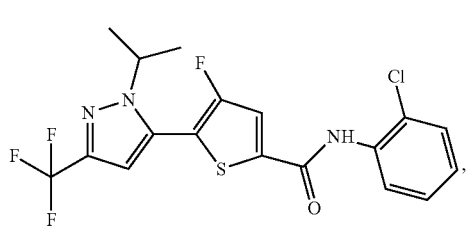
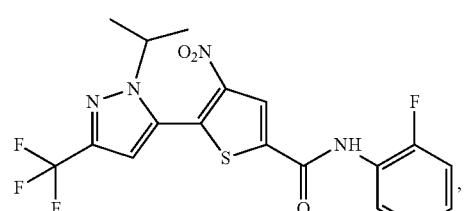
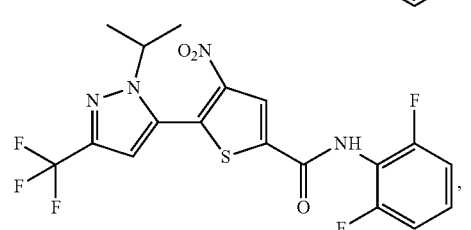
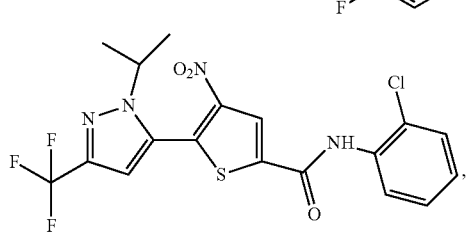

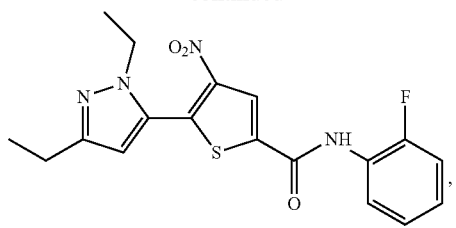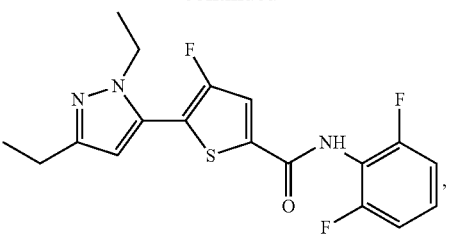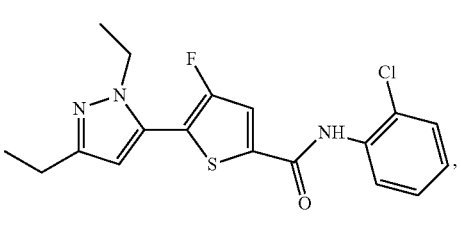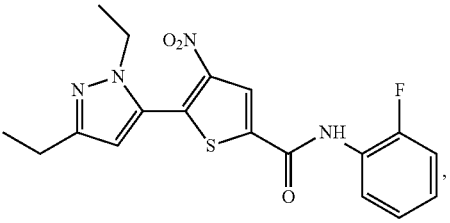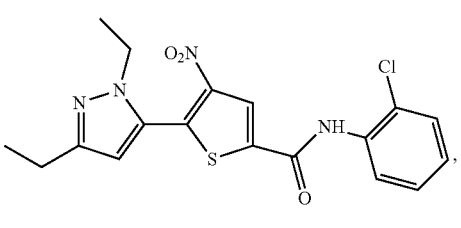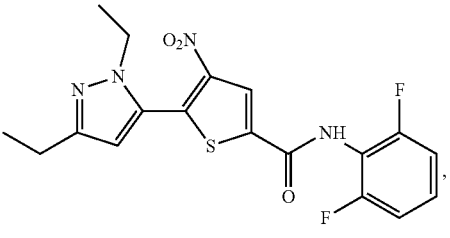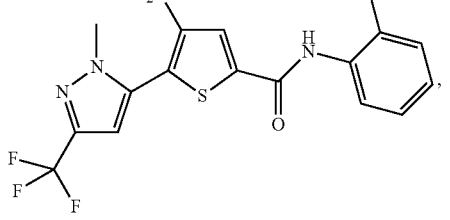

-continued

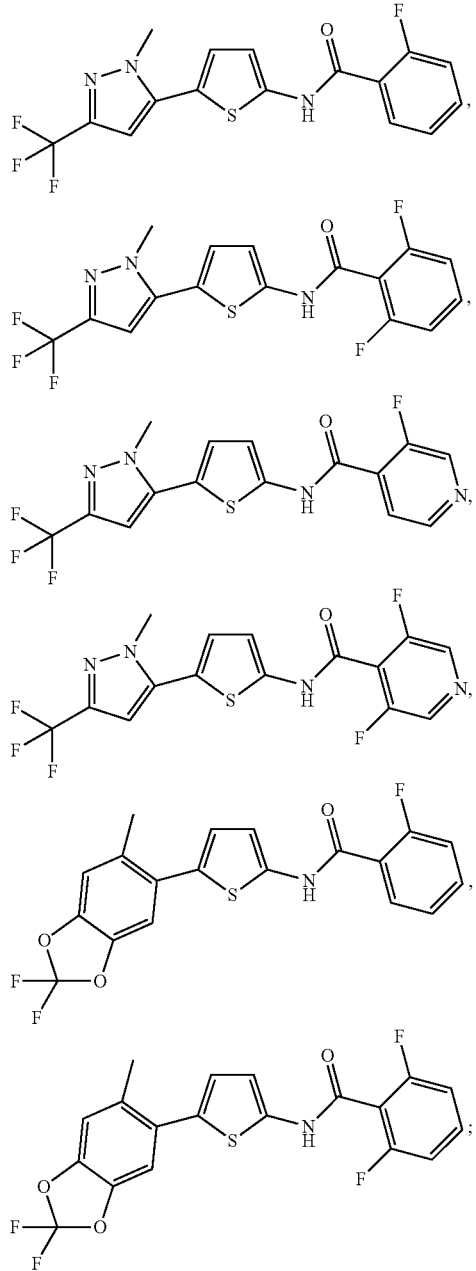

or a pharmaceutically acceptable salt, pharmaceutically acceptable solvate, or pharmaceutically acceptable prodrug thereof.

In one aspect is a compound of Formula (IV) having the structure:

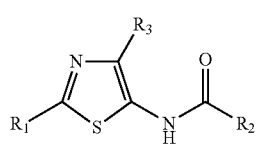

Formula (IV)

wherein:
$R_1$ is

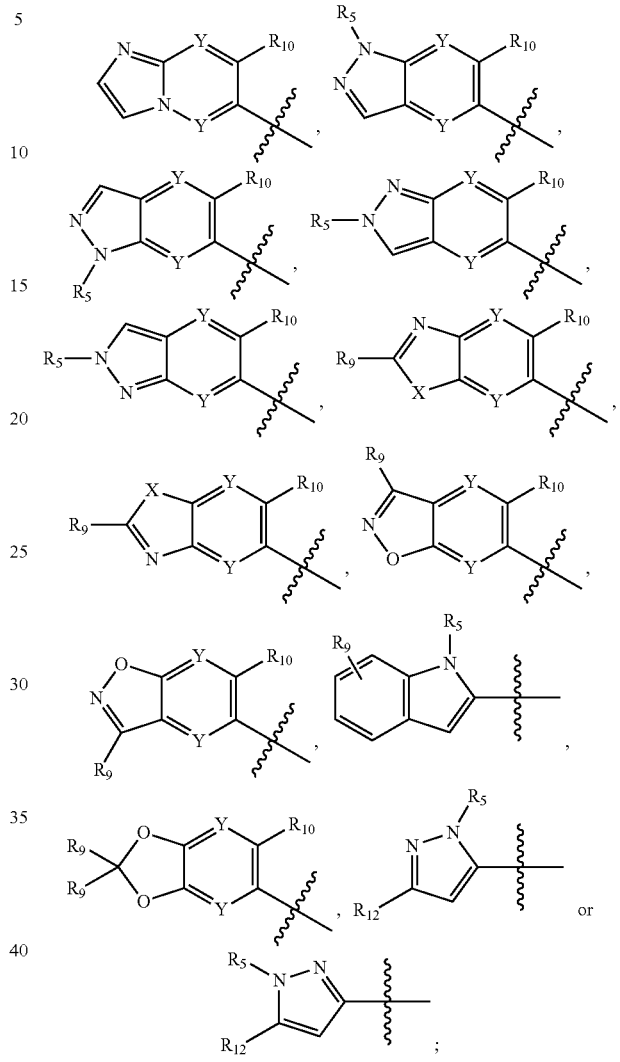

$X$ is S, O, or $NR_5$;
$Y$ is independently selected from $CR_{10}$ or N;
$R_2$ is aryl, heteroaryl, fused aryl or fused heteroaryl; wherein aryl, heteroaryl, fused aryl or fused heteroaryl is optionally substituted with at least one $R_3$;
$R_3$ is independently selected from H, F, D, Cl, Br, I, —CN, —$NO_2$, —OH, —$CF_3$, —$OCF_3$, —$OR_5$, optionally substituted $C_1$-$C_6$alkyl, optionally substituted $C_3$-$C_8$cycloalkyl, optionally substituted $C_1$-$C_6$heteroalkyl, $C_1$-$C_6$haloalkyl, optionally substituted $C_2$-$C_8$heterocycloalkyl, optionally substituted aryl, optionally substituted O-aryl, optionally substituted heteroaryl;
$R_5$ is selected from H, $C_1$-$C_6$alkyl, $C_1$-$C_6$haloalkyl, $C_3$-$C_8$cycloalkyl, phenyl, and benzyl;
$R_9$ and $R_{10}$ are each independently selected from H, D, optionally substituted $C_1$-$C_6$alkyl, halogen, $C_1$-$C_6$ alkylcarbonyl, or $CF_3$;
$R_{12}$ is selected from CN, —$OR_5$, optionally substituted $C_1$-$C_6$alkyl, $C_1$-$C_6$haloalkyl, optionally substituted $C_3$-$C_8$cycloalkyl, optionally substituted aryl, optionally substituted O-aryl, and optionally substituted heteroaryl;

or a pharmaceutically acceptable salt, pharmaceutically acceptable solvate, or pharmaceutically acceptable prodrug thereof.

In a further embodiment $R_2$ is aryl optionally substituted with at least one $R_3$ selected from F, Cl, Br, and I. In another embodiment $R_3$ is selected from —CN, —NO$_2$, —OH, —OCF$_3$, and —OR$_5$, wherein $R_5$ is $C_1$-$C_6$alkyl. In another embodiment $R_3$ is —OH. In a further embodiment, $R_3$ is —CN. In another embodiment is a compound of Formula (IV) wherein $R_{12}$ is selected from H, F, Cl, Br, and I. In another embodiment, $R_{12}$ is $C_1$-$C_6$alkyl. In a further embodiment, $C_1$-$C_6$alkyl is methyl, ethyl, n-propyl, iso-propyl, n-butyl, iso-butyl or tert-butyl. In another embodiment $R_5$ is H or $C_1$-$C_6$alkyl. In another embodiment, $R_5$ is methyl, ethyl, n-propyl, iso-propyl, n-butyl, iso-butyl or tert-butyl. In a further embodiment, $R_5$ is H. In yet a further embodiment, $R_5$ is methyl. In another embodiment is a compound of Formula (IV) wherein $R_2$ is heteroaryl selected from thienyl, thianthrenyl, furyl, pyranyl, thiadiazolyl, benzothiadiazolyl, isobenzofuranyl, chromenyl, xanthenyl, phenoxathiinyl, pyrrolyl, imidazolyl, pyrazolyl, isothiazolyl, isoxazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinoxalinyl, quinazolinyl, oxazolyl, cinnolinyl, pteridinyl, 4aH-carbazolyl, carbazolyl, carbolinyl, phenanthridinyl, acridinyl, perimidinyl, phenanthrolinyl, phenazinyl, phenarsazinyl, phenothiazinyl, furazanyl, and phenoxazinyl. In a further embodiment, $R_2$ is pyridinyl. In another embodiment, $R_2$ is furyl. In a further embodiment, $R_2$ is pyranyl. In one embodiment is a compound of Formula (IV) wherein $R_2$ is heteroaryl substituted with at least one $R_3$ selected from F, Cl, Br, and I. In another embodiment, $R_2$ is heteroaryl substituted with at least two $R_3$ or at least three $R_3$ selected from H, F, Cl, Br, I, —CN, —NO$_2$, —OH, —CF$_3$, —OCF$_3$, —OR$_5$, $C_1$-$C_6$alkyl, and $C_3$-$C_8$cycloalkyl.

Also described herein is a compound of Formula (IV) wherein $R_1$ is

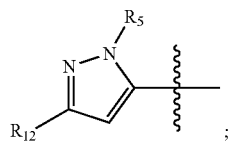

$R_{12}$ is selected from CN, —OR$_5$, $C_1$-$C_6$alkyl, $C_1$-$C_6$haloalkyl, $C_3$-$C_8$cycloalkyl, optionally substituted aryl, optionally substituted O-aryl, and optionally substituted heteroaryl; and $R_5$ is $C_1$-$C_6$alkyl. In one embodiment, $R_{12}$ is —CN. In another embodiment, $R_{12}$ is OH. In yet another embodiment, $R_{12}$ is $C_1$-$C_6$alkyl. In a further embodiment, $R_{12}$ is selected from methyl, ethyl, n-propyl, iso-propyl, n-butyl, iso-butyl, and tert-butyl. In one embodiment, $R_{12}$ is methyl. In another embodiment $R_{12}$ is ethyl.

In another embodiment is a compound of Formula (IV) wherein $R_{12}$ is selected from CF$_3$, $C_1$-$C_6$alkyl, and $C_3$-$C_8$cycloalkyl. In certain embodiments, $R_{12}$ is CF$_3$. In other embodiments, $R_{12}$ is cyclopropyl. In other embodiments, $R_5$ is $C_1$-$C_6$alkyl. In certain embodiments, $R_5$ is CH$_3$. In certain embodiments, $R_5$ is C$_2$H$_5$. In certain embodiments, $R_5$ is isopropyl.

In a further embodiment, $R_1$ is

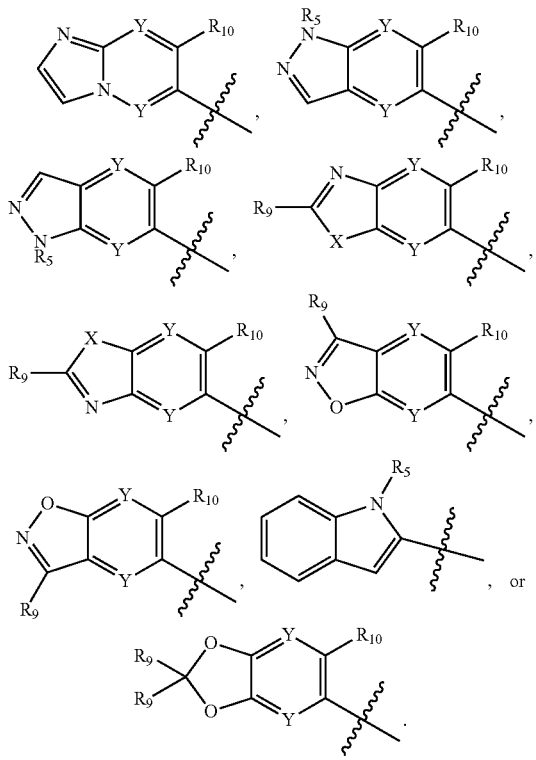

In another aspect is a compound selected from:

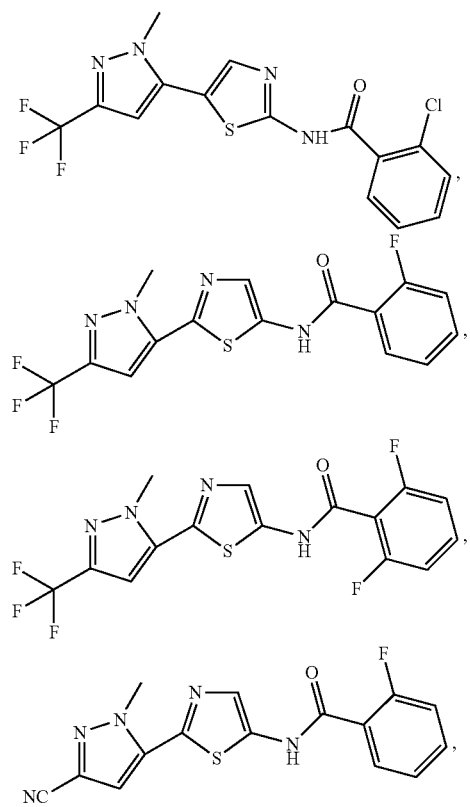

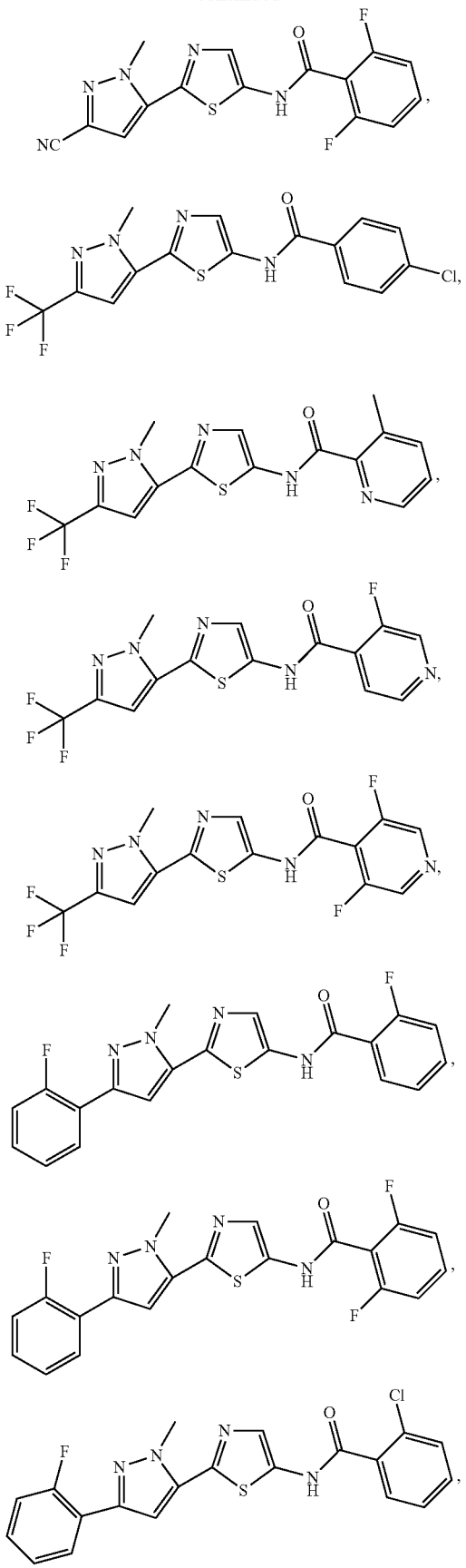
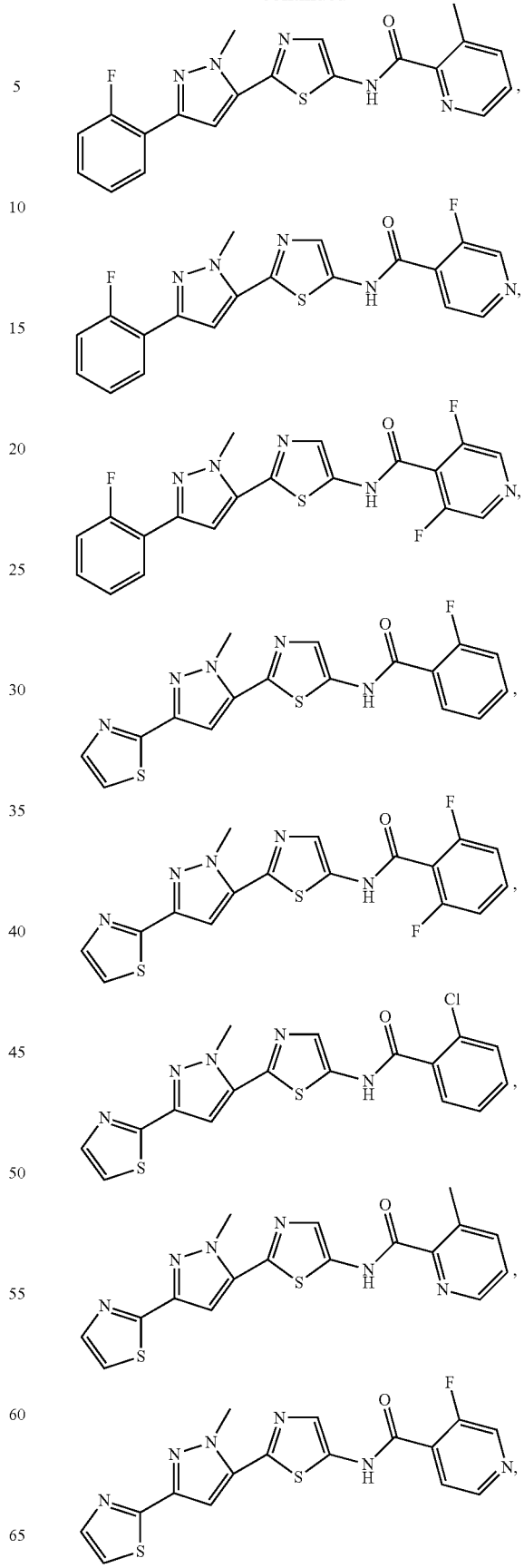

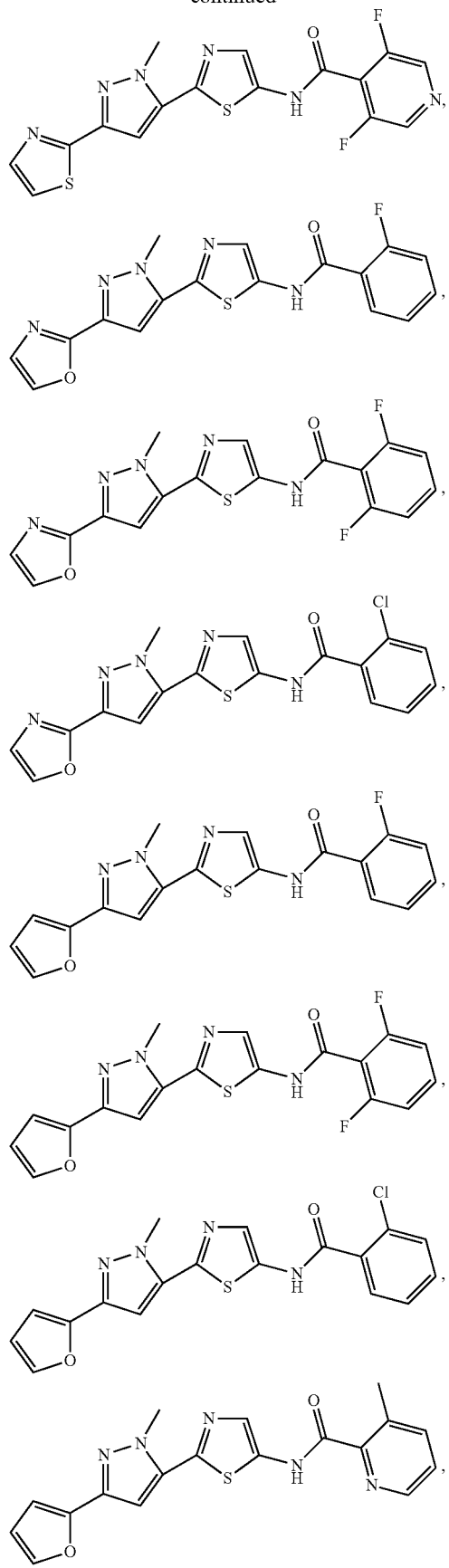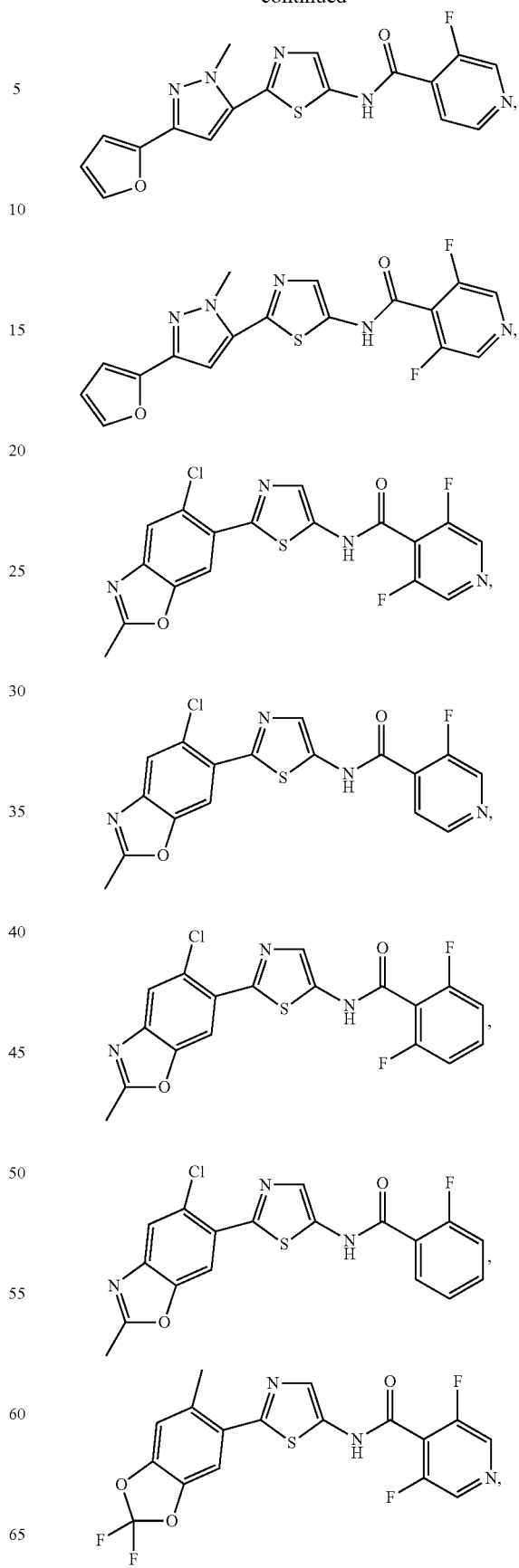

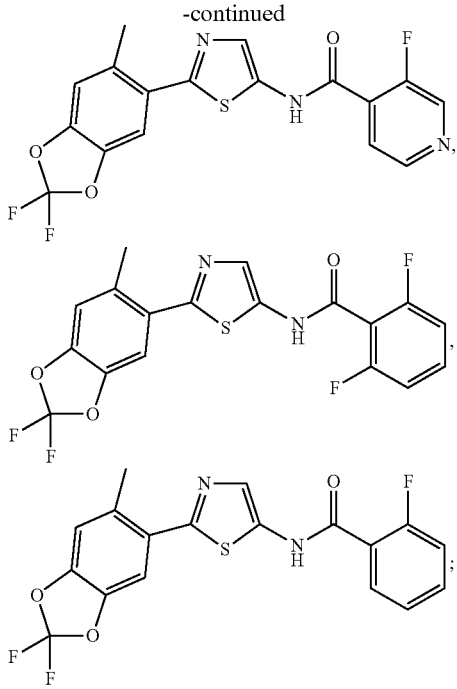

or a pharmaceutically acceptable salt, pharmaceutically acceptable solvate, or pharmaceutically acceptable prodrug thereof.

In another aspect is a pharmaceutical composition comprising a pharmaceutically acceptable diluent, excipient or binder, and a compound having the structure of Formula (I), (II), (III), or (IV) or a pharmaceutically acceptable salt, pharmaceutically acceptable prodrug, or pharmaceutically acceptable solvate thereof.

In another aspect is the use of a compound of Formula (I), (II), or (III), or (IV) or a pharmaceutically acceptable salt, pharmaceutically acceptable solvate, or pharmaceutically acceptable prodrug thereof, for the formulation of a medicament for the modulation of store-operated calcium (SOC) channel activity in a subject or for the treatment of a disease, disorder or condition in a subject that would benefit from the modulation of store-operated calcium (SOC) channel activity. In one embodiment, the compound of Formula (I), (II), (III), or (IV) inhibits store-operated calcium entry (SOCE). In another embodiment, the store-operated calcium channel activity is calcium release activated calcium channel activity.

In another aspect is a method of treating a disease, disorder or condition in a mammal that would benefit from inhibition of store-operated calcium channel activity comprising administering to the mammal a compound having the structure of Formula (I), (II), (III), or (IV) or a pharmaceutically acceptable salt, pharmaceutically acceptable solvate, or pharmaceutically acceptable prodrug thereof, or a pharmaceutical composition comprising same with a pharmaceutically acceptable diluent, excipient or binder.

In certain embodiments, the disease, disorder or condition in a mammal is selected from diseases/disorders involving inflammation, glomerulonephritis, uveitis, hepatic diseases or disorders, renal diseases or disorders, chronic obstructive pulmonary disease, rheumatoid arthritis, inflammatory bowel disease, vasculitis, dermatitis, osteoarthritis, inflammatory muscle disease, allergic rhinitis, vaginitis, interstitial cystitis, scleroderma, osteoporosis, eczema, organ transplant rejection, allogeneic or xenogeneic transplantation, graft rejection, graft-versus-host disease, lupus erythematosus, type I diabetes, pulmonary fibrosis, dermatomyositis, thyroiditis, myasthenia gravis, autoimmune hemolytic anemia, cystic fibrosis, chronic relapsing hepatitis, primary biliary cirrhosis, allergic conjunctivitis, hepatitis and atopic dermatitis, asthma, psoriasis, multiple sclerosis, Sjogren's syndrome, and autoimmune diseases or disorders.

In another aspect is a method of modulating store-operated calcium (SOC) channel activity comprising contacting the SOC channel complex, or portion thereof, with a compound of Formula (I), (II), (III), or (IV) or a pharmaceutically acceptable salt, pharmaceutically acceptable solvate, or pharmaceutically acceptable prodrug thereof, or a pharmaceutical composition comprising same with a pharmaceutically acceptable diluent, excipient or binder.

Also presented herein is a method of modulating calcium release activated calcium channel (CRAC) activity in a mammal comprising administering a compound of Formula (I), (II), (III) or (IV), or a pharmaceutically acceptable salt, pharmaceutically acceptable solvate, or pharmaceutically acceptable prodrug thereof.

In one embodiment is a method of modulating calcium release activated calcium channel (CRAC) activity in a mammal comprising administering a compound of Formula (I), (II), (III) or (IV), or a pharmaceutically acceptable salt, pharmaceutically acceptable solvate, or pharmaceutically acceptable prodrug thereof wherein the compound of Formula (I), (II), (III), or (IV) modulates an activity of, modulates an interaction of, or modulates the level of, or binds to, or interacts with at least one component of the calcium release activated (CRAC) channel complex selected from stromal interaction molecules (STIM) family of proteins.

In another embodiment is a method of modulating calcium release activated calcium channel (CRAC) activity in a mammal comprising administering a compound of Formula (I), (II), (III) or (IV), or a pharmaceutically acceptable salt, pharmaceutically acceptable solvate, or pharmaceutically acceptable prodrug thereof wherein the compound of Formula (I), (II), (III), or (IV) modulates an activity of, modulates an interaction of, or modulates the level of, or binds to, or interacts with STIM1 or STIM2.

In yet another embodiment is a method of modulating calcium release activated calcium channel (CRAC) activity in a mammal comprising administering a compound of Formula (I), (II), (III) or (IV), or a pharmaceutically acceptable salt, pharmaceutically acceptable solvate, or pharmaceutically acceptable prodrug thereof wherein modulating calcium release activated calcium (CRAC) channel activity with a compound of Formula (I), (II), (III), or (IV) inhibits store-operated calcium entry (SOCE).

In a further embodiment is a method of modulating calcium release activated calcium channel (CRAC) activity in a mammal comprising administering a compound of Formula (I), (II), (III) or (IV), or a pharmaceutically acceptable salt, pharmaceutically acceptable solvate, or pharmaceutically acceptable prodrug thereof wherein modulating calcium release activated calcium (CRAC) channel activity with a compound of Formula (I), (II), (III), or (IV) inhibits the electrophysiological current ($I_{CRAC}$) directly associated with activated CRAC channels.

In yet a further embodiment is a method of modulating calcium release activated calcium channel (CRAC) activity in a mammal comprising administering a compound of Formula (I), (II), (III) or (IV), or a pharmaceutically acceptable salt, pharmaceutically acceptable solvate, or pharmaceutically acceptable prodrug thereof wherein the compound of Formula (I), (II), (III), or (IV) inhibits SOCE with an $IC_{50}$ below 10 μM.

In another embodiment is a method of modulating calcium release activated calcium channel (CRAC) activity in a mammal comprising administering a compound of Formula (I), (II), (III) or (IV), or a pharmaceutically acceptable salt, pharmaceutically acceptable solvate, or pharmaceutically acceptable prodrug thereof wherein the compound of Formula (I), (II), (III), or (IV) inhibits electrophysiological current ($I_{CRAC}$) directly associated with activated CRAC channels at a concentration below 10 μM.

In one aspect is a method of treating a disease, disorder or condition in a mammal that would benefit from inhibition of store-operated calcium channel activity comprising administering to the mammal a compound of Formula (I), (II), (III) or (IV), or a pharmaceutically acceptable salt, pharmaceutically acceptable solvate, or pharmaceutically acceptable prodrug thereof.

In one embodiment is a method of treating a disease, disorder or condition in a mammal that would benefit from inhibition of store-operated calcium channel activity comprising administering to the mammal a compound of Formula (I), (II), (III) or (IV), or a pharmaceutically acceptable salt, pharmaceutically acceptable solvate, or pharmaceutically acceptable prodrug thereof wherein the compound of v modulates the activity of, modulates an interaction of, or binds to, or interacts with a mammalian STIM1 protein, or a mammalian STIM2 protein.

In yet another embodiment is a method of treating a disease, disorder or condition in a mammal that would benefit from inhibition of store-operated calcium channel activity comprising administering to the mammal a compound of Formula (I), (II), (III) or (IV), or a pharmaceutically acceptable salt, pharmaceutically acceptable solvate, or pharmaceutically acceptable prodrug thereof wherein the disease, disorder or condition is rheumatoid arthritis.

In a further embodiment is a method of treating a disease, disorder or condition in a mammal that would benefit from inhibition of store-operated calcium channel activity comprising administering to the mammal a compound of Formula (I), (II), (III) or (IV), or a pharmaceutically acceptable salt, pharmaceutically acceptable solvate, or pharmaceutically acceptable prodrug thereof wherein the disease, disorder or condition is psoriasis.

In one embodiment is a method of treating a disease, disorder or condition in a mammal that would benefit from inhibition of store-operated calcium channel activity comprising administering to the mammal a compound of Formula (I), (II), (III) or (IV), or a pharmaceutically acceptable salt, pharmaceutically acceptable solvate, or pharmaceutically acceptable prodrug thereof wherein the disease, disorder or condition is inflammatory bowel disease.

In a further embodiment the inflammatory bowel disease is ulcerative colitis.

In a further embodiment is a method of treating a disease, disorder or condition in a mammal that would benefit from inhibition of store-operated calcium channel activity comprising administering to the mammal a compound of Formula (I), (II), (III) or (IV), or a pharmaceutically acceptable salt, pharmaceutically acceptable solvate, or pharmaceutically acceptable prodrug thereof wherein the disease, disorder or condition is organ transplant rejection.

In a further embodiment is a method of treating a disease, disorder or condition in a mammal that would benefit from inhibition of store-operated calcium channel activity comprising administering to the mammal a compound of Formula (I), (II), (III) or (IV), or a pharmaceutically acceptable salt, pharmaceutically acceptable solvate, or pharmaceutically acceptable prodrug thereof wherein the disease, disorder or condition is multiple sclerosis.

In yet a further embodiment is a method of treating a disease, disorder or condition in a mammal that would benefit from inhibition of store-operated calcium channel activity comprising administering to the mammal a compound of Formula (I), (II), (III) or (IV), or a pharmaceutically acceptable salt, pharmaceutically acceptable solvate, or pharmaceutically acceptable prodrug thereof further comprising administering to the mammal a second therapeutic agent.

In another embodiment is a method of treating a disease, disorder or condition in a mammal that would benefit from inhibition of store-operated calcium channel activity comprising administering to the mammal a compound of Formula (I), (II), (III) or (IV), or a pharmaceutically acceptable salt, pharmaceutically acceptable solvate, or pharmaceutically acceptable prodrug thereof, wherein the second therapeutic agent is selected from immunosuppressants, glucocorticoids, non-steroidal anti-inflammatory drugs, Cox-2-specific inhibitors, leflunomide, gold thioglucose, gold thiomalate, aurofin, sulfasalazine, hydroxychloroquinine, minocycline, anti-TNF-α agents, abatacept, anakinra, interferon-β, interferon-γ, interleukin-2, allergy vaccines, antihistamines, antileukotrienes, beta-agonists, theophylline, and anticholinergics.

In yet another embodiment is a method of treating a disease, disorder or condition in a mammal that would benefit from inhibition of store-operated calcium channel activity comprising administering to the mammal a compound of Formula (I), (II), (III) or (IV), or a pharmaceutically acceptable salt, pharmaceutically acceptable solvate, or pharmaceutically acceptable prodrug thereof, wherein the second therapeutic agent is selected from tacrolimus, cyclosporin, rapamicin, methotrexate, cyclophosphamide, azathioprine, mercaptopurine, mycophenolate, or FTY720, prednisone, cortisone acetate, prednisolone, methylprednisolone, dexamethasone, betamethasone, triamcinolone, beclometasone, fludrocortisone acetate, deoxycorticosterone acetate, aldosterone, aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, fluorobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, celecoxib, rofecoxib, valdecoxib, parecoxib, etoricoxib, lumiracoxib, CS-502, JTE-522, L-745,337 and NS398, leflunomide, gold thioglucose, gold thiomalate, aurofin, sulfasalazine, hydroxychloroquinine, minocycline, infliximab, etanercept, adalimumab, abatacept, anakinra, interferon-β, interferon-γ, interleukin-2, allergy vaccines, antihistamines, antileukotrienes, beta-agonists, theophylline, and anticholinergics.

Also described herein is a method of inhibiting store-operated calcium entry (SOCE) activation of nuclear factor of activated T cells (NFAT) in a mammal comprising administering a compound of Formula (I), (II), (III), or (IV) or a pharmaceutically acceptable salt, pharmaceutically acceptable solvate, or pharmaceutically acceptable prodrug thereof.

In one embodiment is a method of inhibiting store-operated calcium entry (SOCE) activation of nuclear factor of activated T cells (NFAT) in a mammal comprising administering a compound of Formula (I), (II), (III) or (IV), or a pharmaceutically acceptable salt, pharmaceutically acceptable solvate, or pharmaceutically acceptable prodrug thereof, wherein the compound of Formula (I), (II), (III), or (IV) modulates an interaction of, or modulates the level of, or binds to, or interacts with a mammalian STIM1 protein, or a mammalian STIM2 protein.

In another aspect is a method of decreasing cytokine expression by inhibiting the store-operated calcium entry activation of NFAT in a mammal comprising administering a compound of Formula (I), (II), (III) or (IV), or a pharmaceutically acceptable salt, pharmaceutically acceptable solvate, or pharmaceutically acceptable prodrug thereof.

In another embodiment is a method of decreasing cytokine expression by inhibiting the store-operated calcium entry activation of NFAT in a mammal comprising administering a compound of Formula (I), (II), (III) or (IV), or a pharmaceutically acceptable salt, pharmaceutically acceptable solvate, or pharmaceutically acceptable prodrug thereof wherein the compound of Formula (I), (II), (III), or (IV) modulates an interaction of, or modulates the level of, or binds to, or interacts with a mammalian STIM1 protein or a mammalian STIM2 protein.

In yet another embodiment is a method of decreasing cytokine expression by inhibiting the store-operated calcium entry activation of NFAT in a mammal comprising administering a compound of Formula (I), (II), (III) or (IV), or a pharmaceutically acceptable salt, pharmaceutically acceptable solvate, or pharmaceutically acceptable prodrug thereof wherein the cytokine is selected from IL-2, IL-3, IL-4, IL-5, IL-6, IL-7, IL-8, IL-9, IL-10, IL-11, IL-12, IL-13, IL-15, IL-16, IL-17, IL-18, IL-1α, IL-1β, IL-1 RA, granulocyte colony stimulating factor (G-CSF), granulocyte-macrophage colony stimulating factor (GM-CSF), oncostatin M, erythropoietin, leukemia inhibitory factor (LIF), interferons, gamma-interferon (γ-IFN), B7.1 (CD80), B7.2 (B70, CD86), TNF-α, TNF-β, LT-β, CD40 ligand, Fas ligand, CD27 ligand, CD30 ligand, 4-1BBL, Trail, and migration inhibitory factor (MIF).

Further Forms of Compounds

The compounds described herein may in some cases exist as diastereomers, enantiomers, or other stereoisomeric forms. The compounds presented herein include all diastereomeric, enantiomeric, and epimeric forms as well as the appropriate mixtures thereof. Separation of stereoisomers may be performed by chromatography or by the forming diastereomeric and separation by recrystallization, or chromatography, or any combination thereof. (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

In some situations, compounds may exist as tautomers. All tautomers are included within the formulas described herein.

The methods and compositions described herein include the use of amorphous forms as well as crystalline forms (also known as polymorphs). The compounds described herein may be in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In some embodiments, compounds described herein may be prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. In some embodiments, by virtue of knowledge of pharmacodynamic processes and drug metabolism in vivo, once a pharmaceutically active compound is determined, prodrugs of the compound are designed. (see, for example, Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Saulnier et al., (1994), *Bioorganic and Medicinal Chemistry Letters*, Vol. 4, p. 1985; Rooseboom et al., *Pharmacological Reviews*, 56:53-102, 2004; Miller et al., *J. Med. Chem. Vol.* 46, no. 24, 5097-5116, 2003; Aesop Cho, "Recent Advances in Oral Prodrug Discovery", *Annual Reports in Medicinal Chemistry*, Vol. 41, 395-407, 2006).

Prodrug forms of the herein described compounds, wherein the prodrug is metabolized in vivo to produce a compound having the structure of Formula (I), (II), (III), or (IV) as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. Prodrugs may be designed as reversible drug derivatives, for use as modifiers to enhance drug transport to site-specific tissues. In some embodiments, the design of a prodrug increases the effective water solubility. See, e.g., Fedorak et al., *Am. J. Physiol.*, 269:G210-218 (1995); McLoed et al., *Gastroenterol*, 106:405-413 (1994); Hochhaus et al., *Biomed. Chrom.*, 6:283-286 (1992); J. Larsen and H. Bundgaard, *Int. J. Pharmaceutics*, 37, 87 (1987); J. Larsen et al., *Int. J. Pharmaceutics*, 47, 103 (1988); Sinkula et al., *J. Pharm. Sci.*, 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design*, American Pharmaceutical Association and Pergamon Press, 1987, all incorporated herein for such disclosure).

Sites on the aromatic ring portion of compounds described herein can be susceptible to various metabolic reactions, therefore incorporation of appropriate substituents on the aromatic ring structures, such as, by way of example only, halogens can reduce, minimize or eliminate this metabolic pathway.

The compounds described herein may be labeled isotopically (e.g. with a radioisotope) or by other means, including, but not limited to, the use of chromophores or fluorescent moieties, bioluminescent labels, photoactivatable or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^2$H, $^3$H, $^{13}$C, $^{14}$C, $^{15}$N, $^{18}$O, $^{17}$O, $^{35}$S, $^{18}$F, $^{36}$Cl, respectively. Certain isotopically-labeled compounds described herein, for example those into which radioactive isotopes such as $^3$H and $^{14}$C are incorporated, are useful in drug and/or substrate tissue distribution assays. Further, substitution with isotopes such as deuterium, i.e., $^2$H, can afford certain therapeutic advantages resulting from greater metabolic stability, such as, for example, increased in vivo half-life or reduced dosage requirements.

In additional or further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

In some embodiments, compounds described herein, such as compounds of Formula (I), (II), (III) or (IV), are in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, melting points, density, hardness, crystal shape, optical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UV-VIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Throughout the specification, groups and substituents thereof can be chosen to provide stable moieties and compounds.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999) (all of which are incorporated by reference for such disclosure). General methods for the preparation of compound as disclosed herein may be derived from reactions and the reactions may be modified by the use of appropriate reagents and conditions, for the introduction of the various moieties found in the formulae as provided herein. As a guide the following synthetic methods may be utilized.

Formation of Covalent Linkages by Reaction of an Electrophile with a Nucleophile The compounds described herein can be modified using various electrophiles and/or nucleophiles to form new functional groups or substituents. Table 1 entitled "Examples of Covalent Linkages and Precursors Thereof" lists selected non-limiting examples of covalent linkages and precursor functional groups which yield the covalent linkages. Table 1 may be used as guidance toward the variety of electrophiles and nucleophiles combinations available that provide covalent linkages. Precursor functional groups are shown as electrophilic groups and nucleophilic groups.

TABLE 1

Examples of Covalent Linkages and Precursors Thereof

| Covalent Linkage Product | Electrophile | Nucleophile |
|---|---|---|
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ureas | Isocyanates | amines/anilines |
| Urethanes | Isocyanates | alcohols/phenols |

TABLE 1-continued

Examples of Covalent Linkages and Precursors Thereof

| Covalent Linkage Product | Electrophile | Nucleophile |
|---|---|---|
| Thioureas | isothiocyanates | amines/anilines |
| Thioethers | Maleimides | Thiols |
| Alkyl amines | sulfonate esters | amines/anilines |
| Thioethers | sulfonate esters | Thiols |
| Sulfonamides | sulfonyl halides | amines/anilines |
| Sulfonate esters | sulfonyl halides | phenols/alcohols |

Use of Protecting Groups

In the reactions described, it may be necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. It is preferred that each protective group be removable by a different means. Protective groups that are cleaved under totally disparate reaction conditions fulfill the requirement of differential removal.

Protective groups can be removed by acid, base, reducing conditions (such as, for example, hydrogenolysis), and/or oxidative conditions. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, which include conversion to alkyl esters, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and can be subsequently removed by metal or pi-acid catalysts. For example, an allyl-blocked carboxylic acid can be deprotected with a Pd$^0$-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

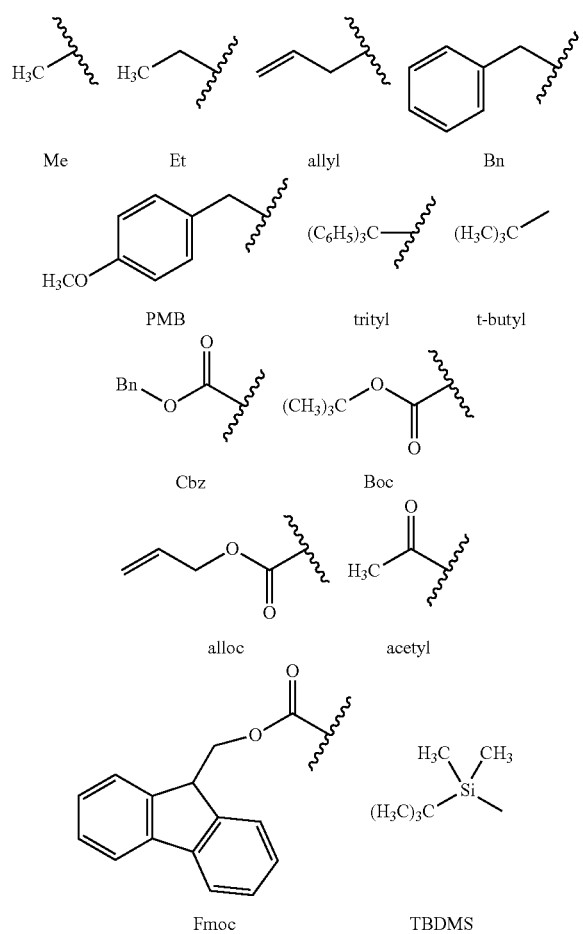

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

Certain Terminology

Unless defined otherwise, all technical and scientific terms used herein have the same meaning as is commonly understood to which the claimed subject matter belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

As used herein, $C_1$-$C_x$ includes $C_1$-$C_2$, $C_1$-$C_3$ ... $C_1$-$C_x$. $C_1$-$C_x$ refers to the number of carbon atoms that make up the moiety to which it designates (excluding optional substituents).

An "alkyl" group refers to an aliphatic hydrocarbon group. The alkyl groups may or may not include units of unsaturation. The alkyl moiety may be a "saturated alkyl" group, which means that it does not contain any units of unsaturation (i.e. a carbon-carbon double bond or a carbon-carbon triple bond). The alkyl group may also be an "unsaturated alkyl" moiety, which means that it contains at least one unit of unsaturation. The alkyl moiety, whether saturated or unsaturated, may be branched, straight chain, or cyclic.

The "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). The alkyl group of the compounds described herein may be designated as "$C_1$-$C_6$ alkyl" or similar designations. By way of example only, "$C_1$-$C_6$ alkyl" indicates that there are one to six carbon atoms in the alkyl chain, i.e., the alkyl chain is selected from the group consisting of methyl, ethyl, n-propyl, iso-propyl, n-butyl, iso-butyl, sec-butyl, t-butyl, n-pentyl, iso-pentyl, neo-pentyl, hexyl, propen-3-yl (allyl), cyclopropylmethyl, cyclobutylmethyl, cyclopentylmethyl, cyclohexylmethyl. Alkyl groups can be substituted or unsubstituted. Depending on the structure, an alkyl group can be a monoradical or a diradical (i.e., an alkylene group).

An "alkoxy" refers to a "—O-alkyl" group, where alkyl is as defined herein.

The term "alkenyl" refers to a type of alkyl group in which the first two atoms of the alkyl group form a double bond that is not part of an aromatic group. That is, an alkenyl group begins with the atoms —C(R)=CR$_2$, wherein R refers to the remaining portions of the alkenyl group, which may be the same or different. Non-limiting examples of an alkenyl group include —CH=CH$_2$, —C(CH$_3$)=CH$_2$, —CH=CHCH$_3$, —CH=C(CH$_3$)$_2$ and —C(CH$_3$)=CHCH$_3$. The alkenyl moiety may be branched, straight chain, or cyclic (in which case, it would also be known as a "cycloalkenyl" group). Alkenyl groups may have 2 to 6 carbons. Alkenyl groups can be substituted or unsubstituted. Depending on the structure, an alkenyl group can be a monoradical or a diradical (i.e., an alkenylene group).

The term "alkynyl" refers to a type of alkyl group in which the first two atoms of the alkyl group form a triple bond. That is, an alkynyl group begins with the atoms —C≡C—R, wherein R refers to the remaining portions of the alkynyl group. Non-limiting examples of an alkynyl group include —C≡CH, —C≡CCH$_3$, —C≡CCH$_2$CH$_3$ and —C≡CCH$_2$CH$_2$CH$_3$. The "R" portion of the alkynyl moiety may be branched, straight chain, or cyclic. An alkynyl group can have 2 to 6 carbons. Alkynyl groups can be substituted or unsubstituted. Depending on the structure, an alkynyl group can be a monoradical or a diradical (i.e., an alkynylene group).

"Amino" refers to a —NH$_2$ group.

The term "alkylamine" or "alkylamino" refers to the —N(alkyl)$_x$H$_y$ group, where alkyl is as defined herein and x and y are selected from the group x=1, y=1 and x=2, y=0. When x=2, the alkyl groups, taken together with the nitrogen to which they are attached, can optionally form a cyclic ring system. "Dialkylamino" refers to a —N(alkyl)$_2$ group, where alkyl is as defined herein.

The term "aromatic" refers to a planar ring having a delocalized π-electron system containing 4n+2 π electrons, where n is an integer. Aromatic rings can be formed from five, six, seven, eight, nine, or more than nine atoms. Aromatics can be optionally substituted. The term "aromatic" includes both aryl groups (e.g., phenyl, naphthalenyl) and heteroaryl groups (e.g., pyridinyl, quinolinyl).

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, and naphthalenyl. Depending on the structure, an aryl group can be a monoradical or a diradical (i.e., an arylene group).

"Carboxy" refers to —CO$_2$H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

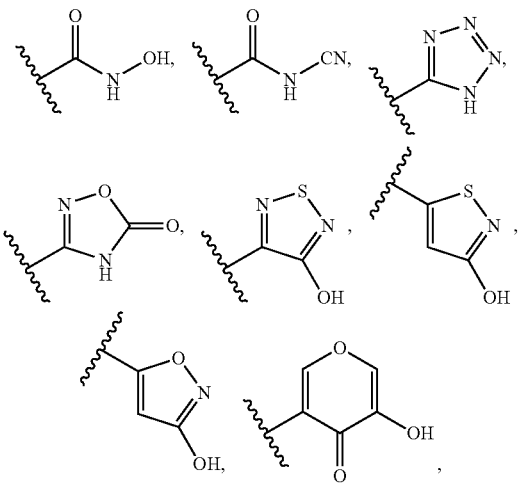

and the like.

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. Illustrative examples of cycloalkyl groups include, but are not limited to, the following moieties:

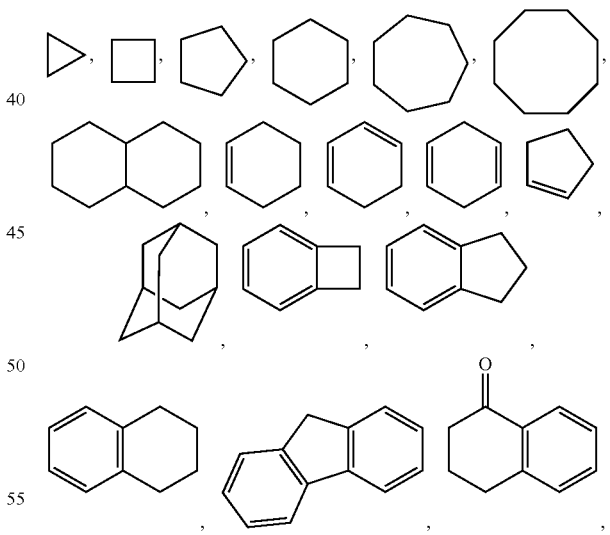

and the like.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. Polycyclic heteroaryl groups may be fused or non-fused. Illustrative examples of heteroaryl groups include the following moieties:

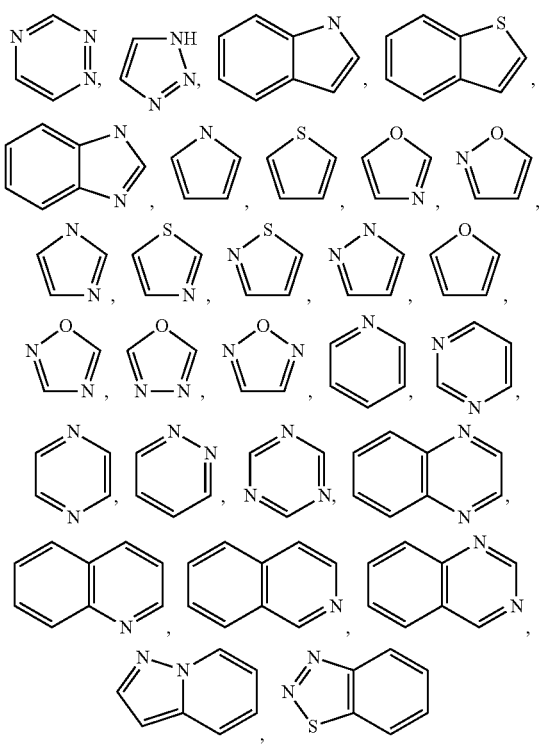

and the like.

A "heterocycloalkyl" group or "heteroalicyclic" group refers to a cycloalkyl group, wherein at least one skeletal ring atom is a heteroatom selected from nitrogen, oxygen and sulfur. The radicals may be fused with an aryl or heteroaryl. Illustrative examples of heterocycloalkyl groups, also referred to as non-aromatic heterocycles, include:

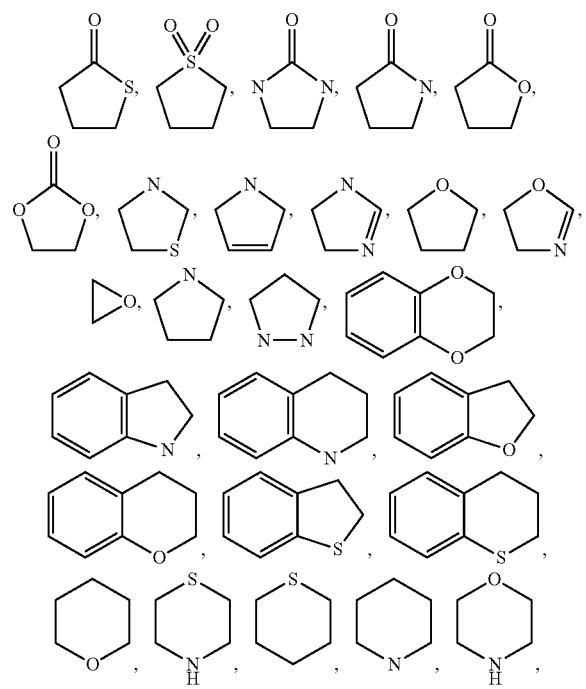

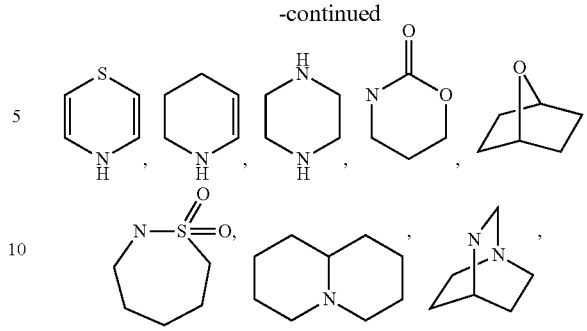

and the like. The term heteroalicyclic also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring).

The term "halo" or, alternatively, "halogen" means fluoro, chloro, bromo and iodo.

The term "haloalkyl" refers to an alkyl group that is substituted with one or more halogens. The halogens may the same or they may be different. Non-limiting examples of haloalkyls include —$CH_2Cl$, —$CF_3$, —$CHF_2$, —$CH_2CF_3$, —$CF_2CF_3$, —$CF(CH_3)_3$, and the like.

The terms "fluoroalkyl" and "fluoroalkoxy" include alkyl and alkoxy groups, respectively, that are substituted with one or more fluorine atoms. Non-limiting examples of fluoroalkyls include —$CF_3$, —$CHF_2$, —$CH_2F$, —$CH_2CF_3$, —$CF_2CF_3$, —$CF_2CF_2CF_3$, —$CF(CH_3)_3$, and the like. Non-limiting examples of fluoroalkoxy groups, include —$OCF_3$, —$OCHF_2$, —$OCH_2F$, —$OCH_2CF_3$, —$OCF_2CF_3$, —$OCF_2CF_2CF_3$, —$OCF(CH_3)_2$, and the like.

The term "heteroalkyl" refers to an alkyl radical where one or more skeletal chain atoms is selected from an atom other than carbon, e.g., oxygen, nitrogen, sulfur, phosphorus, silicon, or combinations thereof. The heteroatom(s) may be placed at any interior position of the heteroalkyl group. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —$CH_2$—NH—$OCH_3$, —$CH_2$—O—Si($CH_3$)$_3$, —$CH_2$—CH=N—$OCH_3$, and —CH=CH—N($CH_3$)—$CH_3$. In addition, up to two heteroatoms may be consecutive, such as, by way of example, —$CH_2$—NH—$OCH_3$ and —$CH_2$—O—Si($CH_3$)$_3$. Excluding the number of heteroatoms, a "heteroalkyl" may have from 1 to 6 carbon atoms.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

As used herein, the substituent "R" appearing by itself and without a number designation refers to a substituent selected from among from alkyl, haloalkyl, heteroalkyl, alkenyl, cycloalkyl, aryl, heteroaryl (bonded through a ring carbon), and heterocycloalkyl.

The term "optionally substituted" or "substituted" means that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halo, acyl, acyloxy, —$CO_2H$, —$CO_2$-alkyl, nitro, haloalkyl, fluoroalkyl, and amino, including mono- and di-substituted amino groups (e.g. —$NH_2$, —NHR, —$N(R)_2$), and the protected derivatives thereof. By way of example, an optional substituents may be $L^sR^s$, wherein each $L^s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, —($C_1$-$C_6$alkyl)-, or —($C_2$-$C_6$alkenyl)-; and each $R^s$ is independently selected from among H, ($C_1$-$C_6$alkyl), ($C_3$-$C_8$cycloalkyl), aryl, heteroaryl, heterocycloalkyl, and $C_1$-$C_6$heteroalkyl. The protecting groups that may form the protective derivatives of the above substituents are found in sources such as Greene and Wuts, above.

The methods and formulations described herein include the use of crystalline forms (also known as polymorphs), or a pharmaceutically acceptable salts of compounds having the structure of Formula (I), (II), (III) or (IV), as well as active metabolites of these compounds having the same type of activity. In some situations, compounds may exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

The terms "kit" and "article of manufacture" are used as synonyms.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," as used herein, include alleviating, abating or ameliorating a disease or condition symptoms, preventing additional symptoms, ameliorating or preventing the underlying causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

As used herein, the term "target protein" refers to a protein or a portion of a protein capable of being bound by, or interacting with a compound described herein, such as a compound of Formula (I), (II), or (III). In certain embodiments, a target protein is a STIM protein. In certain embodiments, a target protein is an Orai protein.

As used herein, "STIM protein" includes but is not limited to, mammalian STIM-1, such as human and rodent (e.g., mouse) STIM-1, *Drosophila melanogaster* D-STIM, *C. elegans* C-STIM, *Anopheles gambiae* STIM and mammalian STIM-2, such as human and rodent (e.g., mouse) STIM-2. (see paragraphs [0211] through [0270] of US 2007/0031814, as well as Table 3 of US 2007/0031814, herein incorporated by reference) As described herein, such proteins have been identified as being involved in, participating in and/or providing for store-operated calcium entry or modulation thereof, cytoplasmic calcium buffering and/or modulation of calcium levels in or movement of calcium into, within or out of intracellular calcium stores (e.g., endoplasmic reticulum).

As used herein, an "Orai protein" includes Orai1 (SEQ ID NO: 1 as described in WO 07/081,804), Orai2 (SEQ ID NO: 2 as described in WO 07/081,804), or Orai3 (SEQ ID NO: 3 as described in WO 07/081,804). Orai1 nucleic acid sequence corresponds to GenBank accession number NM_032790, Orai2 nucleic acid sequence corresponds to GenBank accession number BC069270 and Orai3 nucleic acid sequence corresponds to GenBank accession number NM_152288. As used herein, Orai refers to any one of the Orai genes, e.g., Orai1, Orai2, Orai3 (see Table I of WO 07/081,804). As described herein, such proteins have been identified as being involved in, participating in and/or providing for store-operated calcium entry or modulation thereof, cytoplasmic calcium buffering and/or modulation of calcium levels in or movement of calcium into, within or out of intracellular calcium stores (e.g., endoplasmic reticulum).

The term "fragment" or "derivative" when referring to a protein (e.g. STIM, Orai) means proteins or polypeptides which retain essentially the same biological function or activity in at least one assay as the native protein(s). For example, the fragments or derivatives of the referenced protein maintains at least about 50% of the activity of the native proteins, at least 75%, at least about 95% of the activity of the native proteins, as determined e.g. by a calcium influx assay.

As used herein, amelioration of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

The term "modulate," as used herein, means to interact with a target protein either directly or indirectly so as to alter the activity of the target protein, including, by way of example only, to inhibit the activity of the target, or to limit or reduce the activity of the target.

As used herein, the term "modulator" refers to a compound that alters an activity of a target. For example, a modulator can cause an increase or decrease in the magnitude of a certain activity of a target compared to the magnitude of the activity in the absence of the modulator. In certain embodiments, a modulator is an inhibitor, which decreases the magnitude of one or more activities of a target. In certain embodiments, an inhibitor completely prevents one or more activities of a target.

As used herein, "modulation" with reference to intracellular calcium refers to any alteration or adjustment in intracellular calcium including but not limited to alteration of calcium concentration in the cytoplasm and/or intracellular calcium storage organelles, e.g., endoplasmic reticulum, and alteration of the kinetics of calcium fluxes into, out of and within cells. In aspect, modulation refers to reduction.

As used herein, the term "target activity" refers to a biological activity capable of being modulated by a modulator.

Certain exemplary target activities include, but are not limited to, binding affinity, signal transduction, enzymatic activity, tumor growth, inflammation or inflammation-related processes, and amelioration of one or more symptoms associated with a disease or condition.

The terms "inhibits", "inhibiting", or "inhibitor" of SOC channel activity or CRAC channel activity, as used herein, refer to inhibition of store-operated calcium channel activity or calcium release activated calcium channel activity.

The term "acceptable" with respect to a formulation, composition or ingredient, as used herein, means having no persistent detrimental effect on the general health of the subject being treated.

By "pharmaceutically acceptable," as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutical combination" as used herein, means a product that results from the mixing or combining of more than one active ingredient and includes both fixed and non-fixed combinations of the active ingredients. The term "fixed combination" means that one active ingredient, e.g. a compound of Formula (I), (II), (III) or (IV), and a co-agent, are both administered to a patient simultaneously in the form of a single entity or dosage. The term "non-fixed combination" means that one active ingredient, e.g. a compound of Formula (I), (II), (III) or (IV), and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of a compound of Formula (I), (II), (III), or (IV) described herein with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition that includes a compound of Formula (I), (II), (III), or (IV) described herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "co-administration" or the like, as used herein, are meant to encompass administration of the selected therapeutic agents to a single patient, and are intended to include treatment regimens in which the agents are administered by the same or different route of administration or at the same or different time.

The term "carrier," as used herein, refers to relatively non-toxic chemical compounds or agents that facilitate the incorporation of a compound into cells or tissues.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds.

"Bioavailability" refers to the percentage of the weight of the compound disclosed herein (e.g. compound of Formula (I), (II), or (III)), that is delivered into the general circulation of the animal or human being studied. The total exposure (AUC(0-∞)) of a drug when administered intravenously is usually defined as 100% bioavailable (F %). "Oral bioavailability" refers to the extent to which a compound disclosed herein, is absorbed into the general circulation when the pharmaceutical composition is taken orally as compared to intravenous injection.

"Blood plasma concentration" refers to the concentration of a compound of Formula (I), (II), (III), or (IV) disclosed herein, in the plasma component of blood of a subject. It is understood that the plasma concentration of compounds described herein may vary significantly between subjects, due to variability with respect to metabolism and/or possible interactions with other therapeutic agents. In accordance with one embodiment disclosed herein, the blood plasma concentration of the compounds disclosed herein may vary from subject to subject. Likewise, values such as maximum plasma concentration (Cmax) or time to reach maximum plasma concentration (Tmax), or total area under the plasma concentration time curve (AUC(0-∞)) may vary from subject to subject. Due to this variability, the amount necessary to constitute "a therapeutically effective amount" of a compound may vary from subject to subject.

As used herein, "calcium homeostasis" refers to the maintenance of an overall balance in intracellular calcium levels and movements, including calcium signaling, within a cell.

As used herein, "intracellular calcium" refers to calcium located in a cell without specification of a particular cellular location. In contrast, "cytosolic" or "cytoplasmic" with reference to calcium refers to calcium located in the cell cytoplasm.

As used herein, an effect on intracellular calcium is any alteration of any aspect of intracellular calcium, including but not limited to, an alteration in intracellular calcium levels and location and movement of calcium into, out of or within a cell or intracellular calcium store or organelle. For example, an effect on intracellular calcium can be an alteration of the properties, such as, for example, the kinetics, sensitivities, rate, amplitude, and electrophysiological characteristics, of calcium flux or movement that occurs in a cell or portion thereof. An effect on intracellular calcium can be an alteration in any intracellular calcium-modulating process, including, store-operated calcium entry, cytosolic calcium buffering, and calcium levels in or movement of calcium into, out of or within an intracellular calcium store. Any of these aspects can be assessed in a variety of ways including, but not limited to, evaluation of calcium or other ion (particularly cation) levels, movement of calcium or other ion (particularly cation), fluctuations in calcium or other ion (particularly cation) levels, kinetics of calcium or other ion (particularly cation) fluxes and/or transport of calcium or other ion (particularly cation) through a membrane. An alteration can be any such change that is statistically significant. Thus, for example if intracellular calcium in a test cell and a control cell is said to differ, such difference can be a statistically significant difference.

As used herein, "involved in" with respect to the relationship between a protein and an aspect of intracellular calcium or intracellular calcium regulation means that when expression or activity of the protein in a cell is reduced, altered or eliminated, there is a concomitant or associated reduction, alteration or elimination of one or more aspects of intracellular calcium or intracellular calcium regulation. Such an alteration or reduction in expression or activity can occur by virtue of an alteration of expression of a gene encoding the protein or by altering the levels of the protein. A protein involved in an aspect of intracellular calcium, such as, for example, store-operated calcium entry, thus, can be one that provides for or participates in an aspect of intracellular calcium or intracellular calcium regulation. For example, a protein that provides for store-operated calcium entry can be a STIM protein and/or an Orai protein.

As used herein, a protein that is a component of a calcium channel is a protein that participates in multi-protein complex that forms the channel.

As used herein, "basal" or "resting" with reference to cytosolic calcium levels refers to the concentration of calcium in the cytoplasm of a cell, such as, for example, an unstimulated cell, that has not been subjected to a condition that results in movement of calcium into or out of the cell or within the cell. The basal or resting cytosolic calcium level can be the concentration of free calcium (i.e., calcium that is not bound to a cellular calcium-binding substance) in the cytoplasm of a cell, such as, for example, an unstimulated cell, that has not been subjected to a condition that results in movement of calcium into or out of the cell.

As used herein, "movement" with respect to ions, including cations, e.g., calcium, refers to movement or relocation, such as for example flux, of ions into, out of, or within a cell. Thus, movement of ions can be, for example, movement of ions from the extracellular medium into a cell, from within a cell to the extracellular medium, from within an intracellular organelle or storage site to the cytosol, from the cytosol into an intracellular organelle or storage site, from one intracellular organelle or storage site to another intracellular organelle or storage site, from the extracellular medium into an intracellular organelle or storage site, from an intracellular organelle or storage site to the extracellular medium and from one location to another within the cell cytoplasm.

As used herein, "cation entry" or "calcium entry" into a cell refers to entry of cations, such as calcium, into an intracellular location, such as the cytoplasm of a cell or into the lumen of an intracellular organelle or storage site. Thus, cation entry can be, for example, the movement of cations into the cell cytoplasm from the extracellular medium or from an intracellular organelle or storage site, or the movement of cations into an intracellular organelle or storage site from the cytoplasm or extracellular medium. Movement of calcium into the cytoplasm from an intracellular organelle or storage site is also referred to as "calcium release" from the organelle or storage site.

As used herein, "protein that modulates intracellular calcium" refers to any cellular protein that is involved in regulating, controlling and/or altering intracellular calcium. For example, such a protein can be involved in altering or adjusting intracellular calcium in a number of ways, including, but not limited to, through the maintenance of resting or basal cytoplasmic calcium levels, or through involvement in a cellular response to a signal that is transmitted in a cell through a mechanism that includes a deviation in intracellular calcium from resting or basal states. In the context of a "protein that modulates intracellular calcium," a "cellular" protein is one that is associated with a cell, such as, for example, a cytoplasmic protein, a plasma membrane-associated protein or an intracellular membrane protein. Proteins that modulate intracellular calcium include, but are not limited to, ion transport proteins, calcium-binding proteins and regulatory proteins that regulate ion transport proteins.

As used herein, "amelioration" refers to an improvement in a disease or condition or at least a partial relief of symptoms associated with a disease or condition.

As used herein, "cell response" refers to any cellular response that results from ion movement into or out of a cell or within a cell. The cell response may be associated with any cellular activity that is dependent, at least in part, on ions such as, for example, calcium. Such activities may include, for example, cellular activation, gene expression, endocytosis, exocytosis, cellular trafficking and apoptotic cell death.

As used herein, "immune cells" include cells of the immune system and cells that perform a function or activity in an immune response, such as, but not limited to, T-cells, B-cells, lymphocytes, macrophages, dendritic cells, neutrophils, eosinophils, basophils, mast cells, plasma cells, white blood cells, antigen presenting cells and natural killer cells.

As used herein, "cytokine" refers to small soluble proteins secreted by cells that can alter the behavior or properties of the secreting cell or another cell. Cytokines bind to cytokine receptors and trigger a behavior or property within the cell, for example, cell proliferation, death or differentiation. Exemplary cytokines include, but are not limited to, interleukins (e.g., IL-2, IL-3, IL-4, IL-5, IL-6, IL-7, IL-8, IL-9, IL-10, IL-11, IL-12, IL-13, IL-15, IL-16, IL-17, IL-18, IL-1α, IL-1β, and IL-1 RA), granulocyte colony stimulating factor (G-CSF), granulocyte-macrophage colony stimulating factor (GM-CSF), oncostatin M, erythropoietin, leukemia inhibitory factor (LIF), interferons, B7.1 (also known as CD80), B7.2 (also known as B70, CD86), TNF family members (TNF-α, TNF-β, LT-β, CD40 ligand, Fas ligand, CD27 ligand, CD30 ligand, 4-1BBL, Trail), and MIF.

"Store-operated calcium entry" or "SOCE" refers to the mechanism by which release of calcium ions from intracellular stores is coordinated with ion influx across the plasma membrane.

"Selective inhibitor of SOC channel activity" means that the inhibitor is selective for SOC channels and does not substantially affect the activity of other types of ion channels.

"Selective inhibitor of CRAC channel activity" means that the inhibitor is selective for CRAC channels and does not substantially affect the activity of other types of ion channels and/or other SOC channels.

Monitoring or Assessing Effects on Intracellular Calcium

In monitoring or assessing the effect of a compound of Formula (I), (II), (III), or (IV) on intracellular calcium in any of the screening/identification methods described herein or recognized in the field, a direct or indirect evaluation or measurement of cellular (including cytosolic and intracellular organelle or compartment) calcium and/or movement of ions into, within or out of a cell, organelle, calcium store or portions thereof (e.g., a membrane) can be conducted. A variety of methods are described herein and/or recognized in the field for evaluating calcium levels and ion movements or flux. The particular method used and the conditions employed can depend on whether a particular aspect of intracellular calcium is being monitored or assessed. For example, as described herein in some embodiments, reagents and conditions are used, for specifically evaluating store-operated calcium entry, resting cytosolic calcium levels, calcium buffering and calcium levels and uptake by or release from intracellular organelles and calcium stores. The effect of a compound of Formula (I), (II), (III), or (IV) on intracellular calcium can be monitored or assessed using, for example, a cell, an intracellular organelle or calcium storage compartment, a membrane (including, e.g., a detached membrane patch or a lipid bilayer) or a cell-free assay system (e.g., outside-out membrane vesicle). Generally, some aspect of intracellular calcium is monitored or assessed in the presence of test agent and compared to a control, e.g., intracellular calcium in the absence of test agent.

Methods of Modulating Intracellular Calcium

Modulation of intracellular calcium can be any alteration or adjustment in intracellular calcium including but not limited to alteration of calcium concentration or level in the cytoplasm and/or intracellular calcium storage organelles, e.g., endoplasmic reticulum, alteration in the movement of calcium into, out of and within a cell or intracellular calcium store or organelle, alteration in the location of calcium within a cell, and alteration of the kinetics, or other properties, of calcium fluxes into, out of and within cells. In particular embodiments, intracellular calcium modulation can involve alteration or adjustment, e.g. reduction or inhibition, of store-operated calcium entry, cytosolic calcium buffering, calcium levels in or movement of calcium into, out of or within an intracellular calcium store or organelle, and/or basal or resting cytosolic calcium levels. In some embodiments, modulation of intracellular calcium can involve an alteration or adjustment in receptor-mediated ion (e.g., calcium) movement, second messenger-operated ion (e.g., calcium) movement, calcium influx into or efflux out of a cell, and/or ion (e.g., calcium) uptake into or release from intracellular compartments, including, for example, endosomes and lysosomes.

In one aspect, compounds described herein modulate intracellular calcium, such as but not limited to, modulation (e.g. reduction or inhibition) of SOC channel activity, such as inhibition of CRAC channel activity (e.g. inhibition of $I_{CRAC}$, inhibition of SOCE) in an immune system cell (e.g., a lymphocyte, white blood cell, T cell, B cell), a fibroblast (or a cell derived from a fibroblast), or an epidermal, dermal or skin cell (e.g., a keratinocyte). The step of modulating one or more proteins involved in modulating intracellular calcium (e.g. a STIM protein and/or Orai protein) can involve, for example, reducing the level, expression of, an activity of, function of and/or molecular interactions of a protein. For instance, if a cell exhibits an increase in calcium levels or lack of regulation of an aspect of intracellular calcium modulation, e.g., store-operated calcium entry, then modulating may involve reducing the level of, expression of, an activity or function of, or a molecular interaction of a protein, e.g. a STIM protein and/or Orai protein.

Examples of Pharmaceutical Compositions and Methods of Administration

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Additional details about suitable excipients for pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound of Formula (I), (II), (III), or (IV) described herein, with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds of Formula (I), (II), (III), or (IV) can be used singly or in combination with one or more therapeutic agents as components of mixtures (as in combination therapy).

The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. Moreover, the pharmaceutical compositions described herein, which include a compound of Formula (I), (II), (III), or (IV) described herein, can be formulated into any suitable dosage form, including but not limited to, aqueous oral dispersions, liquids, gels, syrups, elixirs, slurries, suspensions, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

One may administer the compounds and/or compositions in a local rather than systemic manner, for example, via injection of the compound directly into an organ or tissue, often in a depot preparation or sustained release formulation. Such long acting formulations may be administered by implantation (for example subcutaneously or intramuscularly) or by intramuscular injection. Furthermore, one may administer the drug in a targeted drug delivery system, for example, in a liposome coated with organ-specific antibody. The liposomes will be targeted to and taken up selectively by the organ. In addition, the drug may be provided in the form of a rapid release formulation, in the form of an extended release formulation, or in the form of an intermediate release formulation.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formula (I), (II), (III), or (IV) described herein, as an active ingredient in free-acid or free-base form, or in a pharmaceutically acceptable salt form. In addition, the methods and pharmaceutical compositions described herein include the use of crystalline forms (also known as polymorphs), as well as active metabolites of these compounds having the same type of activity. In some situations, compounds may exist as tautomers. All tautomers are included within the scope of the compounds presented herein. Additionally, the compounds described herein can exist in unsolvated as well as solvated forms with pharmaceutically acceptable solvents such as water, ethanol, and the like. The solvated forms of the compounds presented herein are also considered to be disclosed herein.

In certain embodiments, compositions provided herein may also include one or more preservatives to inhibit microbial activity. Suitable preservatives include quaternary ammonium compounds such as benzalkonium chloride, cetyltrimethylammonium bromide and cetylpyridinium chloride.

Pharmaceutical preparations for oral use can be obtained by mixing one or more solid excipient with one or more of the compounds described herein (e.g. compounds of Formula (I), (II), or (III)), optionally grinding the resulting mixture, and processing the mixture of granules, after adding suitable auxiliaries, if desired, to obtain tablets, pills, or capsules. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations of the compounds described herein may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of a compound of Formula (I), (II), (III), or (IV) described herein, with one or more pharmaceutical excipients to form a bulk blend composition. When referring to these bulk blend compositions as homogeneous, it is meant that the particles of the compound of Formula (I), (II), (III), or (IV) described herein, are dispersed evenly throughout the composition so that the composition may be subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

The pharmaceutical solid dosage forms described herein can include a compound of Formula (I), (II), (III), or (IV) described herein, and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in Remington's Pharmaceutical Sciences, 20th Edition (2000), a film coating is provided around the formulation of the compound described herein. In one embodiment, some or all of the particles of the compound described herein are coated. In another embodiment, some or all of the particles of the compound described herein are microencapsulated. In still another embodiment, the particles of the compound described herein are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethylcellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound of Formula (I), (II), (III), or (IV) from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. In some embodiments, formulators determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 5400 to about 7000, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

There is considerable overlap between additives used in the solid dosage forms described herein. Thus, the above-listed additives should be taken as merely exemplary, and not limiting, of the types of additives that can be included in solid dosage forms of the pharmaceutical compositions described herein.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating can provide a delayed release of the compounds of Formula (I), (II), (III), or (IV) described herein from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of the compound of Formula (I), (II), (III), or (IV) described herein and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with compounds described herein, which sufficiently isolate the compound from other non-compatible excipients. Materials compatible with compounds described herein are those that delay the release of the compounds of Formula (I), (II), (III), or (IV) in vivo.

Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG,HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated compounds described herein may be formulated by methods that include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When such salts are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In other embodiments, the formulations described herein, which include a compound described herein, are solid dispersions. Methods of producing such solid dispersions include, but are not limited to, for example, U.S. Pat. Nos. 4,343,789, 5,340,591, 5,456,923, 5,700,485, 5,723,269, and U.S. patent publication no. 2004/0013734. In still other embodiments, the formulations described herein are solid solutions. Solid solutions incorporate a substance together with the active agent and other excipients such that heating the mixture results in dissolution of the drug and the resulting composition is then cooled to provide a solid blend which can be further formulated or directly added to a capsule or compressed into a tablet. Methods of producing such solid solutions include, but are not limited to, for example, U.S. Pat. Nos. 4,151,273, 5,281,420, and 6,083,518.

The pharmaceutical solid oral dosage forms including formulations described herein, which include a compounds described herein, can be further formulated to provide a controlled release of the compound of Formula (I), (II), or (III). Controlled release refers to the release of the compounds described herein from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. Coatings may be made from:

Acrylic polymers. The performance of acrylic polymers (primarily their solubility in biological fluids) can vary based on the degree and type of substitution. Examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine;

Cellulose Derivatives. Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH >6. Aquateric (FMC) is an aqueous based system and is a spray dried CAP pseudolatex with particles <1 μm. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-55S, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions;

Poly Vinyl Acetate Phthalate (PVAP). PVAP dissolves in pH >5, and it is much less permeable to water vapor and gastric fluids.

In some embodiments, the coating can, and usually does, contain a plasticizer and possibly other coating excipients such as colorants, talc, and/or magnesium stearate. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnuba wax or PEG) may be added to the coatings besides plasticizers to solubilize or disperse the coating material, and to improve coating performance and the coated product.

In other embodiments, the formulations described herein, which include a compound of Formula (I), (II), (III), or (IV) described herein, are delivered using a pulsatile dosage form. A pulsatile dosage form is capable of providing one or more immediate release pulses at predetermined time points after a controlled lag time or at specific sites. Pulsatile dosage forms may be administered using a variety of pulsatile formulations including, but are not limited to, those described in U.S. Pat. Nos. 5,011,692; 5,017,381; 5,229,135; 5,840,329; 4,871,549; 5,260,068; 5,260,069; 5,508,040; 5,567,441 and 5,837,284.

Many other types of controlled release systems are suitable for use with the formulations described herein. Examples of such delivery systems include, e.g., polymer-based systems, such as polylactic and polyglycolic acid, polyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., Pharmaceutical Dosage Forms, 2 Ed., Vol. 1, pp. 209-214 (1990); Singh et al., Encyclopedia of Pharmaceutical Technology, 2nd Ed., pp. 751-753 (2002); U.S. Pat. Nos. 4,327,725; 4,624,848; 4,968,509; 5,461,140; 5,456,923; 5,516,527; 5,622,721; 5,686,105; 5,700,410; 5,977,175; 6,465,014; and 6,932,983.

In some embodiments, pharmaceutical formulations are provided that include particles of the compounds described herein, e.g. compounds of Formula (I), (II), (III) or (IV), and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002).

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

The pharmaceutical compositions described herein may include sweetening agents such as, but not limited to, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

In some embodiments, the pharmaceutical formulations described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms include, but are not limited to, for example, U.S. Pat. Nos. 5,858,401, 6,667,048, and 6,960,563.

There is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein.

Potential excipients for intranasal formulations include, for example, U.S. Pat. Nos. 4,476,116, 5,116,817 and 6,391,452. Formulations solutions in saline, employing benzyl alcohol or other suitable preservatives, fluorocarbons, and/or other solubilizing or dispersing agents. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. Preferably, the nasal dosage form should be isotonic with nasal secretions.

For administration by inhalation, the compounds described herein may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Buccal formulations that include compounds described herein may be administered using a variety of formulations which include, but are not limited to, U.S. Pat. Nos. 4,229,447, 4,596,795, 4,755,386, and 5,739,136. In addition, the buccal dosage forms described herein can further include a bioerodible (hydrolysable) polymeric carrier that also serves to adhere the dosage form to the buccal mucosa. The buccal dosage form is fabricated so as to erode gradually over a predetermined time period, wherein the delivery of the compound is provided essentially throughout. Buccal drug delivery avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, virtually any such carrier can be used, so long as the desired drug release profile is not compromised, and the carrier is compatible with the compounds described herein, and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other components may also be incorporated into the buccal dosage forms described herein include, but are not limited to, disintegrants, diluents, binders, lubricants, flavoring, colorants, preservatives, and the like. For buccal or sublingual administration, the compositions may take the form of tablets, lozenges, or gels formulated in a conventional manner.

Transdermal formulations described herein may be administered using a variety of devices including but not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144.

The transdermal dosage forms described herein may incorporate certain pharmaceutically acceptable excipients which are conventional in the art. In one embodiment, the transdermal formulations described herein include at least three components: (1) a formulation of a compound of Formula (I), (II), or (III); (2) a penetration enhancer; and (3) an aqueous adjuvant. In addition, transdermal formulations can include additional components such as, but not limited to, gelling agents, creams and ointment bases, and the like. In some embodiments, the transdermal formulation can further include a woven or non-woven backing material to enhance absorption and prevent the removal of the transdermal formulation from the skin. In other embodiments, the transdermal formulations described herein can maintain a saturated or supersaturated state to promote diffusion into the skin.

Formulations suitable for transdermal administration of compounds described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds described herein can be accomplished by means of iontophoretic patches and the like. Additionally, transdermal patches can provide controlled delivery of the compounds described herein. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Formulations suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally recognized in the field. For other parenteral injections, appropriate formulations may include aqueous or non-aqueous solutions, preferably with physiologically compatible buffers or excipients. Such excipients are generally recognized in the field.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

In certain embodiments, delivery systems for pharmaceutical compounds may be employed, such as, for example, liposomes and emulsions. In certain embodiments, compositions provided herein also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein may be administered topically and are formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

The compounds described herein may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Generally, an agent, such as a compound of Formula (I), (II), (III), or (IV) is administered in an amount effective for amelioration of, or prevention of the development of symptoms of, the disease or disorder (i.e., a therapeutically effective amount). Thus, a therapeutically effective amount can be an amount that is capable of at least partially preventing or reversing a disease or disorder. The dose required to obtain an effective amount may vary depending on the agent, formulation, disease or disorder, and individual to whom the agent is administered.

Determination of effective amounts may also involve in vitro assays in which varying doses of agent are administered to cells in culture and the concentration of agent effective for ameliorating some or all symptoms is determined in order to calculate the concentration required in vivo. Effective amounts may also be based in in vivo animal studies.

An agent can be administered prior to, concurrently with and subsequent to the appearance of symptoms of a disease or disorder. In some embodiments, an agent is administered to a subject with a family history of the disease or disorder, or who has a phenotype that may indicate a predisposition to a disease or disorder, or who has a genotype which predisposes the subject to the disease or disorder.

The particular delivery system used can depend on a number of factors, including, for example, the intended target and the route of administration, e.g., local or systemic. Targets for delivery can be specific cells which are causing or contributing to a disease or disorder, including, for example, cells that have altered intracellular calcium or calcium dysregulation or dyshomeostasis, and cells that do not have altered intracellular calcium but that may have some alteration, defect or deficiency that can be, at least in part, compensated, counteracted, reversed or alleviated or eliminated by altering intracellular calcium of the cell. Particular cells include, for example, immune cells (e.g., lymphocytes, T cells, B cells, white blood cells), fibroblasts (or cells derived from a fibroblast), epidermal, dermal or skin cells (e.g., a keratinocytes), blood cells, kidney or renal cells (e.g., mesangial cells), muscle cells (e.g., a smooth muscle cell such as an airway (tracheal or bronchial) smooth muscle cell) and exocrine or secretory (e.g., salivary, including parotid acinar and submandibular gland) cells. For example, a target cell can be resident or infiltrating cells in the lungs or airways that contribute to an asthmatic illness or disease, resident or infiltrating cells in the nervous system contributing to a neurological, neurodegenerative or demyelinating disease or disorder, resident or infiltrating cells involved in rejection of a kidney graft, grafted cells that when activated lead to graft-versus-host disease, resident or infiltrating cells involved in rejection of a kidney graft, resident or infiltrating cells, activation of which contributes to inflammation, e.g., in arthritis, resident or infiltrating cells in the kidney or renal system (e.g., mesangial cells) involved in neuropathy and glomerulonephritis and resident or infiltrating cells in exocrine glands (e.g., salivary and lacrimal glands) involved in autoimmune disorders (e.g., Sjogren's disease). Administration of an agent can be directed to one or more cell types or subsets of a cell type by methods recognized in the field. For example, an agent can be coupled to an antibody, ligand to a cell surface receptor or a toxin, or can be contained in a particle that is selectively internalized into cells, e.g., liposomes or a virus in which the viral receptor binds specifically to a certain cell type, or a viral particle lacking the viral nucleic acid, or can be administered locally.

Examples of Methods of Dosing and Treatment Regimens

The compounds described herein can be used in the preparation of medicaments for the modulation of intracellular calcium, or for the treatment of diseases or conditions that would benefit, at least in part, from modulation of intracellular calcium. In addition, a method for treating any of the diseases or conditions described herein in a subject in need of such treatment, involves administration of pharmaceutical compositions containing at least one compound described herein, or a pharmaceutically acceptable salt, pharmaceutically acceptable prodrug, or pharmaceutically acceptable solvate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be determined in a manner recognized in the field according to the particular circumstances surrounding the case, including, e.g., the specific agent being administered, the route of administration, the condition being treated, and the subject or host being treated. In general, however, doses employed for adult human treatment will typically be in the range of about 0.02-about 5000 mg per day, in some embodiments, about 1-about 1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The daily dosages appropriate for the compounds described herein described herein are from about 0.01 mg/kg to about 20 mg/kg. In one embodiment, the daily dosages are from about 0.1 mg/kg to about 10 mg/kg. An indicated daily dosage in the larger mammal, including, but not limited to, humans, is in the range from about 0.5 mg to about 1000 mg, conveniently administered in a single dose or in divided doses, including, but not limited to, up to four times a day or in extended release form. Suitable unit dosage forms for oral administration include from about 1 to about 500 mg active ingredient. In one embodiment, the unit dosage is about 1 mg, about 5 mg, about, 10 mg, about 20 mg, about 50 mg, about 100 mg, about 200 mg, about 250 mg, about 400 mg, or about 500 mg. The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Combination Treatments

The compounds of Formula (I), (II), (III) or (IV), and compositions thereof, may also be used in combination with other therapeutic agents that are selected for their therapeutic value for the condition to be treated. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the clinician. The initial administration can be made according to established protocols recognized in the field, and then, based upon the observed effects, the dosage, modes of administration and times of administration can be modified by the clinician.

In certain instances, it may be appropriate to administer at least one compound described herein in combination with another therapeutic agent. By way of example only, if one of the side effects experienced by a patient upon receiving one of the compounds herein, such as a compound of Formula (I), (II), (III) or (IV), is nausea, then it may be appropriate to administer an anti-nausea agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. In any case, regardless of the disease, disorder or condition being treated, the overall benefit experienced by the patient may simply be additive of the two therapeutic agents or the patient may experience a synergistic benefit.

The particular choice of compounds used will depend upon the diagnosis of the attending physicians and their judgment of the condition of the patient and the appropriate treatment protocol. The compounds may be administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the physician after evaluation of the disease being treated and the condition of the patient.

Therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is a compound of Formula (I), (II), (III), or (IV) described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder or condition from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In addition, the compounds described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/ or combinations with other therapeutics are combined with genetic testing to determine whether that individual is a carrier of a mutant gene that is known to be correlated with certain diseases or conditions.

The compounds described herein and combination therapies can be administered before, during or after the occurrence of a disease or condition, and the timing of administering the composition containing a compound can vary. Thus, for example, the compounds can be used as a prophylactic and can be administered continuously to subjects with a propensity to develop conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over about 5 minutes to about 5 hours, a pill, a capsule, transdermal patch, buccal delivery, and the like, or combination thereof. A compound is preferably administered as soon as is practicable after the onset of a disease or condition is detected or suspected, and for a length of time necessary for the treatment of the disease, such as, for example, from 1 day to about 3 months. The length of treatment can vary for each subject, and the length can be determined using the known criteria. For example, the compound or a formulation containing the compound can be administered for at least 2 weeks, preferably about 1 month to about 5 years.

Inhibitors of SOCE

In one aspect, compounds of Formula (I), (II), (III), or (IV) are administered or used in conjunction with other inhibitors of SOCE. In one aspect, the inhibitors of SOCE are non-selective inhibitors.

A variety of inhibitors of SOCE have been described. Inhibitors of SOCE include:
a) Cations, which include lanthanide cations, such as for example, $Gd^{3+}$, $La^{3+}$;
b) P-450 inhibitors, which include econazole, miconazole, clotrimazole, ketoconazole;
c) Cyclooxygenase inhibitors, which include niflumic acid, flufenamic acid, tenidap;
d) Lipoxygenase inhibitors, which include nordihydroguaiaretic acid, eicosatetraynoic acid;
e) Compounds that are channel blockers, which include SK&F 96365, SC38249, LU52396, L-651,582, tetrandrine, 2-APB;
f) Compounds that inhibit SOCE not by an action on the SOC channels themselves, which include U73122 (phospholipase C inhibitor), wortmannin (phosphatidylinositol kinase inhibitor).

Some of these inhibitors of SOCE have non-specific actions and/or multiple modes of action that contribute to the inhibition of SOCE, which include blocking the pore of the SOC channel (Channel blockers), inhibition of mitochondrial ATP synthesis that appears to support SOCE (Gamberucci et al., *J Biol. Chem.*, 269, 23597-23602, 1994; Marriott et al., *Am. J. Physiol.*, 269, C766-C774, 1995), disturbances of cytoplasmic pH (Muallem et al., *Am. J. Physiol.*, 257, G917-G924, 1989), as well as inhibiting the activation of SOC channels.

Immunosuppresants

In one embodiment, compounds described herein are administered as single agents in immunosuppressive therapy to reduce, inhibit, or prevent activity of the immune system. Immunosuppressive therapy is clinically used to: prevent the rejection of transplanted organs and tissues (e.g. bone marrow, heart, kidney, liver); treatment of autoimmune diseases or diseases that are most likely of autoimmune origin (e.g. rheumatoid arthritis, myasthenia gravis, systemic lupus erythematosus, Crohn's disease, and ulcerative colitis); and treatment of some other non-autoimmune inflammatory diseases (e.g. long term allergic asthma control).

In some embodiments, the compounds described herein are administered with other immunosuppresants selected from among: Calcineurin inhibitors (such as, but not limited to, cyclosporin, tacrolimus); mTOR inhibitors (such as, but not limited to, sirolimus, everolimus); anti-proliferatives (such as, but not limited to, azathioprine, mycophenolic acid); corticosteroids (such as, but not limited to, prednisone, cortisone acetate, prednisolone, methylprednisolone, dexamethasone, betamethasone, triamcinolone, beclometasone, fludrocortisone acetate, deoxycorticosterone acetate, aldosterone, hydrocortisone); antibodies (such as, but not limited to, monoclonal anti-IL-2Rα receptor antibodies (basiliximab, daclizumab), polyclonal anti-T-cell antibodies (anti-thymocyte globulin (ATG), anti-lymphocyte globulin (ALG))).

Other immunosuppresants include, but are not limited to: glucocorticoids (alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, Fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone, prednisolone, prednylidene, rimexolone, tixocortol, triamcinolone, ulobetasol), cyclophosphamide, nitrosoureas, cisplatin, carboplatin, oxaliplatin, methotrexate, azathioprine, mercaptopurine, pyrimidine analogues, protein synthesis inhibitors, methotrexate, azathioprine, mercaptopurine, dactinomycin, anthracyclines, mitomycin C, bleomycin, mithramycin, Atgam®, Thymoglobuline®, OKT3®, basiliximab, daclizumab, cyclosporin, tacrolimus, sirolimus, Interferons (IFN-β, IFN-γ), opioids, TNF binding proteins (infliximab, etanercept, adalimumab, golimumab), mycophenolic acid, mycophenolate mofetil, FTY720, as well as those listed in U.S. Pat. No. 7,060,697.

Agents for Treating Autoimmune Diseases, Inflammatory Diseases

Where the subject is suffering from or at risk of suffering from an autoimmune disease, disorder or condition, or an inflammatory disease, disorder or condition, a compound described herein is administered in any combination with one or more of the following therapeutic agents: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, etoricoxib, lumiracoxib, celecoxib, or rofecoxib), leflunomide, gold thioglucose, gold thiomalate, aurofin, sulfasalazine, hydroxychloroquinine, minocycline, TNF-α binding proteins (e.g., infliximab, etanercept, or adalimumab), abatacept, anakinra, interferon-β, interferon-γ, interleukin-2, antileukotrienes, theophylline, or anticholinergics.

In one embodiment, compounds described herein, are administered in combination with inhibitors of NFAT-calcineurin pathway. In one embodiment, the inhibitors of NFAT-calcineurin pathway include, but are not limited to, Cyclosporin A (CsA) and tacrolimus (FK506).

In one embodiment, a compound described herein, or compositions and medicaments that include a compound of Formula (I), (II), (III) or (IV), are administered to a patient in combination with an anti-inflammatory agent including, but not limited to, non-steroidal anti-inflammatory drugs (NSAIDs) and corticosteroids (glucocorticoids).

NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, fluorobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, COX-2 specific inhibitors (such as, but not limited to, celecoxib, rofecoxib, valdecoxib, parecoxib, etoricoxib, lumiracoxib, CS-502, JTE-522, L-745,337 and NS398).

Combinations with NSAIDs, which are selective COX-2 inhibitors, are contemplated herein. Such compounds include, but are not limited to those disclosed in U.S. Pat. Nos. 5,474,995; 5,861,419; 6,001,843; 6,020,343, 5,409,944; 5,436,265; 5,536,752; 5,550,142; 5,604,260; 5,698,584; 5,710,140; WO 94/15932; U.S. Pat. Nos. 5,344,991; 5,134,142; 5,380,738; 5,393,790; 5,466,823; 5,633,272; 5,932,598 and 6,313,138; all of which are hereby incorporated by reference.

Compounds that have been described as selective COX-2 inhibitors and are therefore useful in the methods or pharmaceutical compositions described herein include, but are not limited to, celecoxib, rofecoxib, lumiracoxib, etoricoxib, valdecoxib, and parecoxib, or a pharmaceutically acceptable salt thereof.

Corticosteroids, include, but are not limited to: betamethasone, prednisone, alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

Other agents used as anti-inflammatories include those disclosed in U.S. patent publication 2005/0227929, herein incorporated by reference.

Some commercially available anti-inflammatories include, but are not limited to: Arthrotec® (diclofenac and misoprostol), Asacol® (5-aminosalicyclic acid), Salofalk® (5-aminosalicyclic acid), Auralgan® (antipyrine and benzocaine), Azulfidine® (sulfasalazine), Daypro® (oxaprozin), Lodine® (etodolac), Ponstan® (mefenamic acid), Solumedrol® (methylprednisolone), Bayer® (aspirin), Bufferin® (aspirin), Indocin® (indomethacin), Vioxx® (rofecoxib), Celebrex® (celecoxib), Bextra® (valdecoxib), Arcoxia® (etoricoxib), Prexige® (lumiracoxib), Advil®, Motrin® (ibuprofen), Voltaren® (diclofenac), Orudis® (ketoprofen), Mobic® (meloxicam), Relafen® (nabumetone), Aleve®, Naprosyn® (naproxen), Feldene® (piroxicam).

In one embodiment, compounds described herein are administered in combination with leukotriene receptor antagonists including, but are not limited to, BAY u9773 (see EP 00791576; published 27 Aug. 1997), DUO-LT (Tsuji et al, *Org. Biomol. Chem.*, 1, 3139-3141, 2003), zafirlukast (Accolate®), montelukast (Singulair®), prankulast (Onon®), and derivatives or analogs thereof.

Kits/Articles of Manufacture

For use in the therapeutic applications described herein, kits and articles of manufacture are also described herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products include, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease, disorder, or condition that would benefit by inhibition of CRAC channel activity.

For example, the container(s) can include one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically may include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, the pharmaceutical compositions can be presented in a pack or dispenser device which can contain one or more unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

Assays

Several techniques may be used to evaluate store-operated calcium entry and calcium signaling in cells. Such techniques include, but are not limited to, patch clamp electrophysiology (measurement of calcium ions or other ions across cell membranes, such as plasma membranes), capacitance measurements (allows exocytosis to be followed at the level of single cells), calcium imaging using fluorescent dyes allows patterns of calcium movement within the cytoplasm to be tracked, fluorescence resonance energy transfer (FRET) enables protein-protein interactions to be evaluated, and molecular biology methods allow for the manipulation of the levels of expression of proteins of interest.

A wide variety of assay methods may be used to examine the modulation of intracellular calcium by compounds of Formula (I), (II), or (III). Such assays include in vitro cell based assays as well as in vivo animal models. Any assays that detect, monitor or measure an effect on intracellular calcium, including calcium entry-mediated events can be used. Such assays include, but are not limited to, assays monitoring, measuring and/or detecting intracellular calcium levels, modulation of calcium levels, and movement of calcium into, out of or within cells and intracellular organelles. Assays can also include monitoring, measuring and/or detecting calcium entry-mediated events and molecules involved in calcium entry-mediated events such as, but not limited to, signal transduction molecules, transcription factors, secreted molecules and other molecules that are affected by changes in calcium homeostasis. Assays include, but are not limited to, those described herein and those described in US patent publication no. 2007/0031814 and WO 07/081,804, herein incorporated by reference.

Cells and Cell Models

For in vitro testing of the modulation of intracellular calcium by compounds of Formula (I), (II), (III) or (IV), a wide variety of cell types for such assays are available. In a particular embodiment, the cell is one in which store-operated calcium entry occurs or that can be manipulated such that store-operated calcium entry occurs in the cell. In particular embodiments, the cell contains one or more proteins involved in modulating intracellular calcium (and, in particular, is involved in, participates in and/or provides for store-operated calcium entry, movement of calcium into, out of or within an intracellular organelle or calcium store, modulation of calcium levels in an intracellular organelle or calcium store (e.g., endoplasmic reticulum) and/or calcium buffering), such as those provided herein. In particular embodiments, the protein(s) include STIM proteins (including STIM1, STIM2, DSTIM and CSTIM protein) and/or Orai proteins (Orai1, Orai2, Orai3). The cell may endogenously express the protein(s) or recombinantly express the protein(s).

Cells for use in the methods may be of any species. In one embodiment, the cells can be eukaryotic cells. In one embodiment, the cells can be yeast, insect (e.g., *Drosophila* or Anopheles), or mammalian cells. Mammalian cells include, but are not limited to, rodent (e.g., mouse, rat and hamster), primate, monkey, dog, bovine, rabbit and human cells. A variety of cell types can be used in the methods, including, for example, neuronal, nervous system, brain, immune system cells, e.g., T lymphocytes and B cells, primary cells, blood and hematopoietic cells, stromal cells, myeloid cells, lymphoid cells, and a variety of tumor and cancer cells. Particular cells include Drosophila Schneider 2 or S2 cells, human embryonic kidney (HEK293) cells, rat basophilic leukemia (RBL-2H3) cells, Jurkat cells, epithelial cells, rhabdomyosarcoma cells, rhabdoid cells, retinoblastoma cells, neuroepithelioma cells, neuroblastoma cells, osteosarcoma cells, fibroblasts, bone marrow stroma cells, erythroleukemia cells and lymphoblast cells. Other cell lines include HEK 293 and 293T, CHO (including CHO-K1), LTK-, N2A, H6, and HGB. Many such cells and cell lines are available through cell depositories such as, for example, the American Type Culture Collection (ATCC, Manassas, Va.). Primary cells can be obtained by isolation from tissue sources.

Cells from a known cell line can be used, such as neuroblastoma SH-SY5Y cells, pheochromocytoma PC12 cells, neuroblastoma SK-N-BE(2)C or SK-N-SH cells, human SK-N-MC neuroepithelioma cells, SMS-KCNR cells, human LAN-5 neuroblastoma cells, human GI-CA-N neuroblastoma cells, human GOTO neuroblastoma cells, mouse Neuro 2a (N2A) neuroblastoma cells and/or human IMR 32 neuroblastoma cells, chronic myeloid leukemia cells (e.g., human K562 cells), promyelocytic leukemia cells (e.g., HL60 cells) and histiocytic lymphoma cells (e.g., U937 cells), Burkitt's lymphoma cells (e.g., CA46 cells), B-cells (e.g., NALM6), acute lymphoblastic leukemia cells (e.g., MOLT4 cells), T cells (e.g. Jurkat cells) and early T-ALL (e.g., DU528) cells.

In one embodiment, the choice of a cell for use in an in vitro assay to test the modulation of intracellular calcium by compounds described herein involves several considerations, including, for example, a particular protein that is being used in the method and a particular aspect or activity of intracellular calcium modulation that is being monitored or assessed in the method.

In one embodiment, the modulation of intracellular calcium by a compound described herein, is examined by monitoring or assessing the effect on store-operated calcium entry. Cells typically used in such methods exhibit store-operated calcium entry either naturally or through manipulation of the cells. Cells that endogenously exhibit store-operated calcium entry include some excitable cells and most non-excitable cells and can be identified using methods described herein and/or recognized in the field.

In one embodiment, it may be desirable to utilize a cell that contains components of signaling and messenger systems that can effect release of calcium from intracellular stores. For example, cells containing components of receptor-mediated phospholipase C (PLC) activation systems can be used for physiological activation (via generation of $IP_3$) of store depletion to facilitate monitoring of store-operated calcium entry. Receptor-mediated PLC activation occurs through distinct coupling mechanisms: PLC-β activation by G protein-coupled receptors (GPCRs) and PLC-γ activation by tyrosine kinase receptors and nonreceptor tyrosine kinases. Thus, cells containing a receptor-mediated PLC-activation system can be monitored or assessed for store-operated calcium entry upon agonist activation of one or more receptors known to participate in the system. (see e.g. Bouron (2000) FEBS Lett 470: 269-272; Millar et al. (1995) J. Exp. Biol. 198:1843-1850; Yagodin et al. (1998) Cell Calcium 23:219-228; Yagodin et al. (1999) Cell Calcium 25:429-438; and Patterson et al. (2002) Cell 111:1-20).

An assessment of intracellular calcium after treatment with a compound described herein can be made under a variety of conditions. Conditions can be selected to evaluate the effect of test agent on a specific aspect of intracellular calcium. For example, reagents and conditions are used, for specifically evaluating store-operated calcium entry, resting cytosolic calcium levels, calcium buffering, and calcium levels of and calcium uptake by or release from intracellular organelles. Resting cytosolic calcium levels, intracellular organelle calcium levels and cation movement may be assessed using any of the methods described herein or recognized in the field. Such methods of assessing modulation in intracellular calcium include, but are not limited to, calcium-sensitive indicator-based measurements, such as fluo-3, mag-fura 2 and ER-targeted aequorin, labeled calcium (such as $^{45}Ca^{2+}$)-based measurements, and electrophysiological measurements. Particular aspects of ion flux that may be assessed include, but are not limited to, a reduction (including elimination) in the amount of ion flux, altered biophysical properties of the ion current, and altered sensitivities of the flux to activators or inhibitors of calcium flux processes, such as, for example, store-operated calcium entry. Reagents and conditions for use in specifically evaluating receptor-mediated calcium movement and second messenger-operated calcium movement are also available.

Evaluation of Store-Operated Calcium Entry

In one aspect, compounds described herein are added to cells under conditions that permit store-operated calcium entry to occur in order to assess the effects of Formulas (I)-(III) on store-operated calcium entry. Such conditions are described herein and are recognized in the field.

For example, in one method cells may be treated to reduce the calcium levels of intracellular calcium stores and then analyzed for evidence of ion (e.g., calcium) influx in response thereto in the presence of a compound described herein. Techniques for reducing calcium levels of intracellular stores and for analyzing cells for evidence of ion (e.g., calcium) influx are recognized in the field and described herein.

In other methods, electrophysiological analysis of currents across a cell-detached plasma membrane patch or an outside-out membrane vesicle may be used to detect or monitor store-operated channel currents (e.g., $I_{SOC}$, $I_{CRAC}$) in the presence of a compound described herein.

Evaluation of Calcium Entry-Mediated Events

A number of molecules involved in calcium-regulated pathways are known. Evaluation of molecules involved in calcium-entry mediated events can be used to monitor intracellular calcium, and can be used, for example in screening assays described herein to monitor the effects of the compounds presented herein. Examples of assays include but are not limited to assays which detect, or determine the presence, levels, alteration of levels, production, modification (such as phosphorylation and dephosphorylation), translocation, degradation and activity of molecules involved in calcium-entry mediated events (see for example, Trevillyan et al. (2001) J. Biol. Chem. 276:48118-26). The assays described herein can be used with cells that have been treated with or contacted with a compound presented herein, or that express an altered amount of a test molecule (such as a protein involved in calcium regulation, including a STIM protein, Orai protein), or with control cells. The assays can also be conducted in cells that have been stimulated with a physiological or non-physiological activator, or in unstimulated cells. The following are representative assays for molecules involved in calcium-entry mediated events and are meant to be exemplary only. Other assays for these molecules and assays for other molecules involved in calcium-entry mediated events can also be employed in any of the screening and/or modulation methods described herein.

β-Hexosaminidase Release

In mast cells, $Ca^{2+}$ influx results in degranulation and release of inflammatory mediators such as heparin, histamine and enzymes such as β-hexosaminidase. Detecting and/or measuring release of such molecules can thus be used to monitor intracellular calcium. For example, media from mast cells can be collected. A suitable substrate for β-hexosaminidase (e.g. p-nitrophenyl-acetyl-glucosamide) can then be added and the absorbance of the resulting mixture assessed to measure the relative amount of β-hexosaminidase activity in the samples (Funaba et al. (2003) *Cell Biol. International* 27:879-85).

Calcium/Calmodulin-Dependent CaN Phosphatase Activity

The phosphatase calcineurin (CaN) dephosphorylates various proteins, affecting their activity and localization. CaN activity can be assessed by incubating purified CaN and a CaN substrate, for example a radiolabeled peptide corresponding to a sequence in the RII subunit of cAMP-dependent kinase, either with or without a compound of Formula (I), (II), (III), or (IV) (see, Trevillyan et al. (2001) *J. Biol. Chem.* 276:48118-26). The level of radiolabeled peptide and/or the amount of free inorganic phosphate released can be measured to assess CaN dephosphorylation activity.

NFAT Transcriptional Activity

The NFAT (nuclear factor of activated T cells) transcription factor regulates a number of genes in response to intracellular calcium levels. For example, NFAT proteins regulate the transcription of cytokine genes involved in the immune response. Promoters from NFAT-regulated genes, and/or regulatory regions and elements from these genes, can be used to monitor NFAT regulated expression and thereby monitor intracellular calcium. Reporter gene fusions can be constructed with NFAT regulated promoters or NFAT-regulated elements operably linked to a reporter gene such as luciferase, β-galactosidase, green fluorescent protein (GFP) or any other known reporter in the art (see for example, Published U.S. Application no. 2002-0034728). The amount of reporter protein or activity is a measure of NFAT activity.

NFAT Phosphorylation

NFAT activation is regulated primarily through its phosphorylation, which in turn regulates its subcellular localization. In unstimulated cells, NFAT is a hyperphosphorylated cytosolic protein. An elevation in intracellular $Ca^{2+}$, induced by a variety of mechanisms, increases the activity of the $Ca^{2+}$-calmodulin-dependent phosphatase, calcineurin. Activated calcineurin dephosphorylates multiple serine residues within the regulatory region of the NFAT molecule. NFAT is rephosphorylated in response to decreases in $Ca^{2+}$ levels or CaN inhibition.

The phosphorylation state of NFAT can be monitored for example, by expressing a detectably tagged NFAT protein in cells, such as a His6 tagged-NFAT. Tagged NFAT can be purified from cells using $Ni^{2+}$ chromatography and subjected to gel electrophoresis and staining or western blotting. More highly phosphorylated forms of NFAT can be distinguished by their slower migration. The state of phosphorylated NFAT can be used as a measure of NFAT activation (see, Trevillyan et al. (2001) *J. Biol. Chem.* 276:48118-26).

NFAT Nuclear Localization

NFAT localization between the cytoplasm and nucleus is regulated by the phosphorylation state of NFAT. Phosphorylation of NFAT prevents nuclear localization by masking the nuclear localization sequence. NFAT nuclear localization can be monitored, for example, by expressing fluorescently tagged NFAT, for example, GFP-NFAT, in cells. Confocal microscopy can be used to monitor nuclear localization of the tagged NFAT (see, Trevillyan et al. (2001) *J. Biol. Chem.* 276:48118-26).

Cytokine Secretion

Cytokine secretion, such as IL-2 secretion, can be monitored using protein detection assays. For example, supernatant can be collected from immune cells. An ELISA assay or other suitable format with IL-2 antibodies can be used to detect and/or measure the amount of IL-2 secreted as compared to control cells. Secretion of other cytokines, for example, TNF-α, can also be detected in similar assays.

Cytokine Expression

Expression of cytokines, such as, but not limited to IL-2, can be assessed either directly or indirectly in cells. For example, in indirect methods, an IL-2 promoter can be operably linked to a reporter gene such as luciferase or β-galactosidase, and the reporter construct introduced into cells. Reporter gene expression can be monitored and compared to gene expression in control cells (see, Trevillyan et al. (2001) *J. Biol. Chem.* 276:48118-26). Alternatively, expression of endogenous or recombinant IL-2 mRNA or protein can be assessed.

T Cell Proliferation

Cytokines such as IL-2 are necessary for T-cell proliferation in response to mitogen or alloantigen stimulation, and thus T-cell proliferation is altered by changes in cytokine expression or secretion. T cells can be induced, such as with concanavalin A or alloreactive lymphocytes and T cell proliferation measured, for example, by subjecting cells to a pulse of $^3$H-thymidine and measuring $^3$H-thymidine incorporation (see, Trevillyan et al. (2001) *J. Biol. Chem.* 276:48118-26).

In some embodiments, the modulation (e g inhibition or reduction) of SOCE by compounds presented herein are determined by evaluation of any of the following criteria:

a. there is direct inhibition of increased $[Ca^{2+}]$ as measured by a calcium indicator;
b. there is a direct inhibition of $I_{SOC}$ or $I_{CRAC}$ as measured by patch clamp;
c. there is inhibition of downstream signaling functions such as calcineurin activity, NFAT subcellular localization, NFAT phosphorylation, and/or cytokine, e.g., IL-2, production; or
d. there are modifications in activation-induced cell proliferation, differentiation and/or apoptotic signaling pathways.

Animal Models

Animal models that can be used in embodiments of the methods further include animals, such as, but not limited to non-human animals, which have, in at least some of their cells, an alteration or defect in, or aberrant functioning of, a cellular process which relies on or is regulated by intracellular calcium. Cellular processes that rely on or are regulated by intracellular calcium include, for example, cellular activation, gene expression, cellular trafficking, and apoptosis. Diseases/disorders that involve defects that may be at least partially compensated for by modulation of intracellular calcium include, but are not limited to: autoimmune disorders, including rheumatoid arthritis, inflammatory bowel disease, Sjogren's syndrome (cytokines associated with lymphocyte invasion of salivary epithelial cells can reduce calcium mobilization in parotid cells; also, T-cell activation, including activation of transcription factors, cytokine gene expression and cell proliferation, depends on sustained elevation of intracellular calcium level provided by store-operated calcium influx), asthma (store-operated calcium entry may play an important role in mediating bronchial constriction and bronchial smooth muscle cell proliferation), glomerulonephritis and glomerular inflammation (changes in intracellular calcium, such as by store-operated calcium entry, signal monocyte adhesion in a co-culture model of glomerular inflammation).

Types of animal models include, but are not limited to, non-human animals, such as non-human invertebrates and vertebrates and non-human mammals, rodents (e.g., mice, rat and hamster), cows, chickens, pigs, goats, dogs, sheep, insects, *Drosophila*, nematodes, worms, *C. elegans*, monkeys, gorillas, and other primates.

Animal models include transgenic and non-transgenic animals. One example of such an animal model that can be used in particular embodiments of the methods is a rodent model of airway hyperresponsiveness (AHR), a characteristic of asthma. This model can be generated, for example, by sensitization through immunization with ovalbumin followed by exposure to aerosolized ovalbumin and challenge by cholinergic stimulation (e.g., via administration of methacholine or acetylcholine) (see, e.g., Xu et al. (2002) *J. Appl. Physiol.* 93:1833-1840; Humbles et at (2002) *Proc. Natl. Acad. Sci.* 99:1479-1484). Airway hyperresponsiveness (which can be evaluated using methods, such as for e.g., using barometric plethysmography to record respiratory pressure curves and through measurement of pulmonary parameters such as pulmonary conductance and pulmonary compliance) can be assessed and compared in animals treated and not treated with a compound presented herein. A further example of an animal model that can be used in particular embodiments of the methods is a rodent model of mesangial proliferative glomerulonephritis, which can be generated, for example, by administration of anti-Thy1.1 antibody (see, e.g., Jefferson and Johnson (1999) *J. Nephrol.* 12:297-307). Any number of parameters indicative of glomerulonephritis or renal dysfunction (e.g., mesangial cell proliferation, blood pressure, urinary protein excretion, creatinine clearance, glomerulosclerosis index and other parameters) can be evaluated and compared in animals treated with and not treated with test agent. The non-obese diabetic (NOD) mouse, an inbred mouse strain that spontaneously develops autoimmune diabetes that shares many immunogenetic features with Type 1 diabetes mellitus, is another example of an animal model that can be used in a particular embodiment of the methods. These mice also manifest many characteristics of autoimmune exocrinopathy (such as Sjogren's syndrome) including declining exocrine tissue secretory function (see, e.g., Humphreys-Beher and Peck (1999) *Arch. Oral Biol.* 44 Suppl 1:S21-25 and Brayer et al. (2000) *J Rheumatol.* 27:1896-1904). Characteristics relevant to Sjogren's syndrome (e.g., lymphocytic infiltrates in exocrine glands (e.g., salivary and lacrimal glands), presence of dendritic cells and macrophages in submandibular glands, integrity of the lacrimal gland by measurement of basal and stimulated tear secretion, saliva flow rates and amylase activity) can be evaluated and compared in animals treated with and not treated with a compound described herein. An animal (e.g., rodent) model of autoimmune disease can also be used in particular embodiments of the methods. Such animals include rat models available through the National Institutes of Health (NIH) Autoimmune Rat Model Repository and Development Center (Bethesda, Md.; accessible at www.ors.od.nih.gov/dirs/vrp/ratcenter). One rat model of rheumatoid arthritis (RA) and related chronic/inflammatory autoimmune diseases is the collagen-induced arthritis (CIA) model (see, e.g., Griffiths and Remmers (2001) *Immunol. Rev.* 184:172-183). Characteristic phenotypes of autoimmune disease (e.g. altered levels of immune reactivity to self-antigens, chronic inflammation of autoantigen-expressing target organs, and activation and participation of invading mononuclear cells and tissue fibroblasts in organ damage) can be evaluated and compared in animals treated with and not treated with a compound presented herein. An animal (e.g., rodent) model of neuropathic or inflammatory pain can also be used in a particular embodiment of the methods. For example, one rat model of neuropathic pain involves development of tactile allodynia (exaggerated response to otherwise innocuous stimuli) after ligation of lumbar spinal nerves (see, e.g., Chaplan et al. (1994) *J. Neurosci. Methods* 53:55-63 and Luo et al. (2001) *J. Neurosci.* 21:1868-1875). Tactile allodynia, one characteristic feature of neuropathic pain, can be evaluated (e.g., by evaluating paw withdrawal threshold in response to application of pressure) and compared in animals treated and not treated with a compound described herein.

EXAMPLES

These examples are provided for illustrative purposes only and not to limit the scope of the claims provided herein. The starting materials and reagents used for the synthesis of the compounds described herein may be synthesized or can be obtained from commercial sources, such as, but not limited to, Sigma-Aldrich, Acros Organics, Fluka, and Fischer Scientific.

Synthetic Examples

These examples are provided for illustrative purposes only and not to limit the scope of the claims provided herein. The starting materials and reagents used for the synthesis of the compounds described herein may be synthesized or can be obtained from commercial sources, such as, but not limited to, Sigma-Aldrich, Acros Organics, Fluka, and Fischer Scientific.

Preparation of 2-(5-chloro-2-methylbenzoxazol-6-yl)-4,4,5,5-tetramethyl-1,3,2-dioxaborolane (4)

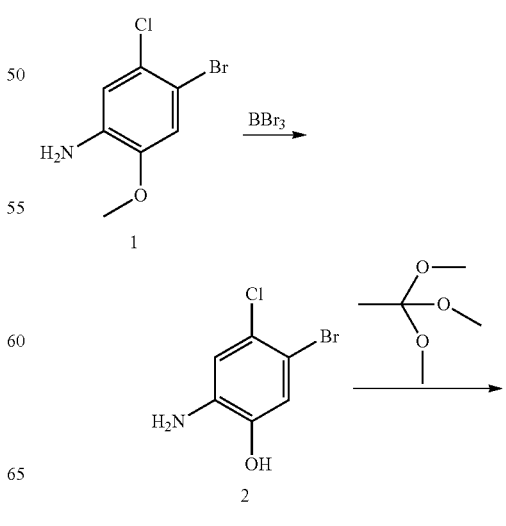

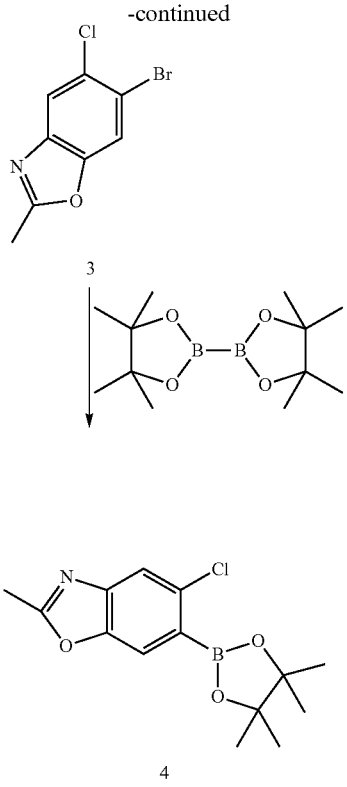

Preparation of 2-amino-5-bromo-4-chlorophenol (2): To a suspension of 4-bromo-3-chloro-6-methoxyaniline (1) (944 mg, 4 mmol) in 10 ml DCM was added 1 M BBr₃ in DCM (8 ml, 8 mmol). The reaction mixture was stirred at r.t. for 2 h, which turned to a brown solution and back to a brown suspension. After quenched with aq. sodium bicarbonate solution, the mixture was extracted with EA. The org. phase was washed with brine, dried over sodium sulfate, concentrated to dryness to give 865 mg 2 as brown solid. Yield: 97.2%, purity>95%.

Preparation of 6-bromo-5-chloro-2-methylbenzoxazole (3): A mixture of 2-amino-5-bromo-4-chlorophenol (2) (865 mg, 3.89 mmol), trifluoromethanesulfonic acid Ytterbium (III) salt (24 mg, 1% mol) and trimethyl orthoacetate (610 μl, 1.2 eq.) in 3 ml EtOH was heated at 90° C. for 1 h. After cooling down to r.t., off-white needles fell off, which were filtered, washed with MeOH, water and dried to give 791 mg title compound as off-white crystalline solid. Yield: 80.2%; purity>95%.

Preparation of 2-(5-chloro-2-methylbenzoxazol-6-yl)-4,4,5,5-tetramethyl-1,3,2-dioxaborolane (4): A mixture of 6-bromo-5-chloro-2-methylbenzoxazole (3, 493 mg, 2 mmol), bis(pinacolato)diboron (1.01 g, 2 mmol), [1,1'-bis(diphenylphosphino)ferrocene]palladium(II) chloride dichloromethane complex (1:1) (163 mg) and potassium acetate (588 mg) in 8 ml dioxane was heated under Ar for 20 h at 90° C. After EA/brine work-up, the org. phase was dried over sodium sulfate, concentrated and subjected to silica gel flash column purification to give 925 mg white solid, which was dissolved in 20 ml THF/MeOH/H₂O (5:4:1) and stirred with 30 ml 1 M HCl at r.t. for 30 min. EA/brine work-up and followed by flash column to give 205 mg of 2-(5-chloro-2-methylbenzoxzzol-6-yl)-4,4,5,5-tetramethyl-1,3,2-dioxaborolane (4) as white solid.

Example 1

Preparation of [5-(5-chloro-2-methylbenzoxazol-6-yl)(2-thienyl)]-N-(2-chlorophenyl)carboxamide (8)

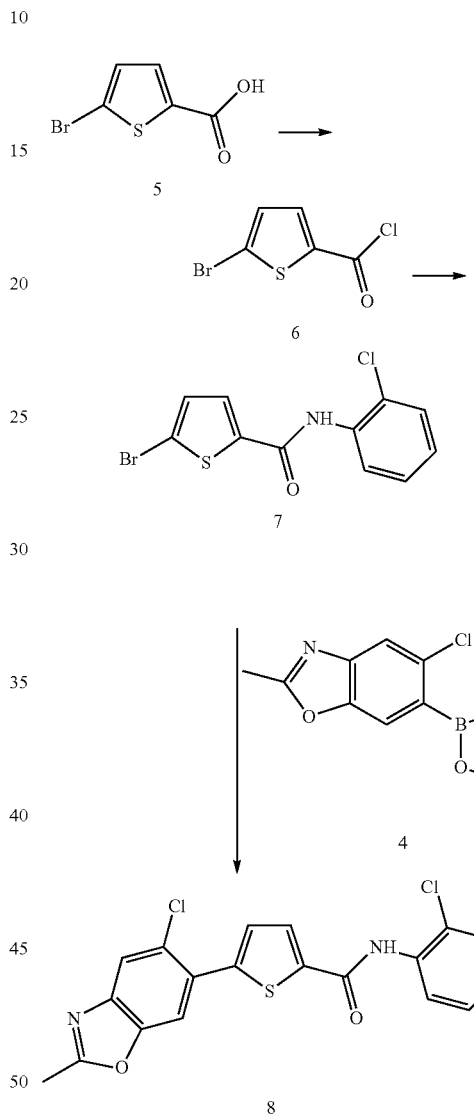

Preparation of (5-bromo(2-thienyl))-N-(2-chlorophenyl)carboxamide (7): A mixture of 5-bromo-thiophene-2-carboxylic acid (5) (207 mg, 1 mmol), oxalyl chloride (420 μl) and catalytic amount of DMF in 5 ml DCM was stirred at r.t for 2 h before evaporation to dryness. The resulting solid residue was dissolved in 5 ml DCM and to which were added 2-chloroaniline (209 μl, 2 eq) and DIEA (522 μl). The reaction mixture was stirred at r.t for overnight before worked up with EA/aq. HCl/brine. The org. phase was concentrated and then purified on a flash silica gel column to give 291 mg (5-bromo(2-thienyl))-N-(2-chlorophenyl)carboxamide (7) as light yellow solid. (yield: 92%, purity>90%).

Preparation of [5-(5-chloro-2-methylbenzoxazol-6-yl)(2-thienyl)]-N-(2-chlorophenyl)carboxamide (8): A mixture of (5-bromo(2-thienyl))-N-(2-chlorophenyl)carboxamide (7) (25 mg, 0.08 mmol), 2-(5-chloro-2-methylbenzoxazol-6-yl)-4,4,5,5-tetramethyl-1,3,2-dioxaborolane (4) (23 mg, 0.08 mmol), tetrakis(triphenylphosphine)-palladium(0) (Pd(Ph$_3$P)$_4$, 12 mg) and sodium carbonate (32 mg) in 0.5 ml DME, 0.5 ml EtOH and 0.25 ml water was heated under Ar in microwave reactor at 110° C. for 30 min. The reaction mixture was worked up with EA/brine. Org. phase was concentrated and then subjected to silica gel flash column chromatography. The isolated crude product was re-purified on prep HPLC to furnish 10.7 mg of [5-(5-chloro-2-methylbenzoxazol-6-yl)(2-thienyl)]-N-(2-chlorophenyl)carboxamide (8) as white solid (yield: 33.1%; purity>95%). LC-MS: calcd. for C$_{19}$H$_{12}$Cl$_2$N$_2$O$_2$S: 404 (M+1).

Example 2

Preparation of [5-(5-chloro-2-methylbenzoxazol-6-yl)(2-thienyl)]-N-(2-fluorophenyl)carboxamide (10)

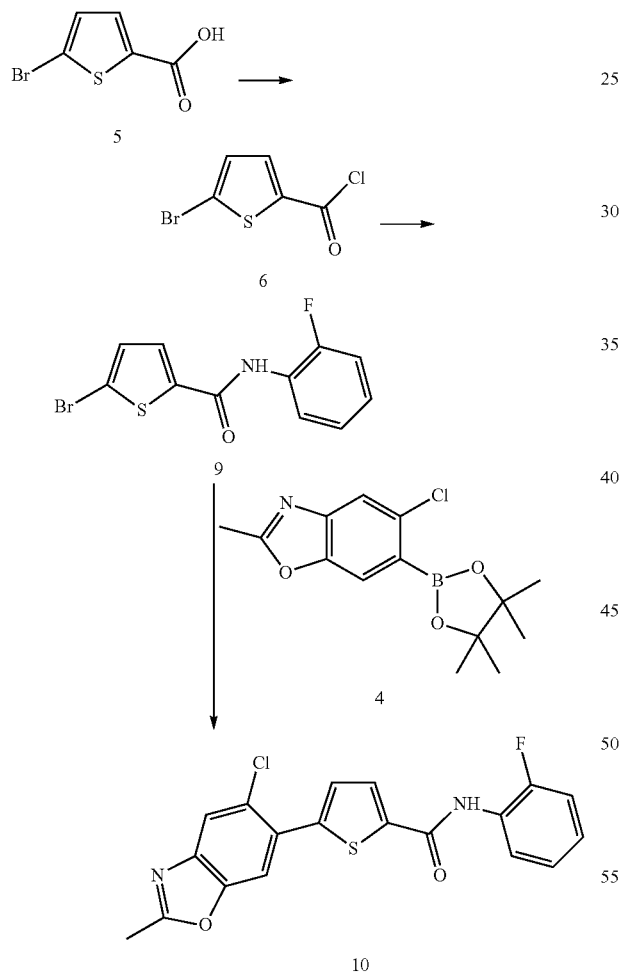

Preparation of (5-bromo(2-thienyl))-N-(2-fluorophenyl)carboxamide (9): A mixture of 5-bromo-thiophene-2-carboxylic acid (5) (207 mg, 1 mmol), oxalyl chloride (420 µl) and catalytic amount of DMF in 5 ml DCM was stirred at r.t for 2 h before evaporation to dryness. The resulting solid residue was dissolved in 5 ml DCM and to which were added 2-fluoroaniline (193 µl, 2 eq) and DIEA (522 µl). The reaction mixture was stirred at r.t for overnight before worked up with EA/aq. HO/brine. The org. phase was concentrated and then purified on a flash silica gel column to give 267 mg (5-bromo(2-thienyl))-N-(2-fluorophenyl)carboxamide (9) as off-white solid. (yield: 89%, purity>95%).

Preparation of [5-(5-chloro-2-methylbenzoxazol-6-yl)(2-thienyl)]-N-(2-fluorophenyl)carboxamide (10): A mixture of (5-bromo(2-thienyl))-N-(2-fluorophenyl)carboxamide (9) (24 mg, 0.08 mmol), 2-(5-chloro-2-methylbenzoxazol-6-yl)-4,4,5,5-tetramethyl-1,3,2-dioxaborolane (4) (23 mg, 0.08 mmol), tetrakis(triphenylphosphine)-palladium(0) (Pd(Ph$_3$P)$_4$, 12 mg) and sodium carbonate (32 mg) in 0.5 ml DME, 0.5 ml EtOH and 0.25 ml water was heated under Ar in microwave reactor at 110° C. for 30 min. The reaction mixture was worked up with EA/brine. Org. phase was concentrated and then subjected to silica gel flash column chromatography. The isolated crude product was re-purified on prep HPLC to furnish 12.1 mg of [5-(5-chloro-2-methylbenzoxazol-6-yl)(2-thienyl)]-N-(2-fluorophenyl)carboxamide (10) as white solid (yield: 39%; purity>95%). LC-MS: calcd. for C$_{19}$H$_{12}$ClFN$_2$O$_2$S: 387 (M+1).

Example 3

Preparation of [5-(5-chloro-2-methylbenzoxazol-6-yl)(2-thienyl)]-N-(2,6-difluorophenyl)carboxamide (11)

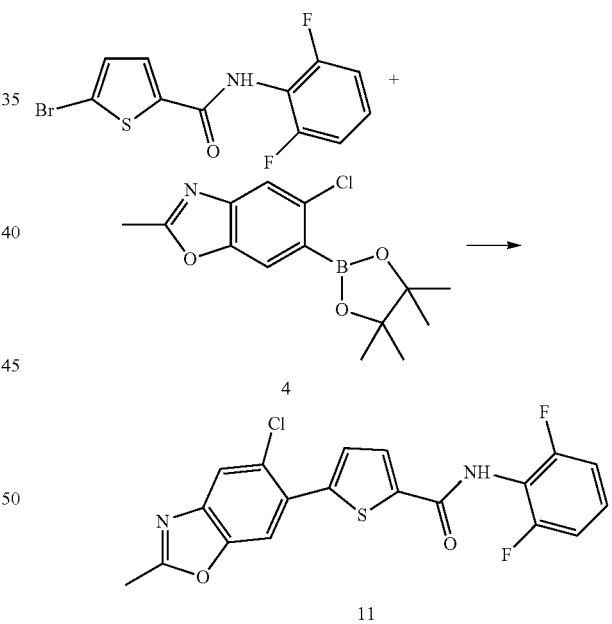

A mixture of (5-bromo(2-thienyl))-N-(2,6-difluorophenyl)carboxamide (25 mg, 0.08 mmol), 2-(5-chloro-2-methylbenzoxazol-6-yl)-4,4,5,5-tetramethyl-1,3,2-dioxaborolane (4) (29 mg, 0.1 mmol), tetrakis(triphenylphosphine)-palladium(0) (Pd(Ph$_3$P)$_4$, 12 mg) and sodium carbonate (32 mg) in 0.5 ml DME, 0.5 ml EtOH and 0.25 ml water was heated under Ar in microwave reactor at 110° C. for 30 min. The reaction mixture was worked up with EA/brine. Org. phase was concentrated and then subjected to silica gel flash column chromatography to furnish 22.4 mg of [5-(5-chloro-2-methylbenzoxazol-6-yl)(2-thienyl)]-N-(2,6-difluorophenyl)carboxamide (11) as yellow solid (yield: 55.3%; purity>95%). LC-MS: calcd. for $C_{19}H_{11}ClF_2N_2O_2S$: 405 (M+1).

Example 4

Preparation of N-(2,6-difluorophenyl)[5-(6-methyl-benzothiazol-5-yl)(2-thienyl)]carboxamide (15)

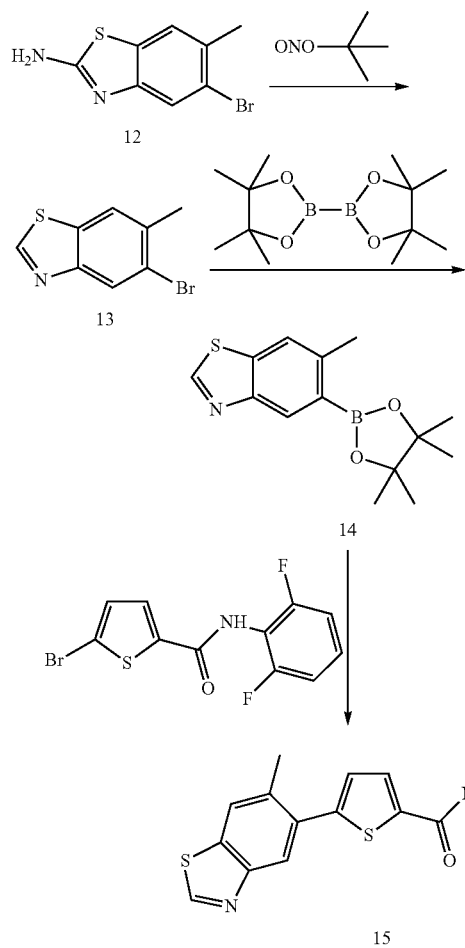

Preparation of 5-bromo-6-methylbenzothiazole (13): A solution of 2-amino-5-bromo-6-methylthiazole (12) (460 mg, 1.89 mmol) and tert-butylnitrite (336 μl, 1.5 eq) in 10 ml DMF was heated at 50° C. to 4 h. After cooling down to r.t., the reaction mixture was diluted with EA, washed with 1N NaOH, brine. Org. phase was dried over sodium sulfate, concentrated and subjected to silica gel flash column chromatography (0-30% B, A: hexane; B: 50% EA in hexane) to give 5-bromo-6-methylbenzothiazole (13) (197 mg, yield: 45.7%, purity>95%) as orange solid.

Preparation of 6-methyl-5-(4,4,5,5-tetramethyl(1,3,2-dioxaborolan-2-yl))benzothiazole (14): A mixture of 5-bromo-6-methylthiazole (13, 114 mg, 0.5 mmol), bis(pinacolato)diboron (152 mg, 0.6 mmol), [1,1'-bis(diphenylphosphino)ferrocene]palladium(II) chloride dichloromethane complex (1:1) (49 mg) and potassium acetate (98 mg, 1 mmol) in 3 ml dioxane was heated under Ar for 16 h at 90° C. After EA/brine work-up, the org. phase was dried over sodium sulfate, concentrated and subjected to silica gel flash column purification to give 100.8 mg 6-methyl-5-(4,4,5,5-tetramethyl(1,3,2-dioxaborolan-2-yl))benzothiazole (14) as white solid (yield: 73.3%; purity>90%).

Preparation of N-(2,6-difluorophenyl)[5-(6-methylbenzothiazol-5-yl)(2-thienyl)]carboxamide (15): A mixture of (5-bromo(2-thienyl)-N-(2,6-difluorophenyl)carboxamide (22 mg, 0.07 mmol), 6-methyl-5-(4,4,5,5-tetramethyl(1,3,2-dioxaborolan-2-yl))benzothiazole (14) (19 mg, 0.07 mmol), tetrakis(triphenylphosphine)-palladium(0) (Pd(Ph$_3$P)$_4$, 8 mg) and sodium carbonate (22 mg) in 0.5 ml DME, 0.5 ml EtOH and 0.25 ml water was heated under Ar in microwave reactor at 110° C. for 30 min. The reaction mixture was worked up with EA/brine. Org. phase was concentrated and then subjected to prep HPLC chromatography to furnish 22.8 mg of N-(2,6-difluorophenyl)[5-(6-methylbenzothiazol-5-yl)(2-thienyl)]carboxamide (15) as white solid (yield: 84.3%; purity>95%). LC-MS: calcd. for $C_{19}H_{12}F_2N_2OS_2$: 387 (M+1).

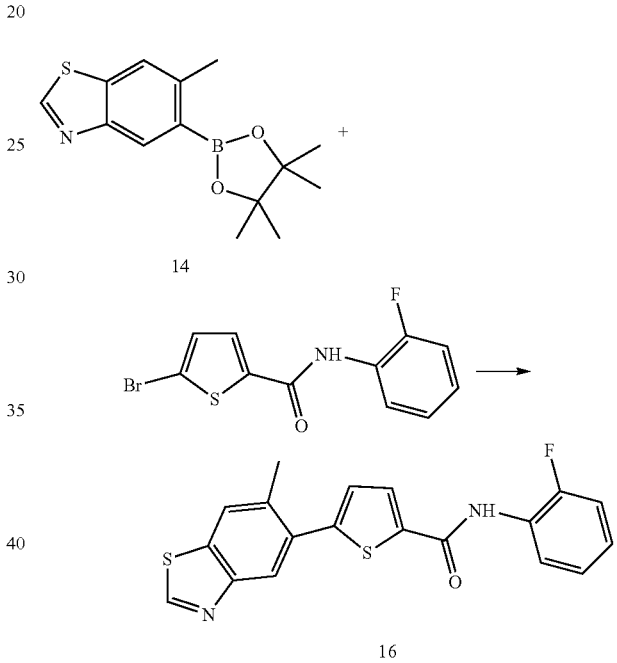

Example 5

Preparation of N-(2-fluorophenyl)[5-(6-methylbenzothiazol-5-yl)(2-thienyl)]carboxamide (16)

A mixture of (5-bromo(2-thienyl))-N-(2-fluorophenyl)carboxamide (9, 21 mg, 0.07 mmol), 6-methyl-5-(4,4,5,5-tetramethyl(1,3,2-dioxaborolan-2-yl))benzothiazole (14) (19 mg, 0.07 mmol), tetrakis(triphenylphosphine)-palladium(0) (Pd(Ph$_3$P)$_4$, 8 mg) and sodium carbonate (22 mg) in 0.5 ml DME, 0.5 ml EtOH and 0.25 ml water was heated under Ar in microwave reactor at 110° C. for 30 min. The reaction mixture was worked up with EA/brine. Org. phase was concentrated and then subjected to prep HPLC chromatography to furnish 23.4 mg of N-(2-fluorophenyl)[5-(6-methylbenzothiazol-5-yl)(2-thienyl)]carboxamide (16) as yellow solid (yield: 90.7%; purity>95%). LC-MS: calcd. for $C_{19}H_{13}FN_2OS_2$: 369 (M+1).

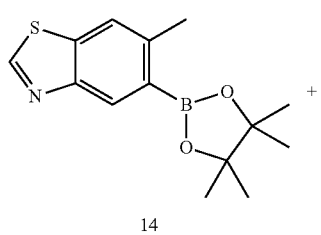

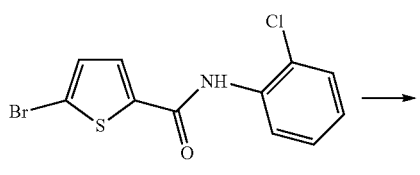

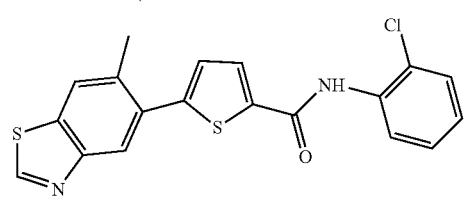

Example 6

Preparation of N-(2-chlorophenyl)[5-(6-methylbenzothiazol-5-yl)(2-thienyl)]carboxamide (17)

A mixture of (5-bromo(2-thienyl))-N-(2-chlorophenyl)carboxamide (7, 21 mg, 0.07 mmol), 6-methyl-5-(4,4,5,5-tetramethyl(1,3,2-dioxaborolan-2-yl))benzothiazole (14) (19 mg, 0.07 mmol), tetrakis(triphenylphosphine)-palladium(0) (Pd(Ph$_3$P)$_4$, 8 mg) and sodium carbonate (22 mg) in 0.5 ml DME, 0.5 ml EtOH and 0.25 ml water was heated under Ar in microwave reactor at 110° C. for 30 min. The reaction mixture was worked up with EA/brine. Org. phase was concentrated and then subjected to prep HPLC chromatography to furnish 22.6 mg of N-(2-chlorophenyl)[5-(6-methylbenzothiazol-5-yl)(2-thienyl)]carboxamide (17) as yellow solid (yield: 83.9%; purity>95%). LC-MS: calcd. for C$_{19}$H$_{13}$ClN$_2$OS$_2$: 385 (M+1).

Example 7

Preparation of N-(2,6-difluorophenyl)[5-(5-chlorobenzothiazol-6-yl)(2-thienyl)]carboxamide (21)

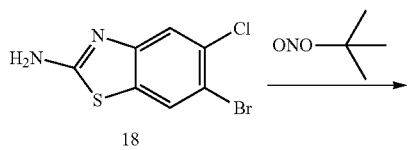

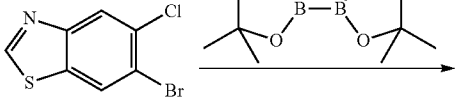

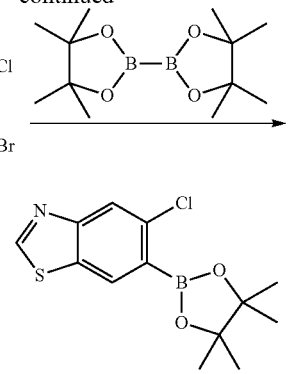

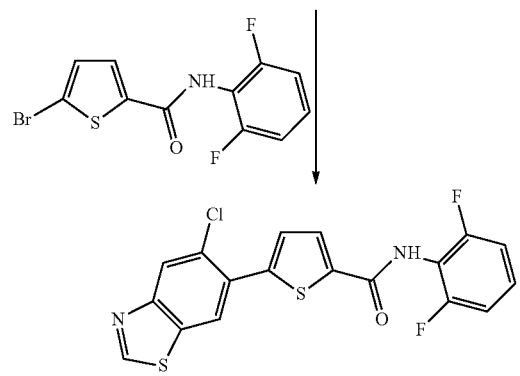

Preparation of 6-bromo-5-chlorobenzothiazole (19): A solution of 2-amino-6-bromo-5-chlorothiazole (18) (210 mg, 0.8 mmol) and tert-butylnitrite (285 µl, 3 eq) in 5 ml DMF was heated at 50° C. to 4 h. After cooling down to r.t., the reaction mixture was diluted with EA, washed with 1N NaOH, saturated NaCO$_3$ then brine. Org. phase was dried over sodium sulfate, concentrated and subjected to silica gel flash column chromatography (0-30% B, A: hexane; B: 50% EA in hexane) to give 6-bromo-5-chlorobenzothiazole (19) (113 mg, yield: 56.8%, purity>95%) as light yellow solid.

Preparation of 5-chloro-6-(4,4,5,5-tetramethyl(1,3,2-dioxaborolan-2-yl))benzothiazole (20): A mixture of 6-bromo-5-chlorobenzothiazole (19, 113 mg, 0.455 mmol), bis(pinacolato)diboron (138 mg, 1.2 eq), [1,1'-bis(diphenylphosphino)ferrocene]palladium(II) chloride dichloromethane complex (1:1) (37 mg) and potassium acetate (89 mg, 2 eq) in 5 ml dioxane was heated under Ar for 16 h at 90° C. After EA/brine work-up, the org. phase was dried over sodium sulfate, concentrated and subjected to silica gel flash column purification (0-40% B, A: hexane; B: 50% EA in hexane) to give 88.4 mg 5-chloro-6-(4,4,5,5-tetramethyl(1,3,2-dioxaborolan-2-yl))benzothiazole (20) as off-white solid (yield: 66.1%; purity>90%).

Preparation of N-(2,6-difluorophenyl)[5-(5-chlorobenzothiazol-6-yl)(2-thienyl)]carboxamide (21): A mixture of (5-bromo(2-thienyl)-N-(2,6-difluorophenyl)carboxamide (19 mg, 0.06 mmol), 5-chloro-6-(4,4,5,5-tetramethyl(1,3,2-dioxaborolan-2-yl))benzothiazole (20) (17 mg, 0.06 mmol), tetrakis(triphenylphosphine)-palladium(0) (Pd(Ph$_3$P)$_4$, 7 mg) and sodium carbonate (19 mg) in 0.5 ml DME, 0.5 ml EtOH and 0.25 ml water was heated under Ar in microwave reactor at 110° C. for 30 min. The reaction mixture was worked up with EA/brine. Org. phase was concentrated and then subjected to silica gel flash chromatography (0-80% B; A: hexane; B: 50% EA in hexane) to furnish 17.8 mg of N-(2,6-difluorophenyl)[5-(5-chlorobenzothiazol-6-yl)(2-thienyl)]carboxamide (21) as white solid (yield: 72.9%; purity>95%). LC-MS: calcd. for $C_{18}H_9F_2ClN_2OS_2$: 407 (M+1).

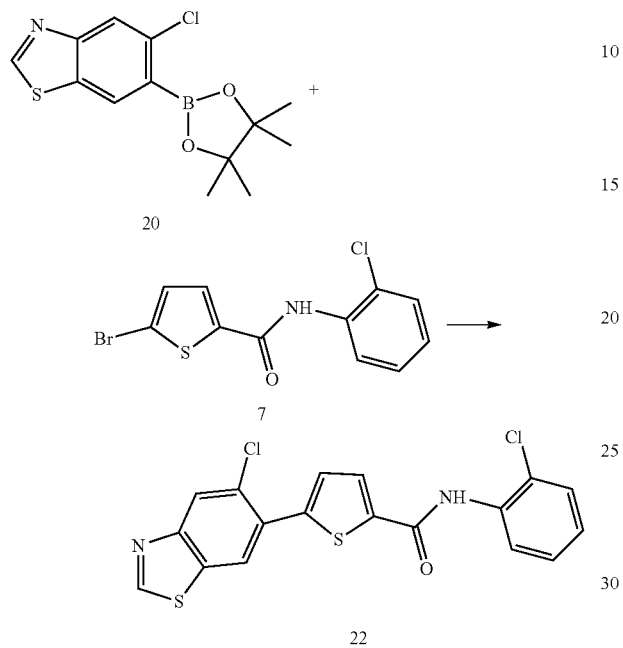

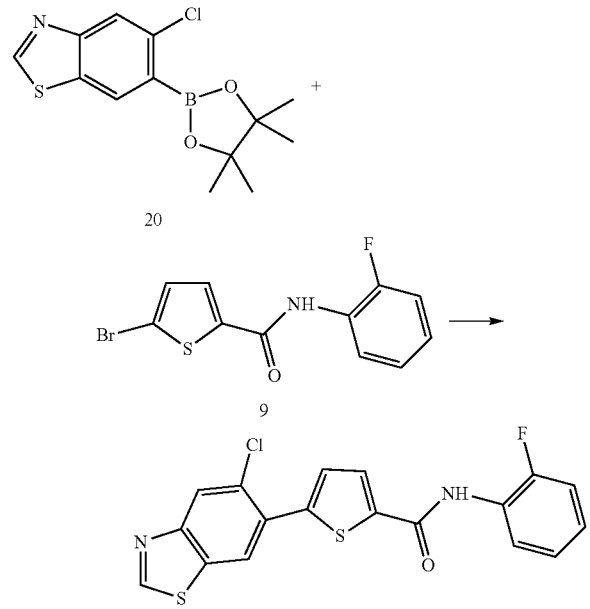

Example 8

Preparation of N-(2-chlorophenyl)[5-(5-chlorobenzothiazol-6-yl)(2-thienyl)]carboxamide (22)

A mixture of (5-bromo(2-thienyl))-N-(2-chlorophenyl)carboxamide (7, 19 mg, 0.06 mmol), 5-chloro-6-(4,4,5,5-tetramethyl(1,3,2-dioxaborolan-2-yl))benzothiazole (20) (17 mg, 0.06 mmol), tetrakis(triphenylphosphine)-palladium(0) (Pd(Ph$_3$P)$_4$, 7 mg) and sodium carbonate (19 mg) in 0.5 ml DME, 0.5 ml EtOH and 0.25 ml water was heated under Ar in microwave reactor at 110° C. for 30 min. The reaction mixture was worked up with EA/brine. Org. phase was concentrated and then subjected to silica gel flash chromatography (0-60% B; A: hexane; B: 50% EA in hexane) to furnish 16.4 mg of N-(2-chlorophenyl)[5-(5-chlorobenzothiazol-6-yl)(2-thienyl)]carboxamide (22) as off-white solid (yield: 67.4%; purity>95%). LC-MS: calcd. for $C_{18}H_{10}Cl_2N_2OS_2$: 406 (M+1).

Example 9

Preparation of [5-(5-chlorobenzothiazol-6-yl)(2-thienyl)]-N-(2-fluorophenyl)carboxamide (23)

A mixture of (5-bromo(2-thienyl))-N-(2-fluorophenyl)carboxamide (9, 18 mg, 0.06 mmol), 5-chloro-6-(4,4,5,5-tetramethyl(1,3,2-dioxaborolan-2-yl))benzothiazole (20) (17 mg, 0.06 mmol), tetrakis(triphenylphosphine)-palladium(0) (Pd(Ph$_3$P)$_4$, 7 mg) and sodium carbonate (19 mg) in 0.5 ml DME, 0.5 ml EtOH and 0.25 ml water was heated under Ar in microwave reactor at 110° C. for 30 min. The reaction mixture was worked up with EA/brine. Org. phase was concentrated and then subjected to silica gel flash chromatography (0-60% B; A: hexane; B: 50% EA in hexane) to furnish 16.7 mg of [5-(5-chlorobenzothiazol-6-yl)(2-thienyl)]-N-(2-fluorophenyl)carboxamide (23) as white solid (yield: 71.6%; purity>95%). LC-MS: calcd. for $C_{18}H_{10}FClN_2OS_2$: 389 (M+1).

Example 10

Preparation of N-(2,6-difluorophenyl)[5-(3,5-dimethylbenzo[d]isoxazol-6-yl)(2-thienyl)]carboxamide (29)

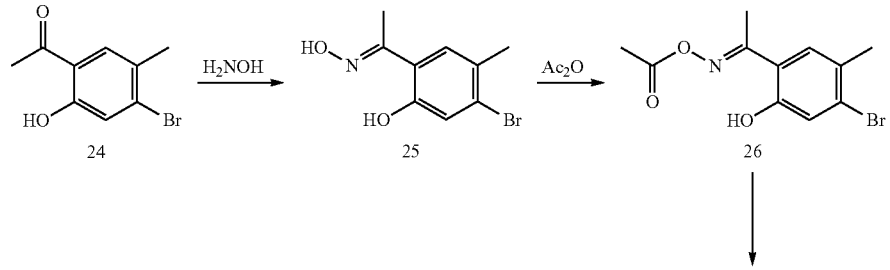

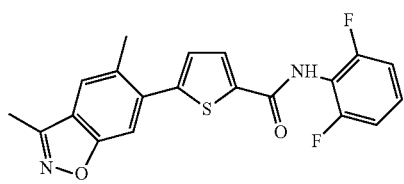 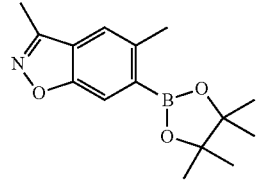 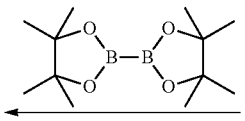

29   28   27

Preparation of 6-bromo-3,5-dimethylbenz[d]isoxazole (27): A solution of hydroxylamine hydrochloride (400 mg, 5 8 mmol) in 1 ml water was added to a solution of NaOAc in 1 ml water. To the resulting solution was added 1-acetyl-4-bromo-2-hydroxy-5-methylbenzene (24) (1.14 g, 5 mmol) followed by addition of 15 ml EtOH. The reaction mixture was stirred at 80° C. for 1 h. After concentrated to half of it's volume, the reaction mixture was poured in to 60 ml ice-water. Precipitate formed was filtered, washed with water and dried to give 1.19 g (yield: 97.5%, purity>95%) 5-bromo-2-((hydroxyimino)ethyl)-4-methylphenol (25) as white solid. The above intermediate 25 (1.19 g, 4.875 mmol) was dissolved in 10 ml Ac$_2$O, stirred at r.t. for 2 h and the reaction mixture turned to a white suspension. After filtration and wash with water 1.0 g 2-(4-bromo-2-hydroxy-5-methylphenyl)-1-azaprop-1-enyl acetate (26) were obtained. EA was added to the filtrate, washed with water. The org. phase was dried over sodium sulfate and concentrated to dryness to give another 370 mg of 26 as off-white solid. (total 1.37 g, yield: 98%, purity>95%). Neat 2-(4-bromo-2-hydroxy-5-methylphenyl)-1-azaprop-1-enyl acetate (26) (0.5 g, 1.748 mmol) was heated at 175° C. for 2 h then at 100° C. for 1 h. After cooling down to r.t., the dark brown solid was dissolved in DCM and subjected to silica gel flash chromatography (0-40% B, A: hexane; B: 50% EA in hexane) to give 6-bromo-3,5-dimethylbenz[d]isoxazole (27) (92 mg, yield: 23.3%; purity>95%) as yellow crystals.

Preparation of 2-(3,5-dimethylbenzo[d]isoxazol-6-yl)-4,4,5,5-tetramethyl(1,3,2-dioxaborolane (28): A mixture of 6-bromo-3,5-dimethylbenz[d]isoxazole (27, 45 mg, 0.2 mmol), bis(pinacolato)diboron (60 mg, 1.2 eq), [1,1'-bis(diphenylphosphino)ferrocene]palladium(II) chloride dichloromethane complex (1:1) (20 mg) and potassium acetate (40 mg, 2 eq) in 2 ml dioxane was heated overnight under Ar at 90° C. After EA/brine work-up, the org. phase was dried over sodium sulfate, concentrated and subjected to silica gel flash column purification (0-40% B, A: hexane; B: 50% EA in hexane) to give 40 mg 2-(3,5-dimethylbenzo[d]isoxazol-6-yl)-4,4,5,5-tetramethyl(1,3,2-dioxaborolane (28) as off-white solid (yield: 73.6%; purity>95%).

Preparation of N-(2,6-difluorophenyl)[5-(3,5-dimethylbenzo[d]isoxazol-6-yl)(2-thienyl)]carboxamide (29): A mixture of (5-bromo(2-thienyl)-N-(2,6-difluorophenyl)carboxamide (23 mg, 0.073 mmol), 2-(3,5-dimethylbenzo[d]isoxazol-6-yl)-4,4,5,5-tetramethyl(1,3,2-dioxaborolane (28) (20 mg, 0.073 mmol), tetrakis(triphenylphosphine)-palladium(0) (Pd(Ph$_3$P)$_4$, 8 mg) and sodium carbonate (29 mg) in 0.5 ml DME, 0.5 ml EtOH and 0.25 ml water was heated under Ar in microwave reactor at 110° C. for 30 min. The reaction mixture was worked up with EA/brine. Org. phase was concentrated and then subjected to silica gel flash chromatography (0-80% B; A: hexane; B: 50% EA in hexane) to furnish 24.9 mg of N-(2,6-difluorophenyl)[5-(3,5-dimethyl-benzo[d]isoxazol-6-yl)(2-thienyl)]carboxamide (29) as white solid (yield: 88.7%; purity>95%). LC-MS: calcd. for C$_{20}$H$_{14}$F$_2$N$_2$O$_2$S: 385 (M+1).

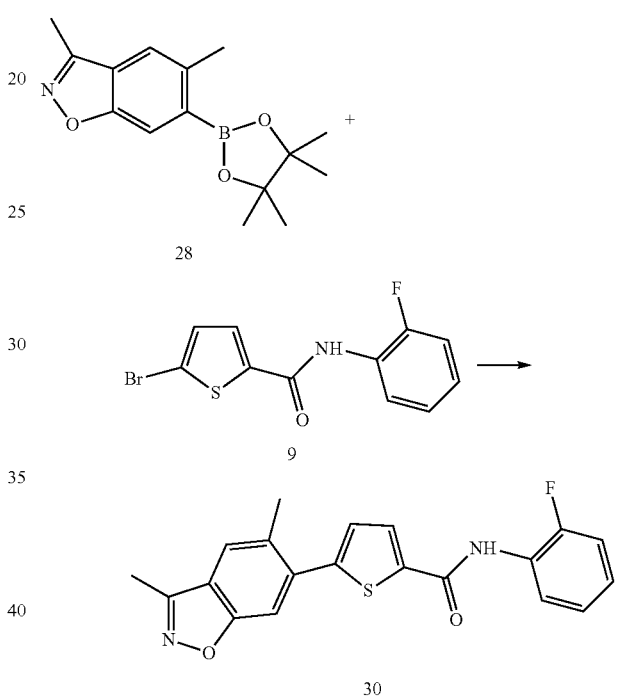

Example 11

Preparation of [5-(3,5-dimethylbenzo[d]isoxazol-6-yl)(2-thienyl)]-N-(2-fluorophenyl)carboxamide (30)

A mixture of (5-bromo(2-thienyl)-N-(2-fluorophenyl)carboxamide (22 mg, 0.073 mmol), 2-(3,5-dimethylbenzo[d]isoxazol-6-yl)-4,4,5,5-tetramethyl(1,3,2-dioxaborolane (28) (20 mg, 0.073 mmol), tetrakis(triphenylphosphine)-palladium(0) (Pd(Ph$_3$P)$_4$, 8 mg) and sodium carbonate (29 mg) in 0.5 ml DME, 0.5 ml EtOH and 0.25 ml water was heated under Ar in microwave reactor at 110° C. for 30 min. The reaction mixture was worked up with EA/brine. Org. phase was concentrated and then subjected to silica gel flash chromatography (0-80% B; A: hexane; B: 50% EA in hexane) to furnish 22.4 mg of [5-(3,5-dimethylbenzo[d]isoxazol-6-yl)(2-thienyl)]-N-(2-fluorophenyl)carboxamide (30) as light yellow solid (yield: 83.7%; purity>95%). LC-MS: calcd. for C$_{20}$H$_{15}$FN$_2$O$_2$S: 367 (M+1).

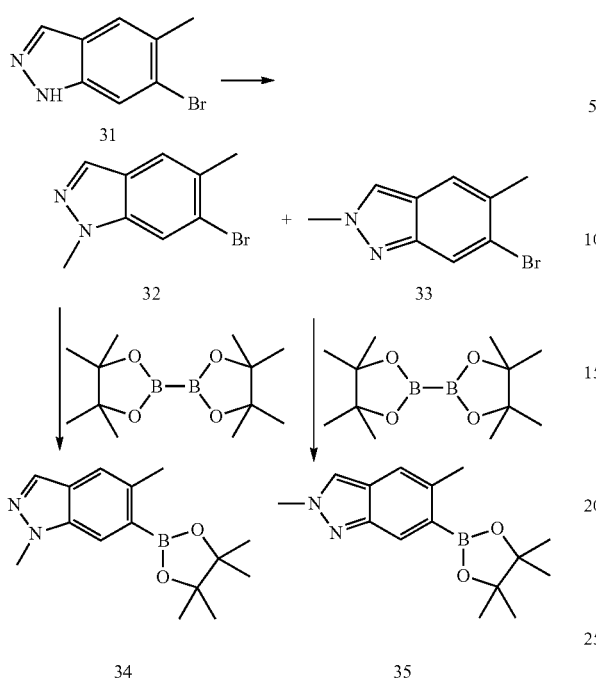

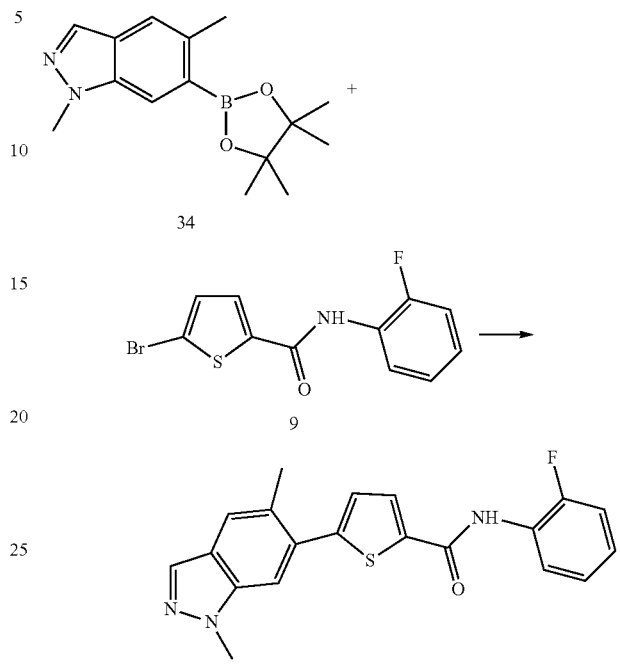

Preparation of 6-bromo-1,5-dimethyl-1H-indazole (32) and 6-bromo-2,5-dimethyl-2H-indazole (33): To a solution of 6-bromo-5-methyl-1H-indazole (31, 211 mg, 1 mmol) in 5 ml dry THF was carefully added sodium hydride (200 mg, 60%). The suspension was stirred at r.t for 2 h before addition of methyl iodide (93 μl, 1.5 eq). After stirring at r.t. for 3 h, the reaction mixture was worked up with EA/brine. Org. phase was dried over sodium sulfate, concentrated and then subjected to silica gel column chromatography (0-50%-100% B; A: hexane; B: 50% EA in hexane) to give 101.4 mg of 6-bromo-1,5-dimethyl-1H-indazole (32) as white solid (yield: 45.0%; purity>95%) and 99.9 mg of 6-bromo-2,5-dimethyl-2H-indazole (33) as white solid (yield: 44.4%; purity>95%).

Preparation of 2-(1,5-dimethyl(1H-indazole-6-yl))-4,4,5,5-tetramethyl-1,3,2-dioxaborolane (34): A mixture of 6-bromo-1,5-dimethyl-1H-indazole (32, 98 mg, 0.44 mmol), bis(pinacolato)diboron (132 mg, 1.2 eq), [1,1'-bis(diphenylphosphino)ferrocene]palladium(II) chloride dichloromethane complex (1:1) (40 mg) and potassium acetate (80 mg, 2 eq) in 4 ml dioxane was heated overnight under Ar at 90° C. After EA/brine work-up, the org. phase was dried over sodium sulfate, concentrated and subjected to silica gel flash column purification (0-70% B, A: hexane; B: 50% EA in hexane) to give 100 mg 2-(1,5-dimethyl(1H-indazole-6-yl))-4,4,5,5-tetramethyl-1,3,2-dioxaborolane (34) as white solid (yield: 83.5%; purity>90%).

Preparation of 2-(2,5-dimethyl(2H-indazole-6-yl))-4,4,5,5-tetramethyl-1,3,2-dioxaborolane (35): A mixture of 6-bromo-2,5-dimethyl-2H-indazole (33, 95 mg, 0.42 mmol), bis(pinacolato)diboron (130 mg, 1.2 eq), [1,1'-bis(diphenylphosphino)ferrocene]palladium(II) chloride dichloromethane complex (1:1) (40 mg) and potassium acetate (80 mg, 2 eq) in 4 ml dioxane was heated overnight under Ar at 90° C. After EA/brine work-up, the org. phase was dried over sodium sulfate, concentrated and subjected to silica gel flash column purification (0-80% B, A: hexane; B: 50% EA in hexane) to give 112 mg 2-(2,5-dimethyl(2H-indazole-6-yl))-4,4,5,5-tetramethyl-1,3,2-dioxaborolane (35) as off-white solid (yield: 97.9%; purity 90%).

Example 12

Preparation of [5-(1,5-dimethyl(1H-indazol-6-yl)(2-thienyl)]-N-(2-fluorophenyl)carboxamide (36)

A mixture of (5-bromo(2-thienyl)-N-(2-fluorophenyl)carboxamide (24 mg, 0.08 mmol), 2-(1,5-dimethyl(1H-indazole-6-yl))-4,4,5,5-tetramethyl-1,3,2-dioxaborolane (34) (20 mg, 0.08 mmol), tetrakis(triphenylphosphine)-palladium(0) (Pd(Ph$_3$P)$_4$, 12 mg) and sodium carbonate (32 mg) in 0.5 ml DME, 0.5 ml EtOH and 0.25 ml water was heated under Ar in microwave reactor at 110° C. for 30 min. The reaction mixture was worked up with EA/brine. Org. phase was concentrated and then subjected to silica gel flash chromatography (0-70% B; A: hexane; B: 50% EA in hexane) to furnish 28.5 mg of [5-(1,5-dimethyl(1H-indazol-6-yl)(2-thienyl)]-N-(2-fluorophenyl)carboxamide (36) as white solid (yield: 97.5%; purity>95%). LC-MS: calcd. for C$_{20}$H$_{16}$FN$_3$OS: 366 (M+1).

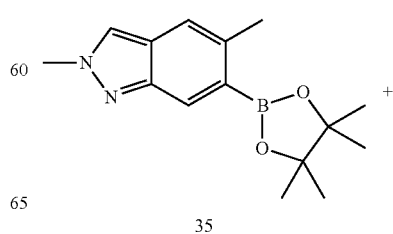

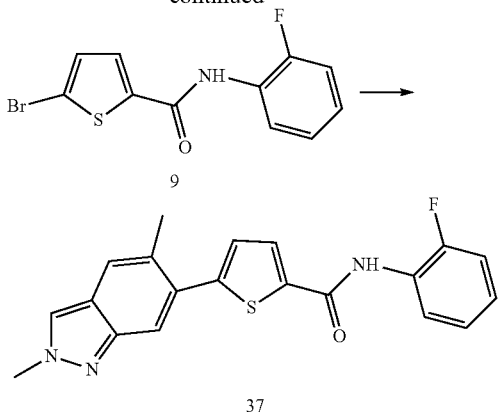

Example 13

Preparation of [5-(2,5-dimethyl(2H-indazol-6-yl)(2-thienyl)]-N-(2-fluorophenyl)carboxamide (37)

A mixture of (5-bromo(2-thienyl)-N-(2-fluorophenyl)carboxamide (24 mg, 0.08 mmol), 2-(2,5-dimethyl(2H-indazole-6-yl))-4,4,5,5-tetramethyl-1,3,2-dioxaborolane (35) (22 mg, 0.08 mmol), tetrakis(triphenylphosphine)-palladium(0) (Pd(Ph$_3$P)$_4$, 12 mg) and sodium carbonate (32 mg) in 0.5 ml DME, 0.5 ml EtOH and 0.25 ml water was heated under Ar in microwave reactor at 110° C. for 30 min. The reaction mixture was worked up with EA/brine. Org. phase was concentrated and then subjected to silica gel flash chromatography (0-80% B; A: hexane; B: 50% EA in hexane) to furnish 22.4 mg of [5-(2,5-dimethyl(2H-indazol-6-yl)(2-thienyl)]-N-(2-fluorophenyl)carboxamide (37) as off-white solid (yield: 76.7%; purity>95%). LC-MS: calcd. for C$_{20}$H$_{16}$FN$_3$OS: 366 (M+1).

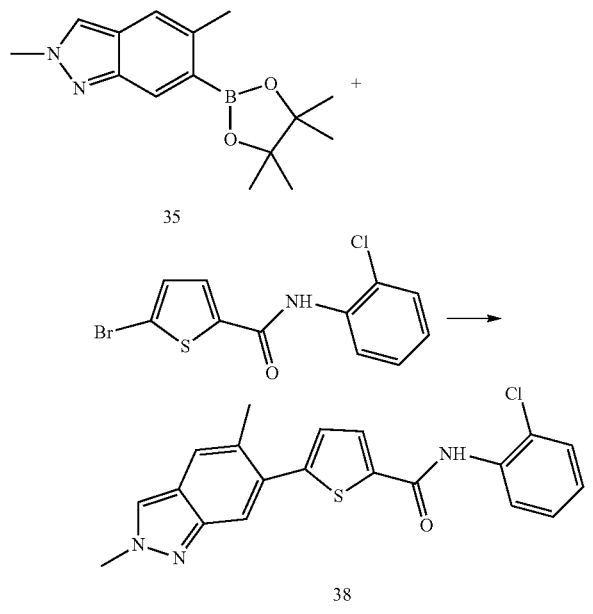

Example 14

Preparation of [5-(2,5-dimethyl(2H-indazol-6-yl)(2-thienyl)]-N-(2-chlorophenyl)carboxamide (38)

A mixture of (5-bromo(2-thienyl)-N-(2-chlorophenyl)carboxamide (25 mg, 0.08 mmol), 2-(2,5-dimethyl(2H-indazole-6-yl))-4,4,5,5-tetramethyl-1,3,2-dioxaborolane (35) (22 mg, 0.08 mmol), tetrakis(triphenylphosphine)-palladium(0) (Pd(Ph$_3$P)$_4$, 12 mg) and sodium carbonate (32 mg) in 0.5 ml DME, 0.5 ml EtOH and 0.25 ml water was heated under Ar in microwave reactor at 110° C. for 30 min. The reaction mixture was worked up with EA/brine. Org. phase was concentrated and then subjected to silica gel flash chromatography (0-80% B; A: hexane; B: 50% EA in hexane) to furnish 21 mg of [5-(2,5-dimethyl(2H-indazol-6-yl)(2-thienyl)]-N-(2-chlorophenyl)carboxamide (38) as yellow solid (yield: 68.7%; purity>95%). LC-MS: calcd. for C$_{20}$H$_{16}$ClN$_3$OS: 382 (M+1).

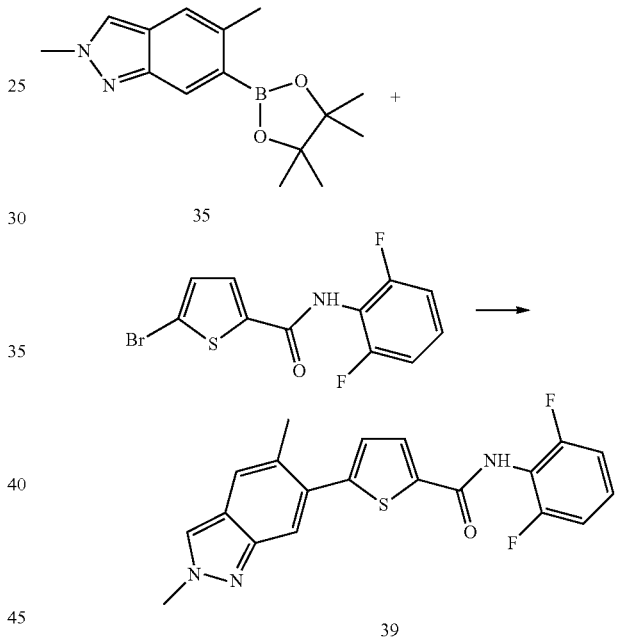

Example 15

Preparation of [5-(2,5-dimethyl(2H-indazol-6-yl)(2-thienyl)]-N-(2,6-difluorophenyl)carboxamide (39)

A mixture of (5-bromo(2-thienyl)-N-(2,6-difluorophenyl)carboxamide (26 mg, 0.08 mmol), 2-(2,5-dimethyl(2H-indazole-6-yl))-4,4,5,5-tetramethyl-1,3,2-dioxaborolane (35) (22 mg, 0.08 mmol), tetrakis(triphenylphosphine)-palladium(0) (Pd(Ph$_3$P)$_4$, 12 mg) and sodium carbonate (32 mg) in 0.5 ml DME, 0.5 ml EtOH and 0.25 ml water was heated under Ar in microwave reactor at 110° C. for 30 min. The reaction mixture was worked up with EA/brine. Org. phase was concentrated and then subjected to silica gel flash chromatography (0-100% B; A: hexane; B: 50% EA in hexane) to furnish 21.4 mg of [5-(2,5-dimethyl(2H-indazol-6-yl)(2-thienyl)]-N-(2,6-difluorophenyl)carboxamide (39) as yellow solid (yield: 69.8%; purity>95%). LC-MS: calcd. for C$_{20}$H$_{15}$F$_2$N$_3$OS: 384 (M+1).

Example 16

Preparation of N-(2,6-difluorophenyl){5-[1-methyl-3-(5-methyl(1,2,4-oxadiazol-3-yl))pyrazol-5-yl](2-thienyl)}carboxamide (44)

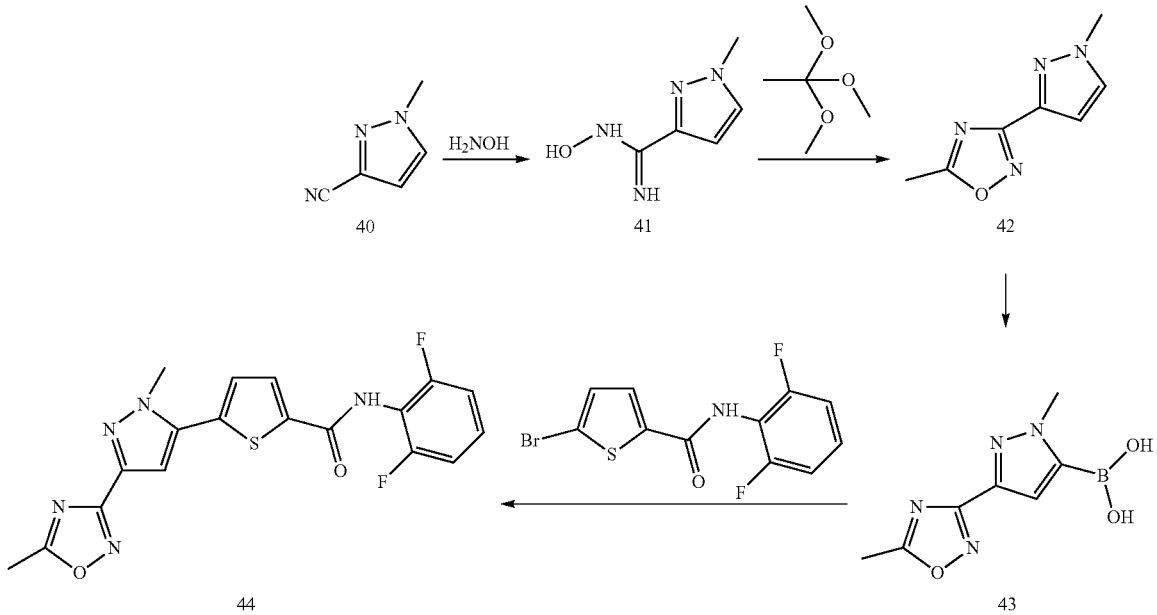

Preparation of 5-methyl-3-(1-methylpyrazol-3-yl)-1,2,4-oxadiazole (42): To a suspension of hydroxylamine hydrochloride (351 mg, 5.05 mmol) in 4 ml EtOH was added 1.86 ml 21% wt sodium ethoxide in ethanol. The resulting mixture was stirred for 10 min at r.t. before addition of 3-cyano-1-methylpyrazole (40) (535 mg, 5 mmol). The resulting suspension was heated overnight at 90° C. After cooling down, the reaction mixture was diluted with EA then washed with brine. Org. phase was concentrated to dryness to give 506 mg crude intermediate 41. A mixture of the above crude intermediate 41, trifluoromethanesulfonic acid Ytterbium (III) salt (22 mg, 1% mol) and trimethyl orthoacetate (550 µl, 1.2 eq.) in 5 ml EtOH was heated at 85° C. for 2 h. After cooling down to r.t., fine needles formed. After filtration and wash with MeOH 166 mg intermediate 41 was recovered as pale yellow needles. The filtrate was concentrated, subjected to silica gel column purification using 0-100% B (A: hexane; B: EA) to furnish 230 mg 5-methyl-3-(1-methylpyrazol-3-yl)-1,2,4-oxadiazole (42) as white solid.

Preparation of [1-methyl-3-(5-methyl-1,2,4-oxadiazol-3-yl)]pyrazol-5-yl-boronic acid (43): A solution of n-butyllithium (1.12 ml, 2.5M in hexane) in hexane was added dropwise to a cold solution of 5-methyl-3-(1-methylpyrazol-3-yl)-1,2,4-oxadiazole (42) (230 mg, 1.4 mmol) in 7 ml dry THF at −70° C. The reaction mixture was stirred at the same temperature for 3 h before addition of trimethyl borate (468 µl, 3 eq). The mixture was allowed to warm up slowly to r.t. and the stirred at r.t. for overnight. The reaction was quenched with 15 ml 1N HCl. After stirred at r.t. for 2 h, EA was added and then washed with brine. Org. phase was extracted with 1N NaOH. The aq. phase was acidified with HCl to pH=2 then extracted with EA. EA phase was washed with brine, dried over sodium sulfate and concentrated to dryness to give 374 mg [1-methyl-3-(5-methyl-1,2,4-oxadiazol-3-yl)]pyrazol-5-yl-boronic acid (43) as yellow solid.

Preparation of N-(2,6-difluorophenyl){5-[1-methyl-3-(5-methyl(1,2,4-oxadiazol-3-yl))pyrazol-5-yl](2-thienyl)}carboxamide (44): A mixture of (5-bromo(2-thienyl)-N-(2,6-difluorophenyl)carboxamide (32 mg, 0.1 mmol), [1-methyl-3-(5-methyl-1,2,4-oxadiazol-3-yl)]pyrazol-5-yl-boronic acid (43) (31 mg, 0.15 mmol), tetrakis(triphenylphosphine)-palladium(0) (Pd(Ph₃P)₄, 18 mg) and sodium carbonate (33 mg) in 0.5 ml DME, 0.5 ml EtOH and 0.25 ml water was heated under Ar in microwave reactor at 110° C. for 30 min. The reaction mixture was worked up with EA/brine. Org. phase was concentrated and then subjected to silica gel flash chromatography (0-100% B; A: hexane; B: 50% EA in hexane) to furnish 14.6 mg of N-(2,6-difluorophenyl){5-[1-methyl-3-(5-methyl(1,2,4-oxadiazol-3-yl))pyrazol-5-yl](2-thienyl)}carboxamide (44) as off-white solid (yield: 36.4%; purity>95%). LC-MS: calcd. for $C_{18}H_{13}F_2N_5O_2S$: 402 (M+1).

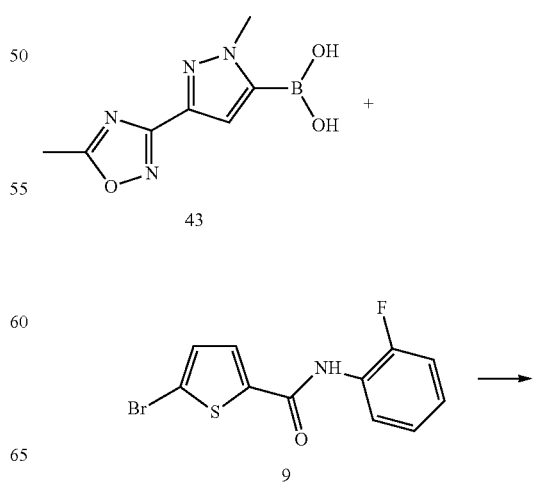

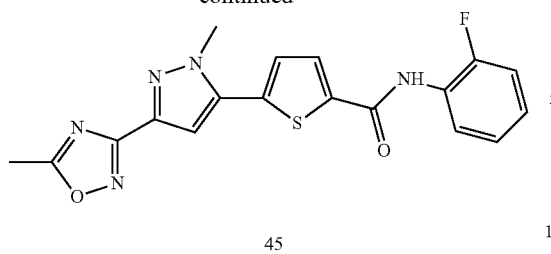

45

Example 17

Preparation of N-(2-fluorophenyl){5-[1-methyl-3-(5-methyl(1,2,4-oxadiazol-3-yl))pyrazol-5-yl](2-thienyl)}carboxamide (45)

A mixture of (5-bromo(2-thienyl)-N-(2-fluorophenyl)carboxamide (15 mg, 0.05 mmol), [1-methyl-3-(5-methyl-1,2,4-oxadiazol-3-yl)]pyrazol-5-yl-boronic acid (43) (21 mg, 0.1 mmol), tetrakis(triphenylphosphine)-palladium(0) (Pd(Ph$_3$P)$_4$, 12 mg) and sodium carbonate (22 mg) in 0.5 ml DME, 0.5 ml EtOH and 0.25 ml water was heated under Ar in microwave reactor at 110° C. for 30 min. The reaction mixture was worked up with EA/brine. Org. phase was concentrated and then subjected to prep HPLC purification to give 4.2 mg product, which was re-purified on a pencil silica column using 50% EA in hexane to give 2.8 mg N-(2-fluorophenyl){5-[1-methyl-3-(5-methyl(1,2,4-oxadiazol-3-yl))pyrazol-5-yl](2-thienyl)}carboxamide (45) as white solid (yield: 7.3%; purity>95%). LC-MS: calcd. for C$_{18}$H$_{14}$FN$_5$O$_2$S: 384 (M+1).

Example 18

Preparation of (2-chlorophenyl)-N-{5-[1-methyl-3-(5-methyl(1,2,4,-oxadiazol-3-yl))pyrazol-5-yl](1,3-thiazol-2-yl)}carboxamide (48)

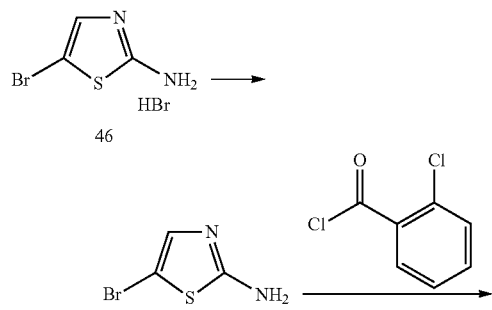

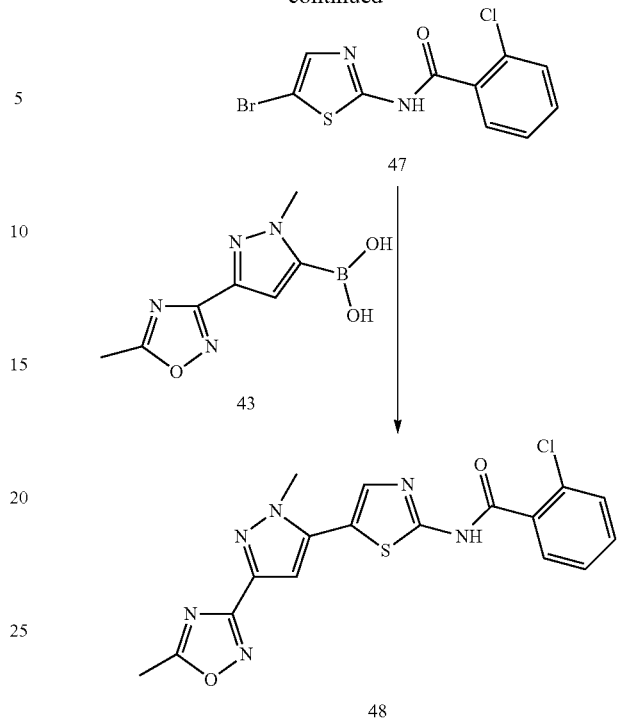

Preparation of N-(5-bromo(1,3-thiazol-2-yl))(2-chlorophenyl)carboxamide (47): A mixture of 2-amino-5-bromothiazole hydrobromide (46, 2.6 g, 10 mmol) in 100 ml EA was shaken with aq. NaCO$_3$. The org. phase was dried over sodium sulfate and concentrated to give free aminobromothiazole, which was dissolved in 25 ml DCM. To the resulting solution were added 2-chlorobenzoyl chloride (1.52 ml, 12 mmol), DIEA (5.2 ml, 3 eq) and DMAP (10 mg). After stirred at r.t for overnight, the reaction mixture was worked up with DCM/aq. NaCO$_3$, the DCM phase was concentrated to dryness. The solid residue was dissolved in 20 ml THF/MeOH/H$_2$O (5:4:1). 10 ml of 1N NaOH were added and mixture was stirred at r.t for 4 h before worked up DCM//aq. NaCO$_3$. DCM phase was concentrated and subjected to silica gel column to give 1.165 g of N-(5-bromo(1,3-thiazol-2-yl))(2-chlorophenyl)carboxamide (47) as yellow solid (yield: 36.9%; purity>95%).

Preparation of (2-chlorophenyl)-N-{5-[1-methyl-3-(5-methyl(1,2,4,-oxadiazol-3-yl))pyrazol-5-yl](1,3-thiazol-2-yl)}carboxamide (48): A mixture of N-(5-bromo(1,3-thiazol-2-yl))(2-chlorophenyl)carboxamide (47, 32 mg, 0.1 mmol), [1-methyl-3-(5-methyl-1,2,4-oxadiazol-3-yl)]pyrazol-5-yl-boronic acid (43) (31 mg, 0.15 mmol), [1,1'-bis(diphenylphosphino)ferrocene]palladium(II) chloride dichloromethane complex (1:1) (12 mg) and potassium phosphate (32 mg) in 1 ml DMF and 0.2 ml water was heated under Ar in microwave reactor at 150° C. for 30 min. The reaction mixture was worked up with EA/brine. Org. phase was concentrated and then subjected to prep HPLC purification to give 5.8 mg (2-chlorophenyl)-N-{5-[1-methyl-3-(5-methyl(1,2,4,-oxadiazol-3-yl))pyrazol-5-yl](1,3-thiazol-2-yl)}carboxamide (48) as light brown solid (yield: 14.5%; purity>95%). LC-MS: calcd. for C$_{17}$H$_{13}$ClN$_6$O$_2$S: 401 (M+1).

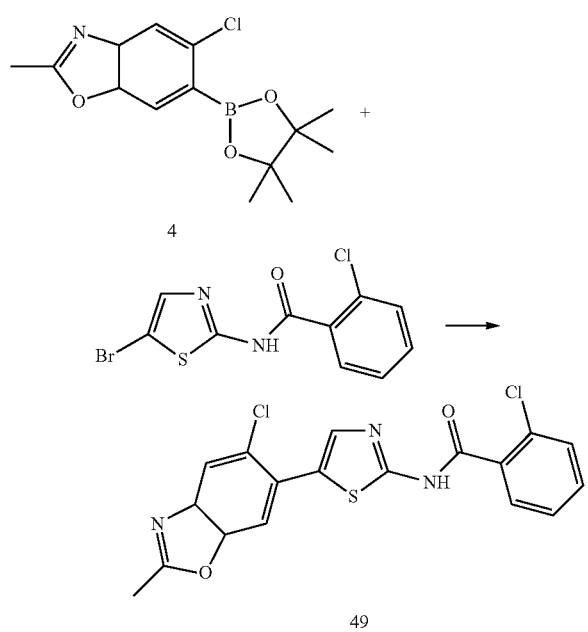

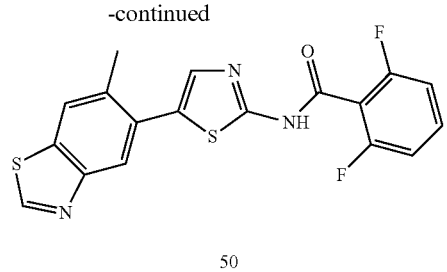

Example 19

Preparation of N-[5-(5-chloro-2-methybenzoxazol-6-yl)(1,3-thiazol-2-yl)](2-chlorophenyl)carboxamide (49)

A mixture of N-(5-bromo(1,3-thiazol-2-yl))(2-chlorophenyl)carboxamide (47, 25 mg, 0.08 mmol), 2-(5-chloro-2-methylbenzoxzzol-6-yl)-4,4,5,5-tetramethyl-1,3,2-dioxaborolane (4) (29 mg, 0.1 mmol), [1,1'-bis(diphenylphosphino)ferrocene]palladium(II) chloride dichloromethane complex (1:1) (12 mg) and potassium phosphate (21 mg) in 1 ml DMF and 0.2 ml water was heated under Ar in microwave reactor at 150° C. for 30 min. The reaction mixture was worked up with EA/brine. Org. phase was concentrated and then subjected to prep HPLC purification to give 3.1 mg N-[5-(5-chloro-2-methybenzoxazol-6-yl)(1,3-thiazol-2-yl)](2-chlorophenyl)carboxamide (49) as pale brown solid (yield: 9.6%; purity>90%). LC-MS: calcd. for $C_{18}H_{11}Cl_2N_3O_2S$: 405 (M+1).

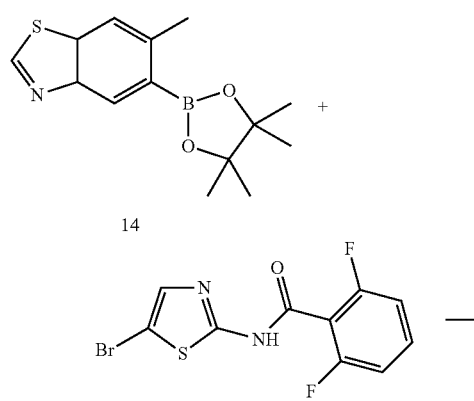

Example 20

Preparation of (2,6-difluorophenyl)-N-[5-(6-methylbenzoxazol-5-yl)(1,3-thiazol-2-yl)]carboxamide (50)

A mixture of N-(5-bromo(1,3-thiazol-2-yl))(2,6-difluorophenyl)carboxamide (31 mg, 0.1 mmol), 6-methyl-5-(4,4,5,5-tetramethyl(1,3,2-dioxaborolan-2-yl))benzothiazole (14) (27 mg, 0.1 mmol), tetrakis(triphenylphosphine)-palladium(0) (Pd(Ph₃P)₄, 12 mg) and sodium carbonate (32 mg) in 0.5 ml DME, 0.5 ml EtOH and 0.2 ml water was heated under Ar in microwave reactor at 110° C. for 30 min. The reaction mixture was worked up with EA/brine. Org. phase was concentrated and then subjected to prep HPLC purification to give 4.6 mg (2,6-difluorophenyl)-N-[5-(6-methylbenzoxazol-5-yl)(1,3-thiazol-2-yl)]carboxamide (50) as pale brown solid (yield: 11.9%; purity>90%). LC-MS: calcd. for $C_{18}H_{11}F_2N_3OS_2$: 388 (M+1).

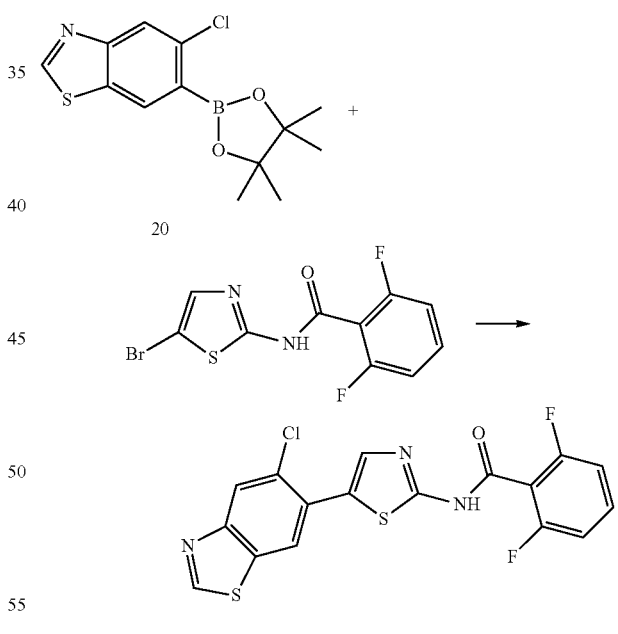

Example 21

Preparation of (2,6-difluorophenyl)-N-[5-(5-chlorobenzoxazol-6-yl)(1,3-thiazol-2-yl)]carboxamide (51)

A mixture of N-(5-bromo(1,3-thiazol-2-yl))(2,6-difluorophenyl)carboxamide (38 mg, 0.12 mmol), 5-chloro-6-(4,4, 5,5-tetramethyl(1,3,2-dioxaborolan-2-yl))benzothiazole (20) (34 mg, 0.12 mmol), tetrakis(triphenylphosphine)-palladium(0) (Pd(Ph₃P)₄, 14 mg) and sodium carbonate (38 mg) in 1.0 ml DME, 0.5 ml EtOH and 0.25 ml water was heated under Ar in microwave reactor at 110° C. for 30 min. The reaction mixture was worked up with EA/brine. Org. phase was concentrated and then subjected to prep HPLC purification to give 7.1 mg (2,6-difluorophenyl)-N-[5-(5-chlorobenzoxazol-6-yl)(1,3-thiazol-2-yl)]carboxamide (51) as pale brown solid (yield: 14.5%; purity>95%). LC-MS: calcd. for $C_{17}H_8ClF_2N_3OS_2$: 408 (M+1).

Example 22

Preparation of (2-chlorophenyl)-N-[5-(1-methylindol-2-yl)(1,3-thiazol-2-yl)]carboxamide (54)

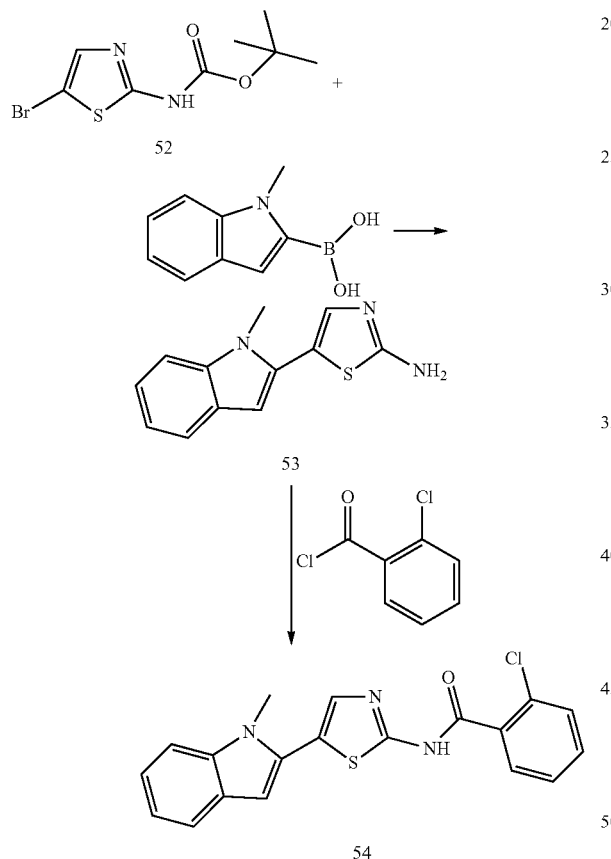

Preparation of 5-(1-methylindol-2-yl)-1,3-thiazole-2-ylamine (53): A mixture of (tert-butoxy)-N-(5-bromo(1,3-thiazol-2-yl)carboxamide (52, 140 mg, 0.5 mmol), 1-methylindol-2-yl boronic acid (88 mg, 0.5 mmol), [1,1'-bis(diphenylphosphino)ferrocene]palladium(II) chloride dichloromethane complex (1:1) (40 mg) and potassium phosphate (106 mg) in 2 ml DMF and 0.5 ml water was heated under Ar in microwave reactor at 150° C. for 30 min. The reaction mixture was worked up with EA/brine. Org. phase was concentrated and then subjected to silica gel flash column purification (0-100% B, A: hexane; B: EA) to give 21 mg 5-(1-methylindol-2-yl)-1,3-thiazole-2-ylamine (53) as brown solid (yield: 18.3%; purity>90%).

Preparation of (2-chlorophenyl)-N-[5-(1-methylindol-2-yl)(1,3-thiazol-2-yl)]carboxamide (54): To a mixture of 5-(1-methylindol-2-yl)-1,3-thiazole-2-ylamine (53, 10 mg, 0.043 mmol) in 1 ml DCM were added 2-chlorobenzoyl chloride (11 μl, 2 eq), DIEA (37 μl, 3 eq) and DMAP (2 mg). After stirred at r.t for overnight, the reaction mixture was worked up with DCM/aq. NaCO₃, the DCM phase was concentrated to dryness. The solid residue was dissolved in 2 ml THF/MeOH/H₂O (5:4:1). 0.1 ml of 1N NaOH were added and mixture was stirred at r.t for 1 h before worked up DCM//aq. NaCO₃. DCM phase was concentrated and subjected to silica gel flash column to give 15.3 mg of (2-chlorophenyl)-N-[5-(1-methylindol-2-yl)(1,3-thiazol-2-yl)]carboxamide (54) as yellow solid (yield: 97%; purity>95%). LC-MS: calcd. for $C_{18}H_{14}ClN_3OS$: 368 (M+1).

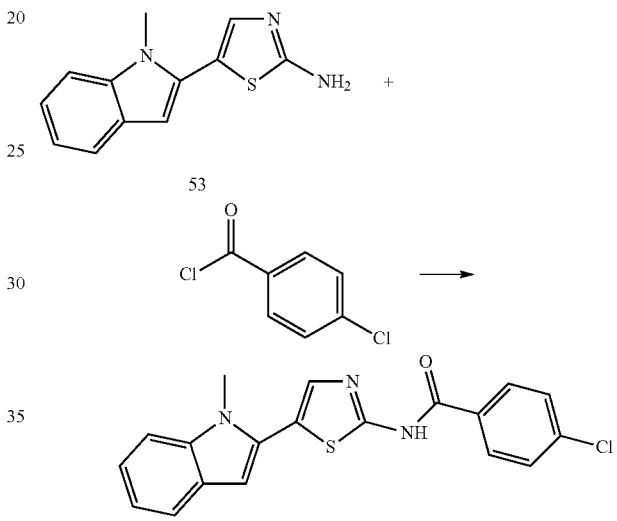

Example 23

Preparation of (4-chlorophenyl)-N-[5-(1-methylindol-2-yl)(1,3-thiazol-2-yl)]carboxamide (55)

In a similar way, (4-chlorophenyl)-N-[5-(1-methylindol-2-yl)(1,3-thiazol-2-yl)]carboxamide (55) (15 mg, yield 94.8%; purity>90%) was synthesized starting from 5-(1-methylindol-2-yl)-1,3-thiazole-2-ylamine (53, 10 mg, 0.043 mmol) by reacting with 4-chlorobenzoyl chloride. LC-MS: calcd. for $C_{18}H_{14}ClN_3OS$: 368 (M+1).

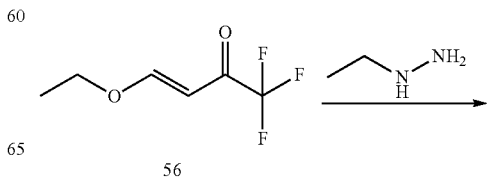

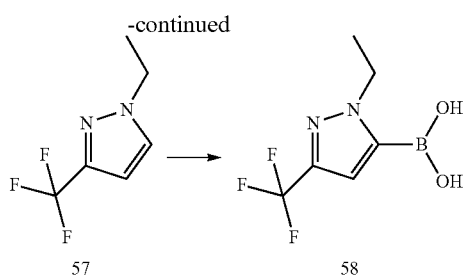

Preparation of (1-ethyl-3-(trifluoromethyl)-1H-pyrazol-5-yl)boronic acid (58): To a mixture of compound 56 (100 g, 0.595 mol) and methanol (400 mL) was added ethyl hydrazine (113 g, 1.2 mol) at r.t. The mixture was refluxed for 4 h. The mixture was poured into water (1 L) and extracted with DCM (600 mL). The organic layer was washed with water (3×400 mL), brine, dried over Na₂SO₄, concentrated. The residue was distillated to give compound 57 (35 g, 35.8%) as a light yellow liquid.

To a solution of compound 57 (35 g, 0.21 mol) in dry THF (400 mL) was added n-BuLi (256 mL, 0.64 mol, 2.5 M) at −78° C. triisopropyl borate (79 g, 0.42 mol) was added after the mixture was stirred at −78° C. for 20 min. The mixture was stirred at r.t. overnight. The mixture was adjusted pH to 5 with 1M HCl. The mixture was separated with EtOAc (500 mL) and water (500 mL). The aqueous layer was extracted with EtOAc (3×500 mL). The organic layers were combined and washed with brine and concentrated to 58 (25 g, 57%) as a yellow oil.

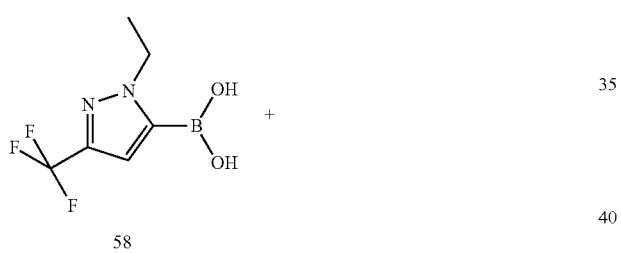

Example 24

Preparation of (2-chlorophenyl)-N-{5-[1-ethyl-3-(trifluoromethyl)pyrazol-5-yl](1,3-thiazol-2-yl)}carboxamide (59)

A mixture of N-(5-bromo(1,3-thiazol-2-yl))(2-chlorophenyl)carboxamide (47, 62 mg, 0.2 mmol), (1-ethyl-3-(trifluoromethyl)-1H-pyrazol-5-yl)boronic acid (58) (62 mg, 0.3 mmol), [1,1'-bis(diphenylphosphino)ferrocene]palladium (II) chloride dichloromethane complex (1:1) (24 mg) and potassium phosphate (63 mg) in 2 ml DMA and 0.5 ml water was heated under Ar in microwave reactor at 150° C. for 30 min. The reaction mixture was worked up with EA/brine. Org. phase was concentrated and then subjected to prep HPLC purification to give 11.5 mg (2-chlorophenyl)-N-{5-[1-ethyl-3-(trifluoromethyl)pyrazol-5-yl](1,3-thiazol-2-yl)}carboxamide (59) as dark brown solid (yield: 14%; purity>90%). LC-MS: calcd. for $C_{16}H_{12}ClF_3N_4OS$: 401 (M+1).

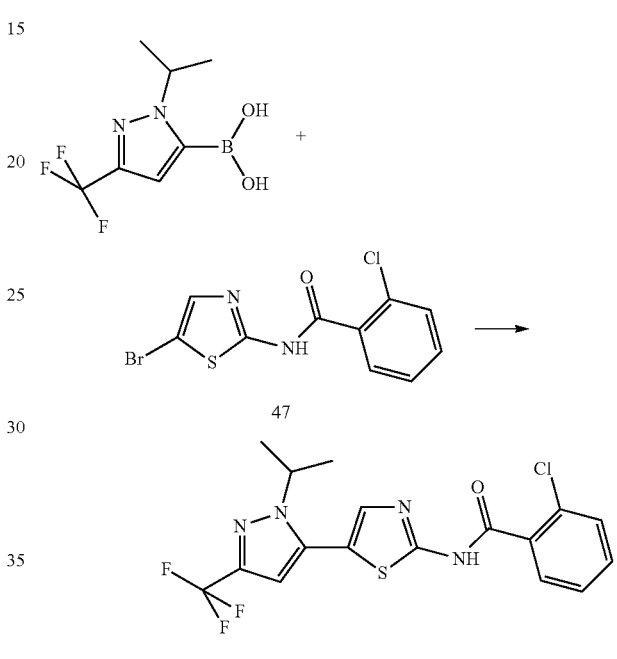

Example 25

Preparation of (2-chlorophenyl)-N-{5-[1-(methylethyl)-3-(trifluoromethyl)pyrazol-5-yl](1,3-thiazol-2-yl)}carboxamide (60)

In a similar way, (2-chlorophenyl)-N-{5-[1-(methylethyl)-3-(trifluoromethyl)pyrazol-5-yl](1,3-thiazol-2-yl)}carboxamide (60) (8.1 mg, dark brown solid, yield 9.8%; yield>95%) was made from N-(5-bromo(1,3-thiazol-2-yl))(2-chlorophenyl)carboxamide (47, 62 mg, 0.2 mmol) by coupling with (1-(methylethyl)-3-(trifluoromethyl)-1H-pyrazol-5-yl)boronic acid (66 mg, 0.3 mmol). LC-MS: calcd. for $C_{17}H_{14}ClF_3N_4OS$: 415 (M+1).

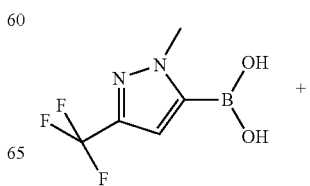

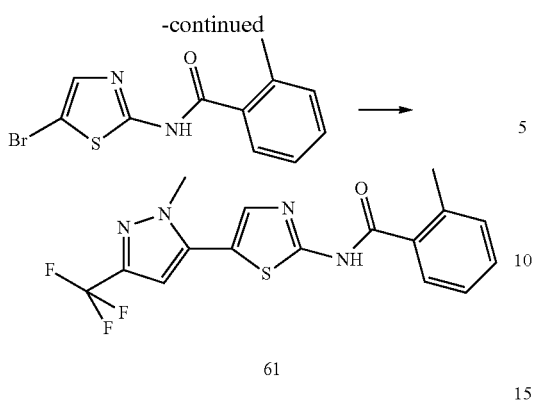

61

Example 26

Preparation of (3-methyl(2-pyridyl))-N-{5-[1-methyl-3-(trifluoromethyl)pyrazol-5-yl](1,3-thiazol-2-yl)}carboxamide (61)

In a similar way, (3-methyl(2-pyridyl))-N-{5-[1-methyl-3-(trifluoromethyl)pyrazol-5-yl] (1,3-thiazol-2-yl)}carboxamide (61) (2.3 mg, yellow solid, yield 7.2%; yield>95%) was made from N-(5-bromo(1,3-thiazol-2-yl))(3-methyl(2-pyridyl))carboxamide (25.9 mg, 0.087 mmol) by coupling with (1-methyl-3-(trifluoromethyl)-1H-pyrazol-5-yl)boronic acid (34 mg, 2 eq). LC-MS: calcd. for $C_{15}H_{12}F_3N_5OS$: 368 (M+1).

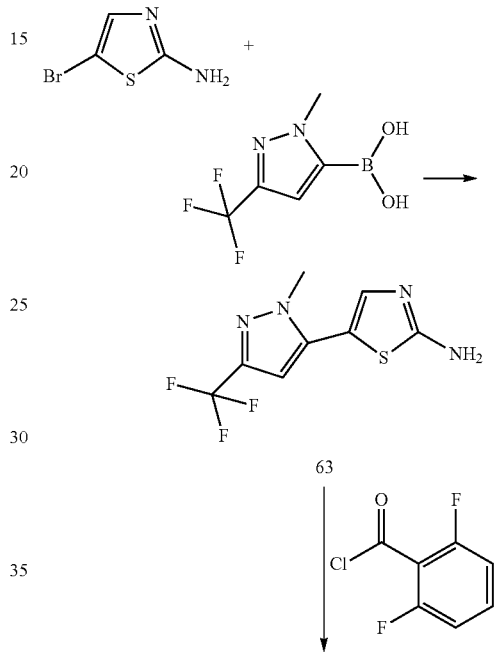

62

Example 27

Preparation of (2-chlorophenyl)-N-{5-[1-methyl-3-(trifluoromethyl)pyrazol-5-yl](1,3-thiazol-2-yl)}carboxamide (62)

In a similar way, (2-chlorophenyl)-N-{5-[1-methyl-3-(trifluoromethyl)pyrazol-5-yl] (1,3-thiazol-2-yl)}carboxamide (62) (10.4 mg, white solid, yield 5.4%; yield>95%) was made from N-(5-bromo(1,3-thiazol-2-yl))(2-chlorophenyl)carboxamide (47, 158 mg, 0.5 mmol) by coupling with (1-methyl-3-(trifluoromethyl)-1H-pyrazol-5-yl)boronic acid (145 mg, 0.75 mmol). LC-MS: calcd. for $C_{15}H_{10}ClF_3N_4OS$: 387 (M+1).

Example 28

Preparation of (2,6-difluorophenyl)-N-{5-[1-methyl-3-(trifluoromethyl)pyrazol-5-yl](1,3-thiazol-2-yl)}carboxamide (64)

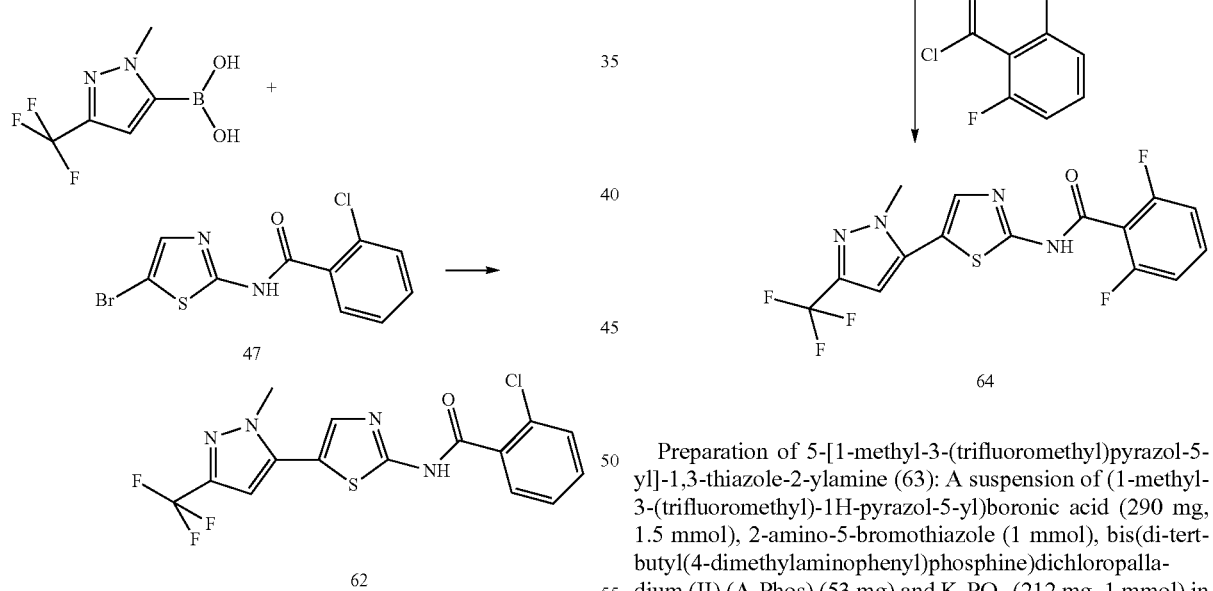

Preparation of 5-[1-methyl-3-(trifluoromethyl)pyrazol-5-yl]-1,3-thiazole-2-ylamine (63): A suspension of (1-methyl-3-(trifluoromethyl)-1H-pyrazol-5-yl)boronic acid (290 mg, 1.5 mmol), 2-amino-5-bromothiazole (1 mmol), bis(di-tert-butyl(4-dimethylaminophenyl)phosphine)dichloropalladium (II) (A-Phos) (53 mg) and $K_3PO_4$ (212 mg, 1 mmol) in 2 ml ACN, 2 ml dioxane, 0.5 ml $H_2O$ was bubbled with argon before heated at 70° C. for 1 h. After cooling down to r.t., the reaction mixture was taken up in EA, washed with aq. $NaHCO_3$ and brine, dried over $Na_2SO_4$, concentrated to dryness. Prep HPLC purification furnished 4.6 mg 5-[1-methyl-3-(trifluoromethyl)pyrazol-5-yl]-1,3-thiazole-2-ylamine (63) as light yellow solid (yield 1.9%; purity>95%).

Preparation of (2,6-difluorophenyl)-N-{5-[1-methyl-3-(trifluoromethyl)pyrazol-5-yl](1,3-thiazol-2-yl)}carboxamide (64): To a mixture of 5-[1-methyl-3-(trifluoromethyl)pyrazol-5-yl]-1,3-thiazole-2-ylamine (63, 4.6 mg, 0.019 mmol) in 0.5 ml DCM were added 2,6-difluorobenzoyl chloride (5 µl, 2 eq), DIEA (17 µl, 3 eq) and DMAP (2 mg). After stirred at r.t for overnight, the reaction mixture was worked up with DCM/aq. NaCO₃, the DCM phase was concentrated to dryness. The solid residue was dissolved in 1 ml THF/MeOH/H₂O (5:4:1). 0.1 ml of 1N NaOH were added and mixture was stirred at r.t for 1 h before worked up DCM//aq. NaCO₃. DCM phase was concentrated and subjected to silica gel flash column to give 5.6 mg of (2,6-difluorophenyl)-N-{5-[1-methyl-3-(trifluoromethyl)pyrazol-5-yl] (1,3-thiazol-2-yl)}carboxamide (64) as white solid (yield: 75.9%; purity>95%). LC-MS: calcd. for $C_{15}H_9F_5N_4OS$: 389 (M+1).

Example 29

Preparation of (2-chlorophenyl)-N-{2-[1-methyl-3-(trifluoromethyl)pyrazol-5-yl](1,3-thiazol-5-yl)}carboxamide (67)

3-(trifluoromethyl)pyrazol-5-yl]-1,3-thiazole (66) as brown thick oil which was used directly used for next step reaction.

Preparation of (2-chlorophenyl)-N-{2-[1-methyl-3-(trifluoromethyl)pyrazol-5-yl](1,3-thiazol-5-yl)}carboxamide (67): To a mixture of 5-amino-2-[1-methyl-3-(trifluoromethyl)pyrazol-5-yl]-1,3-thiazole (66, 8.1 mg, 0.03 mmol) in 1 ml DCM were added 2-chlorobenzoyl chloride (3.8 µl, 2 eq), DIEA (52 µl, 3 eq) and DMAP (2 mg). After stirred at r.t for 2 h, the reaction mixture was worked up with DCM/aq. NaCO₃, the DCM phase was concentrated to dryness. The solid residue was dissolved in 1 ml THF/MeOH/H₂O (5:4:1). 0.06 ml of 1N NaOH were added and mixture was stirred at r.t for 1 h before worked up DCM//aq. NaCO₃. DCM phase was concentrated and subjected to prep HPLC purification to give 3.7 mg of (2-chlorophenyl)-N-{2-[1-methyl-3-(trifluoromethyl)pyrazol-5-yl](1,3-thiazol-5-yl)}carboxamide (67) as

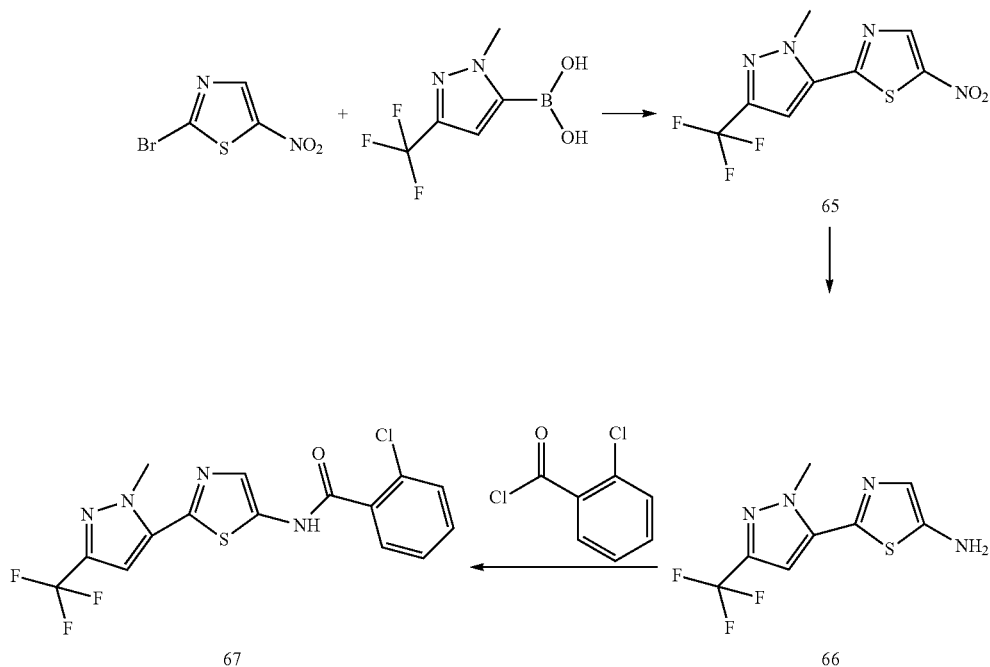

Preparation of 2-[1-methyl-3-(trifluoromethyl)pyrazol-5-yl]-5-nitro-1,3-thiazole (65): A mixture of 2-bromo-5-nitrothiazole (209 mg, 1 mmol), (1-methyl-3-(trifluoromethyl)-1H-pyrazol-5-yl)boronic acid (194 mg, 1 mmol), tetrakis(triphenylphosphine)-palladium(0) (Pd(Ph₃P)₄, 57 mg) and sodium carbonate (212 mg) in 3 ml DME, 0.5 ml EtOH and 0.5 ml water was heated under Ar in microwave reactor at 110° C. for 30 min. The reaction mixture was worked up with EA/brine. Org. phase was concentrated and then subjected to silica gel flash chromatography (0-30% B; A: hexane; B: 50% EA in hexane) to furnish 37.5 mg of 2-[1-methyl-3-(trifluoromethyl)pyrazol-5-yl]-5-nitro-1,3-thiazole (65) as light yellow solid (yield: 13.5%; purity>90%).

Preparation of 5-amino-2-[1-methyl-3-(trifluoromethyl)pyrazol-5-yl]-1,3-thiazole (66): A mixture of 2-[1-methyl-3-(trifluoromethyl)pyrazol-5-yl]-5-nitro-1,3-thiazole (65, 350 mg, 0.13 mmol) and Pd/C in 4 ml MeOH was stirred under H₂ balloon at r.t. for 4 h before filtered thru celite. The filtrate was concentrated to dryness to give 8.1 mg 5-amino-2-[1-methylyellow solid (yield: 31.9%; purity>90%). LC-MS: calcd. for $C_{15}H_{10}ClF_3N_4OS$: 387 (M+1).

Examples 30-34

Preparation of {4-Amino-5-[1-methyl-3-(trifluoromethyl)pyrazol-5-yl](2-thienyl)}-N-(2,6-difluorophenyl)carboxamide (72)

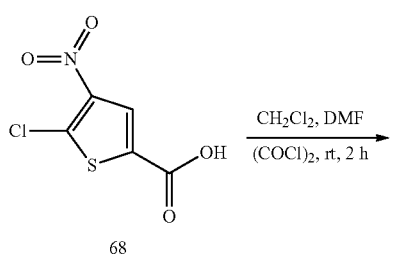

68

-continued

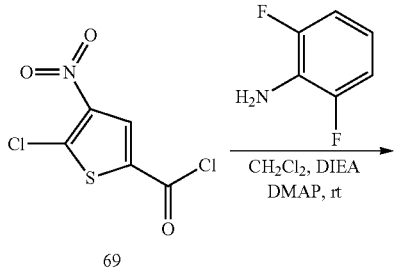

69

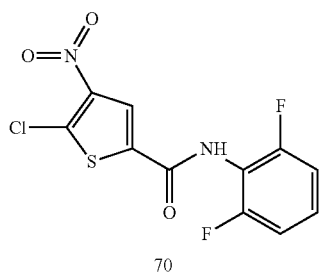

70

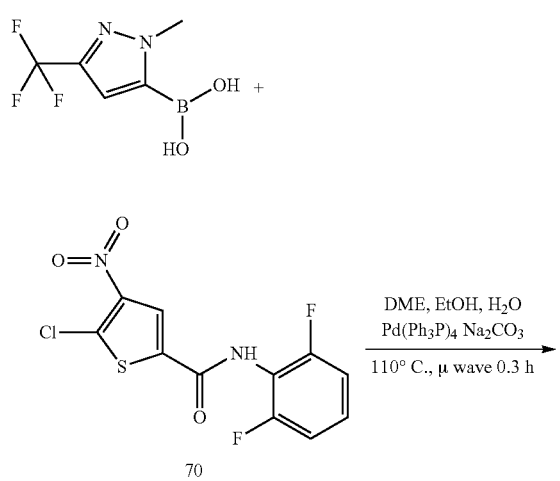

71

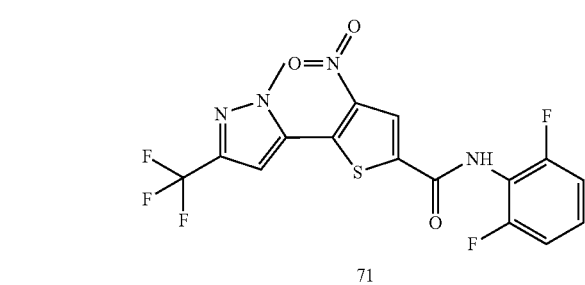

71

-continued

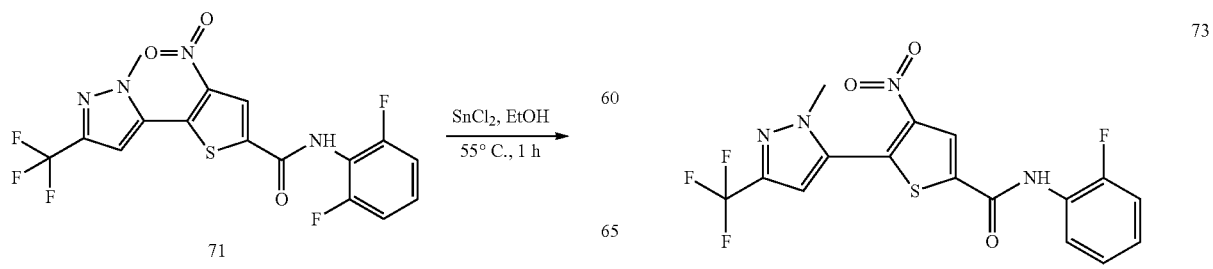

72

To a solution of 68 (414 mg, 2 mmol) in CH$_2$Cl$_2$ (10 ml) was added 1 drop of N,N-dimethylformamide (DMF). The oxalyl chloride (508 mg, 0.34 mL, 4 mmol) was added slowly to above solution. The reaction mixture was stirred overnight at room temperature. The organic solvent was removed in vacuo and dried. The residual 69 was dissolved in CH$_2$Cl$_2$ (10 ml) and 2,6-difluoroaniline (516 mg, 4 mmol) was added along with N,N-diisopropylethylamine (DIEA, 1 g, 1.4 mL, 8 mmol). The mixture was stirred for 2 h at room temperature. The reaction was quenched with saturated NaHCO$_3$ (20 mL) and extracted with EtOAc (20 mL×2). The combined organic layers were dried (Na$_2$SO$_4$) and concentrated in vacuo. The residue was purified by flash column and compound 70 (105 mg, 16%) was obtained as yellow solid.

The (1-methyl-3-(trifluoromethyl)-1H-pyrazol-5-yl)boronic acid (29 mg, 0.15 mmol) and 70 (40 mg, 0.12 mmol) was dissolved in 1 mL dimethoxyethane and 1 mL EtOH. The 0.5 ml of 2 M Na$_2$CO$_3$ was added and the mixture was bubbled with Ar for 1 min before add tetrakis(triphenylphosphine)-palladium(0) (Pd(Ph$_3$P)$_4$, 12 mg, 0.01 mmol). The reaction was heated at 110° C. for 30 min under microwave initiator. The reaction mixture was worked-up with EtOAc extraction and product was purified by flash column and afforded 71 as yellow solid.

To a solution of 71 in EtOH (10 ml) was added SnCl$_2$.2H$_2$O (226 mg, 1 mmol) and reaction mixture was heated at 55° C. for 4 h. The solvent was removed in vacuo and residue was treated with water and EtOAc. The organic phase was separated and aqueous was extracted with EtOAc (20 mL×2). The final product was purified by HPLC and compound 72 (9.5 mg, 20%) was afforded as yellow solid. LC-MS: calcd. for C$_{16}$H$_{11}$F$_5$N$_4$OS: 403 (M+1).

Compounds 73-76 were prepared using similar procedure of 72. For compound 75, LC-MS: calcd. for C$_{16}$H$_{12}$F$_4$N$_4$OS: 385 (M+1). For compound 76, LC-MS: calcd. for C$_{16}$H$_{12}$ClF$_3$N$_4$OS: 401 (M+1).

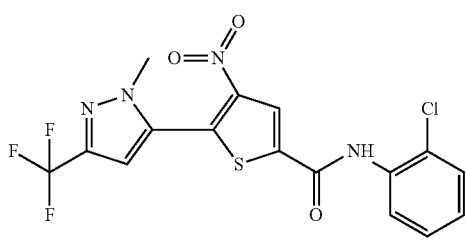

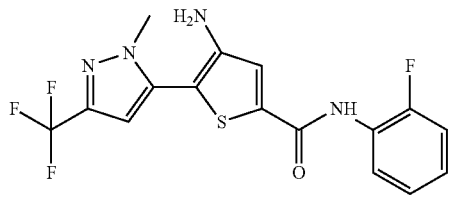

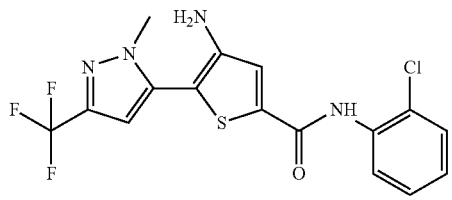

Examples 35-41

Preparation of N-(2,6-difluorophenyl){5-[3-(2-fluorophenyl)-1-methylpyrazol-5-yl](2-thienyl)}carboxamide (83)

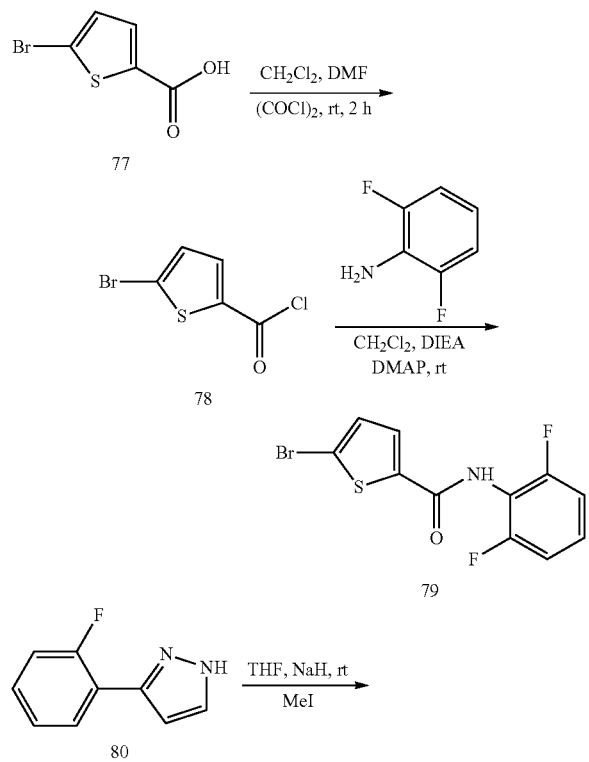

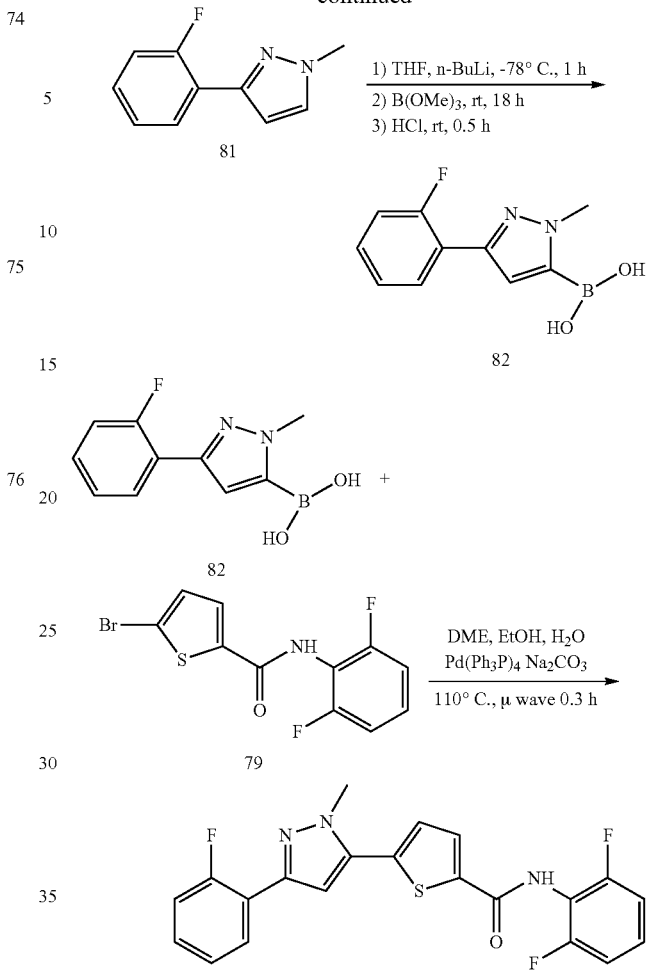

To a solution of 77 (207 mg, 1 mmol) in CH₂Cl₂ (10 ml) was added 1 drop of N,N-dimethylformamide (DMF). The oxalyl chloride (254 mg, 0.17 mL, 2 mmol) was added slowly to above solution. The reaction mixture was stirred overnight at room temperature. The organic solvent was removed in vacuo and dried. The residue was dissolved in CH₂Cl₂ (10 ml) and 2,6-difluoroaniline (258 mg, 2 mmol) was added along with N,N-diisopropylethylamine (DIEA, 0.5 g, 0.7 mL, 4 mmol). The mixture was stirred for 2 h at room temperature. The reaction was quenched with saturated NaHCO₃ (20 mL) and extracted with EtOAc (20 mL×2). The combined organic layers were dried (Na₂SO₄) and concentrated in vacuo. The residue was purified by flash column and compound 79 (105 mg, 16%) was obtained as yellow solid.

To a solution of 80 (1 g, 6.0 mmol) in THF (50 mL) was added NaH (0.57 g, 24 mmol). The mixture was stirred for 1 h and the MeI (1.75 g, 12 mmol) was added in one potion. The reaction mixture was stirred for 18 h at room temperature. The reaction was quenched with MeOH and solvent was removed in vacuo. The residue was treated with water and EtOAc. The organic layer was separated and aqueous was extracted with EtOAc. The combined organic phase was dried over Na₂SO₄, filtered, concentrated to give crude product. The crude product was purified on ISCO columns. Fractions containing pure product were combined and evaporated. The yellow oil 81 (0.97 g, 92%) was obtained.

A solution of 81 (971 mg, 5.51 mmol) in THF (20 ml) was cooled at −78° C. followed by adding 2.5 M n-BuLi (3.3 mL, 8.26 mmol). The mixture was stirred for 4 h at −78° C. and the trimethyl borate (1 mL, 8.96 mmol) was added. The reaction mixture was warmed up to room temperature and stirred overnight. The reaction was quenched with 1M HCl and stirred for 0.5 h. The mixture was extracted with EtOAc (20 mL×2). The organic phase was washed with 1M NaOH. The aqueous was acidified with con. HCl and extracted with EtOAc. The combined organic phase was dried over $Na_2SO_4$, filtered, concentrated to give boronic acid 82 (994 mg, 82%) as yellow solid.

The boronic acid 82 (22 mg, 0.1 mmol) and 79 (32 mg, 0.1 mmol) was dissolved in 1 mL dimethoxyethane and 1 mL EtOH. The 0.5 ml of 2 M $Na_2CO_3$ was added and the mixture was bubbled with Ar for 1 min before add tetrakis(triphenylphosphine)-palladium(0) $(Pd(Ph_3P)_4$, 12 mg, 0.01 mmol). The reaction was heated at 110° C. for 30 min under microwave initiator. The reaction mixture was worked-up with EtOAc extraction and product was purified by HPLC and afforded 83 (26 mg, 63%) as white solid. LC-MS: calcd. for $C_{21}H_{14}F_3N_3OS$: 414 (M+1).

Compounds 84-89 were prepared using similar procedure of 83. For compound 84, LC-MS: calcd. for $C_{20}H_{13}F_3N_4OS$: 415 (M+1). For compound 85, LC-MS: calcd. for $C_{20}H_{14}F_2N_4OS$: 397 (M+1). For compound 86, LC-MS: calcd. for $C_{20}H_{14}F_2N_4OS$: 397 (M+1). For compound 87, LC-MS: calcd. for $C_{20}H_{13}ClF_2N_4OS$: 431 (M+1). For compound 88, LC-MS: calcd. for $C_{21}H_{15}F_2N_3OS$: 396 (M+1). For compound 89, LC-MS: calcd. for $C_{21}H_{15}ClFN_3OS$: 412 (M+1).

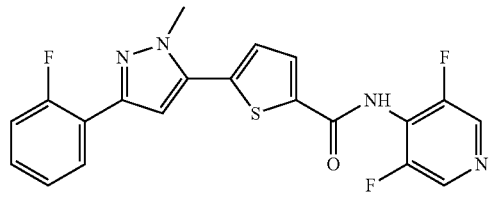

84

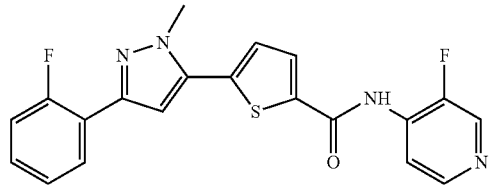

85

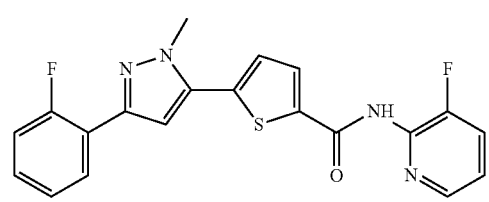

86

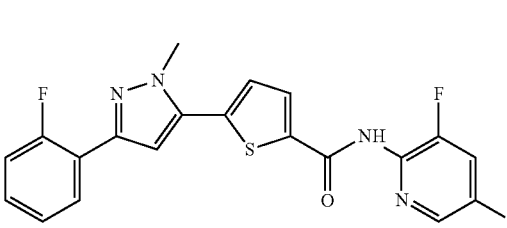

87

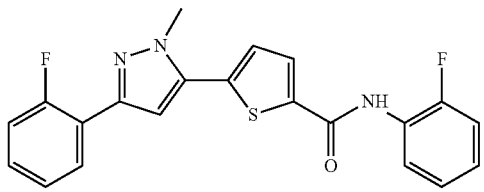

88

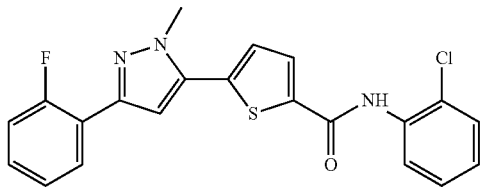

89

Examples 42-48

Preparation of N-(2,6-difluorophenyl)[5-(1-methyl-3-phenylpyrazol-5-yl)(2-thienyl)]carboxamide (93)

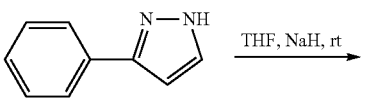

90

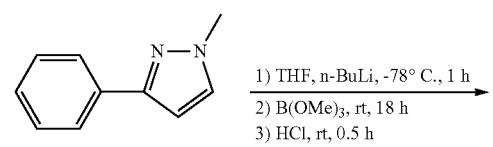

91

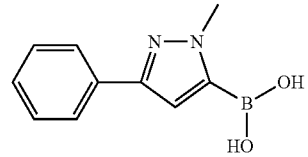

92

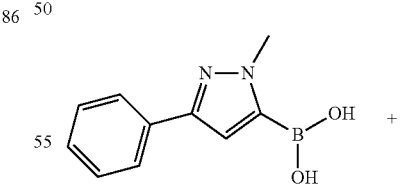

92

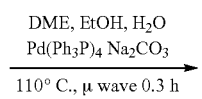

79

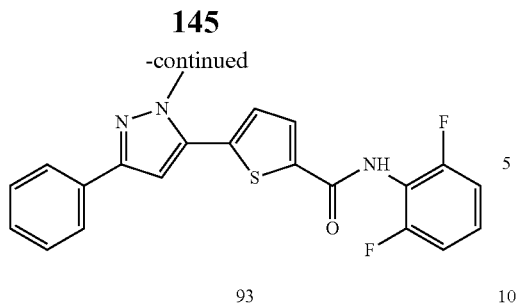

93

To a solution of 90 (1 g, 6.9 mmol) in THF (50 mL) was added NaH (0.66 g, 27.6 mmol). The mixture was stirred for 1 h and the MeI (1.97 g, 13.8 mmol) was added in one potion. The reaction mixture was stirred for 18 h at room temperature. The reaction was quenched with MeOH and solvent was removed in vacuo. The residue was treated with water and EtOAc. The organic layer was separated and aqueous was extracted with EtOAc. The combined organic phase was dried over Na$_2$SO$_4$, filtered, concentrated to give crude product. The crude product was purified on ISCO columns. Fractions containing pure product were combined and evaporated. The yellow oil 91 (0.53 g, 48%) was obtained.

A solution of 91 (185 mg, 1.17 mmol) in THF (5 ml) was cooled at −78° C. followed by adding 2.5 M n-BuLi (0.7 mL, 1.75 mmol). The mixture was stirred for 4 h at −78° C. and the trimethyl borate (2 mL, 1.75 mmol) was added. The reaction mixture was warmed up to room temperature and stirred overnight. The reaction was quenched with 1M HCl and stirred for 0.5 h. The mixture was extracted with EtOAc (20 mL×2). The organic phase was washed with 1M NaOH. The aqueous was acidified with con. HCl and extracted with EtOAc. The combined organic phase was dried over Na$_2$SO$_4$, filtered, concentrated to give boronic acid 92 (121.5 mg, 51%) as yellow solid.

The boronic acid 92 (23 mg, 0.11 mmol) and 79 (32 mg, 0.1 mmol) was dissolved in 1 mL dimethoxyethane and 1 mL EtOH. The 0.5 ml of 2 M Na$_2$CO$_3$ was added and the mixture was bubbled with Ar for 1 min before add tetrakis(triphenylphosphine)-palladium(0) (Pd(Ph$_3$P)$_4$, 12 mg, 0.01 mmol). The reaction was heated at 110° C. for 30 min under microwave initiator. The reaction mixture was worked-up with EtOAc extraction and product was purified by HPLC and afforded 93 (21 mg, 53%) as white solid. LC-MS: calcd. for C$_{21}$H$_{15}$F$_2$N$_3$OS: 396 (M+1).

Compounds 94-99 were prepared using similar procedure of 93. For compound 94, LC-MS: calcd. for C$_{20}$H$_{14}$F$_2$N$_4$OS: 397 (M+1). For compound 95, LC-MS: calcd. for C$_{20}$H$_{15}$FN$_4$OS: 379 (M+1). For compound 96, LC-MS: calcd. for C$_{20}$H$_{15}$FN$_4$OS: 379 (M+1). For compound 97, LC-MS: calcd. for C$_{20}$H$_{14}$ClFN$_4$OS: 413 (M+1). For compound 98, LC-MS: calcd. for C$_{21}$H$_{16}$FN$_3$OS: 378 (M+1). For compound 99, LC-MS: calcd. for C$_{21}$H$_{16}$ClN$_3$OS: 394 (M+1).

95

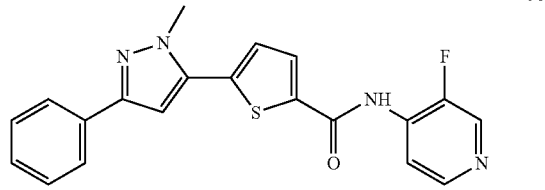

96

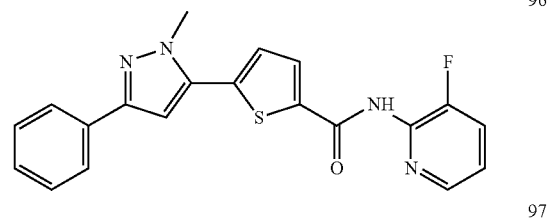

97

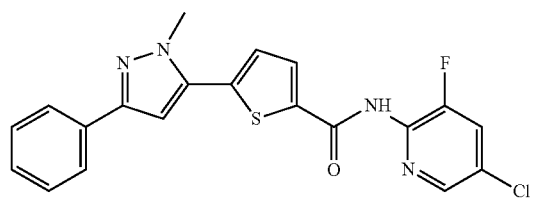

98

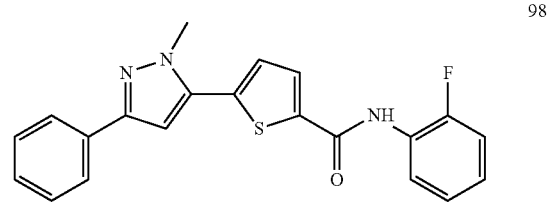

99

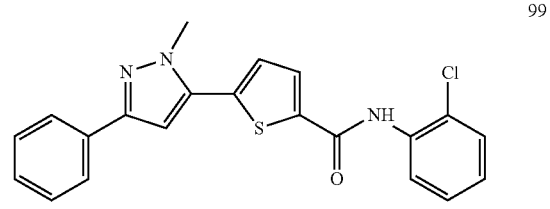

Example 49-55

Preparation of (2,6-difluorophenyl)[5-(1-methyl-3-(1,3-thiazol-2-yl)pyrazol-5-yl](2-thienyl)]carboxamide (103)

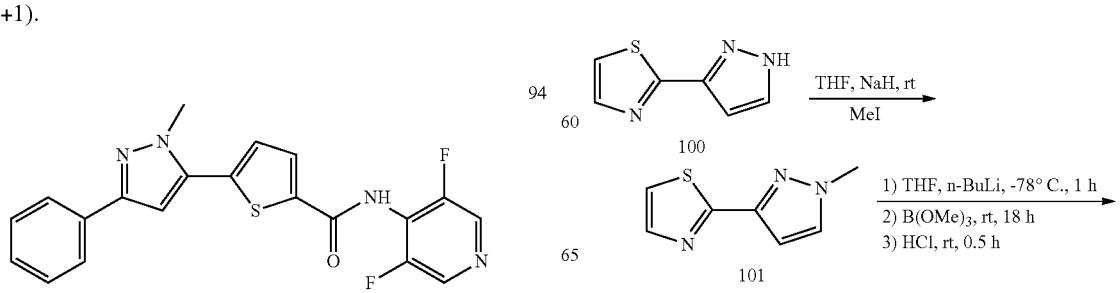

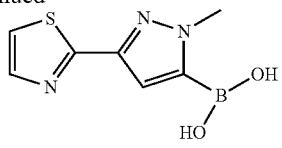

102

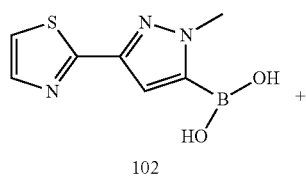

102

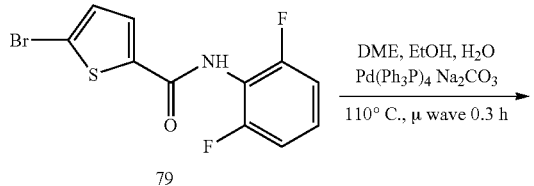

79

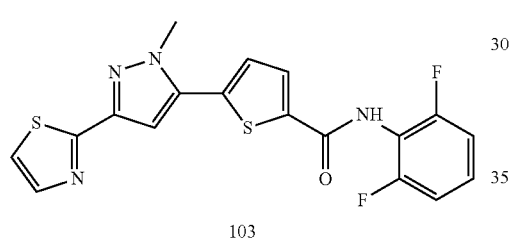

103

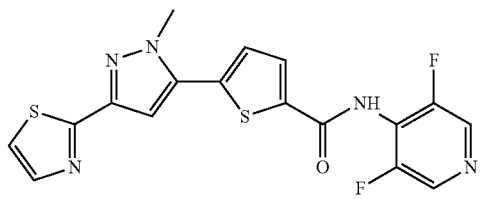

104

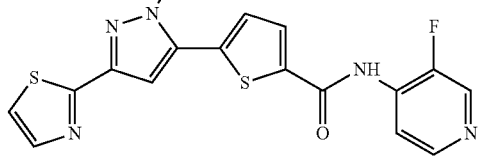

105

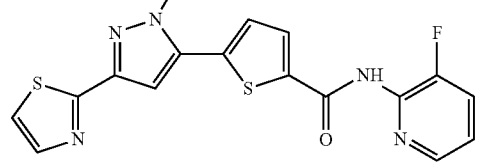

106

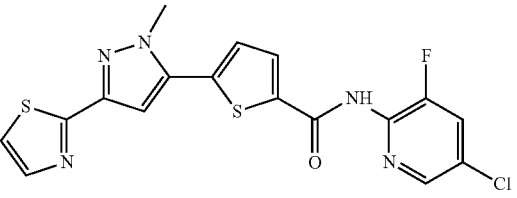

107

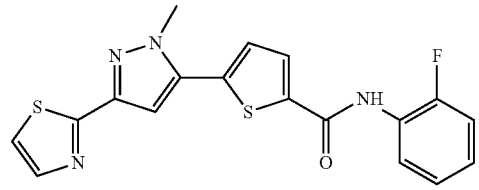

108

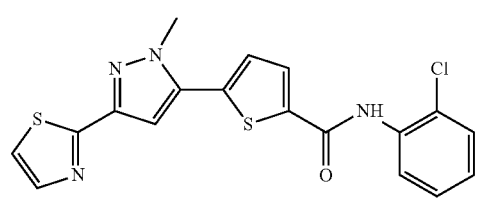

109

To a solution of 100 (1.5 g, 10 mmol) in THF (50 mL) was added NaH (2.4 g, 100 mmol). The mixture was stirred for 1 h and the MeI (2.8 g, 20 mmol) was added in one potion. The reaction mixture was stirred for 18 h at room temperature. The reaction was quenched with MeOH and solvent was removed in vacuo. The residue was treated with water and EtOAc. The organic layer was separated and aqueous was extracted with EtOAc. The combined organic phase was dried over $Na_2SO_4$, filtered, concentrated to give crude product. The crude product was purified on ISCO columns. Fractions containing pure product were combined and evaporated. The yellow oil 101 (1.5 g, 91%) was obtained.

A solution of 101 (395 mg, 2.4 mmol) in THF (20 ml) was cooled at −78° C. followed by adding 2.5 M n-BuLi (1.4 mL, 3.6 mmol). The mixture was stirred for 4 h at −78° C. and the trimethyl borate (0.4 mL, 3.6 mmol) was added. The reaction mixture was warmed up to room temperature and stirred overnight. The reaction was quenched with 1M HCl and stirred for 0.5 h. The mixture was extracted with EtOAc (20 mL×2). The organic phase was washed with 1M NaOH. The aqueous was acidified with con. HCl and extracted with EtOAc. The combined organic phase was dried over $Na_2SO_4$, filtered, concentrated to give boronic acid 102 (317 mg, 63%) as yellow solid.

The boronic acid 102 (23 mg, 0.11 mmol) and 79 (32 mg, 0.1 mmol) was dissolved in 1 mL dimethoxyethane and 1 mL EtOH. The 0.5 ml of 2 M $Na_2CO_3$ was added and the mixture was bubbled with Ar for 1 min before add tetrakis(triphenylphosphine)-palladium(0) $(Pd(Ph_3P)_4$, 12 mg, 0.01 mmol). The reaction was heated at 110° C. for 30 min under microwave initiator. The reaction mixture was worked-up with EtOAc extraction and product was purified by HPLC and afforded 103 (19 mg, 46%) as yellow solid. LC-MS: calcd. for $C_{18}H_{12}F_2N_4OS_2$: 403 (M+1).

Compounds 104-109 were prepared using similar procedure of 103. For compound 104, LC-MS: calcd. for $C_{17}H_{11}F_2N_5OS_2$: 404 (M+1). For compound 105, LC-MS: calcd. for $C_{17}H_{12}FN_5OS_2$: 386 (M+1). For compound 106, LC-MS: calcd. for $C_{17}H_{12}FN_5OS_2$: 386 (M+1). For compound 107, LC-MS: calcd. for $C_{17}H_{11}ClFN_5OS_2$: 420 (M+1). For compound 108, LC-MS: calcd. for $C_{18}H_{13}FN_4OS_2$: 385 (M+1). For compound 99, LC-MS: calcd. for $C_{18}H_{13}ClN_4OS_2$: 401 (M+1).

Examples 56-62

Preparation of N-(2,6-difluorophenyl)[5-(3-(2-furyl)-1-methylpyrazol-5-yl](2-thienyl)]carboxamide (113)

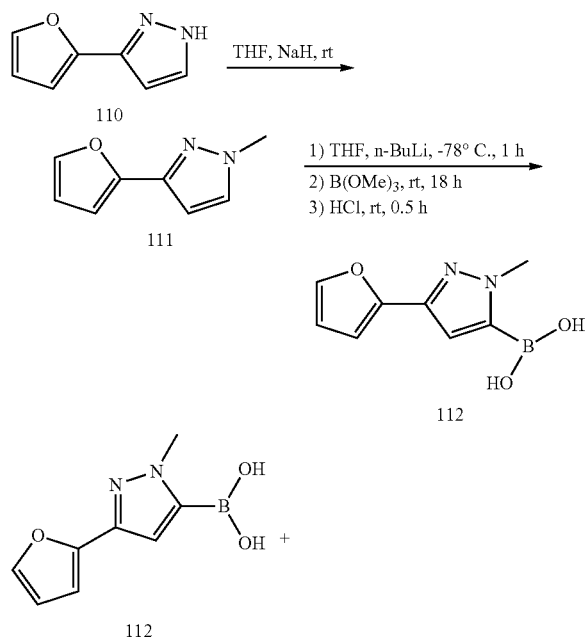

9 mmol). The mixture was stirred for 4 h at −78° C. and the trimethyl borate (1 mL, 9 mmol) was added. The reaction mixture was warmed up to room temperature and stirred overnight. The reaction was quenched with 1M HCl and stirred for 0.5 h. The mixture was extracted with EtOAc (20 mL×2). The organic phase was washed with 1M NaOH. The aqueous was acidified with con. HCl and extracted with EtOAc. The combined organic phase was dried over $Na_2SO_4$, filtered, concentrated to give boronic acid 112 (343 mg, 40%) as yellow solid.

The boronic acid 112 (22 mg, 0.11 mmol) and 79 (32 mg, 0.1 mmol) was dissolved in 1 mL dimethoxyethane and 1 mL EtOH. The 0.5 ml of 2 M $Na_2CO_3$ was added and the mixture was bubbled with Ar for 1 min before add tetrakis(triphenylphosphine)-palladium(0) $(Pd(Ph_3P)_4$, 12 mg, 0.01 mmol). The reaction was heated at 110° C. for 30 min under microwave initiator. The reaction mixture was worked-up with EtOAc extraction and product was purified by HPLC and afforded 113 (21 mg, 53%) as yellow solid. LC-MS: calcd. for $C_{19}H_{13}F_2N_3O_2S$: 386 (M+1).

Compounds 114-119 were prepared using similar procedure of 113. For compound 114, LC-MS: calcd. for $C_{18}H_{12}F_2N_4O_2S$: 387 (M+1). For compound 115, LC-MS: calcd. for $C_{18}H_{13}FN_4O_2S$: 369 (M+1). For compound 116, LC-MS: calcd. for $C_{18}H_{13}FN_4O_2S$: 369 (M+1). For compound 117, LC-MS: calcd. for $C_{18}H_{12}ClFN_4O_2S$: 403 (M+1). For compound 118, LC-MS: calcd. for $C_{19}H_{14}FN_3O_2S$: 368 (M+1). For compound 119, LC-MS: calcd. for $C_{19}H_{14}ClN_3O_2S$: 384 (M+1).

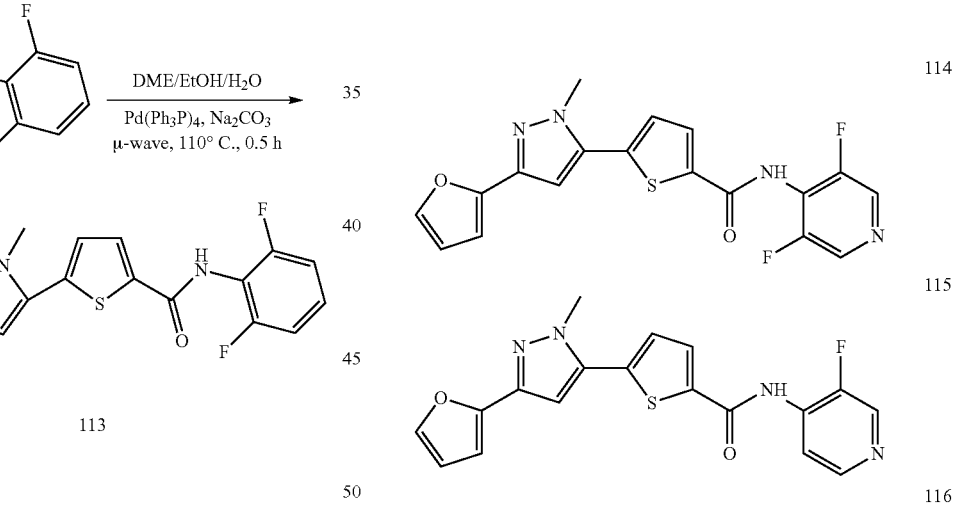

To a solution of 110 (1.4 g, 10.4 mmol) in THF (50 mL) was added NaH (2.4 g, 100 mmol). The mixture was stirred for 1 h and the MeI (3 g, 21 mmol) was added in one potion. The reaction mixture was stirred for 18 h at room temperature. The reaction was quenched with MeOH and solvent was removed in vacuo. The residue was treated with water and EtOAc. The organic layer was separated and aqueous was extracted with EtOAc. The combined organic phase was dried over $Na_2SO_4$, filtered, concentrated to give crude product. The crude product was purified on ISCO columns. Fractions containing pure product were combined and evaporated. The yellow oil 111 (1.45 g, 94%) was obtained.

A solution of 111 (670 mg, 4.5 mmol) in THF (20 ml) was cooled at −78° C. followed by adding 2.5 M n-BuLi (3.6 mL,

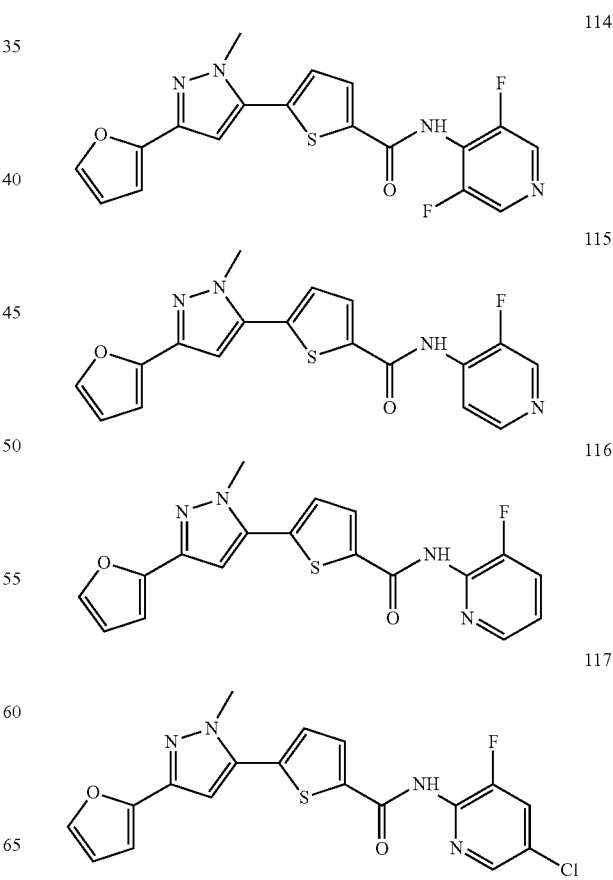

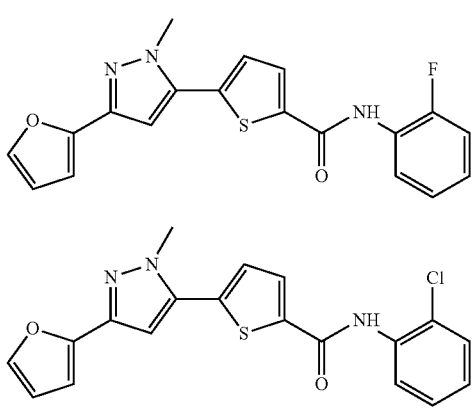

Example 63-65

Preparation of N-(2,6-difluorophenyl)[5-(1-methyl-3-(2-thienyl)pyrazol-5-yl](2-thienyl)]carboxamide (123)

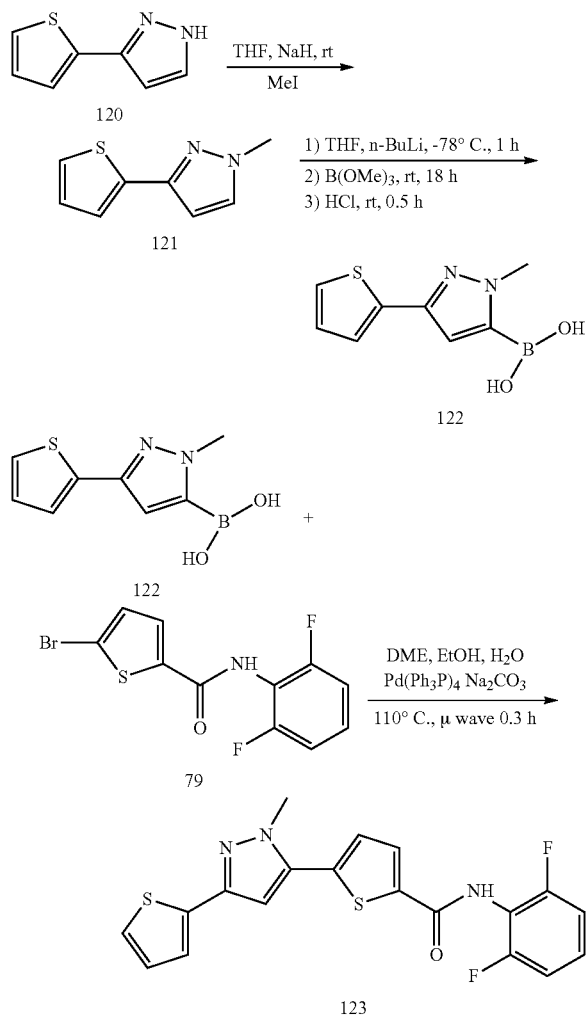

To a solution of 120 (1.5 g, 10 mmol) in THF (50 mL) was added NaH (2.4 g, 100 mmol). The mixture was stirred for 1 h and the MeI (2.8 g, 20 mmol) was added in one potion. The reaction mixture was stirred for 18 h at room temperature. The reaction was quenched with MeOH and solvent was removed in vacuo. The residue was treated with water and EtOAc. The organic layer was separated and aqueous was extracted with EtOAc. The combined organic phase was dried over $Na_2SO_4$, filtered, concentrated to give crude product. The crude product was purified on ISCO columns. Fractions containing pure product were combined and evaporated. The yellow oil 121 (1.5 g, 91%) was obtained.

A solution of 121 (395 mg, 2.4 mmol) in THF (20 ml) was cooled at −78° C. followed by adding 2.5 M n-BuLi (1.4 mL, 3.6 mmol). The mixture was stirred for 4 h at −78° C. and the trimethyl borate (0.4 mL, 3.6 mmol) was added. The reaction mixture was warmed up to room temperature and stirred overnight. The reaction was quenched with 1M HCl and stirred for 0.5 h. The mixture was extracted with EtOAc (20 mL×2). The organic phase was washed with 1M NaOH. The aqueous was acidified with con. HCl and extracted with EtOAc. The combined organic phase was dried over $Na_2SO_4$, filtered, concentrated to give boronic acid 122(317 mg, 63%) as yellow solid.

The boronic acid 122 (22 mg, 0.11 mmol) and 79 (32 mg, 0.1 mmol) was dissolved in 1 mL dimethoxyethane and 1 mL EtOH. The 0.5 ml of 2 M $Na_2CO_3$ was added and the mixture was bubbled with Ar for 1 min before add tetrakis(triphenylphosphine)-palladium(0) $(Pd(Ph_3P)_4,$ 12 mg, 0.01 mmol). The reaction was heated at 110° C. for 30 min under microwave initiator. The reaction mixture was worked-up with EtOAc extraction and product was purified by HPLC and afforded 123 (5.3 mg, 13%) as white solid. LC-MS: calcd. for $C_{19}H_{13}F_2N_3OS_2$: 402 (M+1).

Compounds 124-125 were prepared using similar procedure of 123. For compound 124, LC-MS: calcd. for $C_{19}H_{14}FN_3OS_2$: 384 (M+1). For compound 125, LC-MS: calcd. for $C_{19}H_{14}ClN_3OS_2$: 400 (M+1).

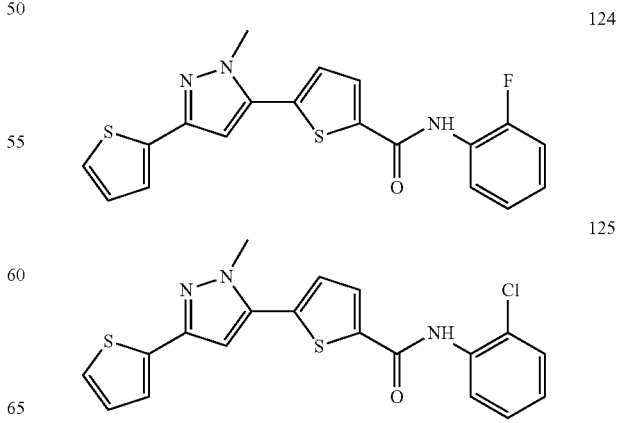

Examples 66-68

Preparation of (2,6-difluorophenyl-N-{5-[2-(fluorophenyl)-1-methylpyrazol-5-yl](1,3-thiazol-2-yl)]carboxamide (127)

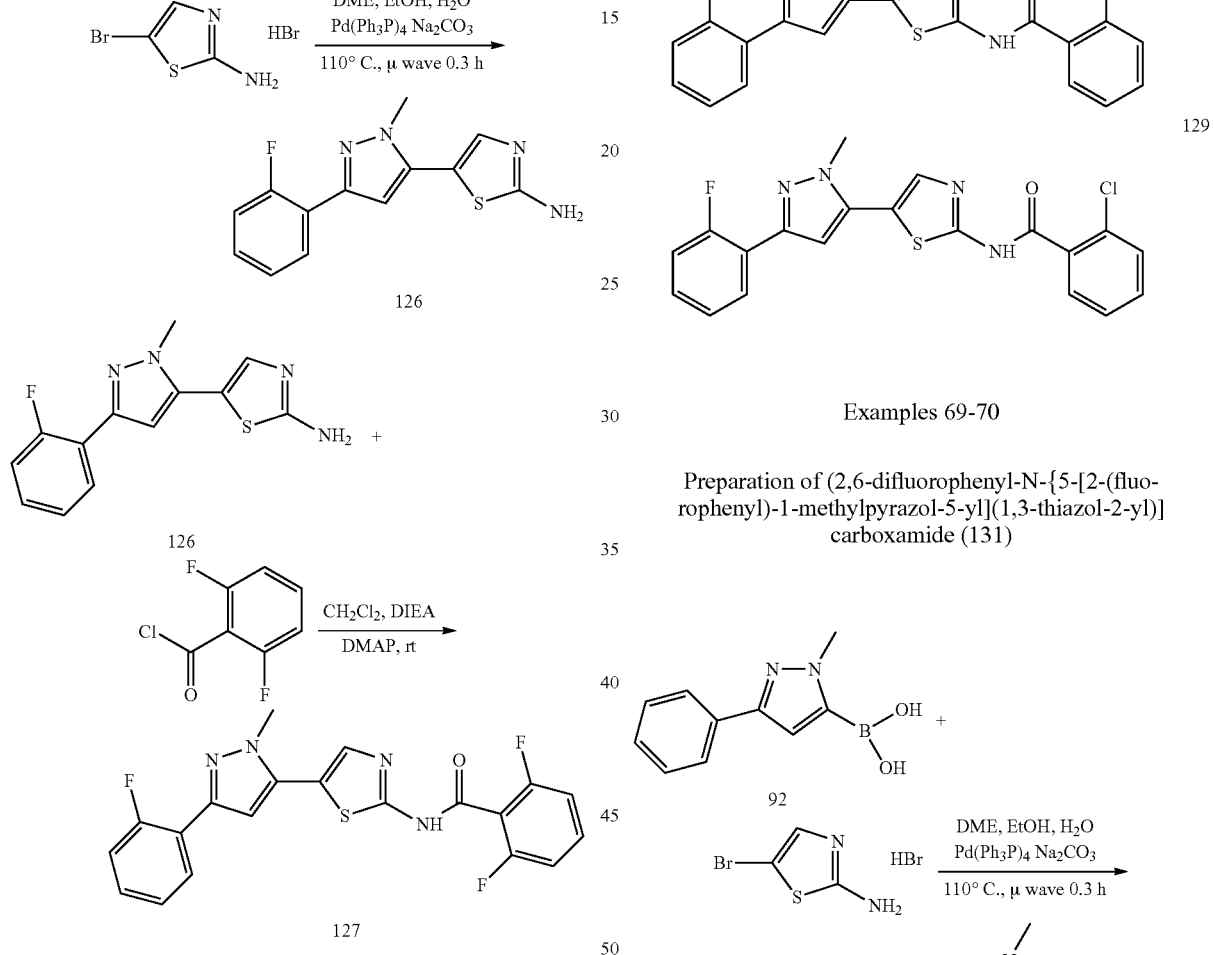

The boronic acid 82 (242 mg, 1.1 mmol) and 2-amino-5-bromothiazole hydrobomide (260 mg, 1 mmol) was dissolved in 5 mL dimethoxyethane and 5 mL EtOH. The 2 ml of 2 M Na₂CO₃ was added and the mixture was bubbled with Ar for 1 min before add tetrakis(triphenylphosphine)-palladium(0) (Pd(Ph₃P)₄, 115 mg, 0.1 mmol). The reaction was heated at 110° C. for 30 min under microwave initiator. The reaction mixture was worked-up with EtOAc extraction and product was purified by flash column and afforded 126 (80 mg, 29%) as white solid.

To a solution of 126 (25 mg, 0.07 mmol) in CH₂Cl₂ (5 ml) was added N,N-diisopropylethylamine (DIEA, 52 mg, 72 µL, 0.4 mmol), 4-dimethylaminopyridine (DMAP, 0.6 mg, 0.05 mmol). The 2,6-difluorobenzoy chloride (18 mg, 0.1 mmol) was dropped into above solution. The mixture was stirred for 2 h at room temperature. The reaction was quenched with saturated NaHCO₃ (20 ml) and extracted with EtOAc. The product was purified by HPLC and afforded 127 (5.4 mg, 19%) as white solid. LC-MS: calcd. for C₂₀H₁₃F₃N₄OS: 415 (M+1).

Compounds 128-129 were prepared using similar procedure of 127. For compound 128, LC-MS: calcd. for C₂₀H₁₄F₂N₄OS: 397 (M+1). For compound 129, LC-MS: calcd. for C₂₀H₁₄ClFN₄OS: 413 (M+1).

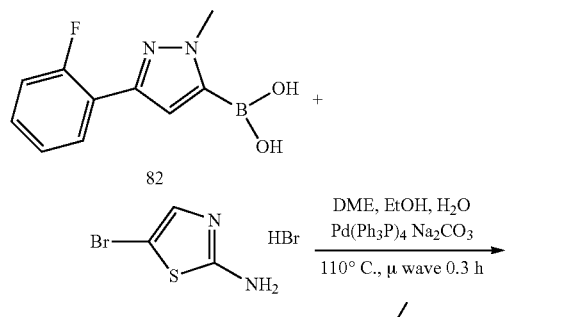

Examples 69-70

Preparation of (2,6-difluorophenyl-N-{5-[2-(fluorophenyl)-1-methylpyrazol-5-yl](1,3-thiazol-2-yl)]carboxamide (131)

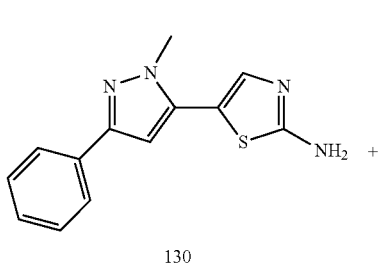

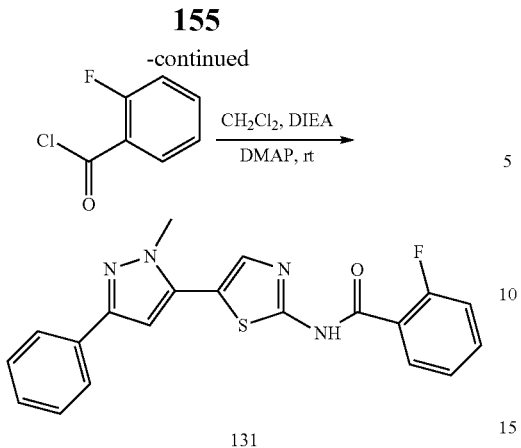

131

The boronic acid 92 (222 mg, 1.1 mmol) and 2-amino-5-bromothiazole hydrobomide (260 mg, 1 mmol) was dissolved in 5 mL dimethoxyethane and 5 mL EtOH. The 2 ml of 2 M $Na_2CO_3$ was added and the mixture was bubbled with Ar for 1 min before add tetrakis(triphenylphosphine)-palladium(0) ($Pd(Ph_3P)_4$, 115 mg, 0.1 mmol). The reaction was heated at 110° C. for 30 min under microwave initiator. The reaction mixture was worked-up with EtOAc extraction and product was purified by flash column and afforded 130 (80 mg, 29%) as white solid.

To a solution of 130 (24 mg, 0.09 mmol) in $CH_2Cl_2$ (5 ml) was added N,N-diisopropylethylamine (DIEA, 52 mg, 72 µL, 0.4 mmol), 4-dimethylaminopyridine (DMAP, 0.6 mg, 0.05 mmol). The 2-fluorobenzoy chloride (18 mg, 0.11 mmol) was dropped into above solution. The mixture was stirred for 2 h at room temperature. The reaction was quenched with saturated $NaHCO_3$ (20 ml) and extracted with EtOAc. The product was purified by HPLC and afforded 131 (0.8 mg, 3%) as white solid. LC-MS: calcd. for $C_{20}H_{15}FN_4OS$: 379 (M+1).

Compound 132 was prepared using similar procedure of 131. For compound 132, LC-MS: calcd. for $C_{20}H_{15}ClN_4OS$: 395 (M+1).

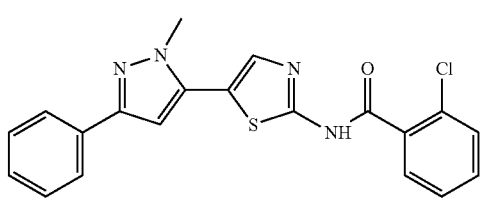

132

Examples 71-73

Preparation of (2-fluorophenyl)-N-{5-[1-methyl-3-(trifluoromethyl)pyrazol-5-yl](2-thienyl)}carboxamide (135)

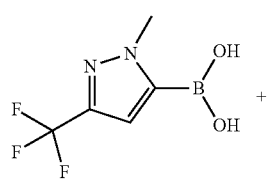

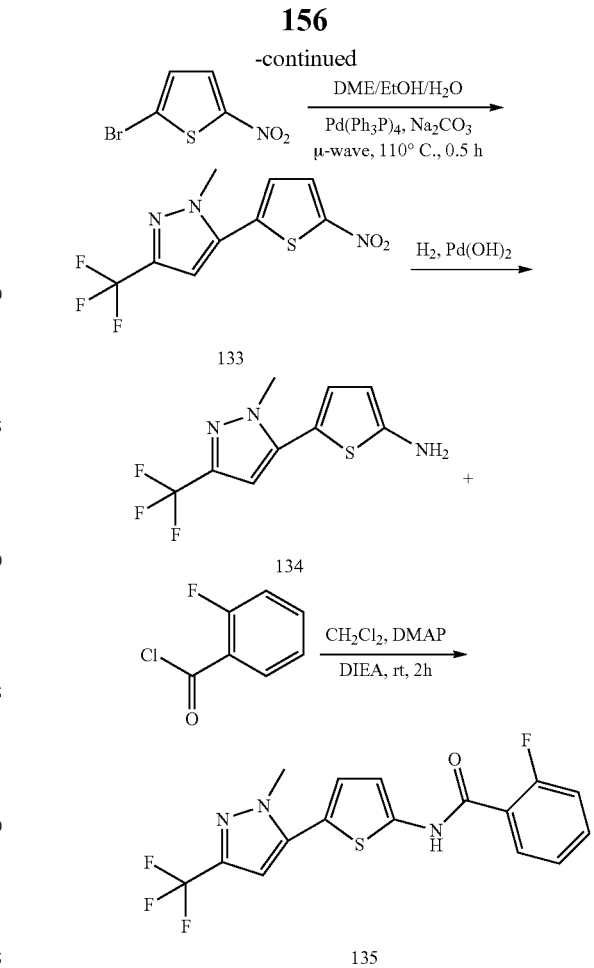

1-Methyl-3-trifluoromethylpyrazole-5-boronic acid (97 mg, 0.5 mmol) and 2-bromo-5-nitrothiophene (104 mg, 0.5 mmol) was dissolved in 2 mL dimethoxyethane and 2 mL EtOH. The 1 mL of 2 M $Na_2CO_3$ was added and the mixture was bubbled with Ar for 1 min before add tetrakis(triphenylphosphine)-palladium(0) ($Pd(Ph_3P)_4$, 60 mg, 0.05 mmol). The reaction was heated at 110° C. for 30 min under microwave initiator. The reaction mixture was worked-up with EtOAc extraction and product was purified by flash column and afforded 133 as yellow solid. Following hydrogenation under standard conditions, to a solution of 134 (37 mg, 0.15 mmol) in $CH_2Cl_2$ (10 mL) was added 2-fluorobenzoyl chloride, N,N-diisopropylethylamine (DIEA, 0.5 g, 0.7 mL, 4 mmol), and a catalytic amount of DMAP. The mixture was stirred for 2 h at room temperature. The reaction was quenched with saturated $NaHCO_3$ (20 mL) and extracted with EtOAc (20 mL×2). The combined organic layers were dried ($Na_2SO_4$) and concentrated in vacuo. The residue was dissolved in THF (2 mL) and MeOH (2 mL). 1M NaOH (2 mL) was added and stirred for 0.5 h at room temperature. The reaction mixture was concentrated and worked-up with EtOAc-Brine. The crude product was purified by flash column and compound 135 (2.7 mg, 5%) was obtained as yellow solid. LC-MS: calcd. for $C_{16}H_{11}F_4N_3OS$: 370 (M+1).

Compounds 136 and 137 were prepared using a similar procedure of 135 by substituting intermediate 63 for intermediate 134. For compound 136, LC-MS: calcd. for $C_{15}H_{10}F_4N_4OS$: 371 (M+1). For compound 137, LC-MS: calcd. for $C_{15}H_{10}ClF_3N_4OS$: 387 (M+1).

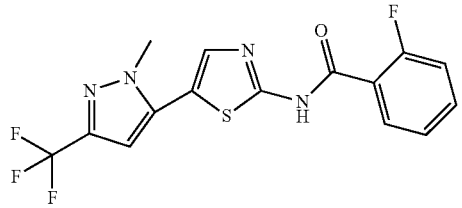

136

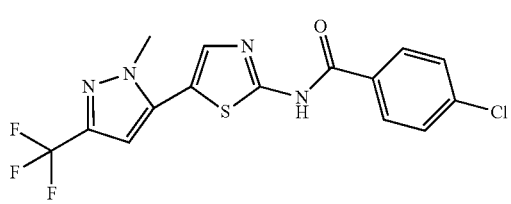

137

Examples 74

Preparation of (2,6-difluorophenyl)-N-{5-[1-methyl-3-(trifluoromethyl)pyrazol-5-yl](2-thienyl)}carboxamide (138)

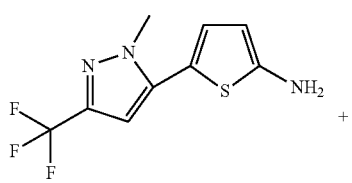

134

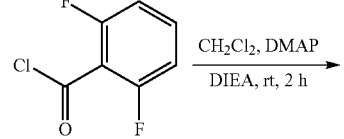

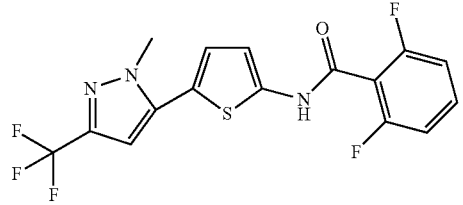

138

To a solution of 134 (37 mg, 0.15 mmol) in $CH_2Cl_2$ (10 mL) was added 2,6-difluorobenzoyl chloride, N,N-diisopropylethylamine (DIEA, 0.5 g, 0.7 mL, 4 mmol), and a catalytic amount of DMAP. The mixture was stirred for 2 h at room temperature. The reaction was quenched with saturated $NaHCO_3$ (20 mL) and extracted with EtOAc (20 mL×2). The combined organic layers were dried ($Na_2SO_4$) and concentrated in vacuo. The residue was dissolved in THF (2 mL) and MeOH (2 mL). 1M NaOH (2 mL) was added and stirred for 0.5 h at room temperature. The reaction mixture was concentrated and worked-up with EtOAc-Brine. The crude product was purified by HPLC and compound 138 (1.7 mg, 3%) was obtained as a green solid. LC-MS: calcd. for $C_{16}H_{10}F_5N_3OS$: 388 (M+1).

Examples 75-76

Preparation of (3-fluoro(4-pyridyl))-N-{5-[1-methyl-3-(trifluoromethyl)pyrazol-5-yl](2-thienyl)}carboxamide (139)

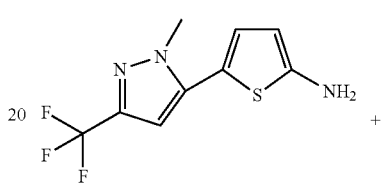

134

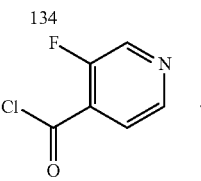

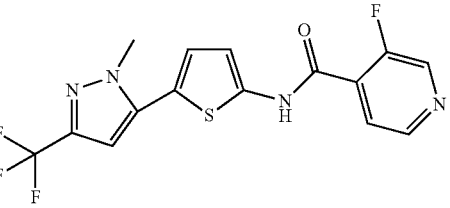

139

To a solution of 134 (25 mg, 0.1 mmol) in $CH_2Cl_2$ (10 mL) was added 3-fluoropyridine-4-carbonyl chloride, N,N-diisopropylethylamine (DIEA, 0.5 g, 0.7 mL, 4 mmol), and a catalytic amount of DMAP. The mixture was stirred for 2 h at room temperature. The reaction was quenched with saturated $NaHCO_3$ (20 mL) and extracted with EtOAc (20 mL×2). The combined organic layers were dried ($Na_2SO_4$) and concentrated in vacuo. The crude product was purified by HPLC and compound 139 (6.7 mg, 18%) was obtained as a brown solid. LC-MS: calcd. for $C_{15}H_{10}F_4N_4OS$: 371 (M+1).

Compound 140 was prepared using a similar procedure of 139 by substituting intermediate 63 for intermediate 134. For compound 140, LC-MS: calcd. for $C_{14}H_9F_4N_5OS$: 372 (M+1).

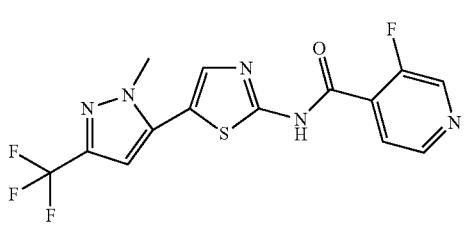

140

Examples 77-78

Preparation of (3,5-difluoro(4-pyridyl))-N-{5-[1-methyl-3-(trifluoromethyl)pyrazol-5-yl](2-thienyl)}carboxamide (141)

Example 79

Preparation of N-[5-(2,2-difluoro-6-methylbenzo[d]1,3-dioxolen-5-yl)(2-thienyl)](2-fluorophenyl)carboxamide (145)

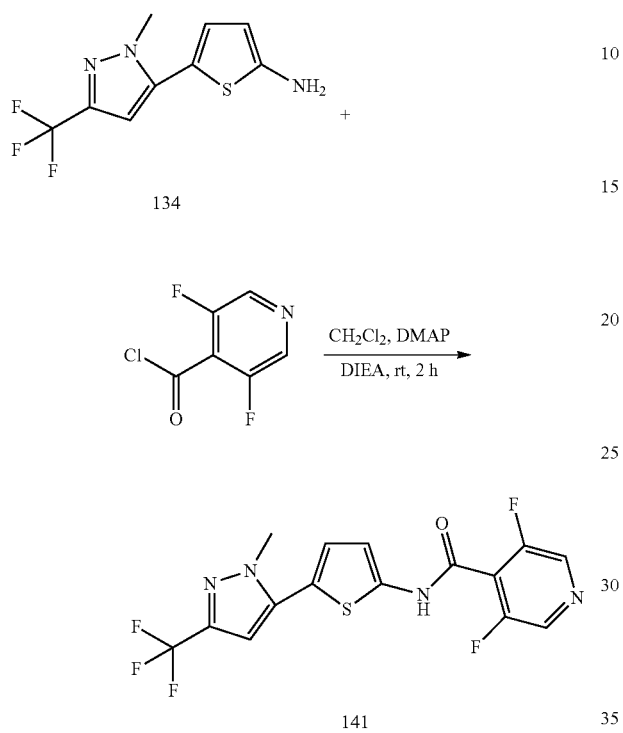

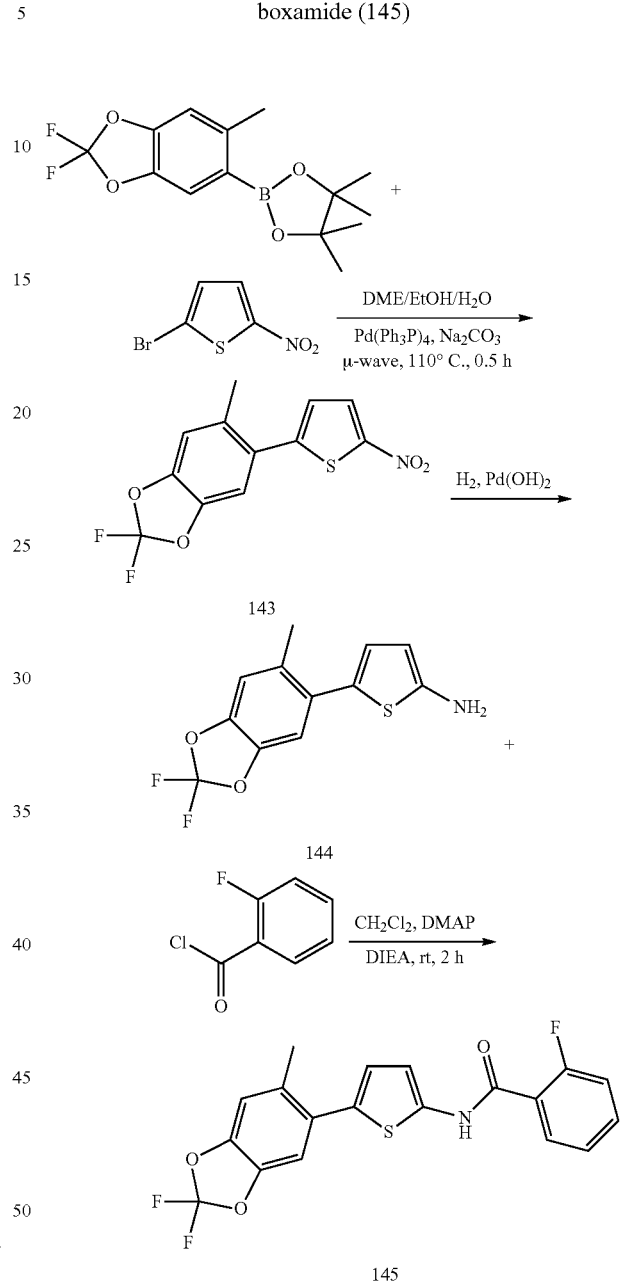

To a solution of 134 (25 mg, 0.1 mmol) in CH$_2$Cl$_2$ (10 mL) was added 3,5-difluoropyridine-4-carbonyl chloride, N,N-diisopropylethylamine (DIEA, 0.5 g, 0.7 mL, 4 mmol), and a catalytic amount of DMAP. The mixture was stirred for 2 h at room temperature. The reaction was quenched with saturated NaHCO$_3$ (20 mL) and extracted with EtOAc (20 mL×2). The combined organic layers were dried (Na$_2$SO$_4$) and concentrated in vacuo. The crude product was purified by flash column and compound 138 (7 mg, 18%) was obtained as a brown solid. LC-MS: calcd. for C$_{15}$H$_9$F$_5$N$_4$OS: 389 (M+1).

Compound 142 was prepared using a similar procedure of 141 by substituting intermediate 63 for intermediate 134. For compound 142, LC-MS: calcd. for C$_{14}$H$_8$F$_5$N$_5$OS: 390 (M+1).

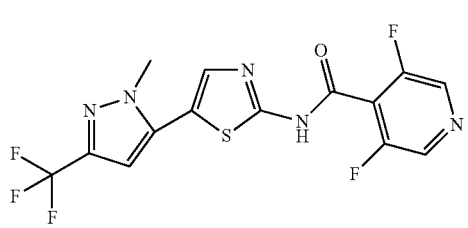

142

2-(2,2-Difluoro-6-methylbenzo[d][1,3]dioxol-5-yl)-4,4,5,5-tetramethyl-1,3,2-dioxaborolane (298 mg, 1 mmol) and 2-bromo-5-nitrothiophene (208 mg, 1 mmol) was dissolved in 4 mL dimethoxyethane and 4 mL EtOH. The 2 mL of 2 M Na$_2$CO$_3$ was added and the mixture was bubbled with Ar for 1 min before add tetrakis(triphenylphosphine)-palladium(0) (Pd(Ph$_3$P)$_4$, 116 mg, 0.1 mmol). The reaction was heated at 110° C. for 30 min under microwave initiator. The reaction mixture was worked-up with EtOAc extraction and the product was purified by flash column and afforded 143 as yellow solid. Following hydrogenation under standard conditions, to a solution of 144 (135 mg, 0.5 mmol) in CH$_2$Cl$_2$ (10 mL) was added 2-fluorobenzoyl chloride, N,N-diisopropylethylamine (DIEA, 0.5 g, 0.7 mL, 4 mmol), and a catalytic amount of DMAP. The mixture was stirred for 2 h at room temperature. The reaction was quenched with saturated NaHCO$_3$ (20 mL) and extracted with EtOAc (20 mL×2). The combined organic layers were dried (Na$_2$SO$_4$) and concentrated in vacuo. The residue was dissolved in THF (2 mL) and MeOH (2 mL). 1M NaOH (2 mL) was added and stirred for 0.5 h at room temperature. The reaction mixture was concentrated and worked-up with EtOAc-Brine. The crude product was purified by flash column and compound 145 (92.7 mg, 47%) was obtained as a brown solid. LC-MS: calcd. for C$_{19}$H$_{12}$F$_3$NO$_3$S: 392 (M+1).

Example 80

Preparation of N-[5-(2,2-difluoro-6-methylbenzo[d]1,3-dioxolen-5-yl)(2-thienyl)](2,6-difluorophenyl)carboxamide (146)

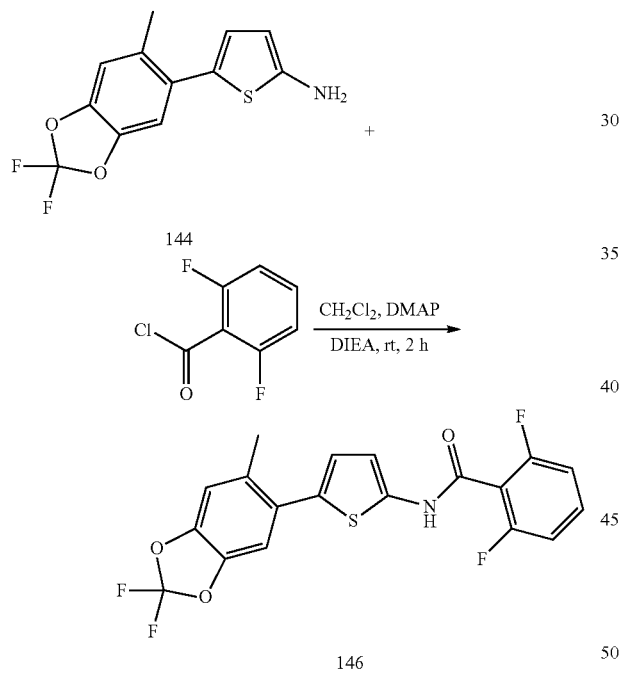

To a solution of 144 (135 mg, 0.5 mmol) in CH$_2$Cl$_2$ (10 mL) was added 2,6-difluorobenzoyl chloride, N,N-diisopropylethylamine (DIEA, 0.5 g, 0.7 mL, 4 mmol), and a catalytic amount of DMAP. The mixture was stirred for 2 h at room temperature. The reaction was quenched with saturated NaHCO$_3$ (20 mL) and extracted with EtOAc (20 mL×2). The combined organic layers were dried (Na$_2$SO$_4$) and concentrated in vacuo. The residue was dissolved in THF (2 mL) and MeOH (2 mL). 1M NaOH (2 mL) was added and stirred for 0.5 h at room temperature. The reaction mixture was concentrated and worked-up with EtOAc-Brine. The crude product was purified by HPLC and compound 146 (50.5 mg, 25%) was obtained as a white solid. LC-MS: calcd. for C$_{19}$H$_{11}$F$_4$NO$_3$S: 410 (M+1).

Examples 81-82

Preparation of (3,5-difluoro(4-pyridyl))-N-[5-(2,2-difluoro-6-methylbenzo[d]1,3-dioxolen-5-yl)(1,3-thiazol-2-yl)]carboxamide (149)

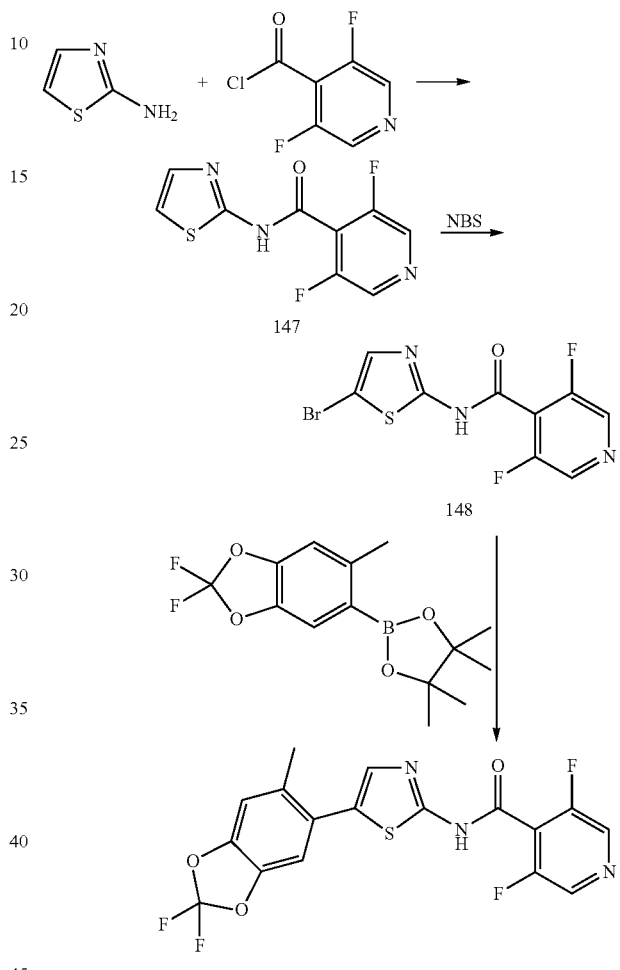

To a mixture of 2-aminothiazole (200 mg, 2 mmol) and N,N-diisopropylethylamine (1.0 mL) in 10 mL DCM was added acid chloride (354 mg, 2 mmol). The resulting mixture was stirred at room temperature for 4 h before worked up with DCM/aqueous NaHCO$_3$/brine. The organic phase was dried (Na$_2$SO$_4$) and concentrated to give intermediate 147 as a brown solid (444 mg, yield: 92%, purity>90%) which was used without further purification.

To a suspension of 147 (444 mg, 1.84 mmol) in 10 mL acetonitrile was added NBS (393 mg, 2.2 mmol, 1.2 eq). The reaction mixture was stirred overnight at room temperature and then worked up with ethyl acetate/aqueous NaHCO$_3$/brine. The organic phase was dried (Na$_2$SO$_4$), concentrated and subjected to silica gel purification to furnish compound 148 as light yellow solid (128 mg, yield: 21.7%, purity>95%) and intermediate 147 (51.6 mg) was recovered from column.

Argon was bubbled through a mixture of (3,5-difluoro(4-pyridyl))-N-(5-bromo(1,3-thiazol-2-yl))carboxamide (148) (32 mg, 0.1 mmol), 2-(2,2-difluoro-6-methylbenzo[d][1,3]dioxol-5-yl)-4,4,5,5-tetramethyl-1,3,2-dioxaborolane (45 mg, 0.15 mmol), bis(ditertbutyl(4-dimethylaminophenyl) phosphine)dichloropalladium (II) (11 mg, 10% mol) and K₃PO₄ (32 mg) in 1 mL ACN, 1 mL dioxane, 0.5 ml H₂O. The reaction mixture was heated at 85° C. for 4 h. After cooling to room temperature, the reaction mixture was taken up in ethyl acetate, washed with aqueous NaHCO₃ and brine. The organic phase was dried (Na₂SO₄), concentrated and then subjected to prep HPLC chromatography to give (3,5-difluoro(4-pyridyl))-N-[5-(2,2-difluoro-6-methylbenzo[d]1,3-dioxolen-5-yl)(1,3-thiazol-2-yl)]carboxamide (149) (16.8 mg, yield: 40.8%, purity>95%). LC-MS: calcd. for $C_{17}H_9F_4N_3O_3S$: 412 (M+1).

Compound 150 was prepared using similar procedure of 149. For compound 150, LC-MS: calcd. for $C_{17}H_{10}F_3N_3O_3S$: 394 (M+1).

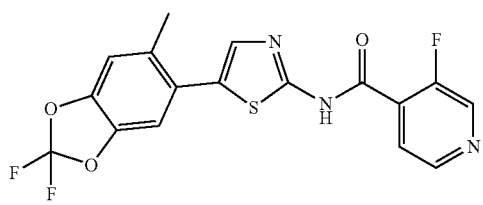

150

Examples 83-84

Preparation of (2,6-difluorophenyl)-N-[5-(2,2-difluoro-6-methylbenzo[d]1,3-dioxolen-5-yl)(1,3-thiazol-2-yl)]carboxamide (153)

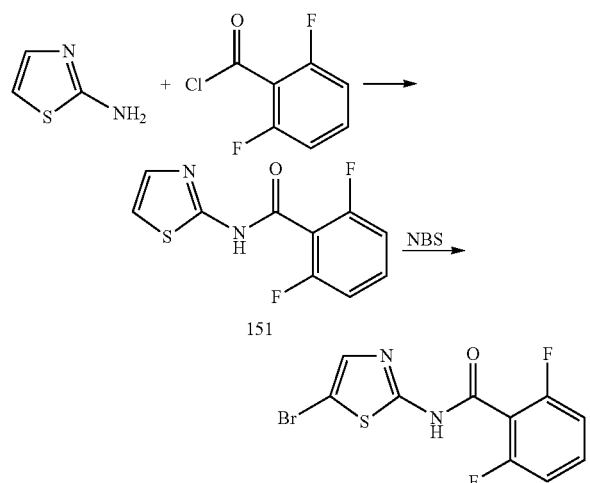

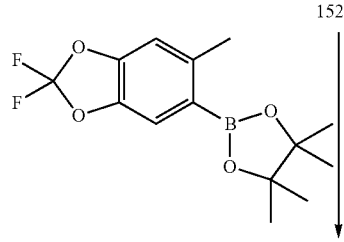

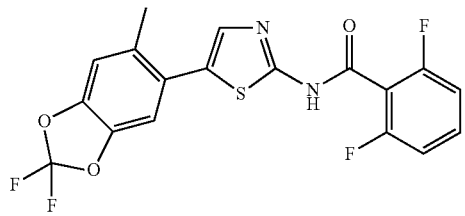

153

To a mixture of 2-aminothiazole (200 mg, 4 mmol) and N,N-diisopropylethylamine (2.1 mL) in 15 ml DCM was added a solution of 2,6-benzoyl chloride (600 µl, 4.8 mmol) in 5 mL DCM at 0° C. The resulting mixture was stirred at 0° C. for 10 min then at room temperature for 1.5 h before worked up with DCM/aqueous NaHCO₃/brine. The organic phase was dried (Na₂SO₄) and concentrated to give intermediate 151 (1.18 g, purity>85%) as yellow solid which was brominated without further purification.

To a suspension of crude 151 (1.18 g) in 20 mL acetonitrile was added NBS (1.07 g, 6 mmol, 1.5 eq). The reaction was stirred overnight at room temperature and then worked up with ethyl acetate/aqueous NaHCO₃/brine. The organic phase was dried (Na₂SO₄), concentrated and subjected to silica gel purification to furnish compound 152 (350 mg, yield: 27.4%, purity>90%) as light yellow solid and intermediate 151 (194 mg) was recovered from column.

Argon was bubbled through a mixture of (2,6-difluorophenyl)-N-(5-bromo(1,3-thiazol-2-yl))carboxamide (152) (64 mg, 0.2 mmol), 2-(2,2-difluoro-6-methylbenzo[d][1,3]dioxol-5-yl)-4,4,5,5-tetramethyl-1,3,2-dioxaborolane (489 mg, 0.3 mmol), bis(ditertbutyl(4-dimethylaminophenyl) phosphine)dichloropalladium (II) (21 mg, 10% mol) and K₃PO₄ (64 mg) in 1 mL ACN, 1 mL dioxane, 0.5 ml H₂O. The reaction mixture was heated at 85° C. for 7 h. After cooling to room temperature, the reaction mixture was taken up in ethyl acetate, washed with aqueous NaHCO₃ and brine. The organic phase was dried over (Na₂SO₄), concentrated and then subjected to prep HPLC chromatography to give (2,6-difluorophenyl)-N-[5-(2,2-difluoro-6-methylbenzo[d]1,3-dioxolen-5-yl)(1,3-thiazol-2-yl)]carboxamide (153) (7.4 mg, yield: 9%, purity>95%) as white solid. LC-MS: calcd. for $C_{18}H_{10}F_4N_2O_3S$: 411 (M+1).

Compound 154 was prepared using similar procedure of 153. For compound 154, LC-MS: calcd. for $C_{18}H_{11}F_3N_2O_3S$: 393 (M+1).

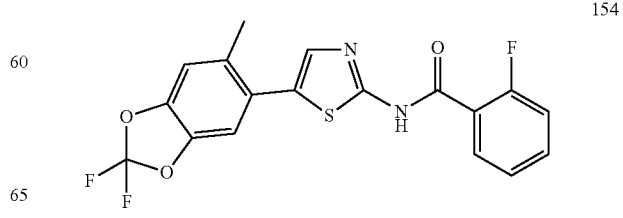

154

IN VITRO EXAMPLES

Example 85

In Vitro Screening for Agents that Modulate Intracellular Calcium Levels

Fluorescence-based assays are used for screening the compounds described herein, such as compounds of Formula (I), (II), (III), or (IV) which modulate intracellular calcium.

A. Fluorescence-Based Assay of Store-Operated Calcium Entry in Orai1/Stim1 Stable Cells.

Cells:

Cells stably expressing recombinant human STIM1 and Orai1 are generated by transfecting a human Orai1 expression plasmid (pcDNA3.1-Orai1-cmyc) into HEK-293 cells stably overexpressing human STIM1 (Roos et al. 2005 JCB 169(3): 435-445). Colonies of cells stably expressing both STIM1 and Orai1 proteins are selected and then subcloned by limiting dilution. Cells were cultured at 37° C./6% $CO_2$ in complete medium with 10% FBS and appropriate selection markers.

Assay

The day prior to performing the assay Orai1/STIM1 stable cells are plated in 50 µL of complete medium at 90-95% confluence in a 384 well plate. Cells are grown at 37° C./6% $CO_2$ overnight. On the day of the assay, 1.5 µM fluo-4-AM (Invitrogen) in complete medium is added to the cells, which are then incubated for 1 hour at RT. Cells are washed once in $Ca^{2+}$-free HBSS (Hank's buffered saline solution) and 35 µl of $Ca^{2+}$-free HBSS is added to each well. Test compounds are added to wells in a 10 µL $Ca^{2+}$-free HBSS solution, prepared at 4.5× the desired final concentration, and incubated for 30 minutes at RT. The initial baseline fluorescence signal is then measured with a FLIPR[384] (Molecular Devices) plate reader. Calcium entry is initiated by adding 5 µl of 10×$CaCl_2$ (10 mM) in HBSS, and changes in cellular fluorescence are measured with the FLIPR[384] plate reader. In each well, the magnitude of the fluorescence signal as a result of calcium entry into the cell is determined by calculating the difference between the peak fluorescence signal measured after calcium addition and the initial baseline fluorescence signal (designated Peak-Basal). $IC_{50}$ values are typically calculated as the concentration that inhibited 50% of the Peak-Basal signal.

B. Fluorescence-Based Assay of Store-Operated Calcium Entry in RBL-2H3 Cells.

Cells:

RBL-2H3 cells are obtained from ATCC and maintained in complete medium with 10% FBS at 37° C./6% $CO_2$.

Assay:

The day prior to performing the assay, RBL-2H3 cells are plated in 50 µl of complete medium in a 384 well plate. Cells are grown at 37° C./6% $CO_2$ overnight and grow to 50-60% confluence by the next day. On the assay day, 1.5 µM Fluo-4-AM dye (Invitrogen) in complete medium is added and incubated for 1 hour at RT. Cells are washed twice in $Ca^{2+}$-free HBSS buffer and 35 µl $Ca^{2+}$-free HBSS buffer is added to each well. 10 µl of a test compound prepared in a $Ca^{2+}$-free HBSS solution at 4.5× of the desired concentration is added to a well and incubated for 5 minutes at RT. 10 µl of thapsigargin prepared in a $Ca^{2+}$-free HBSS solution at 5.5× of the desired concentration (5.5 uM) is added to each well and incubated for an additional 25 minutes. The initial baseline fluorescence signal is measured with a FLIPR[384] (Molecular Devices) plate reader. 5 µl of 12× calcium in HBSS (12 mM) is added and changes in cellular fluorescence are measured with the FLIPR[384] plate reader. In each well, the change in the fluorescent signal as a function of time due to calcium entry into the cell is determined by calculating the difference between the fluorescent signal measured 7 seconds after calcium addition and the initial baseline fluorescence signal at time zero (t=0). This parameter is designated Upslope. The $IC_{50}$ value is calculated as the concentration at which 50% of the Upslope is inhibited.

C. Fluorescence-Based Assay of Store-Operated Calcium Entry in Jurkat Cells.

Cells:

Jurkat E6-1 cells are obtained from ATCC and maintained in complete medium with 10% FBS at 37° C./6% $CO_2$.

Assay:

The day prior to performing the assay, Jurkat E6-1 cells are seeded at a density of 2 million cells/mL in complete medium in a T-175 flask. Cells are grown at 37° C./6% $CO_2$ overnight. On the following day, 1.5 µM Fluo-4-AM dye (Invitrogen) in complete medium is added and incubated for 1 hour at RT. Cells are harvested, washed twice in $Ca^{2+}$-free HBSS buffer and plated in 35 µL $Ca^{2+}$-free HBSS buffer in a 384 well plate. 10 µL of a test compound prepared in a $Ca^{2+}$-free HBSS solution at 4.5× of the desired concentration is added to a well and incubated for 5 minutes at RT. 10 µL of thapsigargin prepared in a $Ca^{2+}$-free HBSS solution at 5.5× of the desired concentration (5.5 uM) is added to each well and incubated for an additional 25 minutes. The initial baseline fluorescence signal is measured with a FLIPR[384] (Molecular Devices) plate reader. 5 µL of 12× calcium in HBSS (12 mM) is added and changes in cellular fluorescence are measured with the FLIPR[384] plate reader. In each well, the change in the fluorescent signal as a function of time due to calcium entry into the cell is determined by calculating the difference between the fluorescent signal measured 7 seconds after calcium addition and the initial baseline fluorescence signal at time zero (t=0). This parameter is designated Upslope. The $IC_{50}$ value is calculated as the concentration at which 50% of the Upslope is inhibited.

TABLE A

In Vitro Fluorescence-based Assay Data

| Example | FLIPR_CRAC: 9 point CRC: O1S1_JR251: IC50: Peak_over_Basal (uM) | FLIPR_CRAC: 9 pt CRC - Fluo4_TG-D: RBL-2H3: IC50: Upslope 0-7 sec (M) |
| --- | --- | --- |
| 1 | A | A |
| 2 | A | A |
| 3 | A | A |
| 4 | A | A |
| 5 | A | A |
| 6 | A | A |
| 7 | A | A |
| 8 | B | A |
| 9 | A | A |
| 10 | A | A |
| 11 | A | A |
| 12 | B | A |
| 13 | A | A |
| 14 | B | A |
| 15 | B | NT |
| 16 | B | NT |
| 17 | B | A |
| 18 | C | NT |
| 19 | A | A |
| 20 | B | A |
| 21 | — | NT |
| 22 | C | A |
| 23 | — | NT |
| 24 | B | A |
| 25 | C | B |

TABLE A-continued

In Vitro Fluorescence-based Assay Data

| Example | FLIPR_CRAC: 9 point CRC: O1S1_JR251: IC50: Peak_over_Basal (uM) | FLIPR_CRAC: 9 pt CRC - Fluo4_TG-D: RBL-2H3: IC50: Upslope 0-7 sec (M) |
|---|---|---|
| 26 | <50% efficacy | A |
| 27 | A | A |
| 28 | A | A |
| 29 | C | C |
| 30 | C | NT |
| 31 | NT | NT |
| 32 | NT | NT |
| 33 | C | A |
| 34 | C | A |
| 35 | A | A |
| 36 | A | A |
| 37 | A | A |
| 38 | A | A |
| 39 | A | B |
| 40 | NT | NT |
| 41 | A | A |
| 42 | A | A |
| 43 | B | B |
| 44 | A | B |
| 45 | B | B |
| 46 | A | A |
| 47 | A | B |
| 48 | A | B |
| 49 | A | A |
| 50 | B | A |
| 51 | A | A |
| 52 | B | B |
| 53 | A | A |
| 54 | A | A |
| 55 | A | A |
| 56 | A | A |
| 57 | A | A |
| 58 | A | A |
| 59 | A | B |
| 60 | A | A |
| 61 | A | A |
| 62 | A | B |
| 63 | C | NT |
| 64 | — | NT |
| 65 | C | NT |
| 66 | — | NT |
| 67 | B | NT |
| 68 | — | NT |
| 69 | B | A |
| 70 | — | NT |
| 71 | A | A |
| 72 | A | A |
| 73 | B | B |
| 74 | A | A |
| 75 | <50% efficacy | C |
| 76 | A | A |
| 77 | B | A |
| 78 | C | B |
| 79 | C | B |
| 80 | C | A |
| 81 | C | A |
| 82 | A | A |
| 83 | C | A |
| 84 | A | A |

A: IC50<0.6 µM; B: IC50=0.6-1.2 µM; C: IC50>1.2 µM; NT=not tested.

Example 86

In Vitro I$_{CRAC}$ Patch Clamp Assay

Objective

The objective of this assay is to examine the in vitro effects of compounds having the structure of Formula (I), (II), (III), or (IV) on cloned CRAC channels (Orai1 and STIM1 genes stably expressed in HEK293 cells), responsible for I$_{CRAC}$, the calcium release activated calcium channel current.

Test and Control Articles

Formulation: Test article stock solutions are prepared in dimethyl sulfoxide (DMSO) and stored frozen. Test article concentrations are prepared fresh daily by diluting stock solutions into an appropriate external recording buffer. If necessary, test article formulations are sonicated (Model 2510, Branson Ultrasonics, Danbury, Conn.), at ambient room temperature to facilitate dissolution. In certain instances, the test solutions contain up to 0.1% DMSO and the presence of 0.1% DMSO does not affect channel current.

Test Article Concentrations and Quantity

Typically, the effects of three (3) concentrations of each test article are evaluated (0.1, 1, and 10 µM). Test articles are weighed and prepared as 30 mM or 10 mM stock solutions in DMSO. The DMSO stock is diluted in external recording buffer to prepare a 10 µM test solution (final DMSO 0.03% or 0.1%). The 10 µM test solution is diluted in external recording buffer to prepare 1 µM and 0.1 µM test solutions. Test solutions contain up to 0.1% DMSO at the highest concentration which are diluted in test solutions at lower concentrations.

Positive Control Article

Stock solutions of the positive control article are prepared in batches, aliquoted for individual use, stored frozen and used within six months. The positive control concentration is prepared fresh daily by diluting stock solutions into external recording buffer. The final DMSO concentration in the test positive control article is up to 0.1% of the solution.

Negative Control Article

The negative control article is 0.1% DMSO in external recording buffer.

Cloned Ion Channel Test Systems

Cells are maintained in tissue culture incubators per CalciMedica standard protocols. Stocks are maintained in cryogenic storage. Cells used for electrophysiology are plated in plastic tissue culture dishes.

HEK293 Cells

HEK293 cells are stably transfected with the appropriate ion channel cDNAs (Orai1/STIM1). Cells are cultured in DMEM (Gibco 11960) supplemented with 10% fetal bovine serum (Gibco 10082), 100 U/mL penicillin G sodium, 1 mM Na pyruvate (Gibco 11360), 100 µg/mL streptomycin sulfate (Gibco 10378), 0.5 mg/ml geneticin (Gibco 10131-035) and 50 µg/ml zeocin (Invitrogen 45-0430). Cells should be maintained at ≤80% confluence. The day before testing, cells in culture dishes are washed once with calcium/magnesium-free D-PBS, treated with trypsin/EDTA and re-suspended in the culture media and counted. Cells are then diluted in culture medium with 1% fetal bovine serum and plated at low density (5-10K) onto poly-D-lysine coated glass coverslips in 24-well tissue culture dishes and placed in a tissue culture incubator set at 37° C. in a humidified 95% air, 6% CO$_2$ atmosphere.

Test Methods

Recording Chamber and Perfusion of Test Articles

Glass coverslips containing cells are transferred to a recording chamber (Warner Instruments) with continuous perfusion of external recording buffer. During recordings of I$_{CRAC}$, all treatments are delivered by gravity-fed bath perfusion from disposable syringe reservoirs via disposable polyethylene tubing feeding into a Teflon manifold. The flow rate is set between 1.2-1.5 ml/min assuring complete solution exchange in ~1 min. All experiments are performed at ambient temperature.

Test Article Treatment Groups

For experiments where the test article is applied for 10 minutes the treatment paradigm is summarized in Table 2. Control recording buffer is perfused for five (5) minutes while $I_{CRAC}$ develops and a stable baseline is established; each cell is used as its own control. Each test article is applied to naïve cells (n≥2, where n=the number cells/concentration; at 1 concentration/cell) for a duration of ten (10) minutes (Table 2). The test article is washed off for ten (10) minutes to look for reversibility of the effect. External recording saline with no calcium is perfused for two (2) minutes to determine the background current in the absence of $I_{CRAC}$. Control saline containing calcium is reapplied for three (3) minutes.

For experiments where the test article is applied for 30 minutes prior to recording of $I_{CRAC}$, the treatment paradigm is summarized in Table 3. Prior to the start of each experiment, cells are incubated with compound for 30 minutes at room temperature, and compound remains present throughout $I_{CRAC}$ recordings. Control cells are exposed to vehicle only. After break-in and establishment of the whole-cell patch clamp configuration, recording buffer±compound is perfused for ten (10) minutes. At the end of the 10 min period the amplitude of $I_{CRAC}$ is measured. The effects of compounds are determined by comparing the $I_{CRAC}$ signal in cells pretreated with compound to the signal in cells pretreated with vehicle.

TABLE 2

Test Article Schedule for 10-minute Application Studies

| Epoch | Solution | Exposure time |
|---|---|---|
| 1 | Baseline control/stabilization | 5 minutes |
| 2 | Test article | 10 minutes |
| 3 | Wash | 10 minutes |
| 4 | 0 calcium | 2 minutes |
| 5 | control | 3 minutes |

TABLE 3

Test Article Schedule for 40-minute Application Studies

| Epoch | Solution | Exposure time |
|---|---|---|
|   | Test article | 30 minutes |
| 1 | Test article | 10 minutes |
| 2 | Wash | 10 minutes |
| 3 | 0 calcium | 2 minutes |
| 4 | control | 3 minutes |

Control Treatment Groups

As a negative control, 0.1% DMSO is applied to naïve cells (n≥2, where n=the number cells. This is used to monitor the magnitude of rundown of $I_{CRAC}$. As a positive control, 1 µM of 4-(4-bromophenyl)-2-(3-fluorobenzamido)thiophene-3-carboxylic acid is routinely applied to naïve cells (n≥2, where n=the number cells).

Whole Cell Patch Clamp Procedures

Standard whole cell patch clamp procedures are used. The compositions of the extracellular and intracellular solutions are shown in Tables 4 and 5. Cells are visualized on an inverted microscope (Olympus IX71) and voltage clamped using a Multiclamp 700B amplifier and PClamp software (Axon Instruments). Briefly, borosilicate patch pipettes filled with intracellular solution (Appendix 1) are positioned onto the cell membrane. Once a GΩ seal is formed, suction is applied until the patch ruptures and the whole cell configuration is established. The quality of the configuration will be evaluated with the "membrane test" in Clampex to determine cell capacitance (Cm), input resistance (Rm), access resistance (Ra), and holding current at −50 mV (Ih). Data are stored on the CalciMedica computer network (and backed-up nightly) for off-line analysis.

TABLE 4

Extracellular Solution Composition (concentration in mM)

| NaCl | 120 |
|---|---|
| TEA-Cl | 10 |
| HEPES | 10 |
| CaCl2 | 10 (and 0) |
| MgCl2 | 2 (and 12) |
| glucose | 10 |

The pH is adjusted to 7.2 with NaOH and the final osmolarity is adjusted to 325 with sucrose. Solutions are prepared daily. Chemicals used in solution preparation are purchased from Sigma-Aldrich (St. Louis, Mo.), unless otherwise noted, and are of ACS reagent grade purity or higher.

TABLE 5

Intracellular Solution Composition (concentration in mM)

| Cs-glutamate | 120 |
|---|---|
| HEPES | 10 |
| BAPTA | 20 |
| MgCl2 | 3 |

The pH is adjusted to 7.2 with CsOH. Solutions are prepared in batches, aliquoted, and refrigerated until use. A fresh aliquot is used each day and stored on ice throughout the day. Chemicals used in solution preparation are purchased from Sigma-Aldrich (St. Louis, Mo.), unless otherwise noted, and are of ACS reagent grade.

Figure 2:
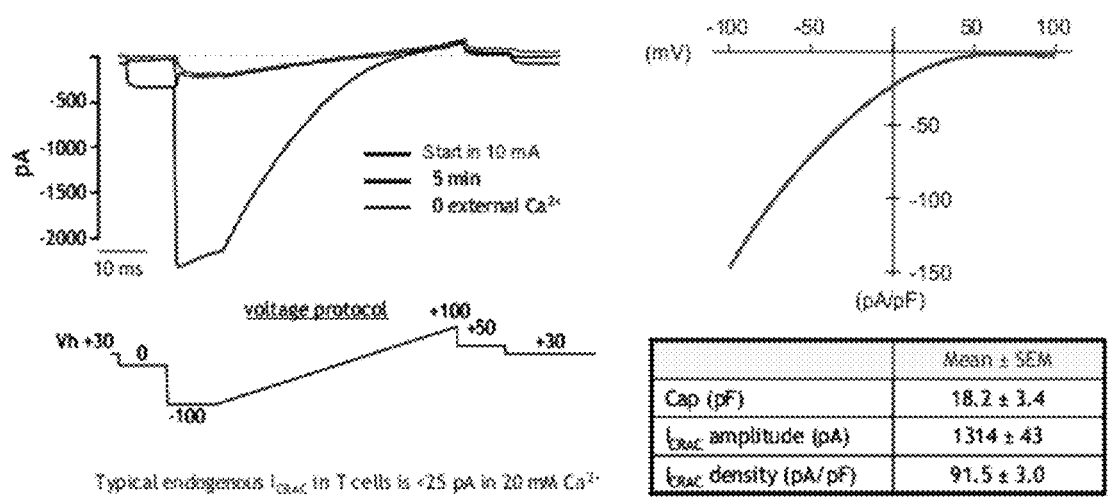
FIG. 2 shows the typical I$_{CRAC}$ traces in cells stably overexpressing human Orai1 and STIM1 in response to the voltage stimulus immediately after break-in, before I$_{CRAC}$ is activated, and at 5 min after I$_{CRAC}$ is fully activated by depletion of intracellular calcium stores.

$I_{CRAC}$ Test Procedures $I_{CRAC}$ from the Orai1/STIM1 channel complex is activated by passive depletion of intracellular calcium stores using 20 mM BAPTA in the intracellular solution. Voltage clamp data is acquired using Clampex software to elicit a stimulus voltage protocol (shown in Table 6) applied every six (6) seconds. Currents are digitized at 10 kHz and filtered at 2 kHz. Whole cell capacitive compensation is employed. Representative $I_{CRAC}$ traces are shown in FIG. 2.

TABLE 6

Voltage Clamp Protocol

| Voltage | Description |
|---|---|
| Vh +30 mV | to minimize calcium entry in-between sweeps |
| Vstep to 0 mV for 10 ms | to evaluate "zero" current |
| Vstep to −100 mV for 10 ms | to measure $I_{CRAC}$ at high driving force |
| Vramp to +100 mV over 50 ms | to monitor inwardly rectifying profile of $I_{CRAC}$ |
| Vstep to +50 mV for 10 ms | to estimate leak current |

Data Analysis

Data analysis is performed using Clampfit software. $I_{CRAC}$ is measured at −100 mV and the current measured after 5 min is used as the baseline control. For 10-minute application studies, the current measured after 10 min application of the test article is normalized to the baseline current and expressed as % control. For 40-min application studies, the current measured at the end of 10 minutes of $I_{CRAC}$ recording time is used as the comparator. The current measured in "0 calcium"

buffer is used to subtract background leak current. Data points for each test article concentration (n≥2) are fitted to a sigmoid function (SigmaPlot) to determine the $IC_{50}$ and Hill slope.

IN VIVO EXAMPLES

Example 87

In Vitro Assay of Mast Cell Degranulation

Cells:
RBL-2H3 cells are obtained from ATCC and maintained in complete medium with 10% FBS at 37° C./6% CO2.
Assay:
a) Stimulation with 1 µM Thapsigargin/20 nM TPA
The day prior to performing the assay, RBL-2H3 cells are plated in a 96 well plate. Cells are grown at 37° C./6% CO2 overnight. On the following day, cells are washed twice in HBSS Buffer with 1.8 mM CaCl2 and 1.75% fetal bovine serum (FBS). 70 µl of a test compound prepared in HBSS Buffer with 1.8 mM CaCl2+1.75% FBS is added and incubated for 10 minutes at 37° C./6% CO2. Cells are stimulated by the addition of 7 µl of 11× thapsigargin/TPA (11 µM thapsigargin/220 nM TPA) and incubated at 37° C./6% CO2 for 120 minutes. Media is collected and cell lysates are prepared by the addition of 70 µL of 0.05% Triton X-100 in HBSS with 1.8 mM CaCl2. Levels of β-hexosaminidase are measured in both the media and the cell lysates. The β-hexosaminidase assay is performed by adding 40 µL of 1 mM p-nitrophenyl-acetyl-glucosamide substrate in 0.05M sodium citrate (pH 4.5) to 10 µL of sample (conditioned medium or cell lysate), incubating 60 minutes at 37° C., then adding 100 µL 0.05M sodium carbonate/0.05M sodium bicarbonate (pH 10.5), mixing thoroughly and reading the absorbance at 405 nm. The percentage of β-hexosaminidase released is calculated as follows: A405 (media)/[A405 (media)+A405 (lysate)]. The $IC_{50}$ value is calculated as the concentration at which 50% of the β-hexosaminidase released in vehicle treated cells is inhibited.

b) Stimulation with IgE-DNP
The day prior to performing the assay, RBL-2H3 cells are plated in 200 µL of complete medium in a 96 well plate for 1 hour. 20 µL of 11×DNP-IgE are added and cells are grown at 37° C./6% CO2 overnight. On the following day, cells are washed twice in HBSS Buffer with 1.8 mM CaCl2 and 1.75% fetal bovine serum (FBS). 70 µL of a test compound prepared in HBSS Buffer with 1.8 mM CaCl2 and 1.75% is added and incubated for 10 minutes at 37° C./6% CO2. Cells are stimulated by the addition of 7 µl of 11×DNP-BSA and incubated at 37° C./6% CO2 for 30 minutes. Media is collected and cell lysates are prepared by the addition of 70 ul of 0.05% Triton X-100 in HBSS with 1.8 mM $CaCl_2$. Levels of β-hexosaminidase are measured in both the media and the cell lysates. The β-hexosaminidase assay is performed by adding 40 µL of 1 mM p-nitrophenyl-acetyl-glucosamide substrate in 0.05M sodium citrate (pH 4.5) to 10 µL of sample (conditioned medium or cell lysate), incubating 60 minutes at 37° C., then adding 100 µL 0.05M sodium carbonate/0.05M sodium bicarbonate (pH 10.5), mixing thoroughly and reading the absorbance at 405 nm. The percentage of β-hexosaminidase released is calculated as follows: A405 (media)/[A405 (media)+A405 (lysate)]. The $IC_{50}$ value is calculated as the concentration at which 50% of the β-hexosaminidase released in vehicle treated cells is inhibited.

Example 88

In Vitro Assay of Cytokine Release from T Cells

Cells:
Jurkat E6-1 cells are obtained from ATCC and maintained in complete medium with 10% FBS at 37° C./6% CO2.
Assay:
The day prior to performing the assay, Jurkat T cells are plated in 90 µL of HBSS Buffer with 1.8 mM $CaCl_2$ and 1.75% fetal bovine serum (FBS) in a 96 well plate at a density of 1.5×105 cells/well for 3 hours. 10 µl of 10× test compound prepared in HBSS is added and incubated for 10 minutes at 37° C./6% CO2. Cells are stimulated by the addition of 10 µl of 11×PHA/TPA (27.5 µg/mL PHA/880 nM TPA) and incubated at 37° C./6% $CO_2$ for 20 hours. On the following day, the supernatants are collected and assayed for IL-2 levels by ELISA according to the manufacturer's protocols. The $IC_{50}$ value is calculated as the concentration at which 50% of secreted IL-2 in vehicle treated cells is inhibited.

TABLE B

In Vitro Assay of Cytokine Release From T Cells Data

| Example | IL-2: PHA/TPA: Jurkat: IC50: (M) |
|---|---|
| 1 | A |
| 2 | A |
| 3 | A |
| 4 | A |
| 5 | A |
| 6 | A |
| 7 | A |
| 8 | NT |
| 9 | A |
| 10 | A |
| 11 | A |
| 12 | NT |
| 13 | A |
| 14 | NT |
| 15 | NT |
| 16 | NT |
| 17 | NT |
| 18 | NT |
| 19 | B |
| 20 | A |
| 21 | NT |
| 22 | NT |
| 23 | NT |
| 24 | A |
| 25 | NT |
| 26 | NT |
| 27 | A |
| 28 | A |
| 29 | NT |
| 30 | NT |
| 31 | NT |
| 32 | NT |
| 33 | NT |
| 34 | NT |
| 35 | A |
| 36 | A |
| 37 | A |
| 38 | B |
| 39 | A |
| 40 | NT |
| 41 | C |
| 42 | A |
| 43 | NT |
| 44 | B |
| 45 | NT |
| 46 | A |
| 47 | C |
| 48 | C |
| 49 | NT |

TABLE B-continued

In Vitro Assay of Cytokine Release From T Cells Data

| Example | IL-2: PHA/TPA: Jurkat: IC50: (M) |
|---|---|
| 50 | NT |
| 51 | A |
| 52 | NT |
| 53 | A |
| 54 | A |
| 55 | A |
| 56 | A |
| 57 | A |
| 58 | A |
| 59 | C |
| 60 | A |
| 61 | A |
| 62 | B |
| 63 | NT |
| 64 | NT |
| 65 | NT |
| 66 | NT |
| 67 | NT |
| 68 | NT |
| 69 | NT |
| 70 | NT |
| 71 | NT |
| 72 | A |
| 73 | NT |
| 74 | A |
| 75 | NT |
| 76 | NT |
| 77 | NT |
| 78 | NT |
| 79 | NT |
| 80 | NT |
| 81 | NT |
| 82 | A |
| 83 | A |
| 84 | A |

A: IC50 < 0.05 µM; B: IC50 = 0.05-0.1 µM; C = IC50 > 0.1 µM; NT = not tested.

Example 89

Dose-Response Effects of a Compound of Formula (I), (II), (III) or (IV), CSA or Rapamycin in Mouse Footpad DTH Purpose: Determine dose-response effects of Test Compound on mBSA induced DTH response in foot pads when dosing is done during the sensitization as well as induction phase.

Animals: Male Swiss Webster Mice approx. 20-25 grams at start of study.

Materials: Methylated BSA (Sigma) Freund's complete adjuvant (Difco) plus supplemental *M. tuberculosis* H37 RA (Difco).

General Study Design: Mice are anesthetized with Isoflurane and given intradermal antigen injections of 0.1 ml at the base of the tail (D0, D07). Antigen is prepared by making a 4 mg/ml solution in sterile water. Equal volumes of antigen and Freund's complete adjuvant to which 4 mg/ml MTB are added (sonicate for 5 minutes after adding MTB to oil), are emulsified by hand mixing until a bead of this material holds its form when placed in water. Treatment with test compound is initiated on day 0, qd (24 hr intervals) and continued through day 10 when challenge is done.

On day 10 animals are injected into the right hind footpad with 20 µl of 10 mg/ml mBSA. Five unsensitized males are injected with mBSA into the footpad. Twenty-four hours later (day 11) the right and left hind paws are transected at the medial and lateral malleolus and weighed and the weight difference induced by injection of antigen is determined.

Statistical Analysis. Paw weights (mean±SE) for each group are analyzed for differences using a Student's t test or ANOVA with Dunnett's post test. Statistical significance is set at $p \leq 0.05$.

TABLE 7

Treatment Groups Males

| Group | N | Treatment 10 ml/kg qd, po |
|---|---|---|
| 1 | 5 | Normal controls (no sensitization) Inject mBSA into right only |
| 2 | 8 | DTH + Vehicle (70% PEG400/30% Water) |
| 3 | 8 | DTH + Test Compound (50 mg/kg, po, qd) |
| 4 | 8 | DTH + Test Compound (100 mg/kg, po, qd) |
| 5 | 8 | DTH + Test Compound (200 mg/kg, po, qd) |
| 6 | 8 | DTH + Test Compound (300 mg/kg, po, qd) |
| 7 | 8 | DTH + CSA (100 mg/kg qd, ip) |
| 8 | 8 | DTH + Rapamycin (5 mg/kg qd, ip) |

Compounds of Formula (I)-(IV) are expected to be effective in this model.

Example 90

Pharmacokinetic Data of a Compound of Formula (I), (II), (III), or (IV) in Rats

The bioavailability and plasma pharmacokinetic properties in rats of Compound of Formula (I), (II), (III), or (IV) administered orally in 25% PEG400/20% ethanol/55% H$_2$O vehicle. Two treatment groups, 1) an i.v. dose group at 2 mg/kg; and 2) an oral dose group at 10 mg/kg are administered to Male Sprague-Dawley rats (3 rats per group), weighing approximately 250-300 gm. Up to 10 time points are collected for each group. Typical time points are: predose, 15, 30 minutes, 1, 2, 4, 6, 8, 12 and 24 hrs. Up to 300 µL of whole blood are collected via jugular vein cannula at each time point. Whole blood is collected into anticoagulant containing microcentrifuge tubes and centrifuged at 5000 rpm in a microcentrifuge for 5 minutes before plasma is transferred to a clean microcentrifuge tube. The plasma samples undergo bioanalytical analysis.

Example 91

Effect of Compound of Formula (I), (II), (III), or (IV) in Rat Collagen Induced Arthritis (CIA) Model Purpose: Determine efficacy of Test Compound administered by oral dosing qd, in inhibiting the inflammation, cartilage destruction and bone resorption of developing type II collagen arthritis in rats.

Animals: Female Lewis rats (Charles River#7246950), weighing 125-150 g at the start of the study. 40 rats are injected with collagen to get solid responders on days 10 and 11. Four nonimmunized animals serve as normal controls.

Materials: Test Compound, Type II collagen, Freund's incomplete adjuvant, acetic acid. Test Compound is prepared at a concentration of 10 mg/ml in 50% PEG400/50% water. Collagen is prepared by making a 4 mg/ml solution in 0.01N Acetic acid. Equal volumes of collagen and Freund's incomplete adjuvant, are emulsified by hand mixing until a bead of this material holds its form when placed in water.

General Study Design: Animals (10 rats/group for arthritis, 4 rats/group for normal control).

Animals in the arthritis groups are anesthetized with isoflurane and given collagen injections (D0); each animal gets 300 μl of the mixture spread over 3 subcutaneous sites on the back. On Day 6 (D6) the animals are anesthetized again and given a second collagen injection, as before.

Oral dosing of a compound of Formula (I), (II), (III), or (IV) at 24 hour intervals (qd) is initiated on Day 0 using a dose volume of 5 ml/kg for oral solutions. Rats are weighed on Days 0, 3, 6, and 9-17 of arthritis, and caliper measurements of ankles taken every day beginning on Day 9. Final body weights are taken on Day 17 of arthritis. On Day 17, all animals are anesthetized for terminal blood draw and then euthanized. Subsequently, hind paws and knees are removed, the hind paws are weighed and then (with knees) placed in formalin for processing for microscopy. Livers, spleen and thymus and kidneys are also removed, trimmed of extraneous tissue and weighed. Kidneys are retained in formalin for histopathology.

Sampling will occur over 1 day and involves groups 2-5 with samples retained from all groups. This results in all animals being treated similarly and is important for clinical parameters and final liver weights.

Example 92

Effect of Compounds of Formula (I), (II), (III), or (IV) on DNBS-Induced Colitis in Rats Procedure: Male Wistar rats weighing 200±20 g are fasted for 24 hours prior to use. Distal colitis is induced by intracolonic instillation of DNBS (2,4-dinotrobenzene sulfonic acid, 20 mg in 0.5 ml ethanol 30%) with a catheter of 12 cm in length, followed by gentle injection of air (2 ml) through the catheter to ensure that the solution remain in the colon. The animals are divided into groups of 5 each. Test substance and vehicle are administered either daily or twice daily by appropriate route of administration 24 hour and 1 hour before DNBS instillation and then for 6 consecutive days thereafter. One normal control group is treated with 0.9% NaCl alone without DNBS challenge. The animals are sacrificed 12 hours after the final bid dose and 24 hours after the final daily dose and the colon is removed and weighed. During the experiment, body weight, fecal occult blood and stool consistency are monitored daily. Furthermore, when the abdominal cavity is opened before removal of the colon, adhesions between the colon and other organs are noted as is the presence of colonic ulceration after removal and weighing of each colon (a macroscopic damage score is recorded according to established score criteria). The colon-to-body weight ratio is calculated according to the formula: Colon (g)/BW×100. The "Net" increase in ratio of Vehicle-control+DNBS group relative to Vehicle-control group is used as a base for comparison with individual treated groups and expressed as "Dec. (%)" (percent decrease). A 30% or more (>30%) reduction in colon-to-body weight ratio, relative to the vehicle treated control group, is considered significant.

Sulfasalazine is used as the standard test agent. (Hogaboam C M, et al., An orally active non-selective endothelin receptor antagonist, bosentan, markedly reduces injury in a rat model of colitis. *Eur J Pharmacol.* 309: 261-269, 1996; Yue G, et al., In some embodiments, the 21-aminosteroid tirilazid mesylate ameliorates inflammatory bowel disease in rats. *J Pharmacol Exp Ther.* 276: 265-270, 1996.)

Compound of Formula (I)-(IV) are expected to reduce colitis in this model.

Example 93

Effect of Compounds of Formula (I), (II), (III), or (IV) on Rejection of Skin Transplants in Rats Procedure. Specific pathogen free Lewis and Brown Norway rats 10 weeks of age are purchased from Charles River and housed under clean conventional conditions. The animals are handled and allowed to acclimatize for a period of two weeks. Skin donors: female Brown Norway rats, 10 weeks of age. Skin recipients: female Lewis rats, 10 weeks of age.

The donor Brown Norway rats are killed to serve as donors of 5 to 8 skin transplants. Directly after killing the Brown Norway rats, the abdominal skin of the rats is shaved and skin transplants of 20 mm in diameter in size are taken. After removal of connective tissue, these grafts are transplanted onto Lewis rats. This is performed by shaving the upper dorsal skin of the Lewis rat under isoflurane anesthesia, removing a piece of skin of 15 mm in diameter by punching and replacement with a skin transplant derived from the Brown Norway rat.

During the study each graft is fixated by 4-6 stitches using Safil 6/0 violet (B Braun, Aesculap) and covered by Paraffin Gauze Dressing BP (3×3 cm, Smith & Nephew), a piece of gauze and surgical tape. This adaptation minimizes the chance of loosing a transplant for reasons different from rejection.

In all cases, transplants are protected with a bandage; these are removed after six days to enable daily inspection of the transplant.

Rejection is monitored by evaluating first signs of inflammation (redness) and necrosis (hardening and blackening of the graft).

Example 94

Phase II Clinical Trial of the Safety and Efficacy of Compounds of Formula (I), (II), (III), or (IV) in Patients with Active Rheumatoid Arthritis The purpose of this phase II trial is to investigate the safety, tolerability, PK, PD, and efficacy of single and repeat intravenous infusions of a compound of Formula (I), (II), (III), or (IV) in patients with active rheumatoid arthritis.

Patients: Eligible subjects will be men and women between the ages of 18 and 75

Criteria:

Inclusion Criteria:

All subjects must use acceptable contraception to ensure that no pregnancies occur during the course of the study and for at least 12 weeks after dosing for males and for 32 weeks after dosing for females;

Body mass index within the range 18.5-35 kg/m$^2$ inclusive, in addition to a weight range of 55-95 kg;

The subject must be capable of giving informed consent and can comply with the study requirements and timetable;

The subject must have a diagnosis of RA according to the revised 1987 criteria of the American College of Rheumatology (ACR);

The subject must have a DAS28 disease activity score of greater than 4.2 at screening and pre-dose;

The subject must have a CRP serum level of >/0.5 mg/dl or an ESR level 28 mm/hour at screening and pre-dose;

The subject has NOT received any biological therapy in the past, including biologicals for the treatment of rheumatoid arthritis;

The subject must have liver function tests including alanine transaminase (ALT) and aspartate transaminase (AST) within 1.5 times the upper limit of normal (ULN) and alkaline phosphatase (ALP) within 3 times ULN at screening. The patient must also have total bilirubin within the ULN at screening;

The subject must have received at least 3 months of methotrexate and must be on a stable dose of methotrexate (up to 25 mg/week) for at least 8 weeks prior to screening and be willing to remain on this dose throughout the study;

If sulfasalazine is being taken in addition to methotrexate, the subject must be on a stable dose for at least 4 weeks prior to screening and be willing to remain on this dose throughout the study;

If hydroxychloroquine or chloroquine is being taken in addition to methotrexate, the subject must be on a stable dose for at least 3 months prior to screening and be willing to remain on this dose throughout the study;

Those subjects on other oral anti-rheumatic therapies, which may include Non Steroidal Anti Inflammatory Drugs (NSAIDs), COX-2 inhibitors, oral glucocorticoids e.g. prednisolone (~10 mg/day) must be on stable dosing regimens for at least 4 weeks prior to screening and be willing to remain on this regime throughout the study. Subjects receiving intramuscular glucocorticoids e.g methylprednisolone (~120 mg/month) must be on a stable dosing regimen for at least 3 months prior to screening and be willing to remain on this regimen throughout the study;

The subject must be on a stable dose of folate supplements (5 mg/week) for at least 4 weeks prior.

Exclusion Criteria:

Any clinically relevant abnormality identified on the screening medical assessment, laboratory examination (e.g. haematology parameter outside the normal limits), or ECG (12 Lead or Holter);

The subject has a positive Hepatitis B surface antigen or Hepatitis C antibody result at screening;

The subject has a history of elevated liver function tests on more than one occasion (ALT, AST and ALP>3×Upper Limit of Normal (ULN); total bilirubin>1.5×ULN) in the past 6 months;

Previous exposure or past infection caused by *Mycobacterium tuberculosis;*

The subject has an acute infection;

The subject has a history of repeated, chronic or opportunistic infections that, in the opinion of the investigator and/or GSK medical monitor, places the subject at an unacceptable risk as a participant in this trial;

The subject has a history of malignancy, except for surgically cured basal cell carcinoma or females with cured cervical carcinoma (>2 yrs prior);

The subject has a history of human immunodeficiency virus (HIV) or other immunodeficiency disease;

The subject whose calculated creatinine clearance is less than 50 ml/min;

The subject has significant cardiac, pulmonary, metabolic, renal, hepatic or gastrointestinal conditions that, in the opinion of the investigator and/or GSK medical monitor, places the subject at an unacceptable risk as a participant in this trial;

The subject has taken cyclosporine, leflonomide, cyclophophamide or azathioprine within 1 month of screening. Subjects that have taken cyclosporine, leflonomide, cyclophophamide or azathioprine in the past must have recovered from all drug related adverse events;

The subject has taken gold salts or d-penicillamine within 1 month prior to screening. Subjects that have taken gold salts or d-penicillamine in the past must have recovered from all drug related adverse events;

The subject has received intra-articular glucocorticoids within 1 month of screening;

Recent history of bleeding disorders, anaemia, peptic ulcer disease, haematemesis or gastrointestinal bleeding;

Subjects with a history of haematological disease or acquired platelet disorders, including drug-induced thrombocytopaenia, acute idiopathic thrombocytopaenia or von Willebrand's disease;

Subjects with a known risk of intra-cranial haemorrhage including Central Nervous System (CNS) surgery within the last 12 months, arterial vascular malformations, aneurysms, significant closed head trauma within 6 months or any other incident the investigator and/or medical monitor considers to be relevant;

The subject has Hb <10 g/deciliter (dL) and platelet count <150×109/Liter (L);

Donation of blood in excess of 500 ml within a 56 day period prior to dosing;

An unwillingness of male subjects to abstain from sexual intercourse with pregnant or lactating women; or an unwillingness of the male subject to use a condom with spermicide in addition to having their female partner use another form of contraception such as an interuterine device (IUD), diaphragm with spermicide, oral contraceptives, injectable progesterone, subdermal implants of levonorgestrel or a tubal ligation if the woman could become pregnant for at least 12 weeks after dosing;

An unwillingness of female subject of child bearing potential to use adequate contraception, as defined in the study restriction section. If necessary, women of non-child bearing potential (i.e. post-menopausal or surgically sterile e.g. tubal ligation or hysterectomy or bilateral oophorectomy) will be confirmed. Postmenopausal status will be confirmed by serum follicle stimulating hormone (FSH) and oestradiol concentrations at screening. Surgical sterility will be defined as females who have had a documented hysterectomy, tubal ligation or bilateral oophorectomy;

The subject has a history of use of drugs of abuse within 12 months prior to screening;

History of regular alcohol consumption exceeding average weekly intake of greater than 21 units or an average daily intake of greater than 3 units (males) or an average weekly intake of greater than 14 units or an average daily intake of greater than 2 units (females). Subjects who regularly consume more than 12 units of alcohol in a 24 h period will also be excluded. 1 unit is equivalent to a half-pint (220 ml) of beer/lager or 1 (25 ml) measure of spirits or 1 glass (125 ml) of wine;

Positive pregnancy test or lactating at screening;

Participation in a trial with any investigational drug within 3 months or 5 half-lives (whichever is longer) before.

Study Design: This is a randomized, double-blinded, placebo-controlled adaptive, dose finding study to investigate the safety, tolerability, PK, PD and efficacy of single and repeat intravenous infusions of a compound of Formula (I), (II), (III), or (IV) in patients with active rheumatoid arthritis. The study is divided into 2 parts: Part A is an adaptive, dose finding phase which will provide safety, tolerability, PK and PD on single intravenous infusions. Part B is a repeat dose phase which will provide safety, tolerability, PK, PD and efficacy following repeat intravenous infusions of a selected dose level.

Primary Outcome Measures:

Safety and Tolerability following single ascending doses of a compound of Formula (I), (II), (III), or (IV) at 1 month and following 3 repeat doses of a compound of Formula (I), (II), (III), or (IV) at 3 months. Clinical Efficacy (DAS28 score) of a compound of Formula (I), (II), (III), or (IV) at 1 month Secondary Outcome Measures:

Weighted mean DAS28 after single and repeat intravenous doses

Plasma PK parameters of a compound of Formula (I), (II), (III), or (IV) after single and repeat intravenous doses including free, and bound a compound of Formula (I), (II), (III), or (IV) (serum) concentrations, $AUC_{(0-\infty)}$, $C_{max}$, clearance, volume of distribution and accumulation ratio DAS28 and EULAR response criteria after single and repeat intravenous doses ACR20/ACR50/ACR70 response after single and repeat intravenous doses Number of swollen joints assessed using 28-joint counts Number of tender/painful joints assessed using 28-joint counts Subject's pain assessment Physician's global assessment of arthritis condition Patients' global assessment of arthritis condition Functional disability index (Health Assessment Questionnaire)

C-reactive Protein (CRP)

ESR

Global Fatigue Index

HAQ disability index

Pharmacodynamic biomarkers after single and repeat intravenous doses

Characteristic $AUC_{50}$ and $EC_{50}$ for clinical endpoint changes with plasma exposure model, as assessed by sigmoid $E_{max}$ and indirect response PK/PD models.

Immunogenicity (Human anti-compound of Formula (I), (II), (III), or (IV) antibodies)

Example 95

Phase II Clinical Trial of the Safety and Efficacy of Compounds of Formula (I), (II), (III), or (IV) in Patients with Severe, Recalcitrant, Plaque-type Psoriasis The purpose of this phase II trial is to investigate the safety, efficacy, and tolerability of a compound of Formula (I), (II), (III), or (IV) in patients with severe, recalcitrant, plaque-type psoriasis.

Patients: Eligible subjects will be men and women between the ages of 18 and 75.

Criteria:

Inclusion Criteria:

The patient has severe, recalcitrant, plaque-type psoriasis and has failed at least 1 systemic therapy (for the purposes of this study psoralen with ultraviolet light A is considered to be a systemic therapy);

The patient has psoriatic involvement of at least 10% of BSA;

The patient has a PSGA score of 4 or greater;

The patient, if a woman, is surgically sterile or 2 years postmenopausal, or if of childbearing potential is currently using a medically accepted method of contraception, and agrees to continue use of this method for the duration of the study (and for 30 days after participation in the study). Acceptable methods of contraception include: abstinence, steroidal contraceptive (oral, transdermal, implanted, or injected) in conjunction with a barrier method, or intrauterine device (IUD);

The patient, if a main, is surgically sterile, or if capable of producing offspring, is currently using an approved method of birth control, and agrees to continued use of this method for the duration of the study (and for 60 days after taking the last dose of a compound of Formula (I), (II), (III), or (IV) because of the possible effects on spermatogenesis);

The patient must be willing and able to comply with study procedures and restrictions and willing to return to the clinic for the follow-up evaluation as specified in this protocol.

Exclusion Criteria:

The patient has received treatment with systemic psoriasis treatments (specifically, retinoids, methotrexate, cyclosporine A, etanercept, efalizumab, other biological agents or other immunomodulators) within 4 weeks, or UV based therapy within 2 weeks, or alefacept within 6 weeks of the planned 1st day of study treatment;

The patient has received treatment with potent CYP3A4 inhibitors including cyclosporine, clotrimazole, fluconazole, itraconazole, ketoconazole, voriconazole, erythromycin, clarithromycin, and troleandomycin, human immunodeficiency virus (HIV) protease inhibitors, or nefazodone within 1 week (7 days) of the planned 1st day of study treatment;

The patient is currently receiving warfarin;

The patient has hypersensitivity to a compound of Formula (I), (II), (III), or (IV) or any component of a compound of Formula (I), (II), or (III);

The patient has one or more of the following serum chemistry values as determined at the screening visit (visit 1):

bilirubin levels greater than 2 times the upper limit of normal (ULN);

ALT or AST levels greater than 2 times the ULN;

serum creatinine levels or more than 2 mg/dL;

The patient requires current treatment for HIV with protease inhibitors;

The patient is taking medication for a clinical diagnosis of gastrointestinal ulceration or has experienced melena or hematoemesis in the previous 3 weeks;

The patient is a woman who is pregnant or lactating;

The patient has received treatment with an investigation drug within 4 weeks of the planned 1st day of study treatment.

Study Design: This is an exploratory, open-label, nonrandomized, dose-escalation study of the efficacy, safety, and tolerability of a compound of Formula (I), (II), (III), or (IV) in patients with severe, recalcitrant, plaque-type psoriasis.

Example 96

Phase II Clinical Trial of the Safety and Efficacy of Compounds of Formula (I), (II), (III), or (IV) for Prophylaxis of Acute Rejection after Renal Transplantation The standard immunosuppressive treatment after renal transplantation is a combination of tacrolimus, mycophenolate mofetil, and prednisolone. With this regimen the incidence of acute rejection within the first six months after transplantation can drop to about 20%. The main challenge at present remains to improve long-term outcome by preventing chronic allograft nephropathy (CAN). Since acute rejection is a strong predictor of CAN, a further decrease in the incidence of acute rejection can improve the long-term graft survival. The purpose of this phase II clinical trial is to investigate the effectiveness and safety of a compound of Formula (I), (II), (III), or (IV) for prophylaxis of acute rejection after renal transplantation.

Patients: Eligible subjects will be men and women ages 18 and older
Criteria:
Inclusion Criteria:
Renal transplant recipients;
Signed, dated, and witnessed IRB approved informed consent;
Exclusion Criteria:
Pregnancy;
Living donor, who is HLA identical;
Hemolytic uremic syndrome as original kidney disease;
Focal segmental glomerulosclerosis that had recurred in a previous graft;
More than two previously failed grafts and/or PRA >85%;
Diabetes mellitus that is currently not treated with insulin;
Total white blood cell count <3,000/mm3 or platelet count <75,000/mm3;
Active infection with hepatitis B, hepatitis C, or HIV;
History of tuberculosis.

Study Design: This is a randomized, double blind, placebo controlled intervention study on the efficacy and safety of the prophylactic use of a compound of Formula (I), (II), or (III). One group will receive a single dose of a compound of Formula (I), (II), (III), or (IV) intravenously at the time of transplantation, and the other group receives a placebo infusion.

Primary Outcome:
To determine the incidence and severity of biopsy-confirmed acute rejection within the first six months after transplantation
Secondary Outcomes:
Renal function as estimated by the endogenous creatinine clearance at 6 months
Occurrence of chronic allograft nephropathy at 6 months
Cumulative incidence of infections and malignancies at 6 months
Medical costs during the first 6 months after transplantation
Patient and graft survival Example 97

Phase II Clinical Trial of the Safety and Tolerability of a Compound of Formula (I), (II), (III), or (IV) in Patients with Active Ulcerative Colitis (UC)

The purpose of this phase II trial is to investigate the safety, tolerability of a compound of Formula (I), (II), (III), or (IV) regimen in patients with active ulcerative colitis.

Patients: Eligible subjects will be men and women aged 18 and older
Criteria:
Inclusion Criteria:
Active UC on 5-ASA therapy and also treated with 6-MP and/or corticosteroids or who have previously been treated with AZA, 6-MP or corticosteroids and could not tolerate them;
Mayo score of 6 to 10 points with moderate to severe disease on endoscopy (Mayo score of at least 2) performed ≤14 days of study drug administration;
Subjects on the following medications may be enrolled into the study if the medications were according to the following schedules prior to study drug administration and if no changes are anticipated during the study;
prednisolone ≤20 mg daily (or equivalent) (dose must be stable for at least 2 weeks prior to study drug administration);
5-ASA (dose must be stable for at least 4 weeks prior to study drug administration);
AZA or 6-MP (dose must be stable for at least 3 months prior to study drug administration);
Rectal steroids or 5-ASA (must have been stable for at least 4 weeks prior to study drug);
Subjects using rectal medications must have visible disease on sigmoidoscopy at ≥20 cm;
Screening laboratory values must meet certain criteria:
Women must be postmenopausal (>12 months without menses) or surgically sterile (e.g., by hysterectomy and/or bilateral oophorectomy) or must be using effective contraception (e.g., oral contraceptives, intrauterine device (IUD), double barrier method of condom and spermicidal) for at least 4 weeks prior to study drug administration and agree to continue contraception for the duration of their participation in the study; and
Sexually active male subjects must use a barrier method of contraception during the duration of the study
Exclusion Criteria:
Anti-TNF therapy within 8 weeks before study drug administration;
Any experimental therapy more therapy ≤4 weeks before study drug administration;
Prior treatment with any monoclonal antibody or immunoglobulin-based fusion proteins ≤8 weeks prior to study treatment;
Presence of Cushing's syndrome;
Toxic megacolon or fulminant disease likely to require colectomy;
Contraindication to colonoscopy or sigmoidoscopy;
Primary or secondary immunodeficiency;
Autoimmune disease besides UC, with the exceptions of Sjogren's syndrome or hypothyroidism;
History of malignancy, excluding adequately treated and cured basal or squamous cell of the skin, or cervical carcinoma in situ;
Major psychiatric disease (subjects with stable depression receiving appropriate management will be permitted in the study);
Evidence of acute or chronic infection as evidenced by:
stool culture positive for pathogens and/or *Clostridium difficile* toxin;
findings on Screening chest radiography such as pulmonary infiltrate(s) or adenopathy;
current treatment for tuberculosis infection, clinical or radiological evidence of active TB, or for subjects in North America, a positive PPD without prior prophylaxis;
Herpes zoster ≤3 months prior to study drug administration;
active infectious disease requiring i.v. antibiotics within 4 weeks prior to study treatment or oral antibiotics at the time of enrollment;
HIV or AIDS;
positive tests for HBV, or HCV indicating active or chronic infection;
Clinically significant cardiac disease requiring medication, unstable angina, myocardial within 6 months, or congestive heart failure;

Arrhythmia requiring active therapy, with the exception of clinically insignificant or minor conduction abnormalities;

History of cerebrovascular disease requiring medication/treatment;

Anticoagulation therapy or a known bleeding disorder;

Seizure disorder requiring active therapy;

Known drug or alcohol abuse;

Pregnant or nursing;

Any underlying medical condition that in the Principal Investigator's opinion will make the study drug hazardous to the subject or would obscure the interpretation of treatment efficacy or safety; or Inability or unwillingness to return for Follow-up visits and comply with study protocol Primary Outcome Measures:

Change in Mayo score at Day 57 compared with Screening

Secondary Outcome Measures:

Remission rate

Study Design: This is a phase II, double-blind, placebo-controlled, randomized, multi-dose study of a compound of Formula (I), (II), (III), or (IV) in subjects with active UC experiencing flare. All subjects will have active disease while on a 5-ASA containing medication and are either on stable doses of corticosteroids and/or azathioprine or 6-mercaptopurine, or who have previously been on these medications but could not tolerate them. Flare is defined as a Mayo score of 6 to 10 with moderate to severe disease activity on endoscopy (Mayo endoscopic subscore of at least 2) within 2 weeks of receiving study drug administration. Doses of permitted concomitant medications (corticosteroids, azathioprine (AZA), 6-mercaptopurine (6-MP), and 5-aminosalicylates (5-ASA) containing compounds) should remain constant during the course of the study. Subjects will be randomized to receive placebo or a compound of Formula (I), (II), (III), or (IV) intravenously on Days 1, 15, 29, and 43. All subjects will be seen in the clinic at regular intervals up to Day 85 for safety, efficacy, pharmacokinetic, and/or pharmacodynamic assessments. All subjects will be contacted 70 days after the last dose of study drug. Assessment of safety will be determined by vital sign measurements, clinical laboratory tests, physical examinations, immunogenicity assessments, chest x-ray, electrocardiograms, and the incidence and severity of treatment emergent adverse events. The primary clinical assessment of activity will be determined by the change in Mayo score at Day 57 compared with Screening. Secondary endpoints include determination of remission rate by the Mayo score at Day 57, evaluation of mucosal healing and change from baseline in the IBDQ score.

Example 98

Phase II Clinical Trial of the Safety and Efficacy of Compounds of Formula (I), (II), (III), or (IV) in Patients with Multiple Sclerosis The purpose of this phase II trial is to investigate the safety, efficacy and tolerability of a compound of Formula (I), (II), (III), or (IV) in patients with Relapsing-Remitting Multiple Sclerosis.

Patients: Eligible subjects will be men and women between the ages of 18 and 65.

Criteria:

Inclusion Criteria:

Have a definite diagnosis of Relapsing remitting Multiple Sclerosis

Have a history of at least 1 of the following: a. A minimum of 2 relapses of MS within the previous 2 years but not within the 1-month period prior to screening. b. A relapse of MS within the previous 6 months but not within the 1-month period prior to screening Exclusion Criteria:

Have a CNS disease (e.g., CNS lymphoma, systemic lupus erythematous)

Have significant bulbar involvement of MS or other neurologic deficits

Have a decubitus ulcer

Have received immunomodulatory therapies within 3 months of screening

Primary Outcome Measures:

The cumulative number of newly Gd-enhancing T1-weighted lesions on cranial MRIs through week 23

Secondary Outcome Measures:

The total number of relapses of MS through week 23; change from baseline in Expanded Disability Status Scale (EDSS) score at week 23

Study Design: This is a phase II, double-blind, placebo-controlled, randomized, dose-ranging study of multiple subcutaneous injections of a compound of Formula (I), (II), (III), or (IV) in patients with relapsing-remitting multiple sclerosis. Patients will receive subcutaneous injections of a compound of Formula (I), (II), (III), or (IV) or placebo at weeks 0, 1, 2, 3, 7, 11, 15, and 19 or 100.

Pharmaceutical Compositions

Parenteral Composition

To prepare a parenteral pharmaceutical composition suitable for administration by injection, 100 mg of a compound of Formula (I), (II), (III), or (IV) is dissolved in DMSO and then mixed with 10 mL of 0.9% sterile saline. The mixture is incorporated into a dosage unit form suitable for administration by injection.

In another embodiment, the following ingredients are mixed to form an injectable formulation:

| Ingredient | Amount |
|---|---|
| Compound of Formula (I), (II), (III), or (IV) | 1.2 g |
| sodium acetate buffer solution (0.4M) | 2.0 mL |
| HCl (1N) or NaOH (1M) | q.s. to suitable pH |
| water (distilled, sterile) | q.s. to 20 mL |

All of the above ingredients, except water, are combined and stirred and if necessary, with slight heating if necessary. A sufficient quantity of water is then added.

Oral Composition

To prepare a pharmaceutical composition for oral delivery, 100 mg of a compound of Formula (I), (II), (III), or (IV) is mixed with 750 mg of starch. The mixture is incorporated into an oral dosage unit, such as a hard gelatin capsule, which is suitable for oral administration.

In another embodiment, the following ingredients are mixed intimately and pressed into single scored tablets.

| Ingredient | Quantity per tablet, mg |
|---|---|
| compound of Formula (I), (II), or (III) | 200 |
| Cornstarch | 50 |
| croscarmellose sodium | 25 |
| Lactose | 120 |
| magnesium stearate | 5 |

185

In yet another embodiment, the following ingredients are mixed intimately and loaded into a hard-shell gelatin capsule.

| Ingredient | Quantity per tablet, mg |
|---|---|
| compound of Formula (I), (II), or (III) | 200 |
| lactose, spray-dried | 148 |
| magnesium stearate | 2 |

Ingredient Quantity per tablet, mg compound of Formula (I), (II), or (III) 200 lactose, spray-dried 148 magnesium stearate 2

In yet another embodiment, the following ingredients are mixed to form a solution/suspension for oral administration:

| Ingredient | Amount |
|---|---|
| Compound of Formula (I), (II), or (III) | 1 g |
| Anhydrous Sodium Carbonate | 0.1 g |
| Ethanol (200 proof), USP | 10 mL |
| Purified Water, USP | 90 mL |
| Aspartame | 0.003 g |

Sublingual (Hard Lozenge) Composition

To prepare a pharmaceutical composition for buccal delivery, such as a hard lozenge, mix 100 mg of a compound of Formula (I), (II), (III), or (IV) with 420 mg of powdered sugar mixed with 1.6 mL of light corn syrup, 2.4 mL distilled water, and 0.42 mL mint extract. The mixture is gently blended and poured into a mold to form a lozenge suitable for buccal administration.

Inhalation Composition

To prepare a pharmaceutical composition for inhalation delivery, 20 mg of a compound of Formula (I), (II), (III), or (IV) is mixed with 50 mg of anhydrous citric acid and 100 mL of 0.9% sodium chloride solution. The mixture is incorporated into an inhalation delivery unit, such as a nebulizer, which is suitable for inhalation administration.

Rectal Gel Composition

To prepare a pharmaceutical composition for rectal delivery, 100 mg of a compound of Formula (I), (II), (III), or (IV) is mixed with 2.5 g of methylcelluose (1500 mPa), 100 mg of methylparapen, 5 g of glycerin and 100 mL of purified water. The resulting gel mixture is then incorporated into rectal delivery units, such as syringes, which are suitable for rectal administration.

Suppository Formulation

A suppository of total weight 2.5 g is prepared by mixing a compound of Formula (I), (II), (III), or (IV) with Witepsol™ H-15 (triglycerides of saturated vegetable fatty acid; Riches-Nelson, Inc., New York), and has the following composition:

| Ingredient | Quantity per suppository, mg |
|---|---|
| compound of Formula (I), (II), or (III) | 500 |
| Witepsol ® H-15 | balance |

Topical Gel Composition

To prepare a pharmaceutical topical gel composition, 100 mg of a compound of Formula (I), (II), (III), or (IV) is mixed with 1.75 g of hydroxypropyl cellulose, 10 mL of propylene glycol, 10 ml, of isopropyl myristate and 100 mL of purified alcohol USP. The resulting gel mixture is then incorporated into containers, such as tubes, which are suitable for topical administration.

186

Ophthalmic Solution Composition

To prepare a pharmaceutical ophthalmic solution composition, 100 mg of a compound of Formula (I), (II), (III), or (IV) is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

The examples and embodiments described herein are for illustrative purposes only and in some embodiments, various modifications or changes are to be included within the purview of disclosure and scope of the appended claims.

What is claimed is:

1. A compound having the structure of Formula (I):

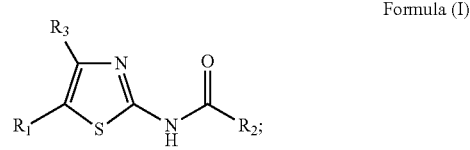

Formula (I)

wherein:

$R_1$ is

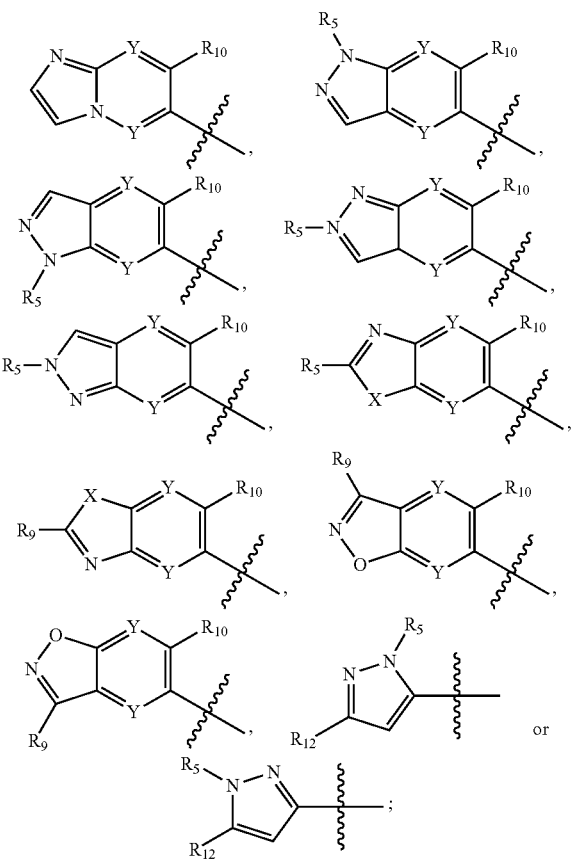

X is S, O, or $NR_5$;
Y is independently selected from $CR_{10}$ or N;
$R_2$ is aryl, heteroaryl, fused aryl or fused heteroaryl; wherein aryl, heteroaryl, fused aryl or fused heteroaryl is optionally substituted with at least one $R_3$;

R₃ is independently selected from H, F, D, Cl, Br, I, —CN, —NO₂, —OH, —CF₃, —OCF₃, —OR₅, optionally substituted $C_1$-$C_6$alkyl, optionally substituted $C_3$-$C_8$cycloalkyl, optionally substituted $C_1$-$C_6$heteroalkyl, $C_1$-$C_6$haloalkyl, optionally substituted $C_2$-$C_8$heterocycloalkyl, optionally substituted aryl, optionally substituted O-aryl, and optionally substituted heteroaryl;

R₅ is selected from H, $C_1$-$C_6$alkyl, $C_1$-$C_6$haloalkyl, $C_3$-$C_8$cycloalkyl, phenyl, and benzyl;

R₉ and R₁₀ are each independently selected from H, D, optionally substituted $C_1$-$C_6$alkyl, halogen, $C_1$-$C_6$ alkylcarbonyl, or CF₃;

R₁₂ is selected from CN, —OR₅, optionally substituted $C_1$-$C_6$alkyl, $C_1$-$C_6$haloalkyl, and optionally substituted $C_3$-$C_8$cycloalkyl, optionally substituted aryl, optionally substituted O-aryl, and optionally substituted heteroaryl;

or a pharmaceutically acceptable salt, pharmaceutically acceptable solvate, or pharmaceutically acceptable prodrug thereof.

2. The compound of claim 1 wherein R₂ is phenyl.

3. The compound of claim 2 wherein phenyl is substituted with at least one R₃ independently selected from F, Cl, Br, and I.

4. The compound of claim 1 wherein R₂ is heteroaryl.

5. The compound of claim 4 wherein heteroaryl is pyridyl.

6. The compound of claim 5 wherein pyridyl is substituted with at least one R₃ independently selected from F and Cl.

7. The compound of claim 1 wherein R₁ is

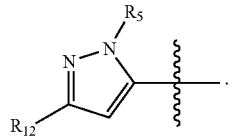

8. The compound of claim 7 wherein R₅ is $C_1$-$C_6$alkyl; and R₁₂ is CF₃.

9. A compound selected from:

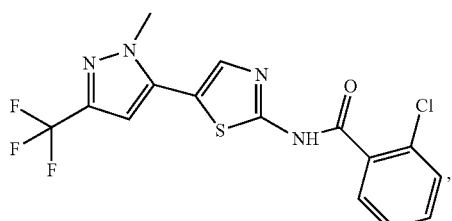

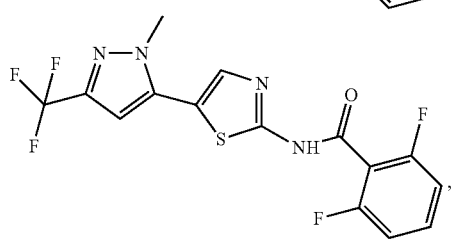

-continued

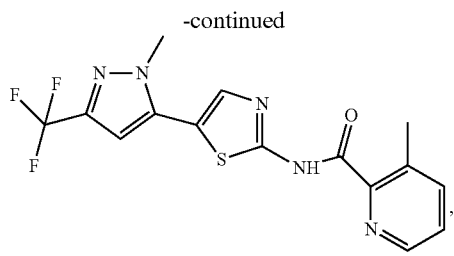

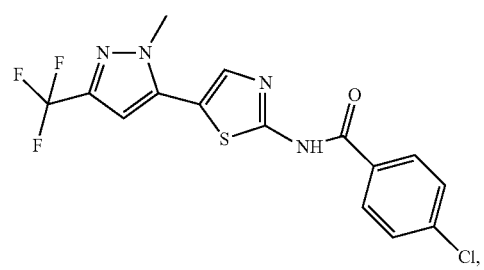

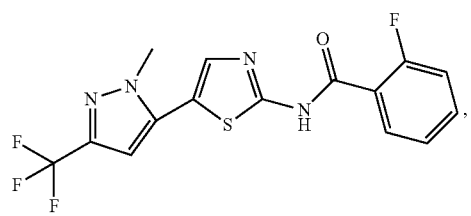

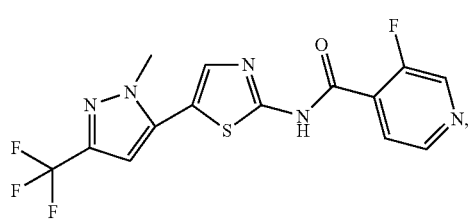

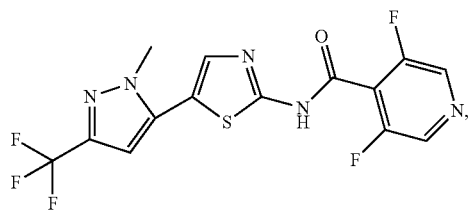

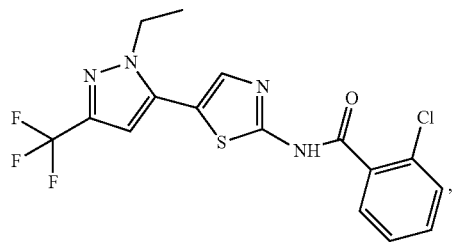

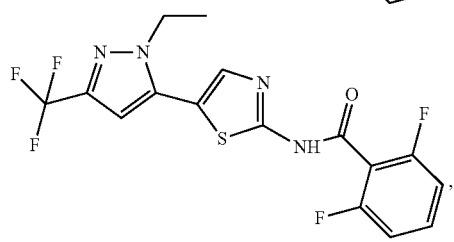

-continued
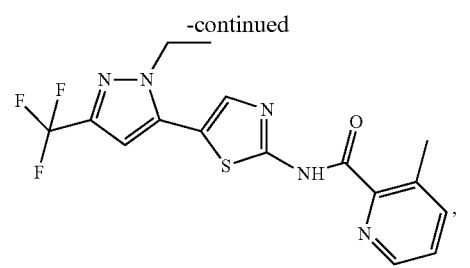
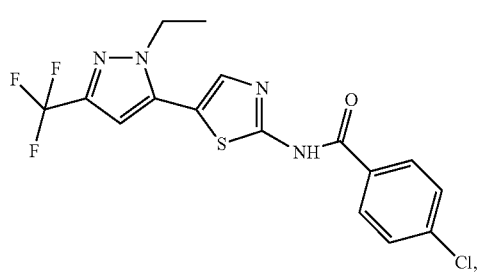
-continued
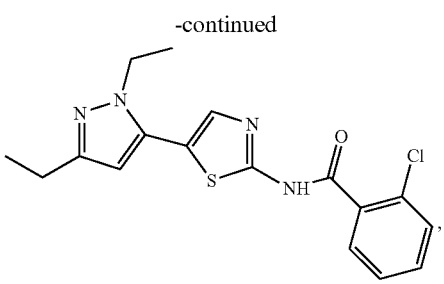
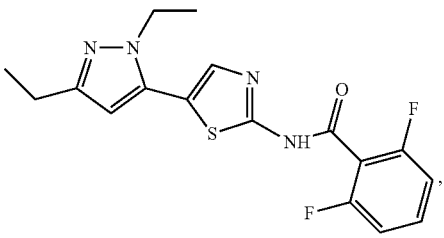
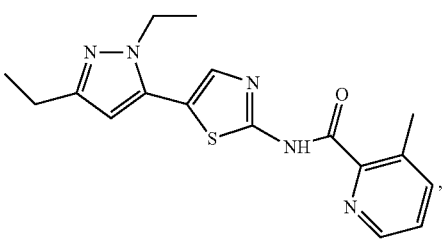
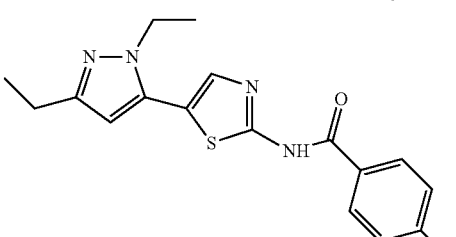
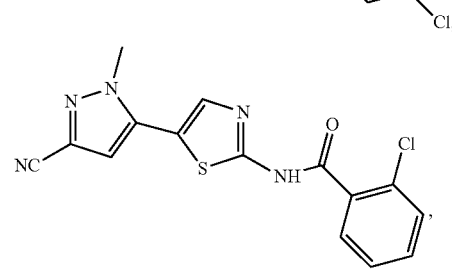
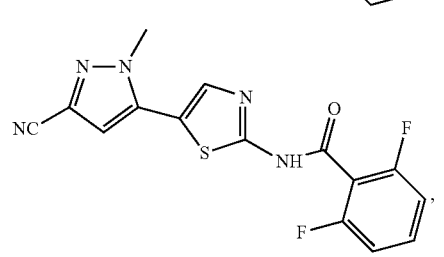
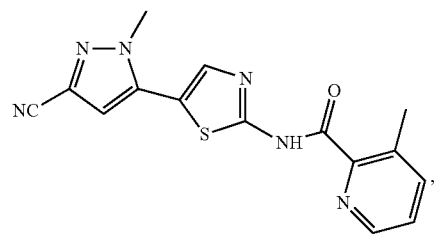

-continued
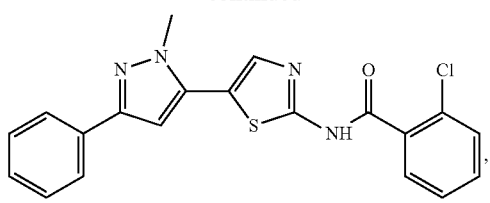,
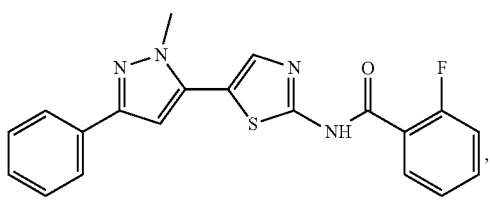,
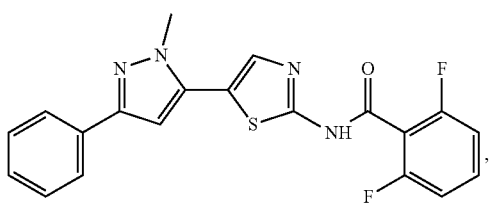,
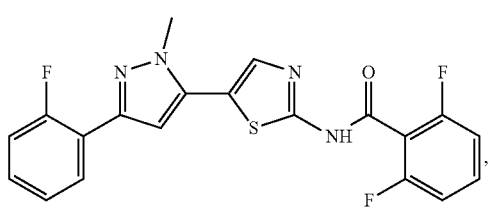,
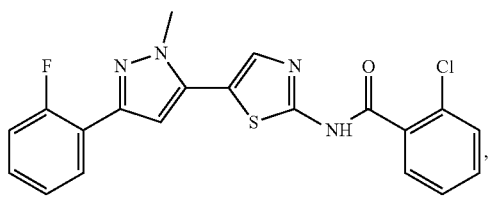,
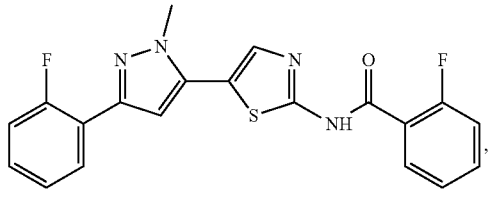,
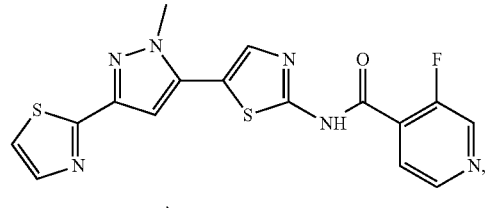,
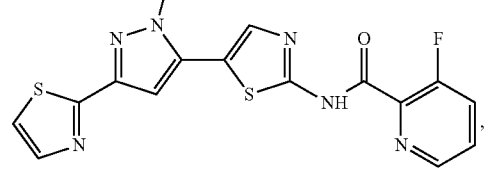,
-continued
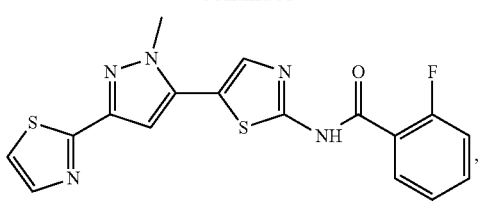,
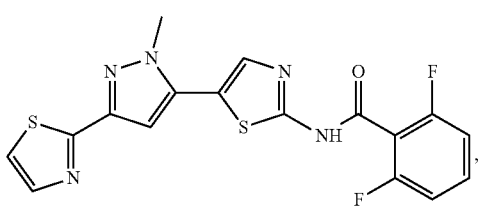,
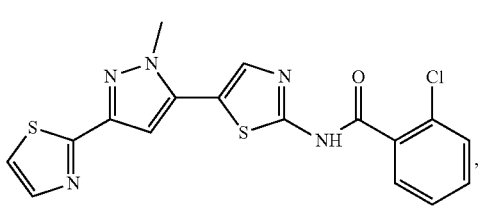,
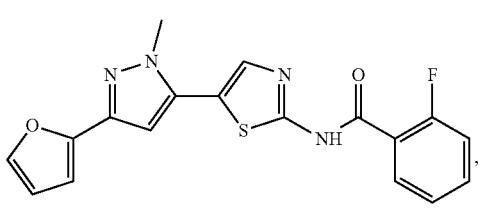,
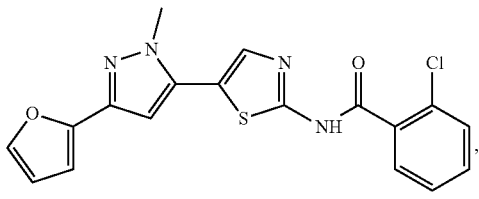,
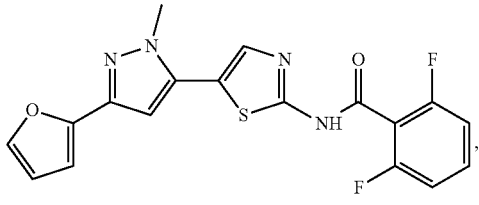,
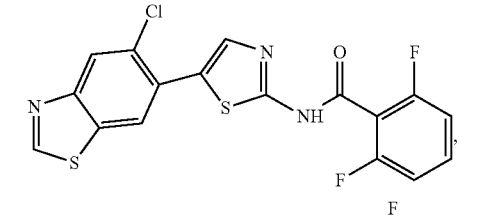,
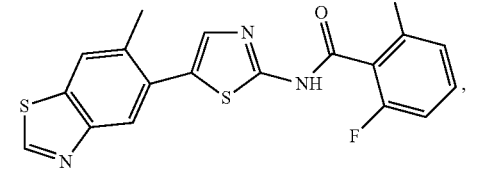,

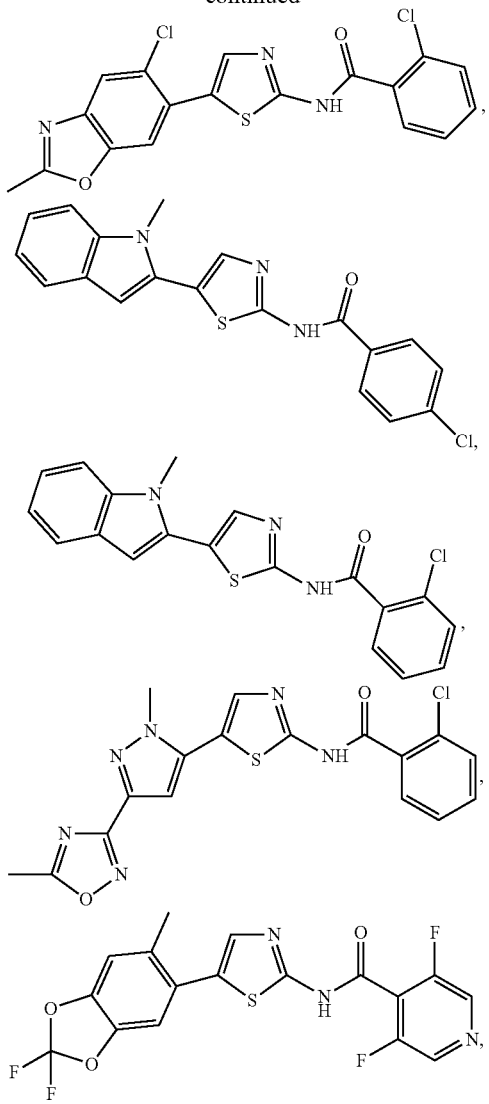

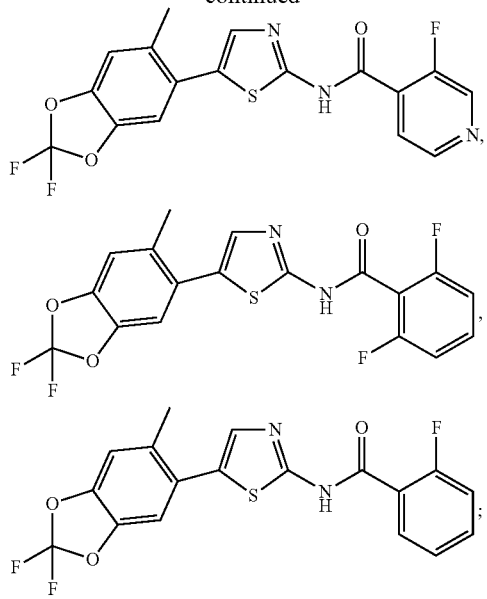

or a pharmaceutically acceptable salt, pharmaceutically acceptable solvate, or pharmaceutically acceptable prodrug thereof.

10. A pharmaceutical composition comprising a pharmaceutically acceptable diluent, excipient or binder, and a compound of claim 1 or a pharmaceutically acceptable salt, pharmaceutically acceptable prodrug, or pharmaceutically acceptable solvate thereof.

11. The compound of claim 8 wherein $R_2$ is phenyl substituted with at least one $R_3$ independently selected from F, Cl, and Br.

12. The compound of claim 11 wherein $R_2$ is phenyl substituted with two $R_3$ and each $R_3$ is F.

13. The compound of claim 11 wherein $R_2$ is phenyl is substituted with three $R_3$ and each $R_3$ is F.

* * * * *